(12) United States Patent
Legrain et al.

(10) Patent No.: US 7,763,254 B2
(45) Date of Patent: Jul. 27, 2010

(54) HUMAN IMMUNODEFICIENCY VIRUS INTEGRASE-LEDGF P75 ISOFORM PROTEIN-PROTEIN INTERACTIONS

(75) Inventors: Pierre Legrain, Paris (FR); Jean-Christophe Rain, Ermont (FR); Richard Benarous, Paris (FR); Stéphane Emiliani, Paris (FR); Clarissa Berlioz-torrent, Paris (FR); Guillaume Blot, Bondy (FR)

(73) Assignee: Cellvir (FR)

( * ) Notice: Subject to any disclaimer, the term of this patent is extended or adjusted under 35 U.S.C. 154(b) by 981 days.

(21) Appl. No.: 10/853,807

(22) Filed: May 26, 2004

(65) Prior Publication Data
US 2006/0034860 A1 Feb. 16, 2006

Related U.S. Application Data

(63) Continuation of application No. PCT/EP02/13868, filed on Nov. 26, 2002.

(60) Provisional application No. 60/333,346, filed on Nov. 26, 2001, provisional application No. 60/385,132, filed on May 31, 2002.

(51) Int. Cl.
A61K 39/385 (2006.01)
A61K 39/21 (2006.01)
(52) U.S. Cl. .............. 424/193.1; 424/188.1; 424/208.1
(58) Field of Classification Search .............. None
See application file for complete search history.

(56) References Cited

U.S. PATENT DOCUMENTS 6,222,024 B1   4/2001   Goff et al.

2006/0275748 A1   12/2006   Debyser et al.

FOREIGN PATENT DOCUMENTS

WO   WO-00/66722         11/2000
WO   WO-2004/029246 A1    4/2004

OTHER PUBLICATIONS

Busschots, K., et al., 2005, "The interaction of LEDGF/p75 with integrase is lentivirus-specific and promotes DNA binding", J. Biol. Chem. 280(18):17841-7.*

2009 Instructions to Authors, 2009, J. Virol. 83(1):1-18.*

Tatusov, R. L., 1997, A Genomic Perspective on Protein Families, Science 278:631-637.*

Tsuchiya et al., "Identification of a novel protein (VBP-1) binding to the von hippel-lindau (VHL) tumor suppressor gene product," 56 Cancer Research (Jul. 1, 1996) pp. 2881-2885.

(Continued)

*Primary Examiner*—Jeffrey S. Parkin
(74) *Attorney, Agent, or Firm*—Lerner, David, Littenberg, Krumholz & Mentlik, LLP

(57) ABSTRACT

The present invention relates to protein-protein interactions involved in AIDS. More specifically, the present invention relates to complexes of polypeptides or polynucleotides encoding the polypeptides, fragments of the polypeptides, antibodies to the complexes, Selected Interacting Domains (SID®) which are identified due to the protein-protein interactions, methods for screening drugs for agents which modulate the interaction of proteins and pharmaceutical compositions that are capable of modulating the protein-protein interactions.

1 Claim, 28 Drawing Sheets

OTHER PUBLICATIONS

Stark & Hay, "Human immunodeficiency virus type 1 (HIV-1) viral protein R (Vpr) interacts with Lys-tRNA synthetase: implications for priming of HIV-1 reverse transcription," 72 J. Virology (Apr. 1998) pp. 3037-3044.

Garrus et al., "Tsg 101 and the vacuolar protein sorting pathway are essential for HIV-1 budding," 107 Cell (Oct. 5, 2001) pp. 55-65.

Holloway, et al., "Functional interaction between the HIV transactivator Tat and the transcriptional coactivator PC4 in T cells," 275 J. Bio. Chem. (Jul. 14, 2000) pp. 21668-21677.

Benichou et al., Use of the two-hybrid system to identify cellular partners of the HIV1 Nef protein, 148 Research in Virology No. 1 (1997) pp. 71-71.

Fields & Sternglanz, The tow0hybrid system: an assay for protein-protein interactions, 10 Trends in Genetics (Aug. 1, 1994) pp. 286-292.

Legrain et al., "Protein-protein interaction maps: a lead towards cellular functions," 17 Trends in Genetics (Jun. 2001) pp. 346-352.

Legrain & Selig, "Genome-wide protein interaction maps using two-hybrid systems," 480 FEBS Letters (Aug. 25, 2000) 32-36.

De Soultrain et al., "A novel short peptide is a specific inhibitor of the human immunodeficiency virus type 1 integrase," 318 J. Molecular Bio. (2002) pp. 45-58.

Brennan & Steitz, "HuR and mRNA stability," 58 Cell. Mol. Life Sci. (2001) pp. 266-277.

Brown et al., "Regulated intramembrane proteolysis: a control mechanism conserved from bacteria to humans," 100 Cell (Feb. 18, 2000) pp. 391-398.

Bukrinskaya et al., "Establishment of a functional human immunodeficiency virus type 1 (HIV-1) reverse transcription complex involves the ctyoskeleton," 188 J. Exp. Med. (Dec. 7, 1998) pp. 2113-2125.

Caron et al., "The HIV protease inhibitor indinavir impairs sterol regulatory element-binding protein-1 intranuclear localization, inhibits preadipocyte differentiation, and induces insulin resistance," 50 Diabetes (Jun. 2001) pp. 1378-1388.

Cherepanov et al., "HIV-1 integrase forms stable tetramers and associates with LEDGF/p95 protein in human cells," 278 J. Bio. Chem. (Jan. 3, 2003) pp. 372-381.

Diaz & Pfeffer, "TIP47: a cargo selection device for mannose 6-phosphate receptor trafficking," 93 Cell (May 1, 1998) pp. 433-443.

Elbashir et al., "Duplexes of 21-nucleotide RNAs mediate RNA interference in clutured mammalian cells," 411 Nature (May 24, 2001) pp. 494-498.

Freed & Martin, "HIV-1 infection of non-dividing cells," 369 Nature (May 12, 1994) pp. 107-108.

Fujita et al., "hCDC47, a Human Member of the MCM Family," 271 J. Bio. Chem. (Feb. 23, 1996) pp. 4349-4354.

Ge et al., "Isolation of cDNAs encoding novel transcription coactivators p52 and p75 reveals an alternate regulatory mechanism of transcriptional activation," 17 EMBO J. (1998) pp. 6723-6729.

Ge et al., "A novel transcriptional coactivator, p52, functionally interacts with the essential splicing factor ASF/SF2," 2 Mol. Cell (Dec. 1998) pp. 751-759.

Gong & Yeh, "Identification of the activating and conjugating enzymes of the NEDD8 conjugation pathway," 274 J. Bio. Chem. (Apr. 23, 1999) pp. 12036-12042.

Graf et al., "Concerted action of multiple cis-acting sequences is required for rev dependence of late human immunodeficiency virus type 1 gene expression," 74 J. Virology (Nov. 2000) pp. 10822-10826.

Greene & Peterlin. "Charting HIV's remarkable voyage through the cell: basic science as a passport to future therapy," 8 Nature Medicine (Jul. 2002) pp. 673-680.

Haneda et al., "Biochemical characterization of casein kinase II as a protein kinase responsible for stimulation of HIV-1 protease in vitro," 275 Biochemical and Biophysical Research Communications (2000) pp. 434-439.

Hartl & Hartl, "Molecular chaperones in the cytosol: from nascent chain to folded protein," 295 Science (Mar. 8, 2002) pp. 1852-1858.

Haze et al., "Mammalian transcription factor ATF6 is synthesized as a transmembrane protein and activated by proteolysis in response to endoplasmic reticulum stress," 10 Molecular Biology of the Cell (Nov. 1999) pp. 3787-3799.

Herberg et al. "Analysis of A-Kinase anchoring protein (AKAP) interactio nwith protein kinase A (PKA) regulatory subunits: PKA isoform specificity in AKAP binding," 298 J. Mol. Biol. (2000) pp. 329-339.

Hoppe et al., "Membrane-bound transcription factors: regulated release by RIP or RUP," 13 Curr Opin Cell Biol (2001) pp. 344-348.

Horton et al., "SREBPs: activators of the complete program of cholesterol and fatty acid synthesis in the liver," 109 J. Clin. Inv. (May 2002) pp. 1125-1131.

Huber et al. "Snurportin 1, an m3G-cap-specific nuclear import receptor with a novel domain structure," 17 EMBO J. (1998) pp. 4114-4126.

Iizuka & Stillman, "Histone acetyltransferase HBO1 interacts with the ORC1 subunit of the human initiator protein," 274 J. Biol. Chem. (Aug. 13, 1999) pp. 23027-23034.

Jensen et al., "BAP1: a novel ubiquitin hydrolase which binds to the BRCA1 RING finger and enhances BRCA1-mediated cell growth suppression," 16 Oncogene (1998) 1097-112.

Kalpana et al. "Binding and stimulation of HIV-1 integrase by a human homolog of yeast transcription factor SNF5," 266 Science (Dec. 23, 1994) pp. 2002-2006.

Kataoka, et al., "Transportin-SR, A nuclear import receptor for SR proteins," 145 J. Cell Biol. (1999) 1145-52.

Leffers et al., "Characterisation of two major cellular poly(rC)-binding human proteins, each containing three K-homologous (KH) domains," 230 Eur. J. Biochem. (1995) pp. 447-453.

Margottin et al., "A novel human WD protein, h-βTRCP, that interacts with HIV-1 Vpu connects CD4 to the ER degradation pathway through an F-Box motif," 1 Mol. Cell (Mar. 1998) 565-574.

Vasu Nair, "HIV integrase as a target for antiviral chemotherapy," 12 Rev mED vIROL (2001) 179-93.

Olsen et al., "Interaction of cellular factors with intragenic cis-acting repressive sequences within the HIV genome," 191 Virology (1992) 709-15.

Paraskeva et al., "CRM1-mediated recycling of snurportin 1 to the cytoplasm," 145 J. Cell Biol. (Apr. 19, 1999) 255-64.

Ratner et al., "Complete nucleotide sequence of the AIDS virus, HTLV-III," 313 Nature (Jan. 24, 1985) 277-84.

Ray et al., "AIM1, a novel non-lens member of the βy-crystallin superfamily, is associated with the control of tumorigenicity in human malignant melanoma," 94 Proc. natl. Acad. Sci USA (Apr. 1997) 3329-34.

Sachdev et al., "PIASγ, a nuclear matrix-associated SUMO E3 ligase, represses LEF1 activity by sequestration into nuclear bodies," 15 Genes & Development (2001) 3088-103.

Schwartz et al., "Distinct RNA sequences in the gag region of human immunodeficiency virus type 1 decrease RNW stability and inhibit expression in the absence of rev protein," 66 J. Virology (Jan. 1992) 150-59.

Singh et al., "LEDGF binds to heat shock and stress-related element to activate the expression of stress-related genes," 283 Bioch Biophys Res Comm (2001) 943-55.

Singh et al., "Lens epithelium-derived growth factor (LEDGF/p75) and p52 are derived from a single gene by alternative splicing," 242 Gene (2000) 265-73.

Trendelenburg et al., "Molecular characterization of AKAP149, a novel a kinase anchor protein with a KH domain," 225 Biochem Biophys Res Commun (1996) 313-19.

Turelli et al., "Cytoplasmic Recruitment of INI1 and PML on Incoming HIV Preintegration Complexes: Interference with Early Steps of Viral Replication," 7 Mol. Cell (Jun. 2001) 1245-54.

Vainberg et al. "Prefoldin, a chaperone that delivers unfolded proteins to cytosolic chaperonin," 93 Cell (1998) 863-73.

Ye et al., "ER stress induces cleavage of membrane-bound ATF6 by the same proteases that process SREBPs." 6 Mol. Cell (2000) 1355-64.

* cited by examiner

EXAMPLE OF PROTEIN INTERACTION MAP

FIG. 18A

```
TGGAAGGGCTAATTCACTCCCAACAAAGACAAGATATCCTTGATCTGTGG
GTCTACCACACACAAGGCTACTTCCCTGATTGGCAGAACTACACACCAGG
GGGGACTAGATGGCCACTGACCTTTGGATGGTGCTTCAAGCTAGTACCAG
TTGAGCCAGAGAAGATAGAAGAGGCCAATGCAGGAGAGAACAACTGCTTG
TTACACCCTATGAGCCAGCATGGAATGGATGACCCGGAGAGAGAAGGGTT
AGAGTGGAGGTTTGACAGCCGCCTAGCATTTCATCACGTGGCCCGAGAGC
TGCATCCGGAGTACTACAAGAACTGATGACCTCGAGCTTTCTACAAGGGA
CTTTCCGCTGGGGACTTTCCAGGGAAGCGTGGCCTGGGCGGGACTGGGGA
GTGGCGAGCCCTCAGATGCTGCATATAAGCAGCTGCTTTTGCCTGTACTG
GGTCTCTCTGGTTAGACCAGATCTGAGCCTGGGAGCTCTCTGGCTAGCTA
GGAAACCCACTGCTTAAGCCTCAATAAAGCTTGCCTTGAGTGCTTTAAGT
AGTGTGTGCCCGTCTGTTGTGTGACTCTGGTAACTAGAGATCCCTCAGAC
CCTTTTAGTCAGTGTGGAAAATCTCTAGCAGTGGCGCCCGAACAGGGACT
TGAAAGCGAAAGGAAAACCAGAGGAGCTCTCTCGACGCAGGACTCGGCTT
GCTGAAGCGCGCACGGCAAGAGGCGAGGGGCGGCGACTGGTGAGTACGCC
AAAAAATTTTTGACTAGCGGAGGCTAGAAGGAGAGAGATGGGTGCGAGAG
CGTCAGTATTAAGTGCGGGGGAATTAGATAAGTGGGAAAAAATTCGGTTA
AGGCCAGGGGGAAAGAAACAATATAGATTAAAACATATAGTATGGGCAAG
CAGGGAGCTAGAACGATTCGCAGTTGATCCTGGCCTGTTAGAAACATCAG
AAGGCTGTAGACAAATACTGGGACAGCTACAACCGTCCCTTCAGACAGGA
TCAGAAGAGCTTAGATCATTATATAATACAGTAGCCACCCTCTATTGTGT
ACATCAAAAGATAGAGGTAAAAGACACCAAGGAAGCTTTAGAGAAGATAG
AGGAAGAGCAAAACAAAAGTAAGAAAAAAGCACAGCAAGCAGCAGCTGAC
ACAGGAAACAGCAGCCAGGTCAGCCAAAATTACCCTATAGTGCAGAACCT
ACAGGGGCAAATGGTACATCAGGCCATATCACCTAGAACTTTAAATGCAT
GGGTAAAAGTAGTGGAAGAGAAGGCGTTCAGCCCAGAAGTAATACCCATG
TTTTCAGCATTATCAGAAGGAGCCACCCCACAAGATTTAAACACCATGCT
AAACACAGTGGGGGGACACCAAGCAGCCATGCAAATGTTAAAAGAGACCA
TCAATGAGGAAGCTGCAGAATGGGATAGATTGCATCCAGTGCATGCAGGG
CCTATTGCACCAGGCCAGATGAGAGAACCAAGGGGAAGTGACATAGCAGG
AACTACTAGTACCCTTCAGGAACAAATAGGATGGATGACAAATAATCCAC
CTATCCCAGTAGGAGAAATCTATAAAAGATGGATAATCCTGGGATTAAAT
AAAATAGTAAGAATGTATAGTCCTACCAGCATTCTGGACATAAGACAAGG
ACCAAAGGAACCCTTTAGAGATTATGTAGACCGGTTCTATAAAACTCTAA
GAGCCGAGCAAGCTTCACAGGAGGTAAAAAATTGGATGACAGAAACCTTG
TTGGTCCAAAATGCGAACCCAGATTGTAAGACTATTTTAAAAGCATTGGG
ACCAGCAGCTACACTAGAAGAAATGATGACAGCATGTCAGGGAGTGGGGG
GACCCGGCCATAAAGCAAGAGTTTTGGCTGAAGCAATGAGCCAAGTAACA
AATTCAGCTACCATAATGATGCAGAGAGGCAATTTTAGGAACCAAAGAAA
AACTGTTAAGTGTTTCAATTGTGGCAAAGAAGGGCACATAGCCAAAAATT
```

FIG. 18B

```
GCAGGGCTCCTAGGAAAAAGGGCTGTTGGAAATGTGGAAAGGAAGGACAC
CAAATGAAAGATTGTACTGAGAGACAGGCTAATTTTTTAGGGAAGATCTG
GCCTTCCCACAAGGGAAGGCCAGGAAATTTTCTTCAGAGCAGACCAGAGC
CAACAGCCCCATCAGAAGAGAGCGTCAGGTTTGGAGAAGAGACAACAACT
CCCTCTCAGAAGCAGGAGCCGATAGACAAGGAACTGTATCCTTTAGCTTC
CCTCAGATCACTCTTTGGCAGCGACCCCTCGTCACAATAAAGATAGGGGG
GCAACTAAAGGAAGCTCTATTAGATACAGGAGCAGATGATACAGTATTAG
AAGAAATGAATTTGCCAGGAAGATGGAAACCAAAAATGATAGGGGGAATT
GGAGGTTTTATCAAAGTAAGACAGTATGATCAGATACCCATAGAAATATG
TGGACATAAAGCTATAGGTACAGTATTAGTAGGACCTACACCTGTCAACA
TAATTGGAAGAAATCTGTTGACTCAGATTGGTTGCACTTTAAATTTTCCC
ATTAGTCCTATTGAAACTGTACCAGTAAAATTAAAGCCAGGAATGGATGG
CCCAAAAGTTAAACAATGGCCATTGACAGAAGAAAAAATAAAAGCATTAG
TAGAAATTTGTACAGAAATGGAAAAGGAAGGGAAAATTTCAAAAATTGGG
CCTGAAAACCCATACAATACTCCAGTATTTGCCATAAAGAAAAAAGACAG
TACTAAATGGAGAAAATTAGTAGATTTCAGAGAACTTAATAAGAGAACTC
AAGACTTCTGGGAAGTTCAATTAGGAATACCACATCCCGCAGGGTTAAAA
AAGAAAAAATCAGTAACAGTACTGGATGTGGGTGATGCATATTTTTCAGT
TCCCTTACATGAAGACTTCAGGAAGTATACTGCATTTACCATACCTAGTA
TAAACAATGAGACACCAGGGACTAGATATCAGTACAATGTGCTTCCACAG
GGATGGAAAGGGTCACCAGCAATATTCCAAAGTAGCATGACAACAATCTT
AGAGCCTTTTAGAAAACAAAATCCAGACCTAGTTATCTATCAGTACATGG
ATGATTTGTACGTAGGATCTGACTTAGAAATAGGGCAGCATAGAACAAAA
ATAGAGGAACTGAGACAACATCTGTTGAGGTGGGGATTTACCACACCAGA
CAAAAAACATCAGAAAGAACCTCCATTCCTTTGGATGGGTTATGAACTCC
ATCCTGATAAATGGACAGTACAGCCTATAGTGCTGCCAGAAAAAGATAGC
TGGACTGTCAATGACATACAGAAGTTAGTGGGAAAATTGAATTGGGCAAG
TCAGATTTATGCAGGGATTAAAGTAAGGCAATTATGTAAACTCCTTAGGG
GAACCAAAGCACTAACAGAAGTAATACCACTAACAGAAGAAGCAGAACTA
GAACTGGCAGAAAACAGGGAAATTCTAAAAGAACCAGTACATGGAGTGTA
TTATGACCCATCAAAAGACTTGATAGCAGAAATACAGAAGCAGGGGCAAG
GCCAATGGACATATCAAATTTATCAAGAGCCATTTAAAAATCTGAAAACA
GGAAAATATGCAAGAACGAGGGGTGCCCACACTAATGATGTAAAACAATT
AACAGAGGCAGTACAAAAAATAGCCACAGAAAGCATAGTAATATGGGGAA
AGACTCCTAAATTTAAACTACCCATACAAAAGAAACATGGGAAACATGG
TGGACAGAATATTGGCAAGCCACCTGGATTCCTGAGTGGGAGTTTGTCAA
TACCCCTCCCTTAGTGAAATTATGGTACCAGTTAGAGAAAGAACCCATAA
TAGGAGCAGAAACTTTCTATGTAGATGGGGCAGCTAACAGGGAGACTAAA
TTAGGAAAAGCAGGATATGTTACTAACAAGGGAAGACAAAAGGTTGTCTC
CCTAACTGACACAACAAATCAGAAGACTGAGTTACAAGCAATTTATCTAG
```

FIG. 18C

```
CTTTGCAGGATTCGGGATTAGAAGTAAACATAGTAACAGACTCACAATAT
GCATTAGGAATCATTCAAGCACAACCAGATAGAAGTGAATCAGAGTTAGT
CAGTCAAATAATAGAGCAGTTAATAAAAAAGGAAAAGGTCTATCTGGCAT
GGGTACCAGCACACAAAGGAATTGGAGGAAATGAACAAGTAGATAAATTA
GTCAGTGCTGGGATCAGGAAAGTACTATTTTTAGATGGAATAGATAAGGC
CCAAGAAGAACATGAGAAATATCACAGTAATTGGAGAGCAATGGCTAGTG
ATTTTAACCTGCCACCTGTAGTAGCAAAAGAAATAGTAGCCAGCTGTGAT
AAATGTCAGCTAAAAGGAGAAGCCATGCATGGGCAAGTAGACTGTAGTCC
AGGAATATGGCAACTAGATTGTACACATTTAGAAGGAAAAGTTATCCTGG
TAGCAGTTCATGTAGCCAGTGGATATATAGAAGCAGAAGTTATTCCAGCA
GAGACAGGGCAGGAAACAGCATACTTTCTCTTAAAATTAGCAGGAAGATG
GCCAGTAACAACAATACATACAGACAATGGCAGCAATTTCACCAGTGCTA
CAGTTAAAGCCGCCTGTTGGTGGGCAGGGATCAAGCAGGAATTTGGCATT
CCCTACAATCCCCAAAGTCAAGGAGTAGTAGAATCTATGAATAAAGAATT
AAAGAAAATTATAGGACAGGTAAGAGATCAGGCTGAACATCTTAAGACAG
CAGTACAAATGGCAGTATTCATCCACAATTTTAAAAGAAAAGGGGGGATT
GGGGGGTACAGTGCAGGGGAAAGAATAGTAGACATAATAGCAACAGACAT
ACAAACTAAAGAACTACAGAAACAAATTACAAAAATTCAAAATTTTCGGG
TTTATTACAGGGACAGCAGAGATCCACTTTGGAAAGGACCAGCAAAGCTC
CTCTGGAAAGGTGAAGGGGCAGTAGTAATACAAGATAATAGTGACATAAA
AGTAGTGCCAAGAAGAAAAGCAAAGATCATTAGGGATTATGGAAAACAGA
TGGCAGGTGATGATTGTGTGGCAGGTAGACAGGATGAGGATTAGAGCATG
GAAAAGTTTAGTAAAACACCATATGTATATTTCAGGGAAAGCTAGGGGAT
GGTTTTATAGACATCACTATGAAAGTCCTCATCCAAGAATAAGTTCAGAA
GTACACATCCCACTAGGGGATGCTAAATTGGTAATAACAACATATTGGGG
TCTGCACACAGGAGAAAGAGACTGGCATTTGGGTCAGGGAGTCTCCATAG
AATGGAGGAAAAAGAGATATAGCACACAAGTAGACCCTGACCTAGCAGAC
CAACTAATTCATCTGTATTACTTTGATTGTTTTTCAGAATCTGCTATAAG
AAAGGCCATATTAGGATATAGAGTTAGTCCTAGGTGTGAATATCAAGCAG
GACATAACAAGGTAGGATCTCTACAGTACTTGGCACTAACAGCATTAATA
ACACCAAAAAAGACAAAGCCACCTTTGCCTAGTGTTAAAAAACTGACAGA
GGATAGATGGAACAAGCCCCAGAAGACCAAGGGCCACAGAGGGAGCCGCA
CAATGAATGGACACTAGAGCTTTTAGAGGAGCTTAAGAGAGAAGCTGTTA
GACATTTTCCTAGGCCATGGCTACATGGCTTAGGACAACATATCTATGAA
ACTTATGGAGATACTTGGGCAGGAGTGGAAGCCATAATAAGAATTCTGCA
ACAACTGCTGTTTATTCATTTCAGAATTGGGTGTCAACATAGCAGAATAG
GCATTATTCAACAGAGGAGAGCAAGAAGAAATGGAGCCAGTAGATCCTAA
CCTAGAGCCCTGGAAGCATCCAGGAAGTCAGCCTAGGACTGCTTGTAACA
ATTGCTATTGTAAAAGTGTTGCTTTCATTGCCAAGTTTGTTTTACAAAA
AAAGGCTTAGGCATCTCCTATGGCAGGAAGAAGCGGAGACAGCGACGAAG
```

FIG. 18D

```
ACCTCCTCAGGACAGTCAGACTCATCAAAGTTCTCTATCAAAGCAGTAAG
TAGTACATGTACTGCAATCTTTACAAGTATTAGCAATAGTAGCATTAGTA
GTAGCAACAATAATAGCAATAGTTGTGTGGACCATAGTATTCATAGAATA
TAGGAAAATATTAAGACAAAGGAAAATAGACAGGTTAATTAATAGAATAA
CAGAAAGAGCAGAAGACAGTGGCAATGAGAGCGACGGAGATCAGGAAGAA
TTATCAGCACTTGTGGAAGGGGGCACCTTGCTCCTTGGGATGTTGATGA
TCTGTAGTGCTGCAGAACAATTGTGGGTCACAGTCTATTATGGGGTACCT
GTGTGGAAAGAAGCAACCACCACTCTATTTTGTGCATCAGATGCTAAAGC
ATATGATACAGAGGTACATAATGTTTGGGCCACACATGCCTGTGTACCCA
CAGACCCCAACCCACAAGAAGTAAAATTGGAAAATGTGACAGAAAATTTT
AACATGTGGAAAAATAACATGGTAGAACAAATGCATGAGGATATAATCAG
TTTATGGGATCAAAGCCTAAAGCCATGTGTAAAATTAACTCCACTCTGTG
TTACTTTAAATTGCACTGATTTAAGGAATGCTACTAATACCACTAGTAGT
AGCTGGGAAACGATGGAGAAAGGAGAAATAAAAAACTGCTCTTTCAATAT
CACCACAAGCATAAGAGATAAGGTACAGAAAGAATATGCACTTTTTTATA
ACCTTGATGTAGTACCAATAGATAATGCTAGCTATAGGTTFATAAGTTGT
AACACCTCAGTCATTACACAGGCCTGTCCAAAGGTATCCTTTGAGCCAAT
TCCCATACATTATTGTGCCCCGGCTGGTTTTGCGATTCTAAAATGTAATG
ATAAAAGTTCAATGGAACAGGACCATGTACAAATGTCAGCACAGTACAA
TGTACACATGGAATTAGGCCAGTAGTATCAACTCAACTGCTGTTAAATGG
CAGTCTAGCAGAAGAAGAGATAGTAATTAGATCTGAAAATTTCACAAACA
ATGCTAAAACTATAATAGTACAGCTGAACGAATCTGTAGTAATTAATTGT
ACAAGACCCAACAACAATACAAGAAAAAGTATAAATATAGGACCAGGGAG
AGCATTGTATACAACAGGAGAAATAATAGGAGATATAAGACAAGCACATT
GTAACCTTAGTAAAACACAATGGGAAAACACTTTAGAACAGATAGCTATA
AAATTAAAAGAACAATTTGGGAATAATAAAACAATAATCTTTAATCCATC
CTCAGGAGGGGACCCAGAAATTGTAACACACAGTTTTAATTGTGGAGGGG
AATTTTTCTACTGTAATTCAACACAACTGTTTACTTGGAATGATACTAGA
AAGTTAAATAACACTGGAAGAAATATCACACTCCCATGTAGAATAAAACA
AATTATAAATATGTGGCAGGAAGTAGGAAAAGCAATGTATGCCCCTCCCA
TCAGAGGACAAATTAGATGTTCATCAAATATTACAGGGCTGCTATTAACA
AGAGATGGTGGTAAGGACACGAACGGGACTGAGATCTTCAGACCTGGAGG
AGGAGATATGAGGGACAATTGGAGAAGTGAATTATATAAATATAAAGTAG
TAAAAATTGAACCATTAGGAGTAGCACCCACCAAGGCAAAGAGAAGAGTG
GTGCAGAGAGAAAAAGAGCAGTGGGACTAGGAGCTTTGTTCCTTGGGTT
CTTGGGAGCAGCAGGAAGCACTATGGGCGCAGCGTCAATAACGCTGACGG
TACAGGCCAGACAATTATTGTCTGGTATAGTGCAACAGCAGAACAATCTG
CTGAGGGCTATTGAGGCGCAACAGCACCTGTTGCAACTCACAGTCTGGGG
CATCAAGCAGCTCCAGGCAAGAGTCCTGGCTGTGGAAAGATACCTAAGGG
ATCAACAGCTCCTAGGGATTTGGGGTTGCTCTGGAAAACTCATTTGCACC
```

FIG. 18E

```
ACTACTGTGCCTTGGAATACTAGTTGGAGTAATAAATCTCTGAATGAAAT
TTGGGATAACATGACTTGGATGAAGTGGGAAAGAGAAATTGACAATTACA
CACACATAATATACTCCTTAATTGAACAATCGCAGAACCAACAAGAAAAG
AATGAACAAGAATTATTGGCATTAGATAAATGGGCAAGTTTGTGGAATTG
GTTTGACATAACAAAATGGCTGTGGTATATAAAAATATTCATAATGATAG
TAGGAGGCTTGATAGGTTTAAGAATAGTTTTTGTTGTACTTTCTATAGTG
AATAGAGTTAGGCAGGGATACTCACCATTATCGTTTCAGACCCACCTCCC
AGCTCAGAGGGGACCCGACAGGCCCGACGGAATCGAAGAAGAAGGTGGAG
AGAGAGACAGAGACAGATCCGGTCCATTAGTGGATGGCTTCTTAGCAATT
ATCTGGGTCGACCTACGGAGCCTGTGCCTTTTCAGCTACCACCGCTTGAG
AGACTTACTCTTGATTGTAACGAGGATTGTGGAACTTCTGGGACGCAGGG
GGTGGGGAGTCCTCAAATATTGGTGGAATCTCCTCCAGTATTGGATTCAG
GAACTAAAGAATAGTGCTGTTAGCTTGCTCAACGCCACAGCTATAGCAGT
AGCTGAGGGAACAGATAGGGTTATAGAAATATTACAAAGAGCTTTTAGAG
CTGTTCTTCACATACCTGTAAGAATAAGACAGGGCTTGGAAAGAGCTTTG
CTATAAGATGGGTGGCAAGTGGTCAAAACGTAGTATGGCTGGATGGCCTA
CTGTAAGGGAAAGAATGAGACGAGCCGAGCCAGCAGCAGAAAGAATGAGA
CGAGCTGAGCCAGCAGCAGATGGGGTGGGAGCAGTATCTCGAGACCTGGA
AAGACATGGAGCAATCACAAGTAGCAATACAGCAGCTACTAATGCTGATT
GTGCCTGGCTAGAAGCACAAGAGGAGGAGGAGGTGGGTTTTCCAGTCAGA
CCTCAGGTACCTTTAAGACCAATGACTCACAAGGCAGCTATGGATCTTAG
CCACTTTTAAAAGAAAAGGGGGGACTGGAAGGGCTAATTCACTCCCAAC
AAAGACAAGATATCCTTGATCTGTGGGTCTACCACACACAAGGCTACTTC
CCTGATTGGCAGAACTACACACCAGGGGGGACTAGATGGCCACTGACCTT
TGGATGGTGCTTCAAGCTAGTACCAGTTGAGCCAGAGAAGATAGAAGAGG
CCAATGCAGGAGAGAACAACTGCTTGTTACACCCTATGAGCCAGCATGGA
ATGGATGACCCGGAGAGAGAAGGGTTAGAGTGGAGGTTTGACAGCCGCCT
AGCATTTCATCACGTGGCCCGAGAGCTGCATCCGGAGTACTACAAGAACT
GATGACCTCGAGCTTTCTACAAGGGACTTTCCGCTGGGGACTTTCCAGGG
AAGCGTGGCCTGGGCGGGACTGGGGAGTGGCGAGCCCTCAGATGCTGCAT
ATAAGCAGCTGCTTTTGCCTGTACTGGGTCTCTCTGGTTAGACCAGATCT
GAGCCTGGGAGCTCTCTGGCTAGCTAGGAAACCCACTGCTTAAGCCTCAA
TAAAGCTTGCCTTGAGTGCTTTAAGTAGTGTGTGCCCGTCTGTTGTGTGA
CTCTCGTAACTAGAGATCCCTCAGACCCTTTTAGTCAGTGTGGAAAATCT
CTAGCA
```

HUMAN IMMUNODEFICIENCY VIRUS INTEGRASE-LEDGF P75 ISOFORM PROTEIN-PROTEIN INTERACTIONS

CROSS-REFERENCE TO RELATED APPLICATIONS

This present application is a continuation of International Application No. PCT/EP02/13868, which was filed on Nov. 26, 2002, published in English, which claims the benefit of U.S. Provisional Patent Application 60/333,346, filed on Nov. 26, 2001 and U.S. Provisional Patent Application 60/385,132, filed on May 31, 2002. The disclosures of said applications are incorporated by reference herein.

BACKGROUND OF THE INVENTION

The present invention relates to proteins that interact with Human Immunodeficiency Virus (HIV) proteins. More specifically, the present invention relates to complexes of polypeptides or polynucleotides encoding the polypeptides, fragments of the polypeptides, antibodies to the complexes, Selected Interacting Domains (SID®) which are identified due to the protein-protein interactions, methods for screening drugs for agents which modulate the interaction of proteins and pharmaceutical compositions that are capable of modulating the protein-protein interactions.

In another embodiment, the present invention provides a protein-protein interaction map called a PIM® which is available in a report relating to the protein-protein interactions of particles from HIV.

In yet another embodiment, the present invention relates to the identification of additional proteins in the pathway common to the proteins described therein, such as pathways involved in HIV.

Most biological processes involve specific protein-protein interactions. Protein-protein interactions enable two or more proteins to associate. A large number of non-covalent bonds form between the proteins when two protein surfaces are precisely matched. These bonds account for the specificity of recognition. Thus, protein-protein interactions are involved, for example, in the assembly of enzyme subunits, in antibody-antigen recognition, in the formation of biochemical complexes, in the correct folding of proteins, in the metabolism of proteins, in the transport of proteins, in the localization of proteins, in protein turnover, in first translation modifications, in the core structures of viruses and in signal transduction.

General methodologies to identify interacting proteins or to study these interactions have been developed. Among these methods are the two-hybrid system originally developed by Fields and co-workers and described, for example, in U.S. Pat. Nos. 5,283,173; 5,468,614; and 5,667,973, which are hereby incorporated by reference.

The earliest and simplest two-hybrid system, which acted as basis for development of other versions, is an in vivo assay between two specifically constructed proteins. The first protein, known in the art as the "bait protein" is a chimeric protein which binds to a site on DNA upstream of a reporter gene by means of a DNA-binding domain or BD. Commonly, the binding domain is the DNA-binding domain from either Gal4 or native E. coli LexA and the sites placed upstream of the reporter are Gal4 binding sites or LexA operators, respectively.

The second protein is also a chimeric protein known as the "prey" in the art. This second chimeric protein carries an activation domain or AD. This activation domain is typically derived from Gal4, from VP16 or from B42.

Besides the two-hybrid systems, other improved systems have been developed to detected protein-protein interactions. For example, a two-hybrid plus one system was developed that allows the use of two proteins as bait to screen available cDNA libraries to detect a third partner. This method permits the detection between proteins that are part of a larger protein complex such as the RNA polymerase II holoenzyme and the TFIIH or TFIID complexes. Therefore, this method, in general, permits the detection of ternary complex formation as well as inhibitors preventing the interaction between the two previously defined fused proteins.

Another advantage of the two-hybrid plus one system is that it allows or prevents the formation of the transcriptional activator since the third partner can be expressed from a conditional promoter such as the methionine-repressed Met25 promoter which is positively regulated in medium lacking methionine. The presence of the methionine-regulated promoter provides an excellent control to evaluate the activation or inhibition properties of the third partner due to its "on" and "off" switch for the formation of the transcriptional activator. The three-hybrid method is described, for example in Tirode et al., *The Journal of Biological Chemistry*, 272, No. 37 pp. 22995-22999 (1997) incorporated herein by reference.

Besides the two and two-hybrid plus one systems, yet another variant is that described in Vidal et al, *Proc. Natl. Sci.* 93 pgs 10315-10320 called the reverse two- and one-hybrid systems where a collection of molecules can be screened that inhibit a specific protein-protein or protein-DNA interactions, respectively.

A summary of the available methodologies for detecting protein-protein interactions is described in Vidal and Legrain, *Nucleic Acids Research* Vol. 27, No. 4, pgs. 919-929 (1999); and Legrain and Selig, FEBS Letters 480, pgs. 32-36 (2000), which references are incorporated herein by reference.

However, the above conventionally used approaches and especially the commonly used two-hybrid methods have their drawbacks. For example, it is known in the art that, more often than not, false positives and false negatives exist in the screening method. In fact, a doctrine has been developed in this field for interpreting the results and in common practice an additional technique such as co-immunoprecipitation or gradient sedimentation of the putative interactors from the appropriate cell or tissue type are generally performed. The methods used for interpreting the results are described by Brent and Finley, Jr. in *Ann. Rev. Genet.*, 31 pgs. 663-704 (1997). Thus, the data interpretation is very questionable using the conventional systems.

One method to overcome the difficulties encountered with the methods in the prior art is described in WO99/42612, incorporated herein by reference. This method is similar to the two-hybrid system described in the prior art in that it also uses bait and prey polypeptides. However, the difference with this method is that a step of mating at least one first haploid recombinant yeast cell containing the prey polypeptide to be assayed with a second haploid recombinant yeast cell containing the bait polynucleotide is performed. Of course the person skilled in the art would appreciate that either the first recombinant yeast cell or the second recombinant yeast cell also contains at least one detectable reporter gene that is activated by a polypeptide including a transcriptional activation domain.

The method described in WO99/42612 permits the screening of more prey polynucleotides with a given bait polynucleotide in a single step than in the prior art systems due to the cell to cell mating strategy between haploid yeast cells. Furthermore, this method is more thorough and reproducible, as well as sensitive. Thus, the presence of false negatives and/or false positives is extremely minimal as compared to the conventional prior art methods.

The etiologic agent of AIDS, namely human immunodeficiency virus (HIV), was discovered in 1984 and reliable tests for HIV antibody as well as for the virus itself are currently available. AIDS is caused by HIV, a human retrovirus of the lentivirus group. The four recognized retroviruses belong to two distinct groups; the human T lymphotropic retrovirus (or leukaemia) such as HTLV-I and HTLV-II or the human immunodeficiency viruses such as HIV-1 and HIV-2. HTLV-I and HTLV-II are transforming viruses, while HIV-1 and HIV-2 are cytopathic viruses. The most common cause of AIDS throughout the world is HIV-1. HIV-2 is more closely related to some members of a group of simian immunodeficiency viruses and has about 40% sequence identity to HIV-1. HIV-2 has been identified predominantly in western Africa and is believed to be less pathogenic than HIV-1.

HIV-1 has the usual retroviral genes such as env, gal and pol. The gag gene encodes the precursor virion core proteins for the matrix protein (MA), the capsid protein (CA), nucleocapsid protein (NC) and P6. The pol gene encodes the precursor for various virion enzymes such as protease (PR), reverse transcriptase (RT), RNAse H and integrase (IN). The env gene encodes the precursors for the envelope glycoprotein (Env gp) such as surface glycoprotein (gp 120/SU) and transmembrane protein (gp 41/TM).

The transcriptional transactivator (tat) and the regulator of viral expression (rev) genes are each encoded by two overlapping exons and produce small nonvirion proteins which are essential for viral replication. Also, several nonessential genes which are not implicated in viral expression are encoded by HIV-1 such as vif, vpr, vpu and nef.

AIDS is a global epidemic with virtually every country in the world reporting cases. In the United States alone by the mid-1990s, approximately 120,000 cases among adults and adolescents, and approximately 2,000 cases among children less than 13 years old had been reported.

Sexual contact is the major mode of transmission of HIV world wide. The virus can also be transmitted via blood or blood products and infected mothers can transmit HIV to their infants perinatally and as early as the first and second trimester of pregnancy. The virus can also be transmitted from the mother to infant via breast feeding. The prevalence of HIV infection among intravenous drug users is exceptionally high.

The clinical manifestations of HIV infection range from an asymptomatic state to severe disease. The majority of individuals experience no recognizable symptoms upon initial infection but some patients suffer from acute illness about three to six weeks after primary infection. This acute illness is characterized by fever, rigors, arthralgias, myalgias, maculopapular rash, urticaria, abdominal cramps, diarrhea and aseptic meningitis. Seroconversion generally occurs between 8 to 12 weeks after infection. Neurologic disease is common in HIV-infected individuals, the most common being encephalopathy or AIDS dementia complex.

Currently. AIDS infected patients are treated with HIV anti-proteases in a three cocktail treatment. However, this medication is very costly and although prolongs the life of the AIDS infected individual, does not cure the HIV infection.

Although the development of potent anti-HIV drugs targeting two viral enzymes, such as Reverse transcriptase (RT) and Protease (PR), has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response. Thus, there is an urgent need for the development of novel anti-HIV therapies to overcome the problems of resistance to the present drugs and to improve treatment efficiency (Greene and Peterlin 2002).

Besides inhibitors of RT and of PR, inhibitors of the third viral enzyme, Integrase (IN) are just entering human clinical trials (Nair 2002). All these inhibitors target the enzymatic activity of these viral enzymes. However, no inhibitors are directed against the interactions between viral proteins and potentially important cellular partners which ensure optimal viral replication in infected cells. HIV having evolved an extraordinary efficient capacity to exploit the cell's molecular machinery in the course of infection, understanding the dynamic interplay of host cell and virus is essential to the effort to control HIV infection.

This shows that it is still needed to explore all mechanisms of HIV particles and to identify drug targets for AIDS.

SUMMARY OF THE INVENTION

Thus, it is an aspect of the present invention to identify protein-protein interactions of proteins expressed in HIV particles involved in AIDS.

Another aspect of the present invention is to develop future anti-HIV therapies by focusing on interrupting key interactions between viral and host proteins during various steps of the virus life cycle.

It is another aspect of the present invention to identify protein-protein interactions involved in AIDS for the development of more effective and better targeted therapeutic treatments.

It is yet another aspect of the present invention to identify complexes of polypeptides or polynucleotides encoding the polypeptides and fragments of the polypeptides of HIV particles.

It is yet another aspect of the present invention to identify antibodies to these complexes of polypeptides or polynucleotides encoding the polypeptides and fragments of the polypeptides of HIV particles including polyclonal, as well as monoclonal antibodies that are used for detection.

It is still another aspect of the present invention to identify selected interacting domains of the polypeptides, called SID® polypeptides.

It is still another aspect of the present invention to identify selected interacting domains of the polynucleotides, called SID® polynucleotides.

It is another aspect of the present invention to generate protein-protein interactions maps called PIM®s.

It is yet another aspect of the present invention to provide a method for screening drugs for agents which modulate the interaction of proteins and pharmaceutical compositions that are capable of modulating the protein-protein interactions involved in AIDS.

It is another aspect to administer the nucleic acids of the present invention via gene therapy.

It is yet another aspect of the present invention to provide protein chips or protein microarrays.

It is yet another aspect of the present invention to provide a report in, for example paper, electronic and/or digital forms, concerning the protein-protein interactions, the modulating compounds and the like as well as a PIM®.

Thus, the present invention relates to a complex of interacting proteins of columns 1 and 4 of Table 2.

Furthermore, the present invention provides SID® polynucleotides and SID® polypeptides of Table 3, as well as a PIM® involved in AIDS.

The present invention also provides antibodies to the protein-protein complexes involved in AIDS.

In another embodiment, the present invention provides a method for screening drugs for agents that modulate the protein-protein interactions and pharmaceutical compositions that are capable of modulating protein-protein interactions.

In another embodiment, the present invention provides protein chips or protein microarrays.

In yet another embodiment, the present invention provides a report in, for example, paper, electronic and/or digital forms.

BRIEF DESCRIPTION OF THE DRAWINGS

FIG. 1 discloses SEQ ID NOS 134-136, respectively, in order of appearance.

FIG. 2 discloses SEQ ID NOS 137 and 135-136, respectively, in order of appearance.

FIG. 3 discloses SEQ ID NOS 138 and 135-136, respectively, in order of appearance.

FIG. 4 discloses SEQ ID NOS 137 and 135-136, respectively, in order of appearance.

FIG. 5 discloses SEQ ID NOS 138 and 135-136, respectively, in order of appearance.

FIG. 6 discloses SEQ ID NO: 139.

FIG. 7 discloses SEQ ID NOS 140-145, respectively, in order of appearance.

FIG. 8 discloses SEQ ID NOS 146 and 141-145, respectively, in order of appearance.

FIG. 9 discloses SEQ ID NOS 147 and 141-145, respectively, in order of appearance.

FIG. 10 discloses SEQ ID NOS 148 and 141-145, respectively, in order of appearance.

FIG. 11 discloses SEQ ID NOS 149 and 141-145, respectively, in order of appearance.

FIG. 12 discloses SEQ ID NOS 150, 151, 150, and 151, respectively, in order of appearance.

FIG. 13 discloses SEQ ID NOS 152-155, respectively, in order of appearance.

FIG. 14 discloses SEQ ID NOS 156-159, respectively, in order of appearance.

FIG. 17 discloses SEQ ID NOS 160-162, respectively, in order of appearance.

FIG. 18 is the nucleotide sequence of a YU2 isolate from HIV-1 (SEQ ID No 133)

DETAILED DESCRIPTION

Figure 1:
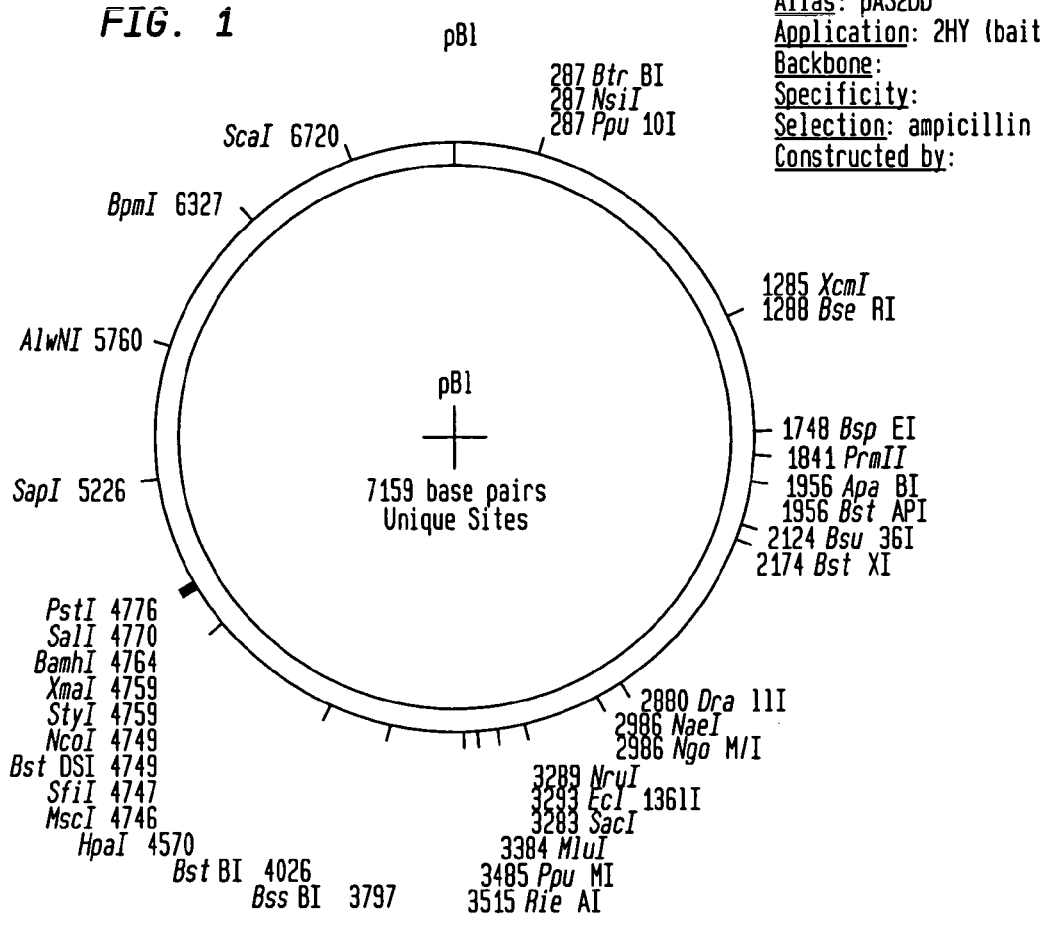
FIG. 1 is a schematic representation of the pB1 plasmid.
Figure 2:
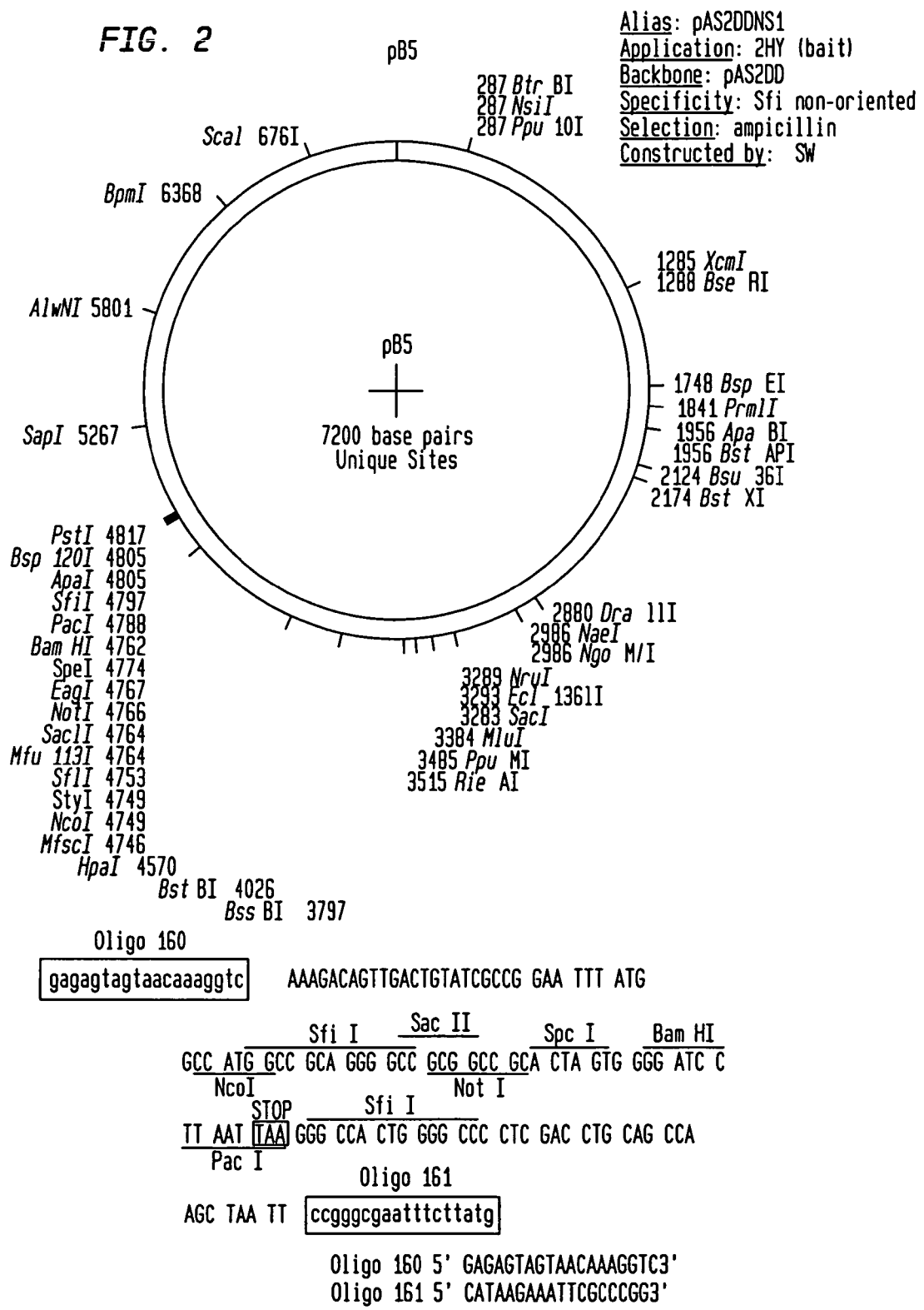
FIG. 2 is a schematic representation of the pB5 plasmid.

As used herein, the terms "polynucleotides", "nucleic acids" and "oligonucleotides" are used interchangeably and include, but are not limited to, RNA, DNA, RNA/DNA sequences of more than one nucleotide in either single chain or duplex form. The polynucleotide sequences of the present invention may be prepared from any known method including, but not limited to, any synthetic method, any recombinant method, any ex vivo generation method and the like, as well as combinations thereof.

The term "polypeptide" means herein a polymer of amino acids having no specific length. Thus, peptides, oligopeptides and proteins are included in the definition of "polypeptide" and these terms are used interchangeably throughout the specification, as well as in the claims. The term "polypeptide" does not exclude post-translational modifications such as polypeptides having covalent attachment of glycosyl groups, acetyl groups, phosphate groups, lipid groups and the like. Also encompassed by this definition of "polypeptide" are homologs thereof.

By the term "homologs" is meant structurally similar genes contained within a given species, orthologs are functionally equivalent genes from a given species or strain, as determined for example, in a standard complementation assay. Thus, a polypeptide of interest can be used not only as a model for identifying similar genes in given strains, but also to identify homologs and orthologs of the polypeptide of interest in other species. The orthologs, for example, can also be identified in a conventional complementation assay. In addition or alternatively, such orthologs can be expected to exist in bacteria (or other kind of cells) in the same branch of the phylogenic tree.

As used herein, the term "prey polynucleotide" means a chimeric polynucleotide encoding a polypeptide comprising (i) a specific domain; and (ii) a polypeptide that is to be tested for interaction with a bait polypeptide. The specific domain is preferably a transcriptional activating domain.

As used herein, a "bait polynucleotide" is a chimeric polynucleotide encoding a chimeric polypeptide comprising (i) a complementary domain; and (ii) a polypeptide that is to be tested for interaction with at least one prey polypeptide. The complementary domain is preferably a DNA-binding domain that recognizes a binding site that is further detected and is contained in the host organism.

As used herein, "complementary domain" is meant a functional constitution of the activity when bait and prey are interacting; for example, enzymatic activity.

As used herein "specific domain" is meant a functional interacting activation domain that may work through different mechanisms by interacting directly or indirectly through intermediary proteins with RNA polymerase II or III-associated proteins in the vicinity of the transcription start site.

As used herein, the term "complementary" means that, for example, each base of a first polynucleotide is paired with the complementary base of a second polynucleotide whose orientation is reversed. The complementary bases are A and T (or A and U) or C and G.

The term "sequence identity" refers to the identity between two peptides or between two nucleic acids. Identity between sequences can be determined by comparing a position in each of the sequences which may be aligned for the purposes of comparison. When a position in the compared sequences is occupied by the same base or amino acid, then the sequences are identical at that position. A degree of sequence identity between nucleic acid sequences is a function of the number of identical nucleotides at positions shared by these sequences. A degree of identity between amino acid sequences is a function of the number of identical amino acid sequences that are shared between these sequences. Since two polypeptides may each (i) comprise a sequence (i.e., a portion of a complete polynucleotide sequence) that is similar between two polynucleotides, and (ii) may further comprise a sequence that is divergent between two polynucleotides, sequence identity comparisons between two or more polynucleotides over a "comparison window" refers to the conceptual segment of at least 20 contiguous nucleotide positions wherein a polynucleotide sequence may be compared to a reference nucleotide sequence of at least 20 contiguous nucleotides and wherein the portion of the polynucleotide sequence in the comparison window may comprise additions or deletions (i.e., gaps) of 20 percent or less compared to the reference sequence (which does not comprise additions or deletions) for optimal alignment of the two sequences.

To determine the percent identity of two amino acids sequences or two nucleic acid sequences, the sequences are aligned for optimal comparison. For example, gaps can be introduced in the sequence of a first amino acid sequence or a first nucleic acid sequence for optimal alignment with the second amino acid sequence or second nucleic acid sequence. The amino acid residues or nucleotides at corresponding amino acid positions or nucleotide positions are then compared. When a position in the first sequence is occupied by the same amino acid residue or nucleotide as the corresponding position in the second sequence, the molecules are identical at that position.

The percent identity between the two sequences is a function of the number of identical positions shared by the sequences. Hence % identity=number of identical positions/ total number of overlapping positions×100.

In this comparison, the sequences can be the same length or may be different in length. Optimal alignment of sequences for determining a comparison window may be conducted by the local homology algorithm of Smith and Waterman (*J. Theor. Biol.*, 91 (2) pgs. 370-380 (1981), by the homology alignment algorithm of Needleman and Wunsch, *J. Mol. Biol.*, 48(3) pgs. 443-453 (1972), by the search for similarity via the method of Pearson and Lipman, *PNAS, USA*, 85(5) pgs. 2444-2448 (1988), by computerized implementations of these algorithms (GAP, BESTFIT, FASTA and TFASTA in the Wisconsin Genetics Software Package Release 7.0, Genetic Computer Group, 575, Science Drive, Madison, Wis.) or by inspection.

The best alignment (i.e., resulting in the highest percentage of identity over the comparison window) generated by the various methods is selected.

The term "sequence identity" means that two polynucleotide sequences are identical (i.e., on a nucleotide by nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size) and multiplying the result by 100 to yield the percentage of sequence identity. The same process can be applied to polypeptide sequences.

The percentage of sequence identity of a nucleic acid sequence or an amino acid sequence can also be calculated using BLAST software (Version 2.06 of September 1998) with the default or user defined parameter.

The term "sequence similarity" means that amino acids can be modified while retaining the same function. It is known that amino acids are classified according to the nature of their side groups and some amino acids such as the basic amino acids can be interchanged for one another while their basic function is maintained.

The term "isolated" as used herein means that a biological material such as a nucleic acid or protein has been removed from its original environment in which it is naturally present. For example, a polynucleotide present in a plant, mammal or animal is present in its natural state and is not considered to be isolated. The same polynucleotide separated from the adjacent nucleic acid sequences in which it is naturally inserted in the genome of the plant or animal is considered as being "isolated."

The term "isolated" is not meant to exclude artificial or synthetic mixtures with other compounds, or the presence of impurities which do not interfere with the biological activity and which may be present, for example, due to incomplete purification, addition of stabilizers or mixtures with pharmaceutically acceptable excipients and the like.

"Isolated polypeptide" or "isolated protein" as used herein means a polypeptide or protein which is substantially free of those compounds that are normally associated with the polypeptide or protein in a naturally state such as other proteins or polypeptides, nucleic acids, carbohydrates, lipids and the like.

The term "purified" as used herein means at least one order of magnitude of purification is achieved, preferably two or three orders of magnitude, most preferably four or five orders of magnitude of purification of the starting material or of the natural material. Thus, the term "purified" as utilized herein does not mean that the material is 100% purified and thus excludes any other material.

The term "variants" when referring to, for example, polynucleotides encoding a polypeptide variant of a given reference polypeptide are polynucleotides that differ from the reference polypeptide but generally maintain their functional characteristics of the reference polypeptide. A variant of a polynucleotide may be a naturally occurring allelic variant or it may be a variant that is known naturally not to occur. Such non-naturally occurring variants of the reference polynucleotide can be made by, for example, mutagenesis techniques, including those mutagenesis techniques that are applied to polynucleotides, cells or organisms.

Generally, differences are limited so that the nucleotide sequences of the reference and variant are closely similar overall and, in many regions identical.

Variants of polynucleotides according to the present invention include, but are not limited to, nucleotide sequences which are at least 95% identical after alignment to the reference polynucleotide encoding the reference polypeptide. These variants can also have 96%, 97%, 98% and 99.999% sequence identity to the reference polynucleotide.

Nucleotide changes present in a variant polynucleotide may be silent, which means that these changes do not alter the amino acid sequences encoded by the reference polynucleotide.

Substitutions, additions and/or deletions can involve one or more nucleic acids. Alterations can produce conservative or non-conservative amino acid substitutions, deletions and/or additions.

Variants of a prey or a SID® polypeptide encoded by a variant polynucleotide can possess a higher affinity of binding and/or a higher specificity of binding to its protein or polypeptide counterpart, against which it has been initially selected. In another context, variants can also loose their ability to bind to their protein or polypeptide counterpart.

By "fragment of a polynucleotide" or "fragment of a SID® polynucleotide" is meant that fragments of these sequences have at least 12 consecutive nucleotides, or between 12 and 5,000 consecutive nucleotides, or between 12 and 10,000 consecutive nucleotides, or between 12 and 20,000 consecutive nucleotides.

By "fragment of a polypeptide" or "fragment of a SID® polypeptide" is meant that fragments of these sequences have at lease 4 consecutive amino acids, or between 4 and 1,700 consecutive amino acids, or between 4 and 3,300 consecutive amino acids, or between 4 and 6,600 consecutive amino acids.

By "anabolic pathway" is meant a reaction or series of reactions in a metabolic pathway that synthesize complex molecules from simpler ones, usually requiring the input of energy. An anabolic pathway is the opposite of a catabolic pathway.

As used herein, a "catabolic pathway" is a series of reactions in a metabolic pathway that break down complex compounds into simpler ones, usually releasing energy in the process. A catabolic pathway is the opposite of an anabolic pathway.

As used herein, "drug metabolism" is meant the study of how drugs are processed and broken down by the body. Drug metabolism can involve the study of enzymes that break down drugs, the study of how different drugs interact within the body and how diet and other ingested compounds affect the way the body processes drugs.

As used herein, "metabolism" means the sum of all of the enzyme-catalyzed reactions in living cells that transform organic molecules.

By "secondary metabolism" is meant pathways producing specialized metabolic products that are not found in every cell.

As used herein, "SID®" means a Selected Interacting Domain and is identified as follows: for each bait polypeptide screened, selected prey polypeptides are compared. Overlapping fragments in the same ORF or CDS define the selected interacting domain.

As used herein, the term "PIM®" means a protein-protein interaction map. This map is obtained from data acquired from a number of separate screens using different bait polypeptides and is designed to map out all of the interactions between the polypeptides.

The term "affinity of binding", as used herein, can be defined as the affinity constant Ka when a given SID® polypeptide of the present invention which binds to a polypeptide and is the following mathematical relationship:

$$Ka = \frac{[SID® / \text{polypeptide complex}]}{[\text{free } SID®][\text{free polypeptide}]}$$

wherein [free SID®], [free polypeptide] and [SID®/polypeptide complex] consist of the concentrations at equilibrium respectively of the free SID® polypeptide, of the free polypeptide onto which the SID® polypeptide binds and of the complex formed between SID® polypeptide and the polypeptide onto which said SID® polypeptide specifically binds.

The affinity of a SID® polypeptide of the present invention or a variant thereof for its polypeptide counterpart can be assessed, for example, on a Biacore™ apparatus marketed by Amersham Pharmacia Biotech Company such as described by Szabo et al. (*Curr. Opin. Struct. Biol.* 5 pgs. 699-705 (1995)) and by Edwards and Leartherbarrow (*Anal. Biochem* 246 pgs. 1-6 (1997)).

As used herein, the phrase "at least the same affinity" with respect to the binding affinity between a SID® polypeptide of the present invention to another polypeptide means that the Ka is identical or can be at least two-fold, at least three-fold or at least five fold greater than the Ka value of reference.

As used herein, the term "modulating compound" means a compound that inhibits or stimulates or can act on another protein which can inhibit or stimulate the protein-protein interaction of a complex of two polypeptides or the protein-protein interaction of two polypeptides.

More specifically, the present invention comprises complexes of polypeptides or polynucleotides encoding the polypeptides composed of a bait polypeptide, or a bait polynucleotide encoding a bait polypeptide and a prey polypeptide or a prey polynucleotide encoding a prey polypeptide. The prey polypeptide or prey polynucleotide encoding the prey polypeptide is capable of interacting with a bait polypeptide of interest in various hybrid systems.

As described in the background of the present invention, there are various methods known in the art to identify prey polypeptides that interact with bait polypeptides of interest. These methods include, but are not limited to, generic two-hybrid systems as described by Fields et al. (*Nature*, 340:245-246 (1989)) and more specifically in U.S. Pat. Nos. 5,283, 173, 5,468,614 and 5,667,973, which are hereby incorporated by reference; the reverse two-hybrid system described by Vidal et al. (supra); the two plus one hybrid method described, for example, in Tirode et al. (supra); the yeast forward and reverse 'n'-hybrid systems as described in Vidal and Legrain (supra); the method described in WO 99/42612; those methods described in Legrain et al. (*FEBS Letters* 480 pgs. 32-36 (2000)) and the like.

The present invention is not limited to the type of method utilized to detect protein-protein interactions and therefore any method known in the art and variants thereof can be used. It is however better to use the method described in WO99/

42612 or WO00/66722, both references incorporated herein by reference due to the methods' sensitivity, reproducibility and reliability.

Protein-protein interactions can also be detected using complementation assays such as those described by WO 00/07038 and WO98/34120.

Although the above methods are described for applications in the yeast system, the present invention is not limited to detecting protein-protein interactions using yeast, but also includes similar methods that can be used in detecting protein-protein interactions in, for example, mammalian systems as described, for example in Takacs et al. (*Proc. Natl. Acad. Sci., USA*, 90 (21):10375-79 (1993)) and Vasavada et al. (*Proc. Natl. Acad. Sci., USA*, 88 (23):10686-90 (1991)), as well as a bacterial two-hybrid system as described in Karimova et al. (1998), WO99/28746, WO00/66722 and Legrain et al. (*FEBS Letters*, 480 pgs. 32-36 (2000)).

Protein-protein interactions can also be detected using fluorescence energy transfer techniques (Fluorescence resonance energy transfer analysis of protein-protein interactions in single living cells by multifocal multiphoton microscopy. Majoul I, Straub M, Duden R, Hell S W, Soling H D J Biotechnol 2002 January; 82(3):267-77).

The above-described methods are limited to the use of yeast, mammalian cells and *Escherichia coli* cells, the present invention is not limited in this manner. Consequently, mammalian and typically human cells, as well as bacterial, yeast, fungus, insect, nematode and plant cells are encompassed by the present invention and may be transfected by the nucleic acid or recombinant vector as defined herein.

Examples of suitable cells include, but are not limited to, VERO cells, HELA cells such as ATCC No. CCL2, CHO cell lines such as ATCC No. CCL61, COS cells such as COS-7 cells and ATCC No. CRL 1650 cells, W138, BHK, HepG2, 3T3 such as ATCC No. CRL6361, A549, PC12, K562 cells, 293 cells, Sf9 cells such as ATCC No. CRL1711 and Cv1 cells such as ATCC No. CCL70.

Other suitable cells that can be used in the present invention include, but are not limited to, prokaryotic host cells strains such as *Escherichia coli*, (e.g., strain DH5-α), *Bacillus subtilis, Salmonella typhimurium*, or strains of the genera of *Pseudomonas, Streptomyces* and *Staphylococcus*.

Further suitable cells that can be used in the present invention include yeast cells such as those of *Saccharomyces* such as *Saccharomyces cerevisiae*.

The bait polynucleotide, as well as the prey polynucleotide can be prepared according to the methods known in the art such as those described above in the publications and patents reciting the known method per se.

The bait polynucleotide of the present invention is obtained from HIV particles cDNA, or variants of cDNA fragment from a library of HIV particles, and fragments from the genome or transcriptome of HIV particles cDNA ranging from about 12 to about 5,000, or about 12 to about 10,000 or from about 12 to about 20,000. The microorganism utilized to make the library of HIV is YU2 described by Li et al (*J. Virol.* 8: 3973-3985 (1991)). The nucleotide sequence of YU2 is shown in FIG. 18 or can be obtained from Genebank Accession No. M93258.

Figure 10:
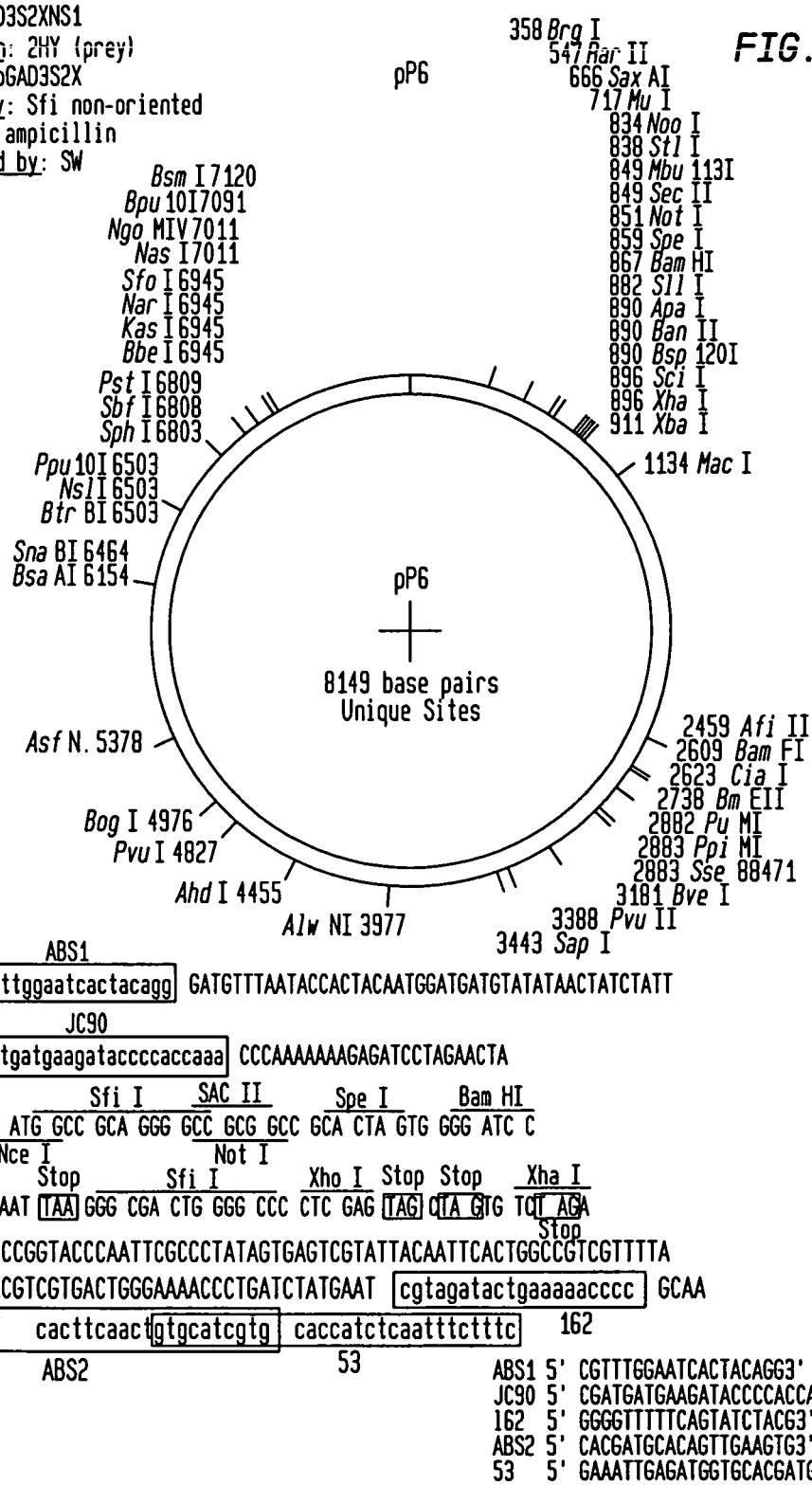
FIG. 10 is a schematic representation of the pP6 plasmid.
Figure 11:
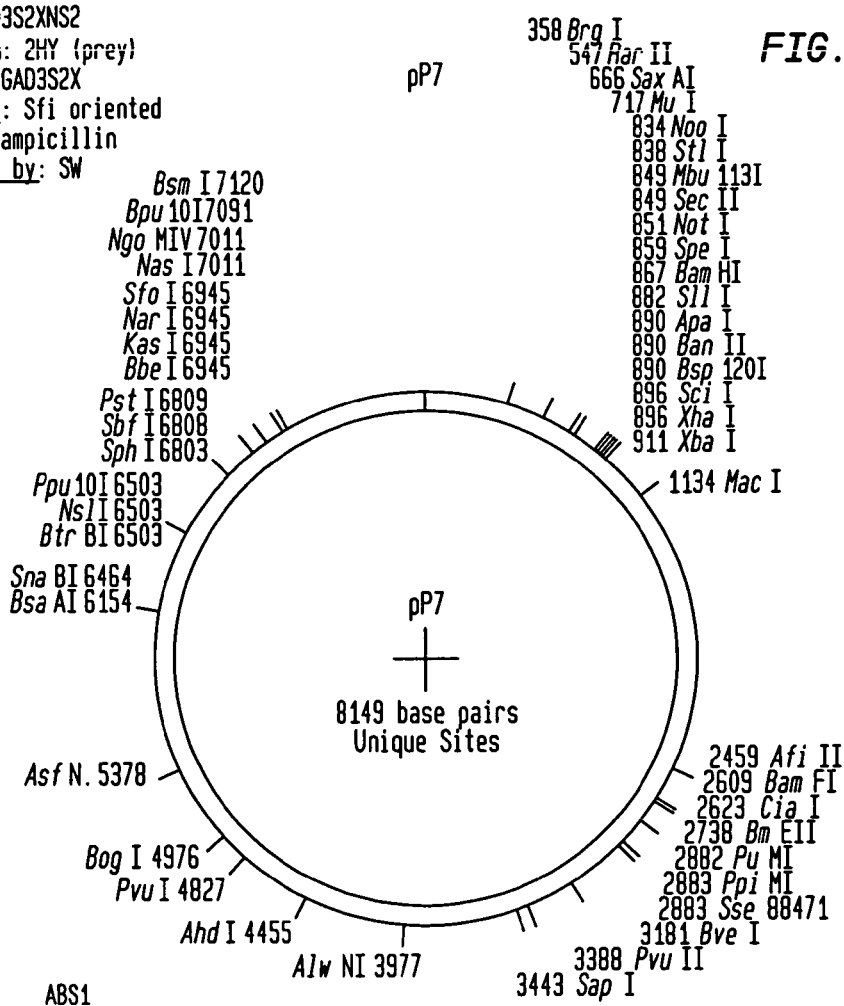
FIG. 11 is a schematic representation of the pP7 plasmid.
Figure 12:
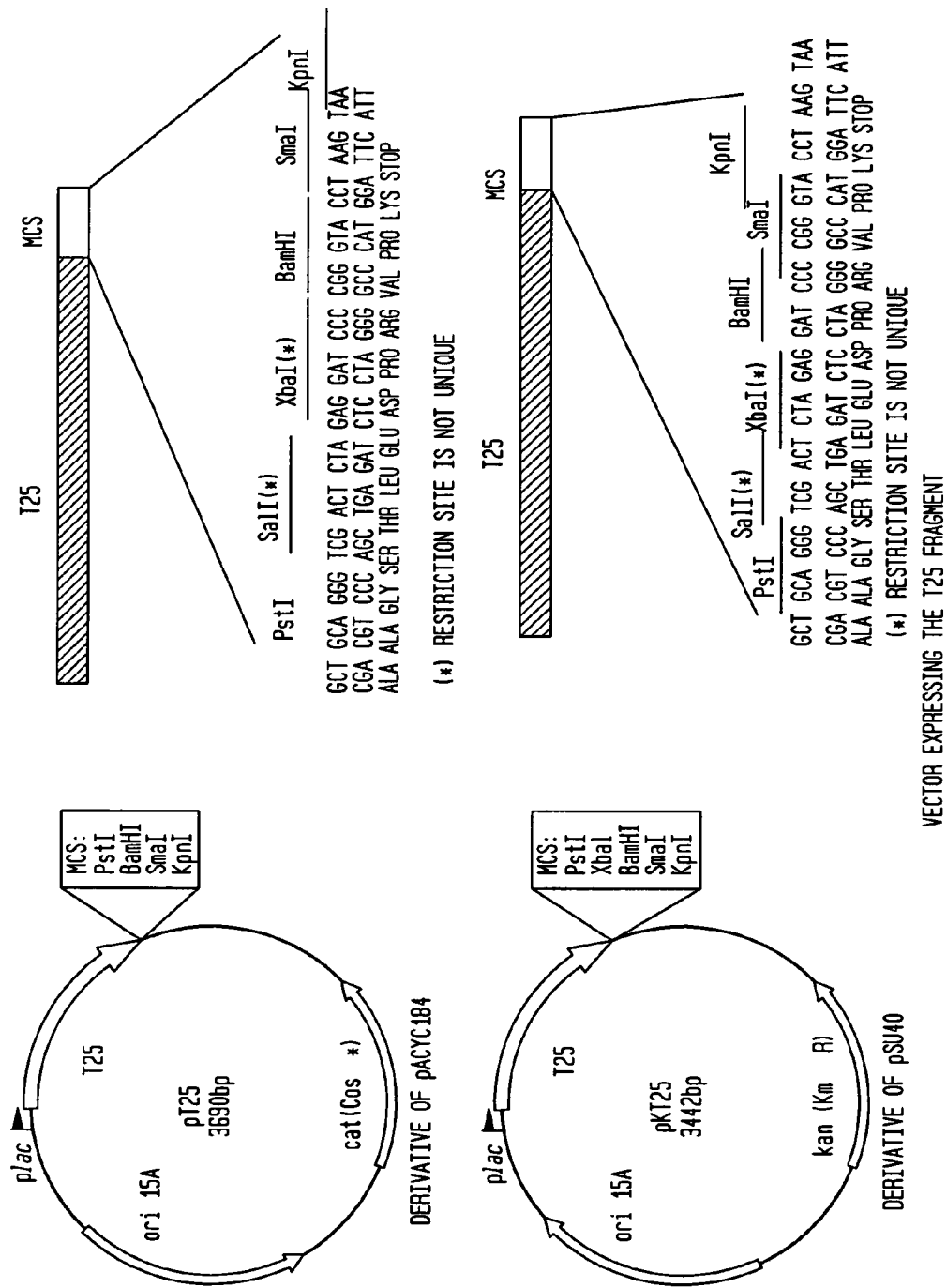
FIG. 12 is a schematic representation of vectors expressing the T25 fragment.
Figure 13:
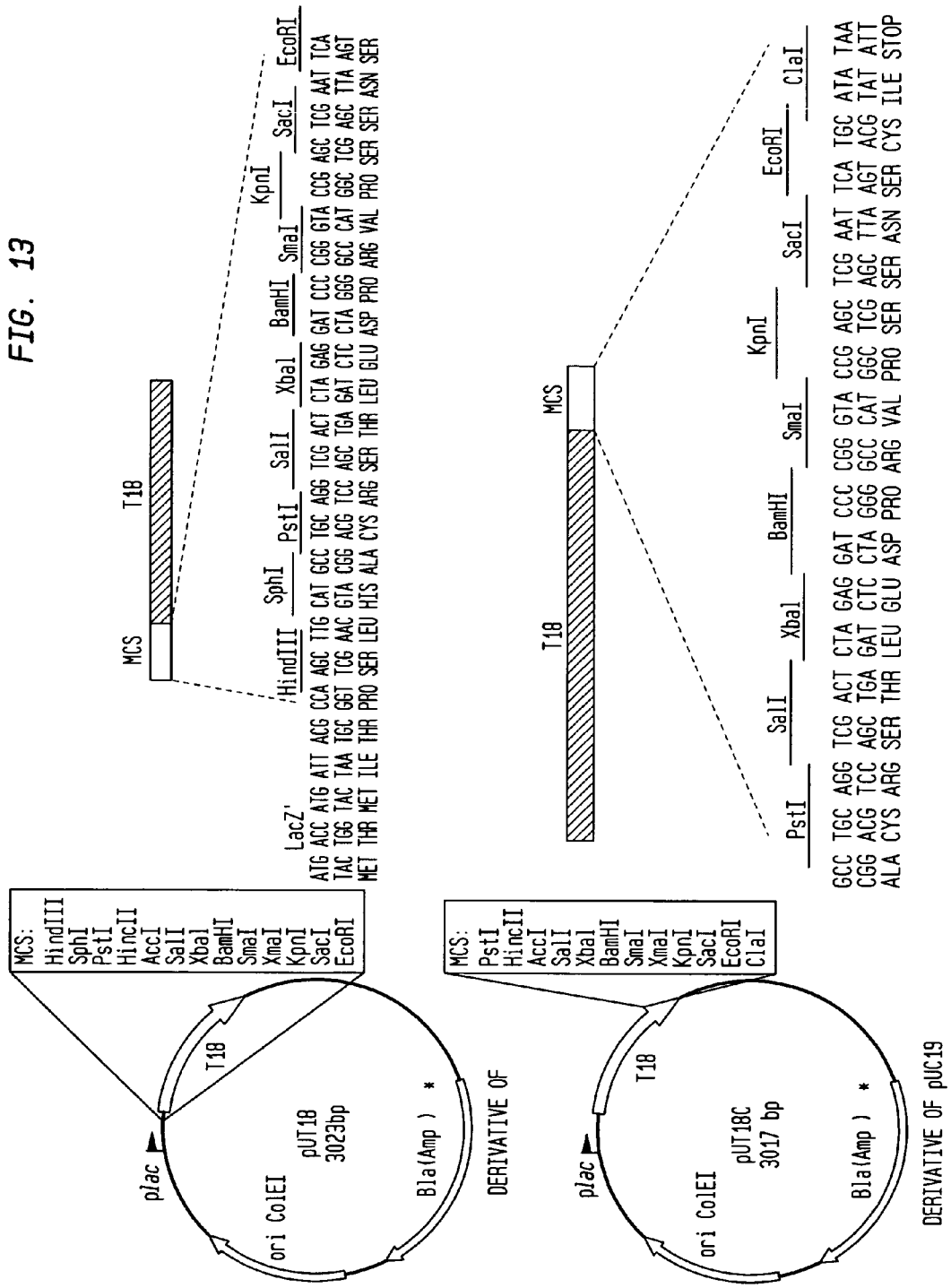
FIG. 13 is a schematic representation of vectors expressing the T18 fragment.
Figure 14:
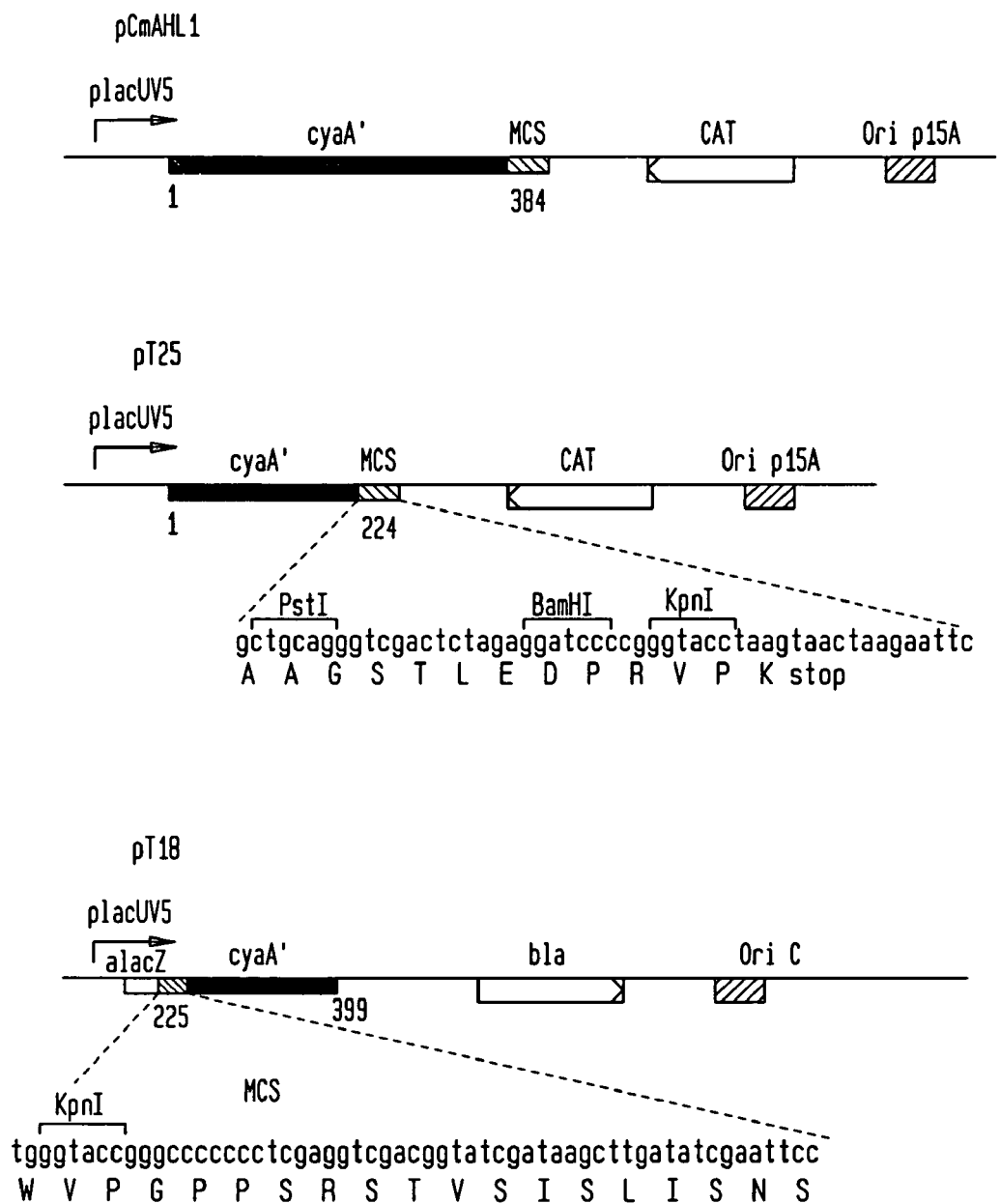
FIG. 14 is a schematic representation of various vectors of pCmAHL1, pT25 and pT18.

A prey library is derived from a cDNA library from poly A+ RNA of CEMC7 cells and constructed in the specially designed prey vector pP6 as shown in FIG. 10 after ligation of suitable linkers such that every cDNA insert is fused to a nucleotide sequence in the vector that encodes the transcription activation domain of a reporter gene. Any transcription activation domain can be used in the present invention. Examples include, but are not limited to, Gal14, VP16, B42, His and the like. Toxic reporter genes, such as $CAT^R$, CYH2, CYH1, URA3, bacterial and fungi toxins and the like can be used in reverse two-hybrid systems.

The polypeptides encoded by the nucleotide inserts of the human CEMC7 prey library thus prepared are termed "prey polypeptides" in the context of the presently described selection method of the prey polynucleotides.

Figure 3:
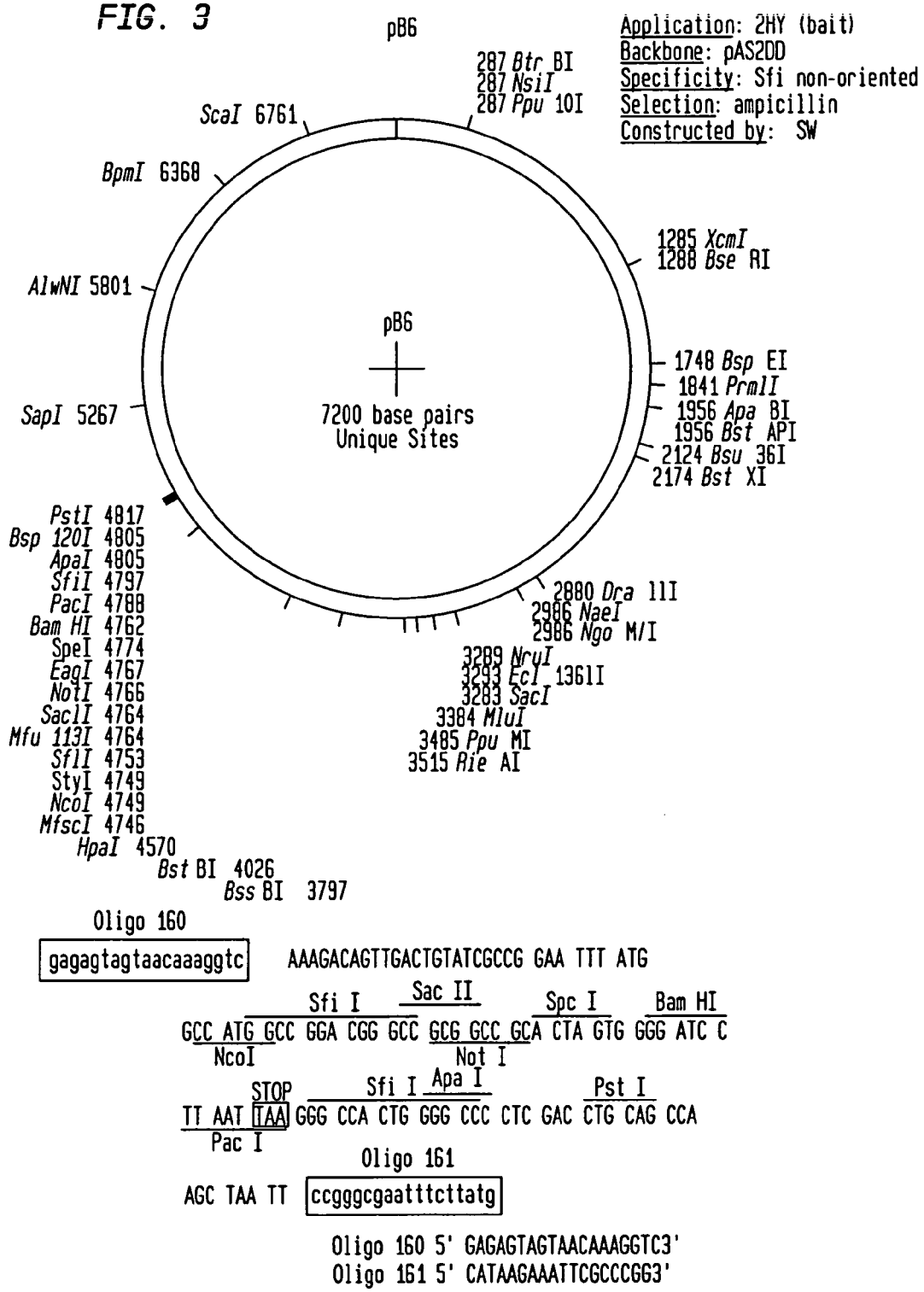
FIG. 3 is a schematic representation of the pB6 plasmid.
Figure 4:
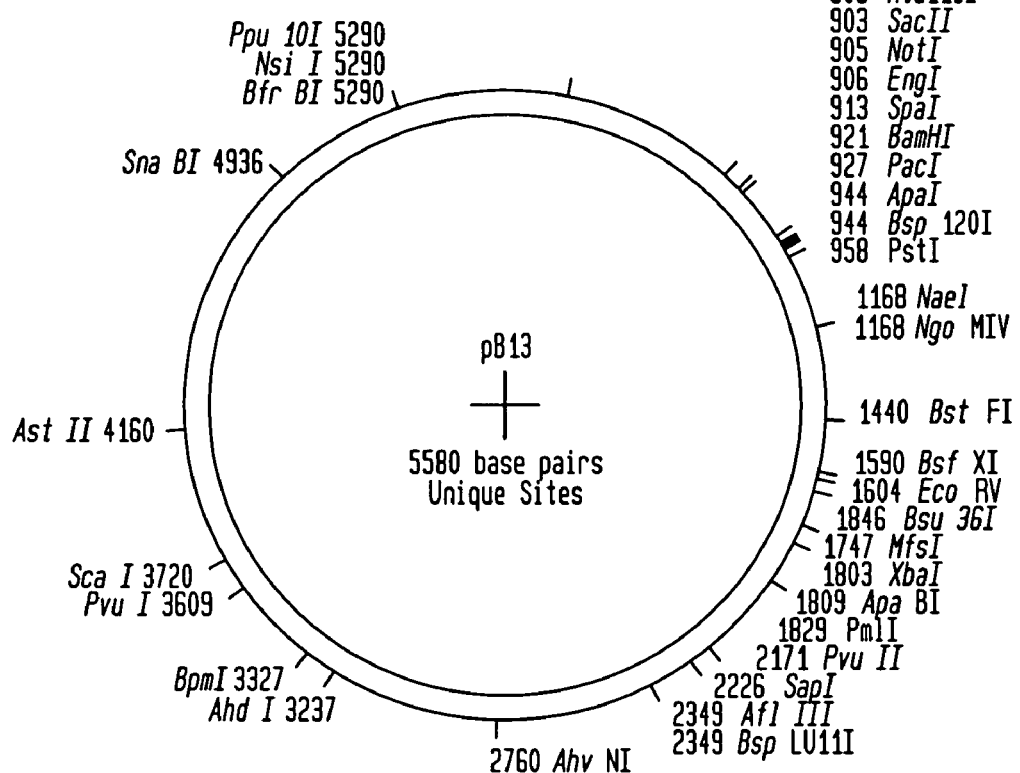
FIG. 4 is a schematic representation of the pB13 plasmid.
Figure 5:
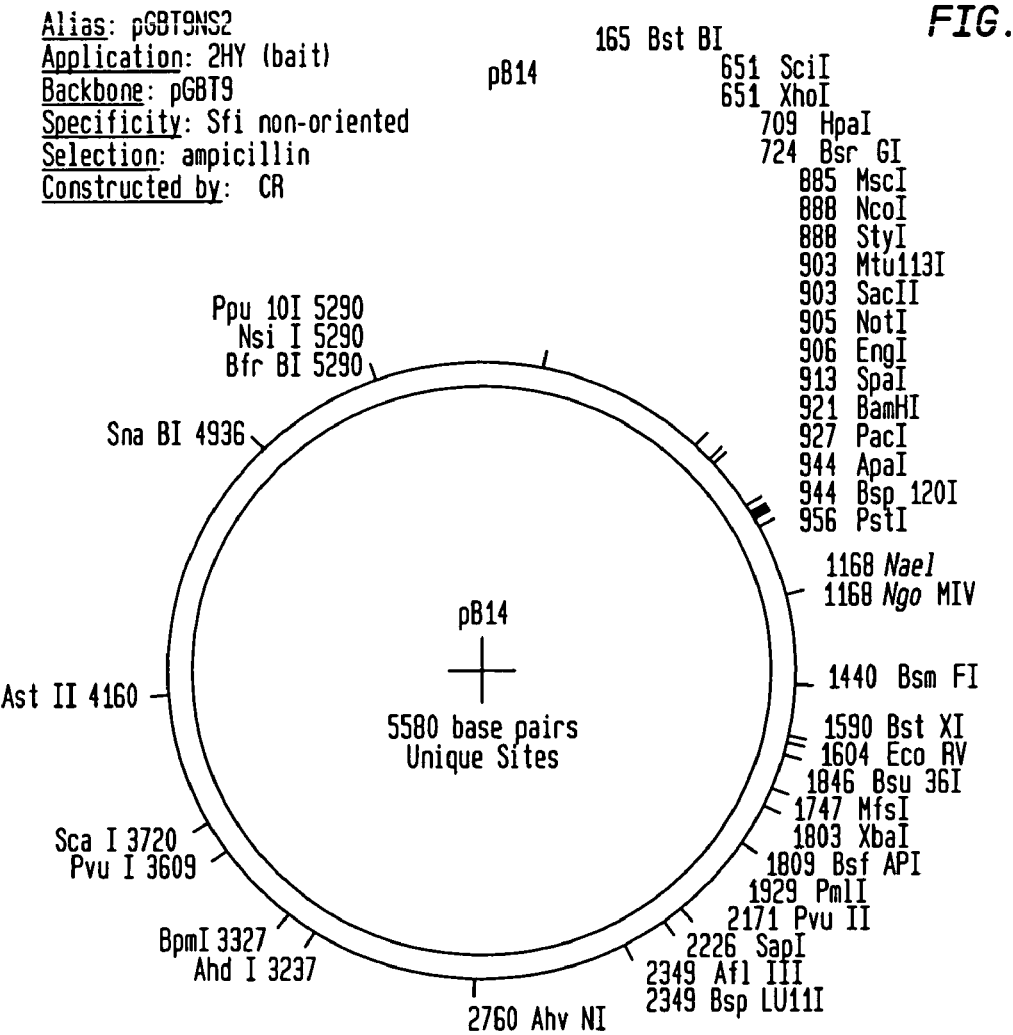
FIG. 5 is a schematic representation of the pB14 plasmid.
Figure 17:
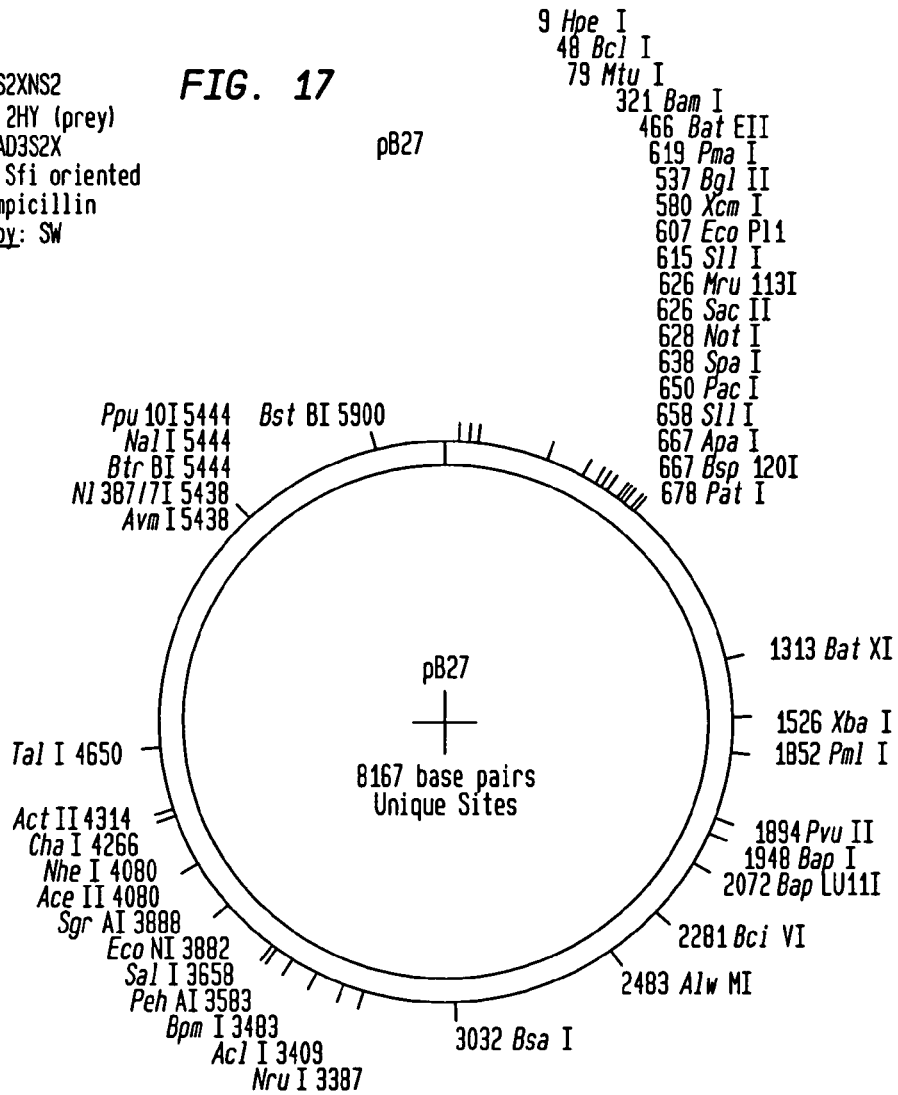
FIG. 17 is a schematic representation of the pB27 plasmid.

The bait polynucleotides can be inserted in bait plasmid pB6 or pB27 as illustrated in FIG. 3 and FIG. 17, respectively. The bait polynucleotide insert is fused to a polynucleotide encoding the binding domain of, for example, the Gal4 DNA binding domain and the shuttle expression vector is used to transform cells.

The bait polynucleotides used in the present invention are described in Table 1.

As stated above, any cells can be utilized in transforming the bait and prey polynucleotides of the present invention including mammalian cells, bacterial cells, yeast cells, insect cells and the like.

In an embodiment, the present invention identifies protein-protein interactions in yeast. In using known methods, a prey positive clone is identified containing a vector which comprises a nucleic acid insert encoding a prey polypeptide which binds to a bait polypeptide of interest. The method in which protein-protein interactions are identified comprises the following steps:

(i) mating at least one first haploid recombinant yeast cell clone from a recombinant yeast cell clone library that has been transformed with a plasmid containing the prey polynucleotide to be assayed with a second haploid recombinant yeast cell clone transformed with a plasmid containing a bait polynucleotide encoding for the bait polypeptide;

(ii) cultivating diploid cell clones obtained in step i) on a selective medium; and (iii) selecting recombinant cell clones which grow on the selective medium.

This method may further comprise the step of:

(iv) characterizing the prey polynucleotide contained in each recombinant cell clone which is selected in step iii).

In yet another embodiment of the present invention, in lieu of yeast, *Escherichia coli* is used in a bacterial two-hybrid system, which encompasses a similar principle to that described above for yeast, but does not involve mating for characterizing the prey polynucleotide.

In yet another embodiment of the present invention, mammalian cells and a method similar to that described above for yeast for characterizing the prey polynucleotide are used.

By performing the yeast, bacterial or mammalian two-hybrid system, it is possible to identify for one particular bait an interacting prey polypeptide. The prey polynucleotide that has been selected by testing the library of preys in a screen using the two-hybrid, two plus one hybrid methods and the like, encodes the polypeptide interacting with the protein of interest.

The present invention is also directed, in a general aspect, to a complex of polypeptides, polynucleotides encoding the polypeptides composed of a bait polypeptide or bait polynucleotide encoding the bait polypeptide and a prey polypeptide or prey polynucleotide encoding the prey polypeptide capable of interacting with the bait polypeptide of interest. These complexes are identified in Table 2.

In another aspect, the present invention relates to a complex of polynucleotides consisting of a first polynucleotide, or a fragment thereof, encoding a prey polypeptide that interacts with a bait polypeptide and a second polynucleotide or a fragment thereof. This fragment has at least 12 consecutive nucleotides, but can have between 12 and 5,000 consecutive nucleotides, or between 12 and 10,000 consecutive nucleotides or between 12 and 20,000 consecutive nucleotides.

The complexes of the two interacting polypeptides listed in Table 2 and the sets of two polynucleotides encoding these polypeptides also form part of the present invention.

In yet another embodiment, the present invention relates to an isolated complex of at least two polypeptides encoded by two polynucleotides wherein said two polypeptides are associated in the complex by affinity binding and are depicted in columns 1 and 4 of Table 2.

In yet another embodiment, the present invention relates to an isolated complex comprising at least a polypeptide as described in column 1 of Table 2 and a polypeptide as described in column 4 of Table 2. The present invention is not limited to these polypeptide complexes alone but also includes the isolated complex of the two polypeptides in which fragments and/or homologous polypeptides exhibit at least 95% sequence identity, as well as from 96% sequence identity to 99.999% sequence identity.

Also encompassed in another embodiment of the present invention is an isolated complex in which the SID® of the prey polypeptides encoded by SEQ ID No 15 to 37 in Table 3 form the isolated complex.

Besides the isolated complexes described above, nucleic acids coding for a Selected Interacting Domain (SID®) polypeptide or a variant thereof or any of the nucleic acids set forth in Table 3 can be inserted into an expression vector which contains the necessary elements for the transcription and translation of the inserted protein-coding sequence. Such transcription elements include a regulatory region and a promoter. Thus, the nucleic acid which may encode a marker compound of the present invention is operably linked to a promoter in the expression vector. The expression vector may also include a replication origin.

A wide variety of host/expression vector combinations are employed in expressing the nucleic acids of the present invention. Useful expression vectors that can be used include, for example, segments of chromosomal, non-chromosomal and synthetic DNA sequences. Suitable vectors include, but are not limited to, derivatives of SV40 and pcDNA and known bacterial plasmids such as Col EI, pCR1, pBR322, pMal-C2, pET, pGEX as described by Smith et al (1988), pMB9 and derivatives thereof, plasmids such as RP4, phage DNAs such as the numerous derivatives of phage I such as NM989, as well as other phage DNA such as M13 and filamentous single stranded phage DNA; yeast plasmids such as the 2 micron plasmid or derivatives of the 2m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like.

For example, in a baculovirus expression system, both non-fusion transfer vectors, such as, but not limited to pVL941 (BamHI cloning site Summers), pVL1393 (BamHI, SmaI, XbaI, EcoRI, NotI, XmaIII, BglII and PstI cloning sites; Invitrogen), pVL1392 (BglII, PstI, NotI, XmaIII, EcoRI, XbaI, SmaI and BamHI cloning site; Summers and Invitrogen) and pBlueBacIII (BamHI, BglII, PstI, NcoI and HindIII cloning site, with blue/white recombinant screening, Invitrogen), and fusion transfer vectors such as, but not limited to, pAc700 (BamHI and KpnI cloning sites, in which the BamHI recognition site begins with the initiation codon; Summers), pAc701 and pAc70-2 (same as pAc700, with different reading frames), pAc360 (BamHI cloning site 36 base pairs downstream of a polyhedrin initiation codon; Invitrogen (1995)) and pBlueBacHisA, B, C (three different reading frames with BamHI, BglII, PstI, NcoI and HindIII cloning site, an N-terminal peptide for ProBond purification and blue/white recombinant screening of plaques; Invitrogen (220) can be used.

Mammalian expression vectors contemplated for use in the invention include vectors with inducible promoters, such as the dihydrofolate reductase promoters, any expression vector with a DHFR expression cassette or a DHFR/methotrexate co-amplification vector such as pED (PstI, SalI, SbaI, SmaI and EcoRI cloning sites, with the vector expressing both the cloned gene and DHFR; Kaufman, 1991). Alternatively a glutamine synthetase/methionine sulfoximine co-amplification vector, such as pEE14 (HindIII, XbaII, SmaI, SbaI, EcoRI and BclI cloning sites in which the vector expresses glutamine synthetase and the cloned gene; Celltech). A vector that directs episomal expression under the control of the Epstein Barr Virus (EBV) or nuclear antigen (EBNA) can be used such as pREP4 (BamHI, SfiI, XhoI, NotI, NheI, HindIII, NheI, PvuII and KpnI cloning sites, constitutive RSV-LTR promoter, hygromycin selectable marker; Invitrogen), pCEP4 (BamHI, SfiI, XhoI, NotI, NheI, HindIII, NheI, PvuII and KpnI cloning sites, constitutive hCMV immediate early gene promoter, hygromycin selectable marker; Invitrogen), pMEP4 (KpnI, PvuI, NheI, HindIII, NotI, XhoI, SfiI, BamHI cloning sites, inducible methallothionein IIa gene promoter, hygromycin selectable marker, Invitrogen), pREP8 (BamHI, XhoI, NotI, HindIII, NheI and KpnI cloning sites, RSV-LTR promoter, histidinol selectable marker; Invitrogen), pREP9 (KpnI, NheI, HindIII, NotI, XhoI, SfiI, BamHI cloning sites, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen).

Selectable mammalian expression vectors for use in the invention include, but are not limited to, pRc/CMV (HindIII, BstXI, NotI, SbaI and ApaI cloning sites, G418 selection, Invitrogen), pRc/RSV (HindIII, SpeI, BstXI, NotI, XbaI cloning sites, G418 selection, Invitrogen) and the like. Vaccinia virus mammalian expression vectors (see, for example Kaufman 1991 that can be used in the present invention include, but are not limited to, pSC11 (SmaI cloning site, TK- and β-gal selection), pMJ601 (SalI, SmaI, AflI, NarI, BspMII, BamHI, ApaI, NheI, SacII, KpnI and HindIII cloning sites; TK- and β-gal selection), pTKgptF1S (EcoRI, PstI, SalII, AccI, HindII, SbaI, BamHI and Hpa cloning sites, TK or XPRT selection) and the like.

Yeast expression systems that can also be used in the present include, but are not limited to, the non-fusion pYES2 vector (XbaI, SphI, ShoI, NotI, GstXI, EcoRI, BstXI, BamHI, SacI, KpnI and HindIII cloning sites, Invitrogen), the fusion pYESHisA, B, C (XbaII, SphI, ShoI, NotI, BstXI, EcoRI, BamHI, SacI, KpnI and HindIII cloning sites, N-terminal peptide purified with ProBond resin and cleaved with enterokinase; Invitrogen), pRS vectors and the like.

Consequently, mammalian and typically human cells, as well as bacterial, yeast, fungi, insect, nematode and plant cells are used in the present invention and may be transfected by the nucleic acid or recombinant vector as defined herein.

Examples of suitable cells include, but are not limited to, VERO cells, HELA cells such as ATCC No. CCL2, CHO cell lines such as ATCC No. CCL61, COS cells such as COS-7 cells and ATCC No. CRL 1650 cells, W138, BHK, HepG2, 3T3 such as ATCC No. CRL6361, A549, PC12, K562 cells, 293 cells, Sf9 cells such as ATCC No. CRL1711 and Cv1 cells such as ATCC No. CCL70.

Other suitable cells that can be used in the present invention include, but are not limited to, prokaryotic host cells strains such as *Escherichia coli*, (e.g., strain DH5-α), *Bacillus subtilis, Salmonella typhimurium*, or strains of the genera of *Pseudomonas, Streptomyces* and *Staphylococcus*.

Further suitable cells that can be used in the present invention include yeast cells such as those of *Saccharomyces* such as *Saccharomyces cerevisiae*.

Besides the specific isolated complexes, as described above, the present invention relates to and also encompasses SID® polynucleotides. As explained above, for each bait polypeptide, several prey polypeptides may be identified by comparing and selecting the intersection of every isolated fragment that are included in the same polypeptide. Thus, the SID® polynucleotides of the present invention are represented by the shared nucleic acid sequences of SEQ ID No 15 to 37 encoding the SID® polypeptides of SEQ ID No 38 to 60 in columns 5 and 7 of Table 3, respectively.

The present invention is not limited to the SID® sequences as described in the above paragraph, but also includes fragments of these sequences having at least 12 consecutive nucleic acids, between 12 and 5,000 consecutive nucleic acids and between 12 and 10,000 consecutive nucleic acids and between 12 and 20,000 consecutive nucleic acids, as well as variants thereof. The fragments or variants of the SID® sequences possess at least the same affinity of binding to its protein or polypeptide counterpart, against which it has been initially selected. Moreover this variant and/or fragments of the SID® sequences alternatively can have between 95% and 99.999% sequence identity to its protein or polypeptide counterpart.

According to the present invention, variants of polynucleotide or polypeptides can be created by known mutagenesis techniques either in vitro or in vivo. Such a variant can be created such that it has altered binding characteristics with respect to the target protein and more specifically that the variant binds the target sequence with either higher or lower affinity.

Polynucleotides that are complementary to the above sequences which include the polynucleotides of the SID®'s, their fragments, variants and those that have specific sequence identity are also included in the present invention.

The polynucleotide encoding the SID® polypeptide, fragment or variant thereof can also be inserted into recombinant vectors which are described in detail above.

The present invention also relates to a composition comprising the above-mentioned recombinant vectors containing the SID® polynucleotides in Table 3, fragments or variants thereof, as well as recombinant host cells transformed by the vectors. The recombinant host cells that can be used in the present invention were discussed in greater detail above.

The compositions comprising the recombinant vectors can contain physiological acceptable carriers such as diluents, adjuvants, excipients and any vehicle in which this composition can be delivered therapeutically and can include, but is are not limited to sterile liquids such as water and oils.

In yet another embodiment, the present invention relates to a method of selecting modulating compounds, as well as the modulating molecules or compounds themselves which may be used in a pharmaceutical composition. These modulating compounds may act as a cofactor, as an inhibitor, as an antibodies, as tags, as a competitive inhibitor, as an activator or alternatively have agonistic or antagonistic activity on the protein-protein interactions.

The activity of the modulating compound does not necessarily, for example, have to be 100% activation or inhibition. Indeed, even partial activation or inhibition can be achieved that is of pharmaceutical interest.

The modulating compound can be selected according to a method which comprises:

(a) cultivating a recombinant host cell with a modulating compound on a selective medium and a reporter gene the expression of which is toxic for said recombinant host cell wherein said recombinant host cell is transformed with two vectors:
   (i) wherein said first vector comprises a polynucleotide encoding a first hybrid polypeptide having a DNA binding domain;
   (ii) wherein said second vector comprises a polynucleotide encoding a second hybrid polypeptide having a transcriptional activating domain that activates said toxic reporter gene when the first and second hybrid polypeptides interact;
(b) selecting said modulating compound which inhibits or permits the growth of said recombinant host cell.

Thus, the present invention relates to a modulating compound that inhibits the protein-protein interactions of a complex of two polypeptides of columns 1 and 4 of Table 2. The present invention also relates to a modulating compound that activates the protein-protein interactions of a complex of two polypeptides of columns 1 and 4 of Table 2.

In yet another embodiment, the present invention relates to a method of selecting a modulating compound, which modulating compound inhibits the interactions of two polypeptides of columns 1 and 4 of Table 2. This method comprises:

(a) cultivating a recombinant host cell with a modulating compound on a selective medium and a reporter gene the expression of which is toxic for said recombinant host cell wherein said recombinant host cell is transformed with two vectors:
   (i) wherein said first vector comprises a polynucleotide encoding a first hybrid polypeptide having a first domain of an enzyme;
   (ii) wherein said second vector comprises a polynucleotide encoding a second hybrid polypeptide having an enzymatic transcriptional activating domain that activates said toxic reporter gene when the first and second hybrid polypeptides interact;
(b) selecting said modulating compound which inhibits or permits the growth of said recombinant host cell.

In the two methods described above, any toxic reporter gene can be utilized including those reporter genes that can be used for negative selection including the URA3 gene, the CYH1 gene, the CYH2 gene and the like.

In yet another embodiment, the present invention provides a kit for screening a modulating compound. This kit comprises a recombinant host cell which comprises a reporter gene the expression of which is toxic for the recombinant host cell. The host cell is transformed with two vectors. The first vector comprises a polynucleotide encoding a first hybrid polypeptide having a DNA binding domain; and the second vector comprises a polynucleotide encoding a second hybrid polypeptide having a transcriptional activating domain that activates said toxic reporter gene when the first and second hybrid polypeptides interact.

In yet another embodiment, a kit is provided for screening a modulating compound by providing a recombinant host cell, as described in the paragraph above, but instead of a DNA binding domain, the first vector encodes a first hybrid polypeptide containing a first domain of a protein. The second vector encodes a second polypeptide containing a second part of a complementary domain of a protein that activates the toxic reporter gene when the first and second hybrid polypeptides interact.

In the selection methods described above, the activating domain can be B42 Gal 4, VP16 (HSV) and the DNA-binding domain can be derived from Gal4 or Lex A. The protein or enzyme can be adenylate cyclase, guanylate cyclase, DHFR and the like.

Examples of modulating compounds are set forth in Table 3.

In yet another embodiment, the present invention relates to a pharmaceutical composition comprising the modulating compounds for preventing or treating AIDS in a human or animal, most preferably in a mammal, or inhibiting HIV replication in indicator cells sensitive to HIV infection.

This pharmaceutical composition comprises a pharmaceutically acceptable amount of the modulating compound. The pharmaceutically acceptable amount can be estimated from cell culture assays. For example, a dose can be formulated in animal models to achieve a circulating concentration range that includes or encompasses a concentration point or range having the desired effect in an in vitro system. This information can thus be used to accurately determine the doses in other mammals, including humans and animals.

The therapeutically effective dose refers to that amount of the compound that results in amelioration of symptoms in a patient. Toxicity and therapeutic efficacy of such compounds can be determined by standard pharmaceutical procedures in cell cultures or in experimental animals. For example, the LD50 (the dose lethal to 50% of the population) as well as the ED50 (the dose therapeutically effective in 50% of the population) can be determined using methods known in the art. The dose ratio between toxic and therapeutic effects is the therapeutic index which can be expressed as the ratio between LD 50 and ED50 compounds that exhibit high therapeutic indexes.

The data obtained from the cell culture and animal studies can be used in formulating a range of dosage of such compounds which lies preferably within a range of circulating concentrations that include the ED50 with little or no toxicity.

The pharmaceutical composition can be administered via any route such as locally, orally, systemically, intravenously, intramuscularly, mucosally, using a patch and can be encapsulated in liposomes, microparticles, microcapsules, and the like. The pharmaceutical composition can be embedded in liposomes or even encapsulated.

Any pharmaceutically acceptable carrier or adjuvant can be used in the pharmaceutical composition. The modulating compound will be preferably in a soluble form combined with a pharmaceutically acceptable carrier. The techniques for formulating and administering these compounds can be found in "Remington's Pharmaceutical Sciences" Mack Publication Co., Easton, Pa., latest edition.

The mode of administration optimum dosages and galenic forms can be determined by the criteria known in the art taken into account the seriousness of the general condition of the mammal, the tolerance of the treatment and the side effects.

The present invention also relates to a method of treating or preventing AIDS in a human or mammal in need of such treatment. This method comprises administering to a mammal in need of such treatment a pharmaceutically effective amount of a modulating compound which binds to a targeted mammalian or human or inner ear cell protein. In a preferred embodiment, the modulating compound is a polynucleotide which may be placed under the control of a regulatory sequence which is functional in the mammal or human.

In yet another embodiment, the present invention relates to a pharmaceutical composition comprising a SID® polypeptide, a fragment or variant thereof. The SID® polypeptide, fragment or variant thereof can be used in a pharmaceutical composition provided that it is endowed with highly specific binding properties to a bait polypeptide of interest.

Thus, the present invention relates to a pharmaceutical composition comprising a pharmaceutically acceptable amount of a SID® polypeptide or variant thereof, provided that the variant has the above-mentioned two characteristics; i.e., that it is endowed with highly specific binding properties to a bait polypeptide of interest and is devoid of biological activity of the naturally occurring protein.

In yet another embodiment, the present invention relates to a pharmaceutical composition comprising a pharmaceutically effective amount of a polynucleotide encoding a SID® polypeptide or a variant thereof wherein the polynucleotide is placed under the control of an appropriate regulatory sequence. Appropriate regulatory sequences that are used are polynucleotide sequences derived from promoter elements and the like.

Polynucleotides that can be used in the pharmaceutical composition of the present invention include the nucleotide sequences of SEQ ID No 15 to 37.

The above described pharmaceutical compositions can be administered by any route such as orally, systemically, intravenously, intramuscularly, intradermally, mucosally, encapsulated, using a patch and the like. Any pharmaceutically acceptable carrier or adjuvant can be used in this pharmaceutical composition.

The SID® polypeptides as active ingredients will be preferably in a soluble form combined with a pharmaceutically acceptable carrier. The techniques for formulating and administering these compounds can be found in "Remington's Pharmaceutical Sciences" supra.

The amount of pharmaceutically acceptable SID® polypeptides can be determined as described above for the modulating compounds using cell culture and animal models.

The primate models of AIDS provide insights into pathogenesis, transmission, and immune responses to infection and are useful in testing vaccines and drugs. The HIV-1/chimpanzee, SIV(mac)/macaque, and SHIV/macaque models are the most widely used. (Primate models of AIDS., Joag S V., Microbes Infect 2000 February; 2(2):223-9; A new approach to AIDS research and prevention: the use of gene-mutated HIV-1/SIV chimeric viruses for anti-HIV-1 live-attenuated vaccines. Haga T, Kuwata T, Ui M, Igarashi T, Miyazaki Y, Hayami M. Microbiol. Immunol. 1998; 42(4):245-51.)

Also, a human CD4/CCR5 transgenic rat model for infection by human immunodeficiency virus type 1 has been recently developed. (J. Exp. Med. 2002 Mar. 18; 195(6):719-36. Progress toward a human CD4/CCR5 transgenic rat model for de novo infection by human immunodeficiency virus type 1 Keppler O T, Welte F J, Ngo T A, Chin P S, Patton K S, Tsou C L, Abbey N W, Sharkey M E, Grant R M, You Y, Scarborough J D, Ellmeier W, Littman D R, Stevenson M, Charo I F, Herndier B G, Speck R F, Goldsmith M A.)

Such compounds can be used in a pharmaceutical composition to treat or prevent AIDS.

Thus, the present invention also relates to a method of preventing or treating AIDS in a mammal said method comprising the steps of administering to a mammal in need of such treatment a pharmaceutically effective amount of:
 (1) a SID® polypeptide of SEQ ID No 38 to 60 or a variant thereof which binds to a targeted HIV protein; or
 (2) SID® polynucleotide encoding a SID® polypeptide of SEQ ID No 15 to 37 or a variant or a fragment thereof wherein said polynucleotide is placed under the control of a regulatory sequence which is functional in said mammal; or (3) a recombinant expression vector comprising a polynucleotide encoding a SID® polypeptide which binds to a HIV protein.

In another embodiment, the present invention nucleic acids comprising a sequence of SEQ ID No 15 to 37 which encodes the protein of sequence SEQ ID No 38 to 60 and/or functional derivatives thereof are administered to modulate complex (from Table 2) function by way of gene therapy. Any of the methodologies relating to gene therapy available within the art may be used in the practice of the present invention such as those described by Goldspiel et al Clin. Pharm. 12 pgs. 488-505 (1993).

Delivery of the therapeutic nucleic acid into a patient may be direct in vivo gene therapy (i.e., the patient is directly exposed to the nucleic acid or nucleic acid-containing vector) or indirect ex vivo gene therapy (i.e., cells are first transformed with the nucleic acid in vitro and then transplanted into the patient).

For example, for in vivo gene therapy, an expression vector containing the nucleic acid is administered in such a manner that it becomes intracellular; i.e., by infection using a defective or attenuated retroviral or other viral vectors as described, for example in U.S. Pat. No. 4,980,286 or by Robbins et al, Pharmacol. Ther., 80 No. 1 pgs. 35-47 (1998).

The various retroviral vectors that are known in the art are such as those described in Miller et al. (Meth. Enzymol. 217 pgs. 581-599 (1993)) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (Human Gene Therapy, 10, pgs. 2451-2459 (1999)). Chimeric viral vectors that can be used are those described by Reynolds et al. (Molecular Medicine Today, pgs. 25-31 (1999)). Hybrid vectors can also be used and are described by Jacoby et al. (Gene Therapy, 4, pgs. 1282-1283 (1997)).

Direct injection of naked DNA, or through the use of microparticle bombardment (e.g., Gene Gun®; Biolistic, Dupont) or by coating it with lipids can also be used in gene therapy. Cell-surface receptors/transfecting agents or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu & Wu, J. Biol. Chem., 262 pgs. 4429-4432 (1987)) can be used to target cell types which specifically express the receptors of interest.

In another embodiment, a nucleic acid ligand compound may be produced in which the ligand comprises a fusogenic viral peptide designed so as to disrupt endosomes, thus allowing the nucleic acid to avoid subsequent lysosomal degradation. The nucleic acid may be targeted in vivo for cell specific endocytosis and expression by targeting a specific receptor such as that described in WO92/06180, WO93/14188 and WO 93/20221. Alternatively, the nucleic acid may be introduced intracellularly and incorporated within the host cell genome for expression by homologous recombination (See Zijlstra et al, Nature, 342, pgs. 435-428 (1989)).

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as hematopoietic stem or progenitor cells.

Cells into which a nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryotcytes, granulocytes, hematopoietic cells or progenitor cells and the like.

In yet another embodiment, the present invention relates to protein chips or protein microarrays. It is well known in the art that microarrays can contain more than 10,000 spots of a protein that can be robotically deposited on a surface of a glass slide or nylon filter. The proteins attach covalently to the slide surface, yet retain their ability to interact with other proteins or small molecules in solution. In some instances, the protein samples can be made to adhere to glass slides by coating the slides with an aldehyde-containing reagent that attaches to primary amines. A process for creating microarrays is described, for example by MacBeath and Schreiber (Science, Volume 289, Number 5485, pgs, 1760-1763 (2000)) or (Service, Science, Vol, 289, Number 5485 pg. 1673 (2000)). An apparatus for controlling, dispensing and measuring small quantities of fluid is described, for example, in U.S. Pat. No. 6,112,605.

The present invention also provides a record of protein-protein interactions, PIM®'s and any data encompassed in the following Tables. It will be appreciated that this record can be provided in paper or electronic or digital form.

As seen below in the examples, the present invention relates to the development of future anti-HIV therapies by focusing on interrupting key interactions between viral and host proteins during various steps of the virus life cycle. To identify these key cellular factors essential for HIV-1 replication, systematic, exhaustive and large-scale two-hybrid screens with all proteins of the R5 HIV-1 isolate YU2 listed in Table 1, using highly complex random and oligo dT primed cDNA libraries from CEM cells was performed. Results of these screens are reported below in detail and are listed in Table 2. In order to demonstrate that these interactions are required for viral replication and viral spread, gene silencing experiments according (Elbashir, Harborth et al. 2001), using transfection of double stranded silencing RNAs (siRNAs) specifically directed against mRNAs coding for, selected cellular partners of viral proteins was performed. The protocols used in these experiments are described in detail in the examples. Briefly, cells used as targets for infection with HIV-1 virions were transfected twice (Day 1 and day 2) with a particular siRNA targeting a specific partner of a given viral protein prior infection with HIV-1 virions. After infection, virus production was checked by p24 assay in the medium. The different siRNAs used, their respective target cellular genes, and their sequences are listed in Table 2. The effects of these siRNAs on viral replication in indicator cells were appreciated by p24 assays (see FIGS. 19 to 21), and compared to that of the siRNA against luciferase used as a negative control, and to the effects provoked by siRNA against Tsg101, which was used as a positive control since siRNA against Tsg101 was previously reported in the literature as being responsible for more than 80% decrease in virus production (Garrus, von Schwedler et al. 2001). The selectivity of the effects of siRNAs on their cognate mRNA, but not on a control mRNA (GAPDH mRNA), was checked by Q-RT PCR assay of each cellular mRNA targets. Also checked was the viability and the cell cycle of the indicator cells used for viral infection were not affected by treatment with the siR-NAs (FIG. 22), indicating that the effect of inhibition of virus production resulting from the treatment with some siRNAs was not due to a toxic effect of these siRNAs on the indicator cells for HIV infection.

Furthermore, a highly complex library of two hundred thousand of small HIV DNA random fragments of the 5' half of the HIV-1 YU2 DNA obtained after breakage at random of this 5' half part of the HIV-1 YU2 DNA was constructed, using a procedure of DNA nebulisation. In some cases, this library was used in secondary screens with some of the cellular preys identified in the primary screens. The very high number of viral protein fragments often selected in these secondary screens due to the very high complexity of the library used, allowed us to define very precisely the Selected Interacting Domain (SID®) on these viral proteins.

Use of a SID® or an interaction or a prey to screen molecules that inhibit human immunodeficiency virus also is another embodiment of the present invention, as well as molecules that inhibits human immunodeficiency virus obtained by this screening method. The screening can occur in mammalian or yeast cells. Furthermore, the inhibition can be detected by fluorescence polarization, FRET, BRET, filter binding assays or radioactive techniques.

In order to fully illustrate the present invention and advantages thereof, the following specific examples are given, it being understood that the same are intended only as illustrative and in nowise limitative.

EXAMPLES

Example 1

Preparation of a Collection of Random-Primed cDNA Fragments

1.A. Collection Preparation and Transformation in *Escherichia coli*

1.A.1. Random-Primed cDNA Fragment Preparation

For mRNA sample from CEMC7 cells, random-primed 2 cDNA was prepared from 5 µg of polyA+ mRNA using a TimeSaver cDNA Synthesis Kit (Amersham Pharmacia Biotech) and with 5 µg of random N9-mers or 1 µg of oligo dT 18-mers, respectively, according to the manufacturer's instructions. Following phenolic extraction, the cDNA was precipitated and resuspended in water. The resuspended cDNA was phosphorylated by incubating in the presence of T4 DNA Kinase (Biolabs) and ATP for 30 minutes at 37° C. The resulting phosphorylated cDNA was then purified over a separation column (Chromaspin TE 400, Clontech), according to the manufacturer's protocol.

1.A.2. Genomic DNA Preparation

The first 5080 bp of Genomic DNA from U2 clone was amplify by PCR using:

(SEQ ID No. 61)
oli3285 geno_YU2_5p1
TCCCCCGGGCGGAGGCTAGAAGGAGAGAGATGGGTG (SEQ ID No. 62)
oli3286 geno_YU2_3p1
TCCCCCGGGGCTCTAGGTTAGGATCTACTGGCTCCAT The amplification was digested by SmaI and then cloned in SK vector (Stratagene) digest by SmaI. The insert containing the first 5080 bp has been validated by full sequencing. It is call U2-F1 clone.

1.A.3. Fragmenting of Genomic DNA Preparation

ADN from U2-F1 clone was extracted by maxiprep (Qiagen). 100 µg of plasmidic DNA was digested by SmaI and gel purified 2 times (KIT gelextract Bio101). 75 µg of DNA was recovered and ligated in 50 µl with T4 DNA ligase. This concatenation of the F1 fragment reduced the ligation bias due to over representation of natural extremity.

This concatena of the first 5080 bp of Genomic DNA from U2 clone was fragmented in a nebulizer (GATC) for 1 minute, precipitated and resuspended in water.

The obtained nebulized genomic DNA was successively treated with Mung Bean Nuclease (Biolabs) for 30 minutes at 30° C., with T4 DNA polymerase (Biolabs) for 10 minutes at 37° C., and Klenow enzyme (Pharmacia) for 10 minutes at room temperature and for 1 hour at 16° C.

DNA was then extracted, precipitated and resuspended in water.

1.A.4. Ligation of Linkers to Blunt-Ended cDNA

Oligonucleotide HGX931 (5' end phosphorylated) 1 µg/µl and HGX932 1 µg/µl were used.

Sequence of the oligo HGX931: 5'-GGGCCACGAA-3' (SEQ ID No.63)

Sequence of the oligo HGX932: 5'-TTCGTGGCCCCTG-3' (SEQ ID No.64)

Linkers were preincubated (5 minutes at 95° C., 10 minutes at 68° C., 15 minutes at 42° C.) then cooled down at room temperature and ligated with cDNA fragments at 16° C. overnight.

Linkers were removed on a separation column (Chromaspin TE 400, Clontech), according to the manufacturer's protocol.

1.A.5. Ligation of Linkers to Blunt-Ended Genomic DNA

Oligonucleotide PL160 (5' end phosphorylated) 1 µg/µl and PL159 2 µg/µl.

Sequence of the oligo PL160: 5'-ATCCCGGACGAAG-GCC-3' (SEQ ID No. 65)

Sequence of the oligo PL159: 5'-GGCCTTCGTCCGG-3' (SEQ ID No. 66)

Linkers were preincubated (5 minutes at 95° C., 10 minutes at 68° C., 15 minutes at 42° C.) then cooled down at room temperature and ligated with genomic DNA inserts at 4° C. overnight.

Linkers were removed on a separation column (Chromaspin TE 400, Clontech), according to the manufacturer's protocol.

1.A.6. Vector Preparation

Plasmid pP6 (see FIG. 10) was prepared by replacing the SpeI-XhoI fragment of pGAD3S2X with the double-stranded oligonucleotide:

(SEQ ID No. 67)
5'-TAGCCATGGCCGCAGGGGCCGCGGCCGCACTAGTGGGGATCCTTAAT
TAAGGGCCACTGGGGCCCCC-3'

(SEQ ID No. 68)
5'-TCGAGGGGCCCCAGTGGCCCTTAATTAAGGATCCCCACTAGTGCGG
CCGCGGCCCCTGCGGCCATGG-3'

The pP6 vector was successively digested with SfiI and BamHI restriction enzymes (Biolabs) for 1 hour at 37° C., extracted, precipitated, and resuspended in water. Digested plasmid vector backbones were purified on a separation column (Chromaspin TE 400, Clontech), according to the manufacturer's protocol.

1.A.7. Vector Preparation

Plasmid pP6 (see FIG. 10) was prepared by replacing the SpeI/XhoI fragment of pGAD3S2X with the double-stranded oligonucleotide:

(SEQ ID No. 69)
5'CTAGCCATGGCCGCAGGGGCCGCGGCCGCACTAGTGGGGATCCTTAAT
TAAGGGCCACTGGGGCCCC 3'

(SEQ ID No. 70)
5'TCGAGGGGGCCCCAGTGGCCCTTAATTAAGGATCCCCACTAGTGCGGC
CGCGGCCCCTGCGGCCATGGC 3'

The pP6 vector was successively digested with SfiI and BamHI restriction enzymes (Biolabs) for 1 hour at 37° C., extracted, precipitated and resuspended in water. Digested plasmid vector backbones were purified on a separation column (Chromaspin TE 400, Clontech), according to the manufacturer's protocol.

1.A.8. Ligation Between Vector and Insert of cDNA

The prepared vector was ligated overnight at 15° C. with the blunt-ended cDNA described in section 2 using T4 DNA ligase (Biolabs). The DNA was then precipitated and resuspended in water.

1.A.9. Ligation Between Vector and Insert of Genomic DNA

The prepared vector was ligated overnight at 15° C. with the blunt-ended genomic DNA described in section 2 using T4 DNA ligase (Biolabs). The DNA was then precipitated and resuspended in water.

1.A.10. Library Transformation in *Escherichia coli*

The DNA from section 1.A.4 was transformed into Electromax DH10B electrocompetent cells (Gibco BRL) with a Cell Porator apparatus (Gibco BRL). 1 ml SOC medium was added and the transformed cells were incubated at 37° C. for 1 hour. 9 mls of SOC medium per tube was added and the cells were plated on LB+ampicillin medium. The colonies were scraped with liquid LB medium, aliquoted and frozen at −80° C.

1.B. Collection Transformation in *Saccharomyces cerevisiae*

The *Saccharomyces cerevisiae* strain (YHGX13 (MATα Gal4Δ Gal80Δ ade2-101::KAN$^R$, his3, leu2-3, -112, trp1-901, ura3-52 URA3::UASGAL1-LacZ, Met)) was transformed with the cDNA library.

The plasmid DNA contained in *E. coli* were extracted (Qiagen) from aliquoted *E. coli* frozen cells (1.A.5.). *Saccharomyces cerevisiae* yeast YHGX13 in YPGlu were grown.

Yeast transformation was performed according to standard protocol (Giest et al. Yeast, 11, 355-360, 1995) using yeast carrier DNA (Clontech). This experiment leads to $10^4$ to $5\times10^4$ cells/μg DNA. $2\times10^4$ cells were spread on DO-Leu medium per plate. The cells were aliquoted into vials containing 1 ml of cells and frozen at −80° C.

1.B.1 Collection Transformation in *Saccharomyces cerevisiae*

The *Saccharomyces cerevisiae* strain (Y187 (MATα Gal4Δ Gal18Δ ade2-101, his3, leu2-3, -112, trp1-901, ura3-52 URA3::UASGAL1-LacZ Met)) was transformed with the *Staphylococcus aureus* genomic DNA library.

The plasmid DNAs contained in *E. coli* were extracted (Qiagen) from aliquoted *E. coli* frozen cells (1.A.5.). *Saccharomyces cerevisiae* yeast Y187 were grown in YPGlu.

Yeast transformation was performed according to standard protocol (Giest et al. Yeast, 11, 355-360, 1995) using yeast carrier DNA (Clontech). This experiment leads to $10^4$ to $5\times10^4$ cells/μg DNA. $2\times10^4$ cells per plate were spread on DO-Leu medium. The cells were aliquoted into vials containing 1 ml of cells and frozen at −80° C.

For fusions of the bait protein to the DNA-binding domain of the GAL4 protein of *S. cerevisiae*, bait fragments were cloned into plasmid pB6 or plasmid pB27.

Plasmid pB6 (see FIG. 3) was prepared by replacing the NcoI/SalI polylinker fragment of pASΔΔ with the double-stranded DNA fragment:

(SEQ ID No. 71)
5'-CTAGCCATGGCCGCAGGGGCCGCGGCCGCACTAGTGGGGATCCTTAA
TTAAGGGCCACTGGGGCCCCC-3'

(SEQ ID No. 72)
5'-TCGAGGGGGCCCCAGTGGCCCTTAATTAAGGATCCCCACTAG
TGCGGCCGCGGCCCCTGCGGCCATGG-3'

Plasmid pB27 (see FIG. 17) was prepared by replacing the ampicillin resistance of pB20 with the tetracyclin resistance.

MCS sequence EcoRI/PstI:

(SEQ ID No 73)
5'AATTCGGGGCCGGACGGGCCGCGGCCGCACTAGTGGGGATCCTTAAT
TAAGGGCCACTGGGGCCCCTCGACCTGCA 3'

(SEQ ID No. 74)
5'GGTCGAGGGGCCCCAGTGGCCCTTAATTAAGGATCCCCACTAGTGCG
GCCGCGGCCCGTCCGGCCCCG 3'

The amplification of the bait ORF was obtained by PCR using the Pfu proof-reading Taq polymerase (Stratagene), 10 pmol of each specific amplification primer and 200 ng of plasmid DNA as template.

The PCR program was set up as follows:

| | |
|---|---|
| 94° | 45" |
| 94° | 45" ⎫ |
| 48° | 45" ⎬ x30 cycles |
| 72° | 6' ⎭ |
| 72° | 10' |
| 15° | ∞ |

The amplification was checked by agarose gel electrophoresis.

The PCR fragments were purified with Qiaquick column (Qiagen) according to the manufacturer's protocol.

Purified PCR fragments were digested with adequate restriction enzymes.

The PCR fragments were purified with Qiaquick column (Qiagen) according to the manufacturer's protocol.

The digested PCR fragments were ligated into an adequately digested and dephosphorylated bait vector (pB6 or pB27) according to standard protocol (Sambrook et al.) and were transformed into competent bacterial cells. The cells were grown, the DNA extracted and the plasmid was sequenced.

Example 2

Screening the Collection with the Two-Hybrid in Yeast System

2.A. The Mating Protocol

The mating two-hybrid in yeast system (as described by Legrain et al., *Nature Genetics*, vol. 16, 277-282 (1997), *Toward a functional analysis of the yeast genome through exhaustive two-hybrid screens*) was used for its advantages but one could also screen the cDNA collection in classical two-hybrid system as described in Fields et al. or in a yeast reverse two-hybrid system.

The mating procedure allows a direct selection on selective plates because the two fusion proteins are already produced in the parental cells. No replica plating is required.

This protocol was written for the use of the library transformed into the YHGX13 strain.

For bait proteins fused to the DNA-binding domain of GAL4, bait-encoding plasmids were first transformed into *S. cerevisiae* (CG1945 strain (MATa Gal4-542 Gal180-538 ade2-101 his3Δ200, leu2-3,112, trp1-901, ura3-52, lys2-801, URA3::GAL4 17mers (X3)-CyC1TATA-LacZ, LYS2:: GAL1UAS-GAL1TATA-HIS3 CYH$^R$)) according to step 1.B. and spread on DO-Trp medium.

For bait proteins fused to the DNA-binding domain of LexA, bait-encoding plasmids were first transformed into *S. cerevisiae* (L40Δgal4 strain (MATa ade2, trp1-901, leu2 3,112, lys2-801, his3Δ200, LYS2::(lexAop)$_4$-HIS3, ura3-52::URA3 (lexAop)$_8$-LacZ, GAL4::Kan$^R$)) according to step 1.B. and spread on DO-Trp medium.

Day 1, Morning: Preculture

The cells carrying the bait plasmid obtained at step 1.C. were precultured in 20 ml DO-Trp medium and grown at 30° C. with vigorous agitation.

Day 1, Late Afternoon: Culture

The $OD_{600nm}$ of the DO-Trp pre-culture of cells carrying the bait plasmid was measured. The $OD_{600nm}$ must lie between 0.1 and 0.5 in order to correspond to a linear measurement.

50 ml DO-Trp at $OD_{600nm}$ 0.006/ml was inoculated and grown overnight at 30° C. with vigorous agitation.

Day 2: Mating

Medium and Plates

2 YPGlu 15 cm plates 50 ml tube with 13 ml DO-Leu-Trp-His 100 ml flask with 5 ml of YPGlu 8 DO-Leu-Trp-His plates 2 DO-Leu-Trp Plates The $OD_{600nm}$ of the DO-Trp culture was measured. It should be around 1.

For the mating, twice as many bait cells as library cells were used. To get a good mating efficiency, one must collect the cells at $10^8$ cells per cm$^2$.

The amount of bait culture (in ml) that makes up 50 $OD_{600nm}$ units for the mating with the prey library was estimated.

A vial containing the library of step 1B was thawed slowly on ice. 1.0 ml of the vial was added to 20 ml YPGlu. Those cells were recovered at 30° C., under gentle agitation for 10 minutes.

Mating

The 50 $OD_{600nm}$ units of bait culture was placed into a 50 ml falcon tube.

The library of step 1B culture was added to the bait culture, then centrifuged, the supernatant discarded and resuspended in 1.6 ml YPGlu medium.

The cells were distributed onto two 15 cm YPGlu plates with glass beads. The cells were spread by shaking the plates. The plate cells-up at 30° C. for 4 h 30 min were incubated.

Collection of Mated Cells

The plates were washed and rinsed with 6 ml and 7 ml respectively of DO-Leu-Trp-His. Two parallel serial ten-fold dilutions were performed in 500 µl DO-Leu-Trp-His up to ¹⁄₁₀,₀₀₀. 50 µl of each 1/1,000 dilution was spread onto DO-Leu-Trp plates. 22.4 ml of collected cells were spread in 400 µl aliquots on DO-Leu-Trp-His+Tet plates.

Day 4

Clones that were able to grow on DO-Leu-Trp-His+Tetracyclin were then selected. This medium allows one to isolate diploid clones presenting an interaction.

The His+ colonies were counted on control plates.

The number of His+ cell clones will define which protocol is to be processed:

Upon $60 \cdot 10^6$ Trp+Leu+ colonies:

if the number His+ cell clones <285: then use the process stamp overlay protocol on all colonies if the number of His+ cell clones >285 and <5000: then process via overlay and then stamp overlay protocols on blue colonies (2.B and 2.C).

if number of His+ cell clones >5000: repeat screen using DO-Leu-Trp-His+ Tetracyclin plates containing 3-aminotriazol.

2.B. The X-Gal Overlay Assay

The X-Gal overlay assay was performed directly on the selective medium plates after scoring the number of His$^+$ colonies.

A water bath was set up. The water temperature should be 50° C.

0.5 M $Na_2HPO_4$ pH 7.5.

1.2% Bacto-agar.

2% X-Gal in DMF.

Overlay mixture: 0.25 M $Na_2HPO_4$ pH 7.5, 0.5% agar, 0.1% SDS, 7% DMF (LABOSI), 0.04% X-Gal (ICN).

For each plate, 10 ml overlay mixture are needed.

DO-Leu-Trp-His plates.

Sterile toothpicks.

The temperature of the overlay mix should be between 45° C. and 50° C. The overlay-mix was poured over the plates in portions of 10 ml. When the top layer was settled, they were collected. The plates were incubated overlay-up at 30° C. and the time was noted. Blue colonies were checked for regularly. If no blue colony appeared, overnight incubation was performed. Using a pen the number of positives was marked. The positives colonies were streaked on fresh DO-Leu-Trp-His plates with a sterile toothpick.

2.C. The Stamp Overlay Assay

His+ colonies were grown overnight at 30° C. in microtiter plates containing DO-Leu-Trp-His+ Tetracyclin medium with shaking. The day after the overnight culture, the 96 colonies were stamped on a 15 cm plate of DO-Leu-Trp-His. 4 control yeast colonies were spotted on the same plate. After 2 days of growing at 30° C., an overlay assay was performed on this plate with 80 ml of overlay mixture (see step 2.B.). After 2 hours of incubation, the plate was photographed with a CCD camera. The blue intensity was quantified by Genetools® software (SYNGENE) and normalized to the control spots.

Example 3

Identification of Positive Clones

3.A. PCR on Yeast Colonies
Introduction

PCR amplification of fragments of plasmid DNA directly on yeast colonies is a quick and efficient procedure to identify sequences cloned into this plasmid. It is directly derived from a published protocol (Wang H. et al., *Analytical Biochemistry*, 237, 145-146, (1996)). However, it is not a standardized protocol and it varies from strain to strain and it is dependent of experimental conditions (number of cells, Taq polymerase source, etc). This protocol should be optimized to specific local conditions.

Materials
For 1 well, PCR mix composition was:
32.5 µl water,
5 µl 10×PCR buffer (Pharmacia),
1 µl dNTP 10 mM,
0.5 µl Taq polymerase (5 u/µl) (Pharmacia),
0.5 µl oligonucleotide ABS1 10 pmole/µl: 5'-GCGTTTG-GAATCACTACAGG-3' (SEQ ID No.75)
0.5 µl oligonucleotide ABS2 10 pmole/µl: 5'-CACGATG-CACGTTGAAGTG-3' (SEQ ID No.76)
1 N NaOH.

Experiment

The positive colonies were grown overnight at 30° C. on a 96 well cell culture cluster (Costar), containing 150 µl DO-Leu-Trp-His+ Tetracyclin with shaking. The culture was resuspended and 100 µl was transferred immediately on a Thermowell 96 (Costar) and centrifuged for 5 minutes at 4,000 rpm at room temperature. The supernatant was removed. 5 µl NaOH was added to each well and shaken for 1 minute.

The Thermowell was placed in the thermocycler (Gene-Amp 9700, Perkin Elmer) for 5 minutes at 99.9° C. and then 10 minutes at 4° C. In each well, the PCR mix was added and shaken well.

The PCR program was set up as followed:

| | | |
|---|---|---|
| 94° C. | 3 minutes | |
| 94° C. | 30 seconds | |
| 53° C. | 1 minute 30 seconds | ×35 cycles |
| 72° C. | 3 minutes | |
| 72° C. | 5 minutes | |
| 15° C. | ∞ | |

The quality, the quantity and the length of the PCR fragment was checked on an agarose gel. The length of the cloned fragment was the estimated length of the PCR fragment minus 300 base pairs that corresponded to the amplified flanking plasmid sequences.

3.B. Plasmids Rescue from Yeast by Electroporation

The previous protocol of PCR on yeast cell may not be successful, in such a case, plasmids from yeast by electroporation can be rescued. This experiment allows the recovery of prey plasmids from yeast cells by transformation of *E. coli* with a yeast cellular extract. The prey plasmid can then be amplified and the cloned fragment can be sequenced.

Plasmid Rescue
Glass beads 425-600 µm (Sigma)
Phenol/chloroform (1/1) premixed with isoamyl alcohol (Amresco)
Extraction buffer: 2% Triton X100, 1% SDS, 100 mM NaCl, 10 mM TrisHCl pH 8.0, 1 mM EDTA pH 8.0.
Mix ethanol/NH$_4$Ac: 6 volumes ethanol with 7.5 M NH$_4$ Acetate, 70% Ethanol and yeast cells in patches on plates.
Electroporation
SOC medium
M9 medium
Selective plates: M9-Leu+Ampicillin
2 mm electroporation cuvettes (Eurogentech)

Plasmid Rescue

The cell patch on DO-Leu-Trp-His was prepared with the cell culture of section 2.C. The cell of each patch was scraped into an Eppendorf tube, 300 µl of glass beads was added in each tube, then, 200 µl extraction buffer and 200 µl phenol: chloroform:isoamyl alcohol (25:24:1) was added.

The tubes were centrifuged for 10 minutes at 15,000 rpm.

180 µl supernatant was transferred to a sterile Eppendorf tube and 500 µl each of ethanol/NH$_4$Ac was added and the tubes were vortexed. The tubes were centrifuged for 15 minutes at 15,000 rpm at 4° C. The pellet was washed with 200 µl 70% ethanol and the ethanol was removed and the pellet was dried. The pellet was resuspended in 10 µl water. Extracts were stored at −20° C.

Electroporation

Materials: Electrocompetent MC1066 cells prepared according to standard protocols (Sambrook et al. supra).

1 µl of yeast plasmid DNA-extract was added to a pre-chilled Eppendorf tube, and kept on ice.

1 µl plasmid yeast DNA-extract sample was mixed and 20 µl electrocompetent cells was added and transferred in a cold electroporation cuvette.

The Biorad electroporator was set on 200 ohms resistance, 25 µF capacity; 2.5 kV. The cuvette was placed in the cuvette holder and electroporation was performed.

1 ml of SOC was added into the cuvette and the cell-mix was transferred into a sterile Eppendorf tube. The cells were recovered for 30 minutes at 37° C., then spun down for 1 minute at 4,000×g and the supernatant was poured off. About 100 µl medium was kept and used to resuspend the cells and spread them on selective plates (e.g., M9-Leu plates). The plates were then incubated for 36 hours at 37° C.

One colony was grown and the plasmids were extracted. The presence and the size of the insert were checked for through enzymatic digestion and agarose gel electrophoresis. The insert was then sequenced.

Example 4

Protein-Protein Interaction

For each bait, the previous protocol leads to the identification of prey polynucleotide sequences. Using a suitable software program (e.g., Blastwun, available on the Internet site of the University of Washington), the mRNA transcript that is encoded by the prey fragment may be identified and whether the fusion protein encoded is in the same open reading frame of translation as the predicted protein or not can be determined.

Alternatively, prey nucleotide sequences can be compared with one another and those which share identity over a significant region (60 nt) can be grouped together to form a contiguous sequence (Contig) whose identity can be ascertained in the same manner as for individual prey fragments described above.

Example 5

Identification of SID®

Figure 15:
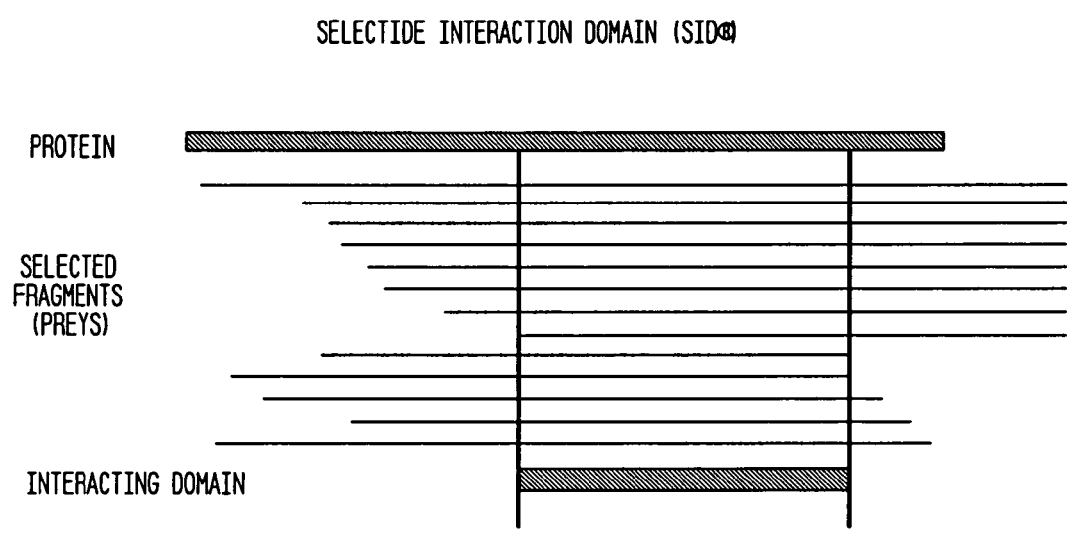
FIG. 15 is a schematic representation identifying the SID®'s of proteins of the present invention. In this figure, the "Full-length prey protein" is the Open Reading Frame (ORF) or coding sequence (CDS) where the identified prey polypeptides are included. The Selected Interaction Domain (SID®) is determined by the commonly shared polypeptide domain of every selected prey fragment.
Figure 16:
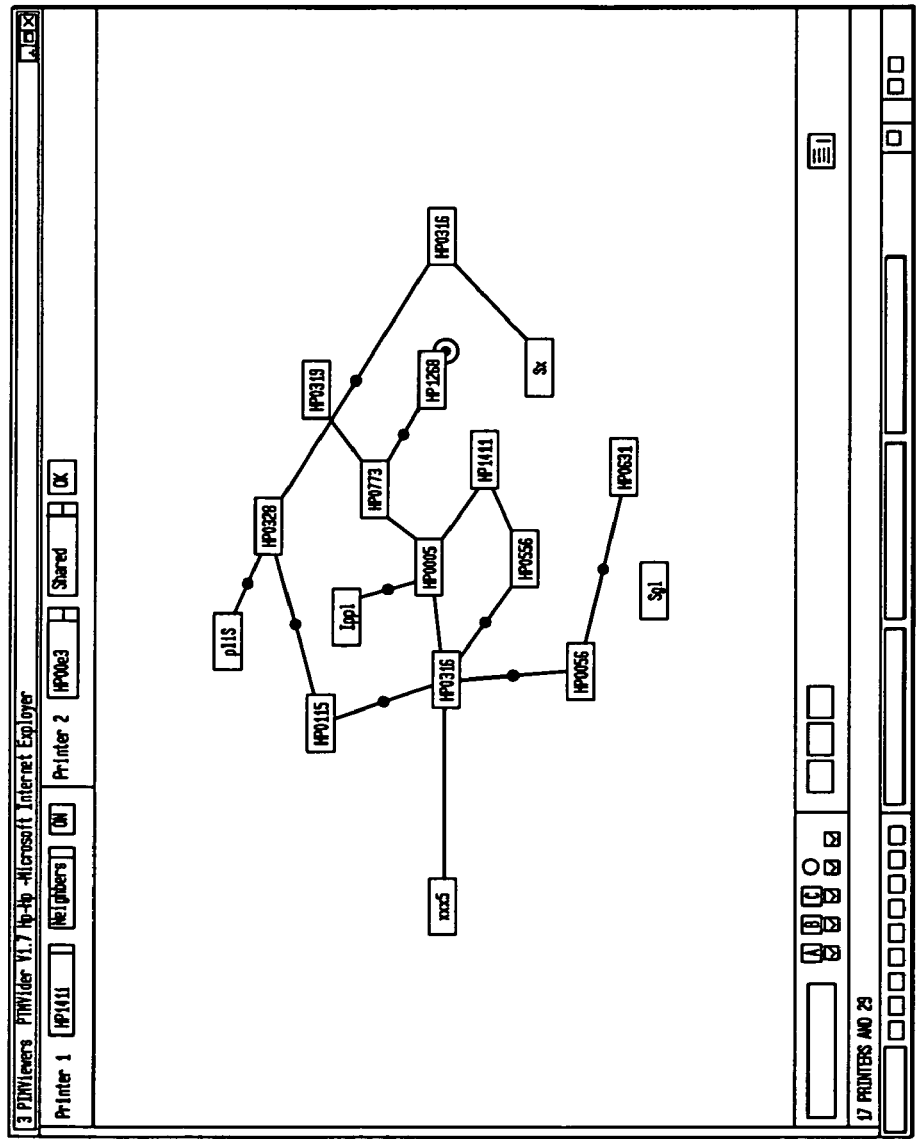
FIG. 16 is a protein map (PIM®).

By comparing and selecting the intersection of all isolated fragments that are included in the same polypeptide, one can define the Selected Interacting Domain (SID®) is determined as illustrated in FIG. 15. The SID® is illustrated in Table 3.

Example 6

Making of Polyclonal and Monoclonal Antibodies

The protein-protein complex of columns 1 and 4 of Table 2 is injected into mice and polyclonal and monoclonal antibodies are made following the procedure set forth in Sambrook et al supra.

More specifically, mice are immunized with an immunogen comprising the above mentioned complexes conjugated to keyhole limpet hemocyanin using glutaraldehyde or EDC as is well known in the art. The complexes can also be stabilized by crosslinking as described in WO 00/37483. The immunogen is then mixed with an adjuvant. Each mouse receives four injections of 10 µg to 100 µg of immunogen, and after the fourth injection, blood samples are taken from the mice to determine if the serum contains antibodies to the immunogen. Serum titer is determined by ELISA or RIA. Mice with sera indicating the presence of antibody to the immunogen are selected for hybridoma production.

Spleens are removed from immune mice and single-cell suspension is prepared (Harlow et al. 1988). Cell fusions are performed essentially as described by Kohler et al. Briefly, P365.3 myeloma cells (ATTC Rockville, Md.) or NS-1 myeloma cells are fused with spleen cells using polyethylene glycol as described by Harlow et al (1989). Cells are plated at a density of $2 \times 10^5$ cells/well in 96-well tissue culture plates. Individual wells are examined for growth and the supernatants of wells with growth are tested for the presence of complex-specific antibodies by ELISA or RIA using the protein-protein complex of columns 1 and 4 of Table 2 as a target protein. Cells in positive wells are expanded and subcloned to establish and confirm monoclonality.

Clones with the desired specificities are expanded and grown as ascites in mice or in a hollow fiber system to produce sufficient quantities of antibodies for characterization and assay development. Antibodies are tested for binding to bait polypeptide of column 1 of Table 2 alone or to prey polypeptide of column 4 of Table 2 alone, to determine which are specific for the protein-protein complex of columns 1 and 4 of Table 2, as opposed to those that bind to the individual proteins.

Monoclonal antibodies against each of the complexes set forth in columns 1 and 4 of Table 2 are prepared in a similar manner by mixing specified proteins together, immunizing an animal, fusing spleen cells with myeloma cells and isolating clones which produce antibodies specific for the protein complex, but not for individual proteins.

Example 7

Modulating Compounds Identification

Each specific protein-protein complex of columns 1 and 4 of Table 2 may be used to screen for modulating compounds.

One appropriate construction for this modulating compound screening may be:
 bait polynucleotide inserted in pB6 or pB27;
 prey polynucleotide inserted in pP6;
 transformation of these two vectors in a permeable yeast cell;
 growth of the transformed yeast cell on a medium containing compound to be tested,
 and observation of the growth of the yeast cells.

Example 8

List of siRNA Used to Obtain the Results Set Forth and Further Described in More Detail Below (S Means Sense Strand and as Means Anti-Sense Strand)

```
EIF3S3 S       GGAGUGCUUUUGGGUCUGGTT    (SEQ ID NO. 77)
EIF3S3 AS      CCAGACCCAAAAGCACUCCTT    (SEQ ID NO. 78)

HBO1 S         GUGAUGGCACAUCCCGACGTT    (SEQ ID NO. 79)
HBO1 AS        CGUCGGGAUGUGCCAUCACTT    (SEQ ID NO. 80)

LEDGF S        GUUCCUGAUGGAGCUGUAATT    (SEQ ID NO. 81)
LEDGF AS       UUACAGCUCCAUCAGGAACTT    (SEQ ID NO. 82)

MCM7 S         GAAGCAGUUCAAGUAUGGGTT    (SEQ ID NO. 83)
MCM7 AS        CCCAUACUUGAACUGCUUCTT    (SEQ ID NO. 84)

SNUPORTIN S    CCAUGCCAGAAGACUGGCUTT    (SEQ ID NO. 85)
SNUPORTIN AS   AGCCAGUCUUCUGGCAUGGTT    (SEQ ID NO. 86)

TRANSPORTIN S  GGAGCGCGCCUCUUUUUGGTT    (SEQ ID NO. 87)
TRANSPORTIN AS CCAAAAAGAGGCGCGCUCCTT    (SEQ ID NO. 88)

TSG101 S       CCUCCAGUCUUCUCUCGUCTT    (SEQ ID NO. 89)
TSG101 AS      GACGAGAGAAGACUGGAGGTT    (SEQ ID NO. 90)

VBP1 S         CAGCCUGGGAAUGAGACUGTT    (SEQ ID NO. 91)
VBP1 AS        CAGUCUCAUUCCCAGGCUGTT    (SEQ ID NO. 92)
```

```
                     -continued
or from Eurogentech:
AIMS            GAAAGUGAAAUCUCCGCGGTT 200   (SEQ ID NO. 93)
AIMAS           CCGCGGAGAUUUCACUUUCTT 200   (SEQ ID NO. 94)

AKAP1S          GGAACCUCUCCCCGUGGAATT 200   (SEQ ID NO. 95)
AKAP1AS         UUCCACGGGGAGAGGUUCCTT 200   (SEQ ID NO. 96)

ATF6S           UGAGACGUAUGAAAACAAUTT 200   (SEQ ID NO. 97)
ATF6AS          AUUGUUUUCAUACGUCUCATT 200   (SEQ ID NO. 98)

BAP1S           GUGGAGGAGAUCUACGACCTT 200   (SEQ ID NO. 99)
BAP1AS          GGUCGUAGAUCUCCUCCACTT 200   (SEQ ID NO. 100)

CK2S            GAACUGGAAGACAACCCCATT 200   (SEQ ID NO. 101)
CK2AS           UGGGGUUGUCUUCCAGUUCTT 200   (SEQ ID NO. 102)

ELAVS           GCCUGUUCAGCAGCAUUGGTT       (SEQ ID NO. 103)
ELAVAS          CCAAUGCUGCUGAACAGGCTT       (SEQ ID NO. 104)

HIV5' S         CUAGAGAUCCCUCAGACCCTT       (SEQ ID NO. 105)
HIV5' AS        GGGUCUGAGGGAUCUCUAGTT       (SEQ ID NO. 106)

LUC S           CGUACGCGGAAUACUUCGATT       (SEQ ID NO. 107)
LUC AS          UCGAAGUAUUCCGCGUACGTT       (SEQ ID NO. 108)

NEF S           CAAUGACUUACAAGGCAGCTT       (SEQ ID NO. 109)
NEF AS          GCUGCCUUGUAAGUCAUUGTT       (SEQ ID NO. 110)

PIASYS          GAGUGGACUGAAGCACGAGTT       (SEQ ID NO. 111)
PIASYAS         CUCGUGCUUCAGUCCACUCTT       (SEQ ID NO. 112)

RCBP1S          GGAAGUAGGAAGCAUCAUUTT       (SEQ ID NO. 113)
RCBP1AS         AAUGAUGCUUCCUACUUCCTT       (SEQ ID NO. 114)

SNF5S           GAGAUACCCCUCACUCUGGTT       (SEQ ID NO. 115)
SNF5AS          CCAGAGUGAGGGGUAUCUCTT       (SEQ ID NO. 116)

SREBP1S         GACAUGCUUCAGCUUAUCATT       (SEQ ID NO. 117)
SREBP1AS        UGAUAAGCUGAAGCAUGUCTT       (SEQ ID NO. 118)

SREBP2S         UCAAGUGGGAGAGUUCCCUTT       (SEQ ID NO. 119)
SREBP2AS        AGGGAACUCUCCCACUUGATT       (SEQ ID NO. 120)

UBE1S           CCAACGGAAUGGCCAAGAATT       (SEQ ID NO. 121)
UEB1AS          UUCUUGGCCAUUCCGUUGGTT       (SEQ ID NO. 122)

TIP47S          GACUGUCUGCGACGCAGCATT       (SEQ ID NO. 123)
TIP47AS         UGCUGCGUCGCAGACAGUCTT       (SEQ ID NO. 124)
```

Each lyophylized S and AS single strand of a siRNA pair was resuspended in water at 100 mM. For annealing, 20 mM single strands were incubated in annealing buffer (100 mM potassium acetate, 30 mM HEPES-KOH at pH 7.4, 2 mM magnesium acetate) for 1 min at 90° C. and cooled down to 37° C. over a 4 hour period. The formation of duplex was verified on 15% acrylamide 1× TBE gels.

Example 9

Effect of siRNAs Against the Novel Cellular Proteins Interacting with HIV-1 Integrase on HIV-1 Infection in Hela Cells Transiently Expressing CD4 and CCR5

200,000 HeLa cells (ATCC#CCL-2) were co-transfected using Lipofectamine Plus (Invitrogen) with 0.5 µg of each expression plasmids encoding CD4 and CCR5, together with 30 nM of siRNA according Elbashir et al (2001). Two days after transfection, cells were washed three times with PBS and infected with the pNLAD8 strain of HIV-1 (Freed and Martin 1994) using 25 ng of p24 antigen per well. Three days later, supernatants were collected and viral replication was quantified by measuring the p24 antigen in supernatants using the Beckman Coulter P24 antigen detection kit. Each effect of siRNA was measured in duplicate. Cells untransfected with neither CD4 nor CCR5 expression vectors are not permissive for HIV-1 NLAD8 infection and are the negative control of infection. siRNA Luc directed against the exogenous Luciferase gene not expressed neither in HeLa cells nor in the HIV-1 genome is a negative control for siRNA. Therefore, the level of HIV-1 infection reached in the presence of the siRNA Luc was taken as the reference corresponding to the control point of 100% infection. The level of p24 production reached 5 ng of p24/ml in this control. All the effects of the other siRNAs used in this experiment were calculated by reference to siRNA Luc. siRNA HIV5' and siRNA Nef are directed against pNLAD8 sequences in the Nef gene and in the 5' region of Gag and are positive controls for effects of siRNAs targeting directly viral sequences. siRNA against the cellular gene coding for Tsg101 was previously reported as inhibitory for HIV infection (Garrus, von Schwedler et al. 2001) since Tsg101 is needed for the budding of HIV-1. This Tsg101 siRNA is therefore a positive control for the effect of siRNA directed against a cellular gene required for HIV-1 infection. Treatment by siRNA against INI1/SNF5 has a positive effect on HIV-1 infection. Treatment with siRNAs against novel cellular proteins interacting with HIV-1 Integrase, LEDGF, MCM7, HBO1, Snurportin, VBP1, Transportin-SR, EIF3S3, have an inhibitory effect on HIV-1 infection, showing that these Integrase interacting proteins are needed for optimal HIV-1 replication and infection.

Figure 19:
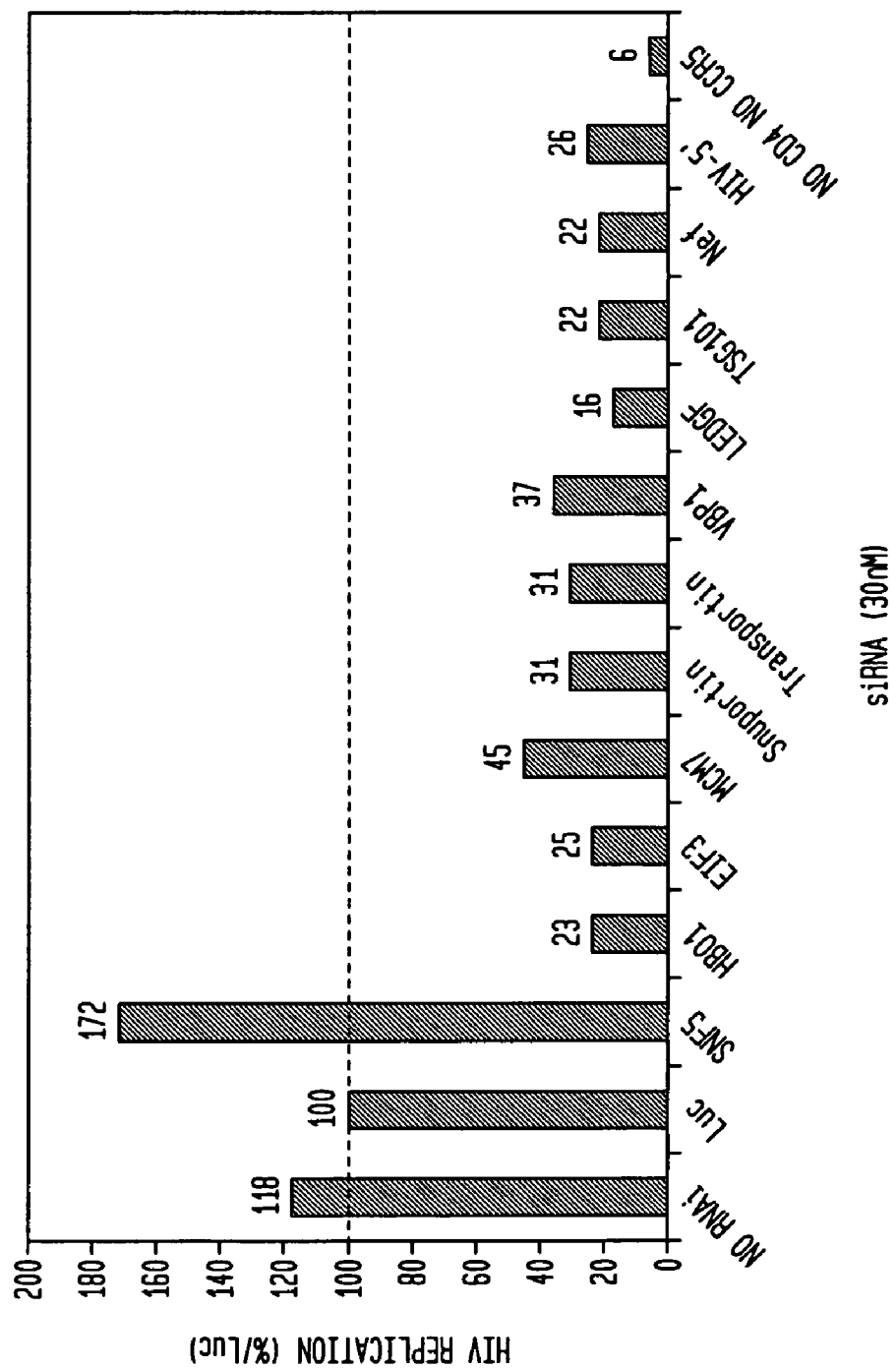
FIG. 19 is a graph showing the effects of siRNAs against the novel cellular proteins interacting with HIV-1 Integrase on HIV-1 infection in HeLa cells transiently expressing CD4 and CCR5.

The results are shown in FIG. 19.

Example 10

Effect of siRNAs Against the Novel Cellular Proteins Interacting with HIV-1 Proteins RT, Protease, Pr55 Gag on HIV-1 Infection in HeLa Cells Transiently Expressing CD4 and CCR5

Figure 20:
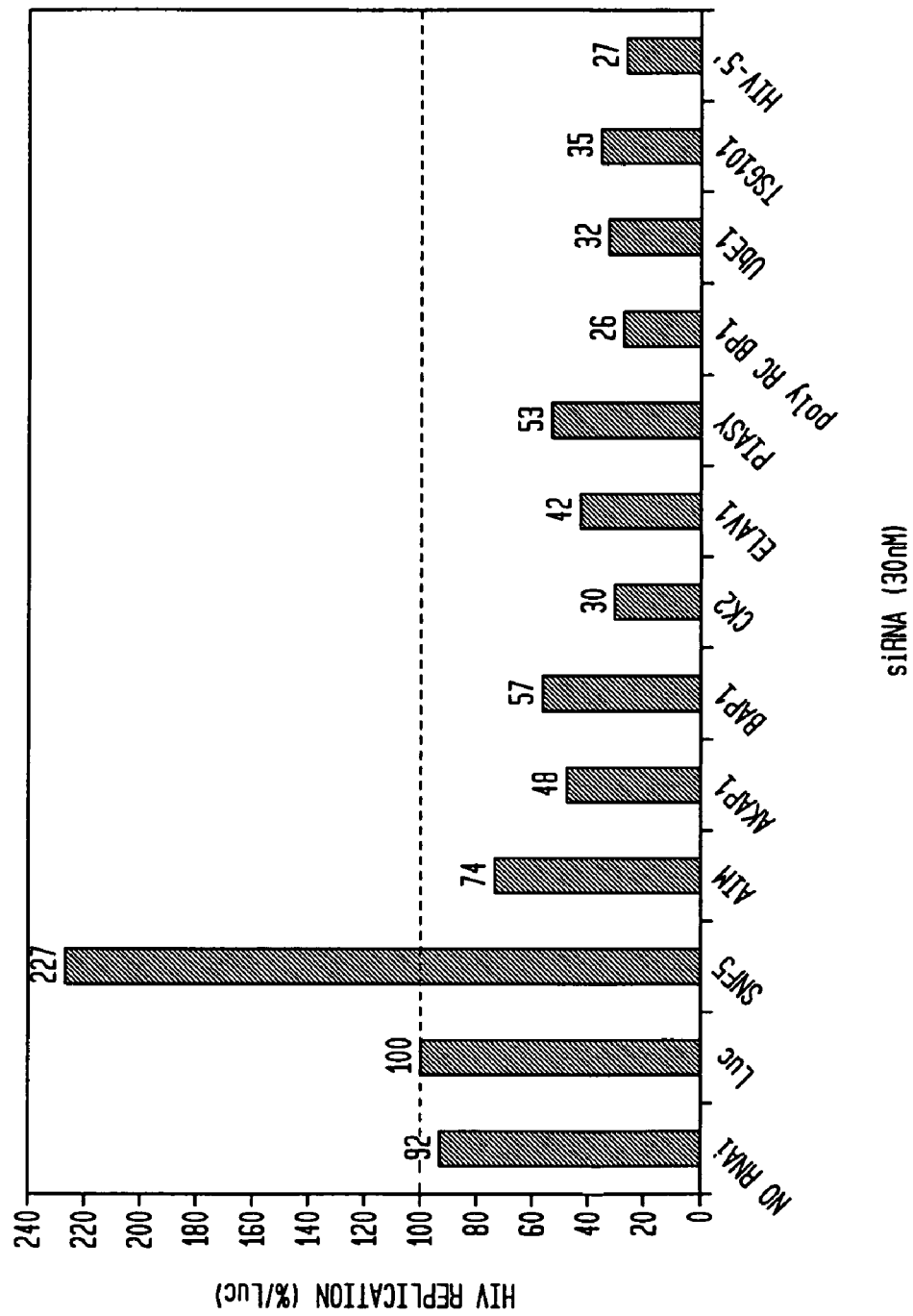
FIG. 20 is a graph showing the effects of siRNAs against the novel cellular proteins interacting with HIV-1 proteins RT, Protease, Pr55 Gag, on HIV-1 infection in HeLa cells transiently expressing CD4 and CCR5.

The experiment illustrated in FIG. 20 was performed and the results were expressed identically to those shown in FIG. 19. The same controls as those described in the legend of FIG. 19 were also used with similar results (control siRNAs HIV5' and Nef which target directly the virus sequence are not shown). The level of p24 production reached in the 100% control in the presence of siRNA Luc was 4 ng of p24/ml in this experiment. The inhibitory effects on HIV-1 infection, of treatments with siRNAs against novel cellular proteins interacting with HIV-1 RT (Akap1 and ELAV1), HIV-1 protease (AIM1, CSNK2B) HIV-1 Integrase (Piasy), HIV-1 Gag precursor and NCp7 (Bap1), and HIV-1 Vpu (polyRC BP1) respectively are shown. These results indicate that these cellular partners of the HIV-1 proteins listed above, are needed for optimal HIV-1 replication and infection.

Example 11

Figure 21:
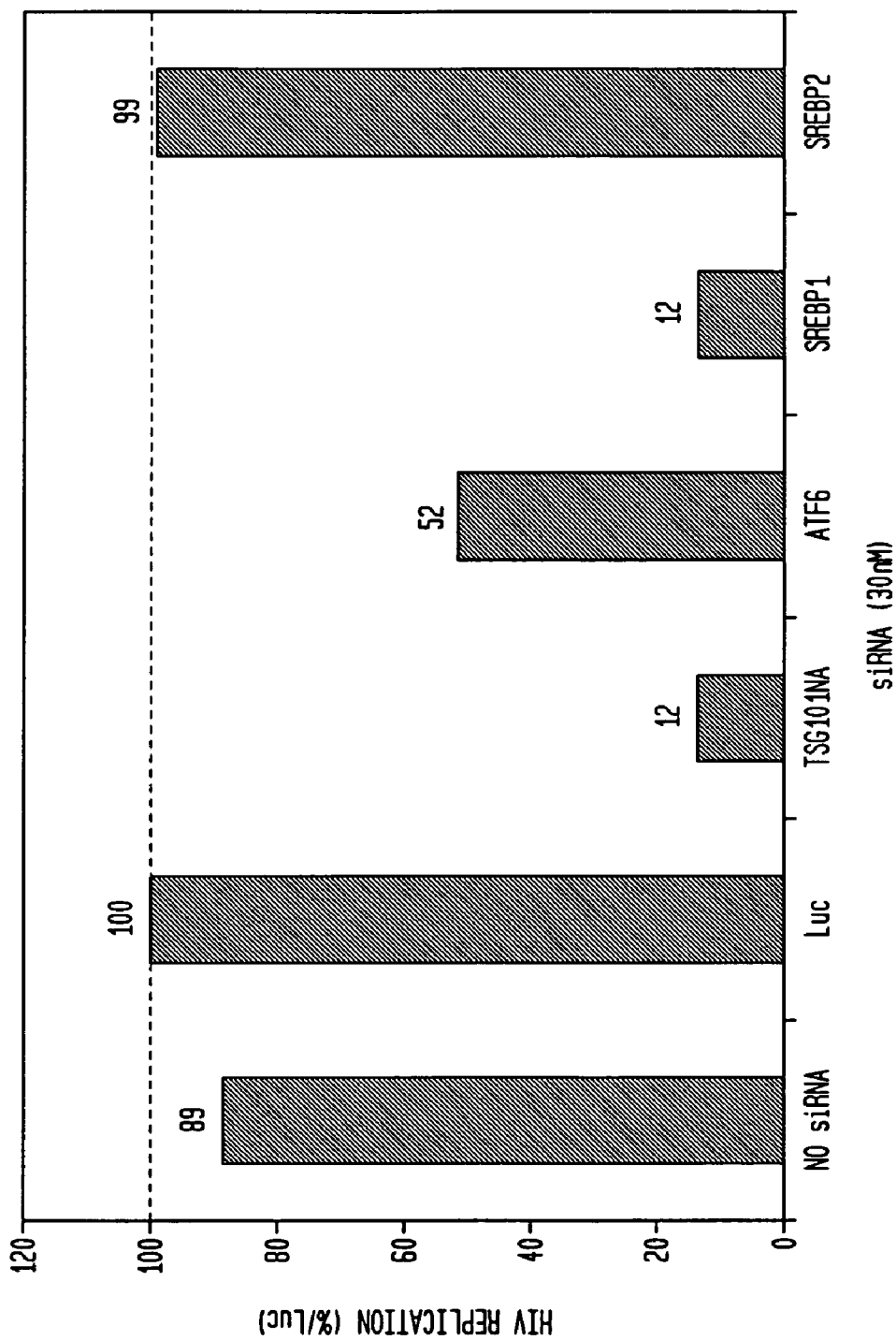
FIG. 21 is a graph showing the effects of siRNA-directed inhibition of HIV-1 infection by the X4 HIV-1 isolate HXB2 in HeLa P4-2 cells.

Effect of siRNAs Against the Novel Cellular Proteins Interacting with HIV-1 TMgp41 on HIV-1 Infection by the X4 HIV-1 Isolate HXB2 in HeLa P4-2 Cells 200,000 HeLa P4-2 cells expressing CD4 (NIH-AIDS program) were transfected two times in 24 h interval using Oligofectamine with 30 nM of siRNA. One day after the second transfection, cells were washed three times with PBS and infected with the HXB2 strain of HIV-1 (Ratner, Haseltine et al. 1985) using 25 ng of p24 antigen per well. Three days later, supernatants were collected and viral replication was quantified by measuring the p24 antigen in supernatants using a P24 antigen detection kit (Beckman Coulter). As in FIGS. 19 and 20, results obtained in the presence of siRNA Luc were taken as the reference point 100% infection. In this experiment, since all cells expressed constitutively CD4 and the co-receptor for X4 viruses CXCR4, the level of infection reached were higher (45 ng of p24/ml in the 100% control point). The effects on HIV-1 infection, of treatments with siRNAs against novel cellular proteins interacting with HIV-1 Env TM Gp41 cytoplasmic domain (SREBP1, SREBP2 and ATF6 alpha) are shown. These results as shown in FIG. 21 indicate that SREBP1 and ATF6, but not SREBP2 are the cellular partners of the HIV-1 Env TM Gp41 cytoplasmic domain, which are required for optimal HIV-1 replication and infection.

Example 12

P24 Assay

The p24 antigen detection kit uses a murine monoclonal antibody to HIV-1 p24 antigen coated onto microtiter strip wells. Diluted supernatant from infected cell cultures were lysed and added to the coated wells. Following a wash step, biotinylated human anti-HIV-1 IgG was added to the well. Following another wash, streptavidin-horseradish peroxidase was added which complexes with biotinylated antibodies. In a final step, a substrate reagent containing tetramethylbenzidine and hydrogen peroxide was added which react with complexed peroxidase. Absorbance is measured spectrophotometrically at 450/570 nm.

Example 13

Figure 22:
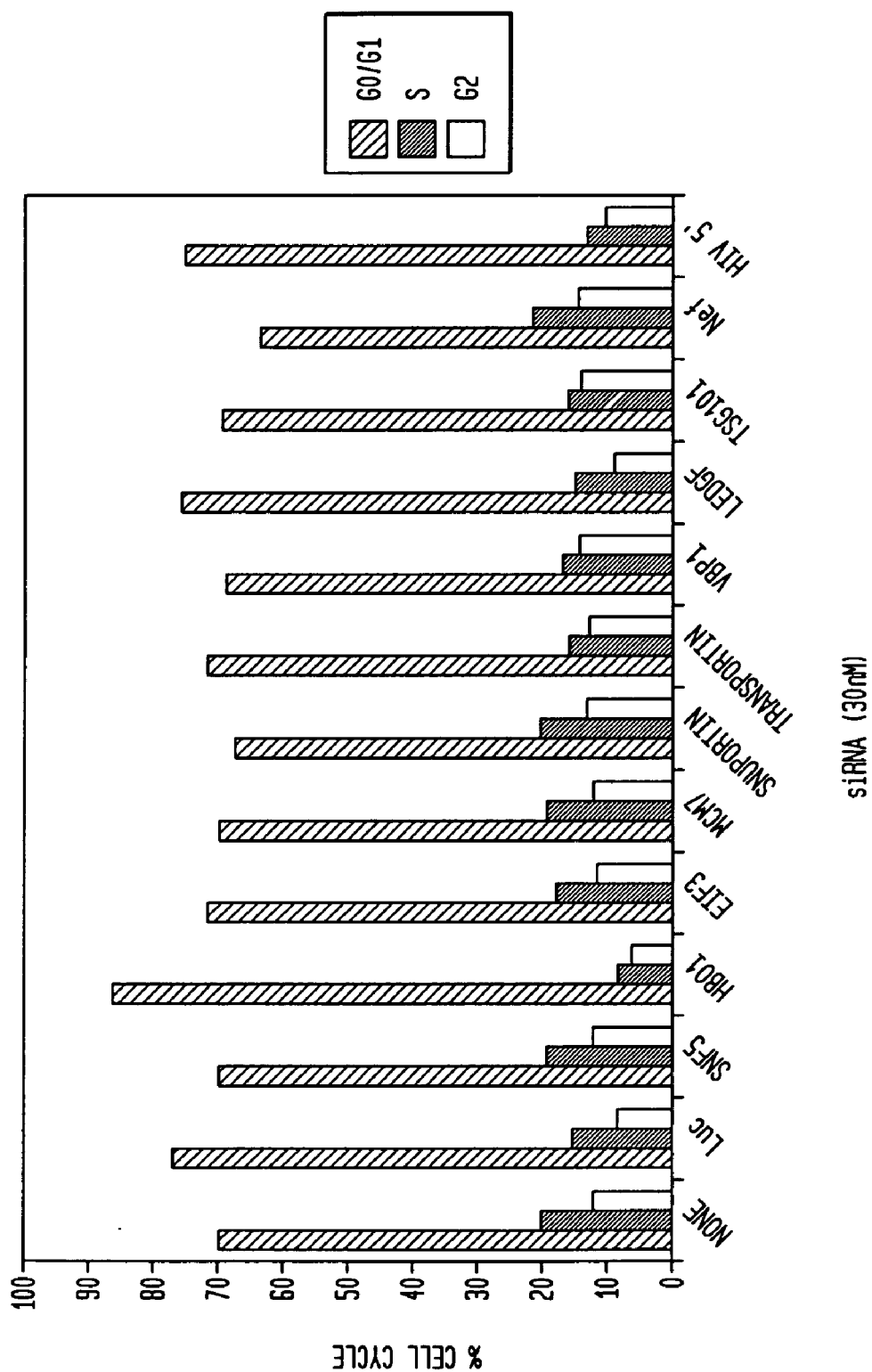
FIG. 22 is a graph showing a FACS analysis of cell cycle showing that cell cycle and cell viability were not affected by transfection of siRNA against the novel cellular partners of HIV-1 proteins described in the present invention.

FACS Analysis of Cell Cycle Showing that Cell Cycle and Cell Viability were not Affected by Transfection of siRNA Against the Novel Cellular Partners of HIV-1 Proteins Described Herein 200,000 HeLa were transfected two times in 24 h interval using Oligofectamine with 30 nM of siRNA. One day after the second transfection, cells were trypsinized, resuspended in PBS and fixed in cold Ethanol for an 1 h at 4° C. Cells were then resuspended in PBS containing 100 µg/ml of RNAse A and 10 µg/ml of propidium iodide. The cell cycle was analyzed by Fluorescence-Activated Cell Sorting (FACS) using a coultroncis Epics Elite instrument. The peaks corresponding to the different phases of the cell cycle, G0-G1, S, and G2 were quantified according to Sherwood et al., Exp. Cell. Res. 1994 211:275-281. As an example FIG. 22 shows results of treatment of cells with 11 siRNAs. Identical results were obtained with all the other siRNAs used in experiments shown in FIGS. 19 to 21 and not shown in FIG. 22.

Example 14

Western Blot Analysis of the Effects of siRNAs Against SREBP1, SREBP2, ATF6 Alpha, the Cellular Gene Tip47, and Luciferase, on the Expression of SREBP1, ATF6 Alpha, HIV-1 Env, and HIV-1 Gag Products on HIV-1 HXB2 Infected Cells 200,000 HeLa cells were transfected two times in 24 h interval using Oligofectamine (Invitrogen) with or without 30 nM of siRNAs as indicated. As a control siRNA Luc targeting the luciferase mRNA described in (Elbashir, Harborth et al. 2001) was used. One day after the second transfection, cells were washed three times with PBS and infected with the HXB2 strain of HIV-1 using 25 ng of p24 antigen per well. Three days later, cells were washed in PBS and lysed in buffer (50 mM Tris HCl ph 7.5, 1 mM EDTA, 150 mM NaCl, 10% glycerol, 1% NP40, 1% antiprotease cocktail (Sigma). Cell lysates were submitted to SDS PAGE electrophoresis. Expression of Gag proteins (p160Gag-Pol, p41, p55Gag, CAp24) and Env proteins (Pr160 Env and SU gp120) of HXB2 HIV-1 virus in infected P4-2 cells was verified by western blot analysis using mouse anti-CA p24 mAb (Hybridolabs) and mouse anti-SU gp120 (110H) (Hybridolab). Expression of SREBP-1 and ATF6 was verified by western blot analysis using rabbit anti-ATF6 antibodies (Haze, Yoshida et al. 1999) and mouse anti-SREBP-1 2A4 (Santa cruz). Lane 1: mock transfected and mock infected cells; lane 2: HXB2 infected cells without siRNA; lane 3 to 7: HXB2 infected cells with siRNA against Luciferase (luc), ATF6 alpha, Tip47, SREBP1, SREBP2 respectively. Tip 47 is a cellular protein which is a putative partner of TM Gp41 used here as a control (Diaz and Pfeffer 1998).

Figure 23:
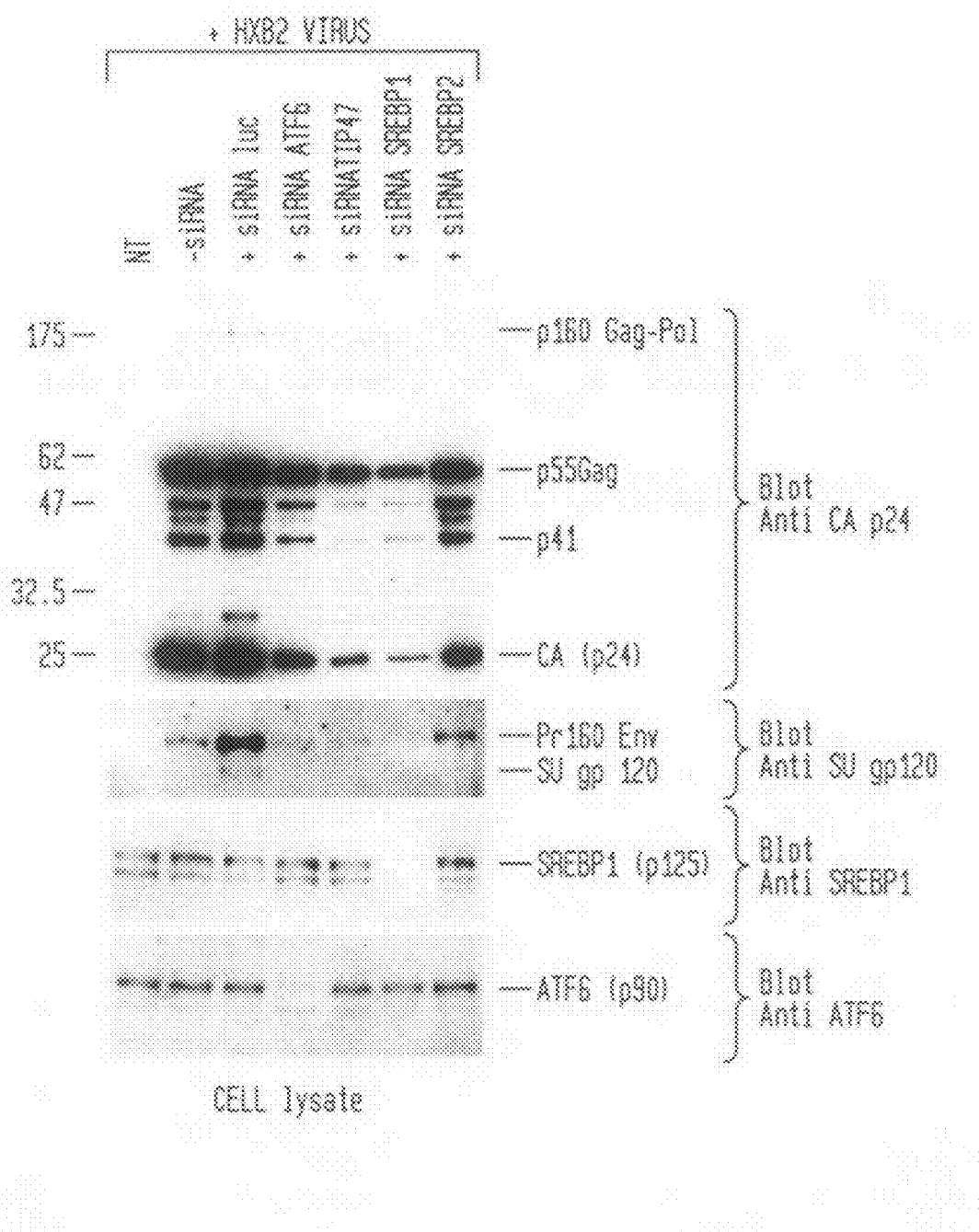
FIG. 23 is a Western blot analysis of the effects of siRNAs against SREBP1, SREBP2, ATF6 alpha, the cellular gene Tip47, and Luciferase, on the expression of SREBP1, ATF6 alpha, HIV-1 env, and HIV-1 Gag products on HIV-1 HXB2 infected cells.

The results are shown in FIG. 23.

Example 15

Figure 24:
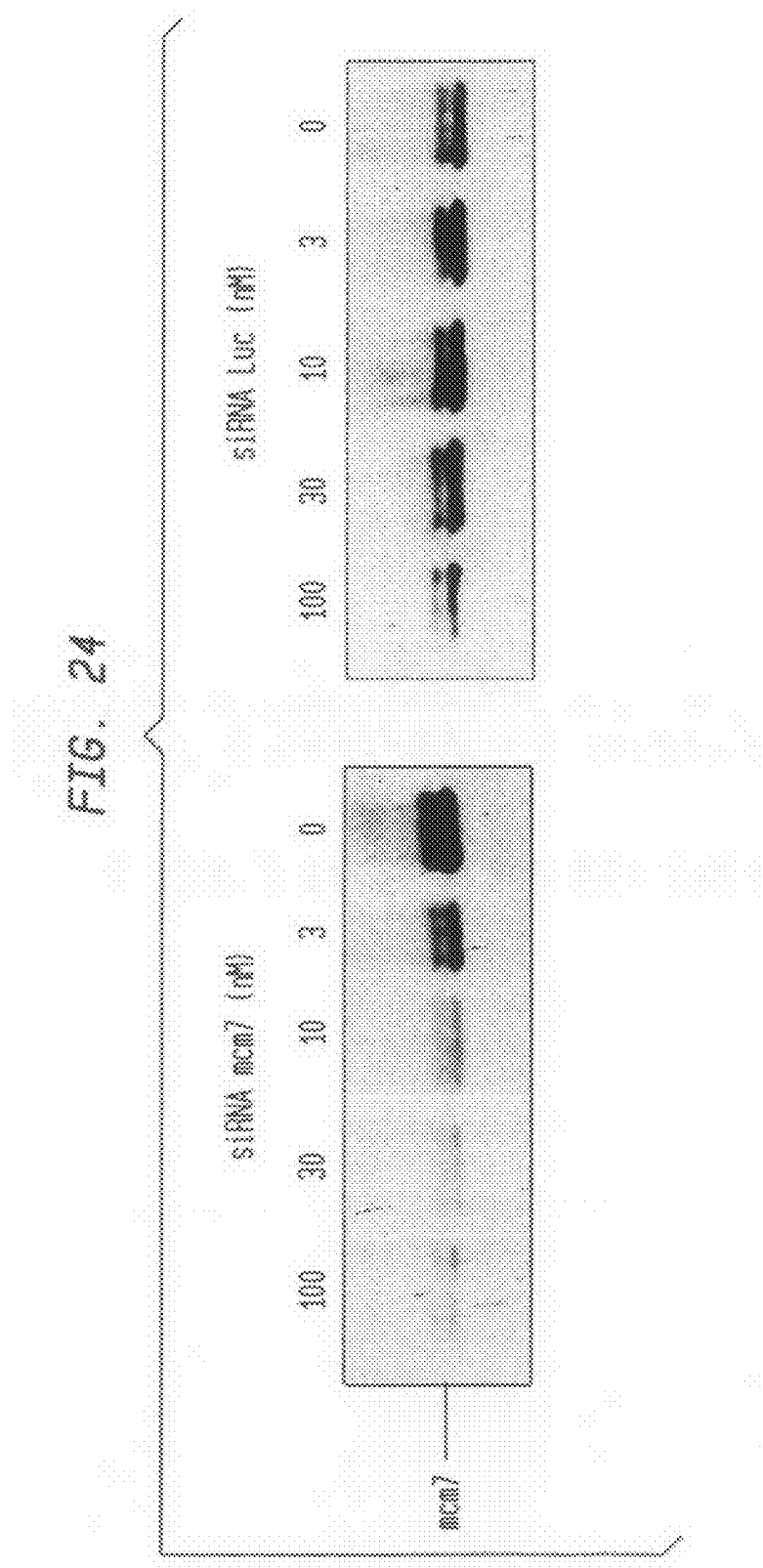
FIG. 24 is a Western blot analysis of the effects of siRNAs against MCM7 and Luciferase, on the expression of MCM7 in HeLa cells.

Western Blot Analysis of the Effects of siRNAs Against MCM7 and Luciferase, on the Expression of MCM7 in HeLa Cells Treatment with siRNA against MCM7 resulted in strong inhibition of MCM7 protein expression detected by western blot using anti-MCM7 antibodies. As soon as cells were treated with 10 nM of MCM7 siRNA, more than 80% decrease of MCM7 expression level was obtained. The results are shown in FIG. 24. At 30 nM MCM7 siRNA, MCM7 expression became almost undetectable (left panel). This effect was specific for MCM7 siRNA since the siRNA Luc which targets Luciferase had no effect on the level of MCM7 (right panel).

Example 16

Quantitative PCR

To monitor the effect of siRNA on target genes, quantitative-PCR was carried-out using an Applied Biosystems 7000 SDS machine. Transfected cells are lysed and RNA was extracted using the Rneasy Minikit and the Qia Shredder from Qiagen following the recommendations of the manufacturer. 1 mg of RNA was then used for a reverse transcription reaction to generate the cDNA which served as template in the following Q-PCR reaction. The reverse transcription step was realized in 96 wells-plate with the TaqMan reverse transcription kit (Applied Biosystems) following the recommendations of the manufacturer. The cDNA of the gene of interest was then quantified in 96 wells-plate by the SyBR green methodology using the SyBR Green PCR master Mix kit (Applied Bisosystems) in an ABI 7000 machine following the recommendations of the manufacturer. For each reaction, 8 ng of cDNA was used as template and 300 nM of forward and reverse oligonucleotides probing specifically the gene for which the mRNA was quantified were added. Values were normalized with the value obtained for the mRNA of the hGAPDH or hGUS genes which serve as internal experimental controls.

The forward and reverse oligonucleotides probing the gene of interest were designed using the Primer Express software (Applied Biosystems). These oligonucleotides were validated by Q-PCR experiments showing that they allow a quantitative measurement (quantification of cDNA diluted in cascade and PCR efficacy determination).

The efficacy of all siRNA has been validated by Q-PCR in duplicate. The siRNA transfection has been performed in the same condition as before the HIV infection process.

Example 17

HIV-1 Integrase

HIV-1 integrase is a protein of 289 amino acid residues, with a MW of the integrase monomer of 31 KD. It is essential for integration of the proviral DNA in the genome of infected cells. Integrase is composed of three domains which have been individually determined by x-ray crystallography or NMR, but the structure of the complete protein has not been solved yet. The core domain contains the catalytic site. A triad of acidic residues, the D,D-35-E motif, plays a key role in catalysis. This domain is well conserved not only among retroviruses but also among many DNA transposons in both prokaryotes and eukaryotes. The N-terminal domain includes the conserved HHCC motif, which binds zinc. Although this domain does indeed bind zinc its structure is totally different from that of zinc fingers. It has an SH3 fold, although there is no known functional relationship with the SH3 domains of other proteins. The function of the N-terminal domain of integrase is at present unknown. The C-terminal domain is less well conserved. Although the core domain of integrase is clearly responsible for catalysis, the functional roles of the other two domains are less clear. The C-terminal domain binds DNA nonspecifically. Integrase is a karyophilic protein, member of the pre-integration complex (PIC) with Vpr, the Nucleocapsid protein (NC) and the matrix protein (MA). The motifs and the mechanism involved in integrase import into the nucleus remain to be elucidated.

Prior to this invention, Ini1, the human homolog of the yeast SNF5 chromatin remodeling factor, was the only cellular protein which has been shown to interact with HIV-1 IN (Kalpana, Marmon at al. 1994). However the functional implication of INI1/SNF5 in the functions of HIV-1 integrase has not been demonstrated yet. Turelli et al. have shown that the SWI/SNF component INI1 trigger the export of the nuclear body constituent PML (Turelli, Doucas at al. 2001) Sequestration of PML in the nucleus, for example by arsenic treatment, provokes a marked increase in the efficiency of HIV-1 transduction. Therefore, (Turelli, Doucas et al. 2001) have raised the hypothesis that, by inducing export of PML INI1 in fact mediates an antiviral response opposing retroviral integration. This effect of INI1 could explain why, using the early phase of the retroviral life cycle, only a fraction of internalized virions end up integrating proviral DNA into the genome of infected cells. Interestingly, the positive effects of siRNA against SNF5/INI detected repetitively herein, although at a magnitude varying slightly from 172% in the experiment shown in FIG. 19 to 227% in the experiment shown in FIG. 20), confirm that INI1/SNF5 may have an inhibitory role in HIV-1 integration and infection. These results reveal a so far unsuspected cellular response that interferes with the early steps of HIV replication.

Example 18

1/VBP1 or Prefoldin 3

Numerous VBP1 polypeptide fragments from the random primed and the oligo dT primed CEM cDNA libraries interacted with HIV-1 IN, demonstrating that this interaction of VBP1 with IN is highly specific. The selective interacting domain (SID®) on VBP1 for interaction with HIV-1 IN could be mapped between amino acid residues 8 to 199 in VBP1 sequence (see Table 2). Secondary screen with VBP1 full length as a bait against the library of HIV genome DNA random fragments shows that VBP1 interacts only with IN and not with any other protein of HIV-1 represented in the library. The great number of positive fragments found in this screen (96 fragments) allows us to define precisely the VBP1-SID® on the HIV-1 IN protein as being located between residues 43 to 195:

(SEQ ID NO. 125)
SEQ: CAGCTAAAAGGAGAAGCCATGCATGGGCAAGTAGACTGTAGTCCA
GGAATATGGCAACTAGATTGTACACATTTAGAAGGAAAAGTTATCCTGGT
AGCAGTTCATGTAGCCAGTGGATATATAGAAGCAGAAGTTATTCCAGCAG
AGACAGGGCAGGAAACAGCATACTTTCTCTTAAAATTAGCAGGAAGATGG
CCAGTAACAACAATACATACAGACAATGGCAGCAATTTCACCAGTGCTAC
AGTTAAAGCCGCCTGTTGGTGGGCAGGGATCAAGCAGGAATTTGGCATTC
CCTACAATCCCCAAAGTCAAGGAGTAGTAGAATCTATGAATAAAGAATTA

-continued
AAGAAAATTATAGGACAGGTAAGAGATCAGGCTGAACATCTTAAGACAGC
AGTACAAATGGCAGTATTCATCCACAATTTTAAAAGAAAAGGGGGATTG
GGGGGTACAGTGC (SEQ ID NO. 126)
SEQ: QLKGEAMHGQVDCSPGIWQLDCTHLEGKVILVAVHVASGYIEAEV
IPAETGQETAYFLLKLAGRWPVTTIHTDNGSNFTSATVKAACWWAGIKQEF
GIPYNPQSQGVVESMNKELKKIIGQVRDQAEHLKTAVQMAVFIHNFKRKGG
IGGYS Thus, both SID®s on VBP1 and IN are precisely defined. Silencing of VBP1 gene expression with specific siRNA prior HIV-1 infection, shows that HIV-1 infection and production of virus particles is strongly inhibited when VBP1 expression is impaired (see FIG. 19), to an extent, 63%, not far from the inhibition induced by siRNA against Tsg101 which gave 78% inhibition (FIG. 19). By contrast, siRNA against the previously described IN interacting protein, Ini1 the homolog of SNF5, has a positive effect on HIV replication (172%). The unrelated siRNA against Luciferase had no effect and was taken as a 100% reference. This experiment demonstrated that the VBP1 protein is required for efficient infection and production of HIV-1 virion particles. Thus, targeting VBP1 or its cellular partners and disrupting the VBP1-IN interaction should allow to isolate novel anti-HIV molecules. VBP1 as a strong binder of HIV-1 IN, may play a role in the folding and in vivo activity of IN. In vitro, VBP1 could help to solubilize purified recombinant IN which usually aggregates in these conditions, and could allow crystallization of the full length IN protein which has not been yet realized.

VBP1 or Prefoldin 3 is a chaperone that delivers unfolded proteins to cytosolic chaperonin (Vainberg, Lewis et al. 1998; Hartl and Hayer-Hartl 2002). The protein encoded by this gene interacts with the Von Hippel-Lindau protein to form an intracellular complex. Because it functions as a chaperone protein, it is suspected that it may play a role in the folding, activity and transport of IN as it does on the folding and transport of the Von Hippel-Lindau protein from the perinuclear granules to the nucleus or cytoplasm. In vitro, VBP1 can help to solubilize IN which give aggregates when expressed alone, and can help to crystallize full length IN protein which has not been yet realized.

2/ Snurportin1

As shown in Table 2, Snurportin1 fragments selected from the IN screen with the random primed cDNA library indicate that Snurportin1 interact with HIV-1 Integrase. The selective interacting domain (SID®) on Snurportin for interaction with HIV-1 IN could be mapped between amino acid residues 33-269 in the Snurportin sequence (see Table 2). Silencing of Snurportin1 gene expression with specific siRNA prior HIV-1 infection, shows that HIV-1 infection and production of virus particles is strongly inhibited when Snurportin1 expression is impaired, to an extent, 69%, comparable to that obtained with siRNA against Tsg101 (FIG. 19). This experiment demonstrates that the Snurportin1 protein is required for efficient infection and production of HIV-1 virion particles. Thus, targeting Snurportin1 or its cellular partners and disrupting the Snurportin1-IN interaction should allow to isolate novel anti-HIV molecules.

Snurportin1 is an m3G-cap-specific nuclear import receptor with a novel domain structure. Snurportin interacts specifically with m3G-cap but not m7G-cap structures. Snurportin1 enhances the m3G-cap dependent nuclear import of U snRNPs. Snurportin functions as an snRNP-specific nuclear import receptor (Huber, Cronshagen et al. 1998). Recycling of snurportin 1 to the cytoplasm. has been shown to be dependent of CRM1 (Paraskeva, Izaurralde et al. 1999). Thus, Snurportin can play a role in the nuclear transport of IN and of the HIV-1 pre-integration complex (PIC) of which Integrase is an important component.

3/ Transportin-SR:

As shown in Table 2, Transportin-SR fragments selected from the IN screen with the random primed cDNA library indicate that Transportin-SR interact with HIV-1 Integrase. The multiple transportin polypeptide fragments from the random primed and the oligo dT primed CEM cDNA library interacting with HIV-1 IN, demonstrate that this interaction of Transportin-SR with IN is highly specific, and allow to map the SID® on Transportin-SR for interaction with HIV-1 IN between Transportin SR amino acid residues 62-334 (see Table 2). Secondary screen with Transportin-SR (fragment aa61-aa333) as a bait against the library of HIV genome DNA random fragments shows that Transportin-SR interacts only with IN and not with any other protein of HIV-1 represented in the library. The great number of positive fragments found in this screen allows us to define precisely the Transportin-SR SID® on the HIV-1 IN protein as being located between residues 62 and 176:

(SEQ ID NO. 127)
SEQ: ACTAGATTGTACACATTTAGAAGGAAAAGTTATCCTGGTAGCAGT
TCATGTAGCCAGTGGATATATAGAAGCAGAAGTTATTCCAGCAGAGACAG
GGCAGGAAACAGCATACTTTCTCTTAAAATTAGCAGGAAGATGGCCAGTA
ACAACAATACATAC (SEQ ID NO. 128)
SEQ: LDCTHLEGKVILVAVHVASGYIEAEVIPAETGQETAYFLLKLAGR
WPVTTIH

Thus, both SID®s on Transportin-SR and IN are precisely defined. Silencing of Transportin-SR gene expression with specific siRNA prior HIV-1 infection, shows that HIV-1 infection and production of virus particles is strongly inhibited when Transportin-SR expression is impaired, to an extent identical to that obtained with siRNA against Snurportin, and comparable to that obtained with siRNA against Tsg101 (FIG. 19). This experiment demonstrates that the Transportin-SR protein is required for efficient infection and production of HIV-1 virion particles. Thus, targeting Transportin-SR or its cellular partners and disrupting the Transportin-SR-IN interaction should allow to isolate novel anti-HIV molecules. Quantitative PCR experiments show that siRNA against Transportin-SR reduce specifically the amount of Transportin-SR RNA of more than 95%.

Transportin-SR is a nuclear receptor for SR proteins (Kataoka, Bachorik et al. 1999). Thus, taking into account its known function, transportin-SR can play, together with Snurportin, a role in the nuclear transport of IN and of the HIV-1 pre-integration complex (PIC) of which Integrase is an important component.

4/ HBO1:

As shown in Table 2, HBO1 (named also HBOA) fragments selected from the IN screen with the random primed and the oligo dT cDNA libraries indicate that HBO1 interacts with HIV-1 Integrase. The SID® on HBO1 for interaction with HIV-1 IN is located between amino acid 337 and 605 of HBO1, as shown on Table 2. Silencing of HBO1 gene expression with specific siRNA prior HIV-1 infection, shows that HIV-1 infection and production of virus particles is strongly inhibited when HBO1 expression is impaired, to an extent, 77% comparable to that obtained with siRNA against Tsg101 (FIG. 1). This experiment demonstrates that the HBO1 protein is required for efficient infection and production of HIV-1 virion particles. Thus, targeting HBO1 or its cellular partners and disrupting the HBO1-IN interaction should allow to isolate novel anti-HIV molecules.

HBO1 is an Histone acetyltransferase which interacts with the ORC1 subunit of the human initiator (Lizuka and Stillman 1999). HBO1 by its acetyl transferase activity participate to Chromatin remodeling. HBOA could therefore participate to the chromatin remodeling which is required for and concomitant to the integration of proviral HIV-1 DNA in the genome of HIV-1 infected cells.

5/ MCM7

Figure 6:
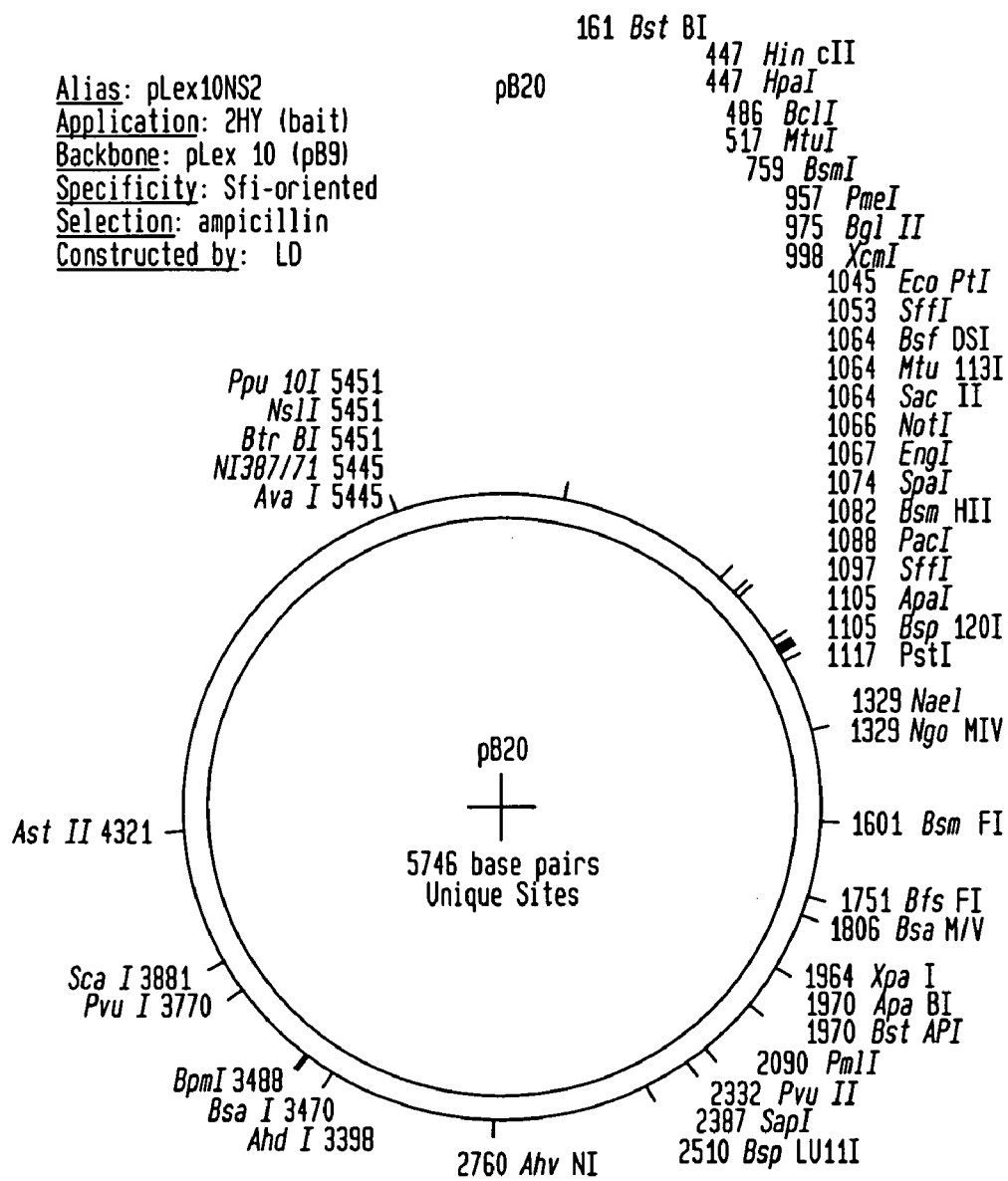
FIG. 6 is a schematic representation of the pB20 plasmid.
Figure 7:
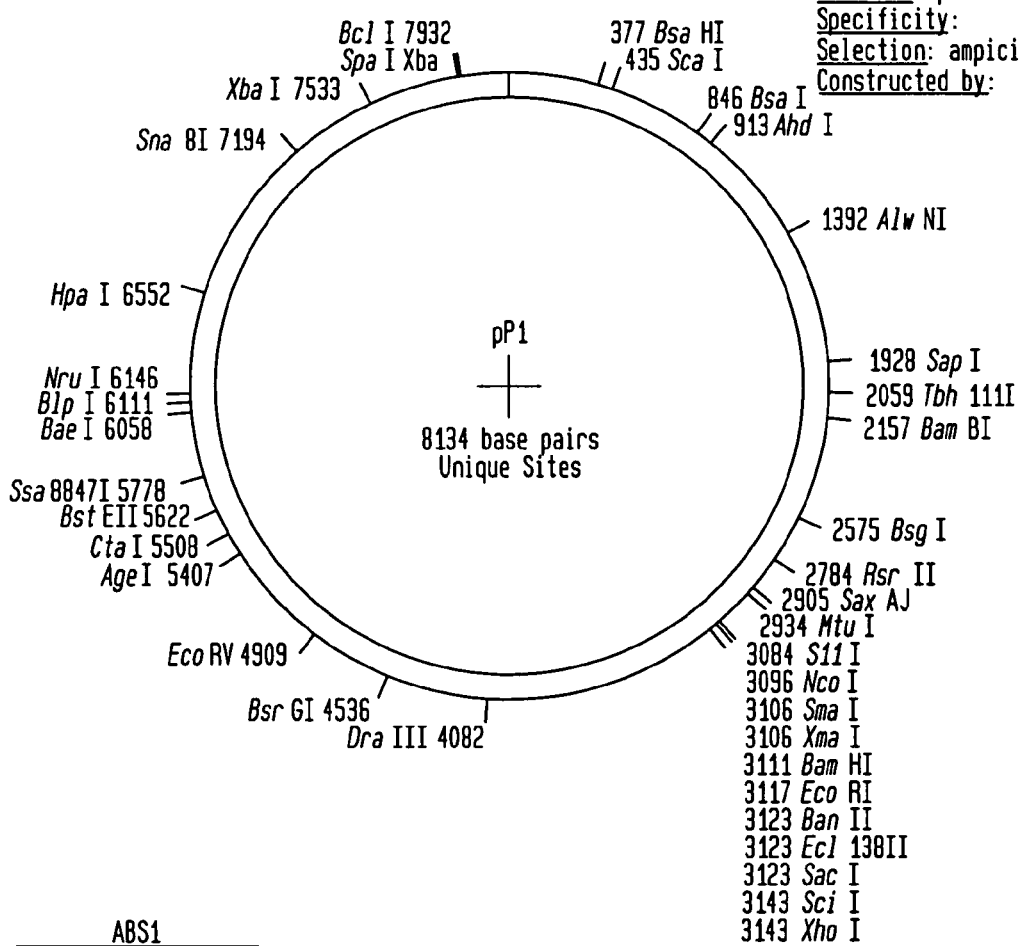
FIG. 7 is a schematic representation of the pP1 plasmid.
Figure 8:
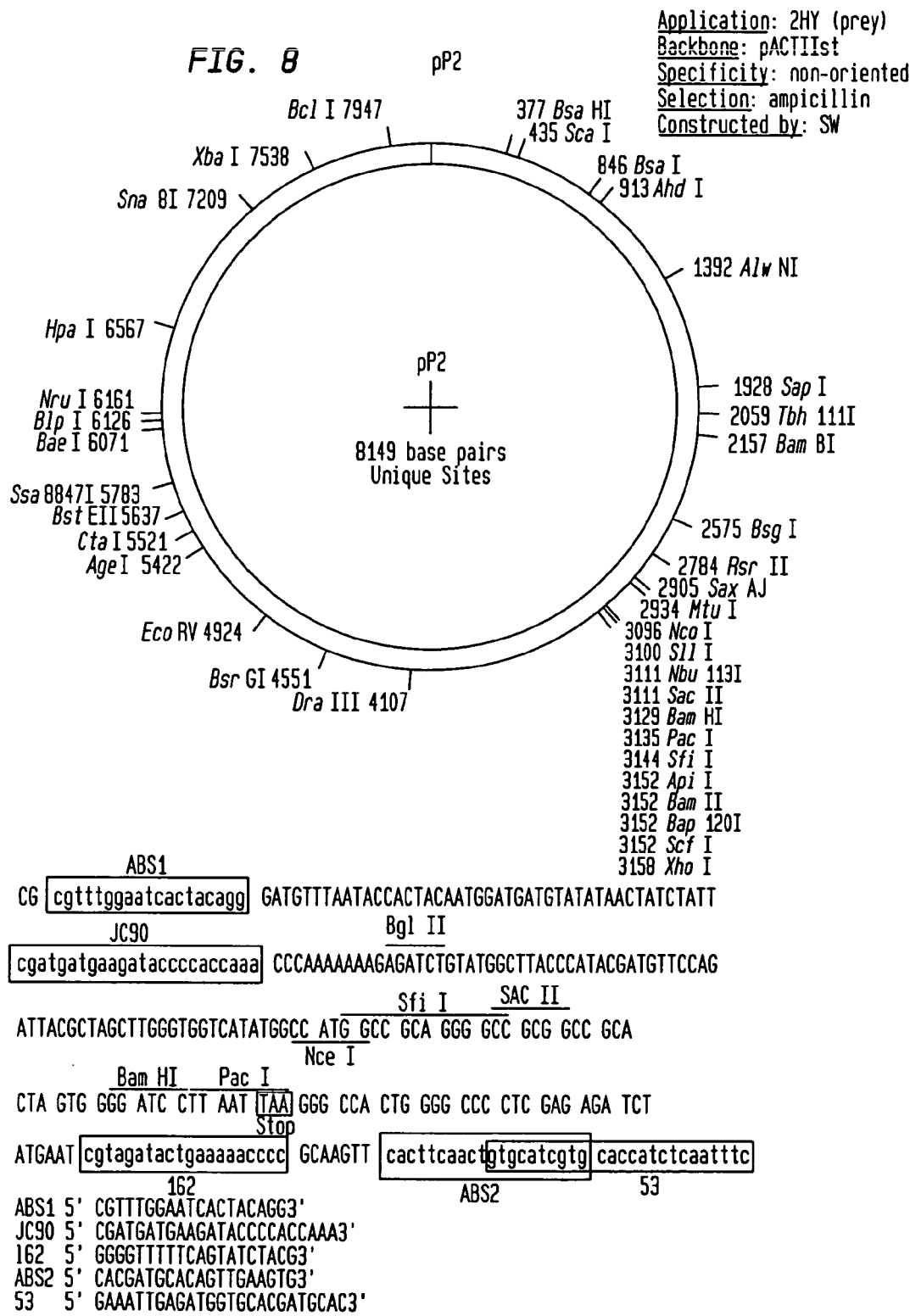
FIG. 8 is a schematic representation of the pP2 plasmid.
Figure 9:
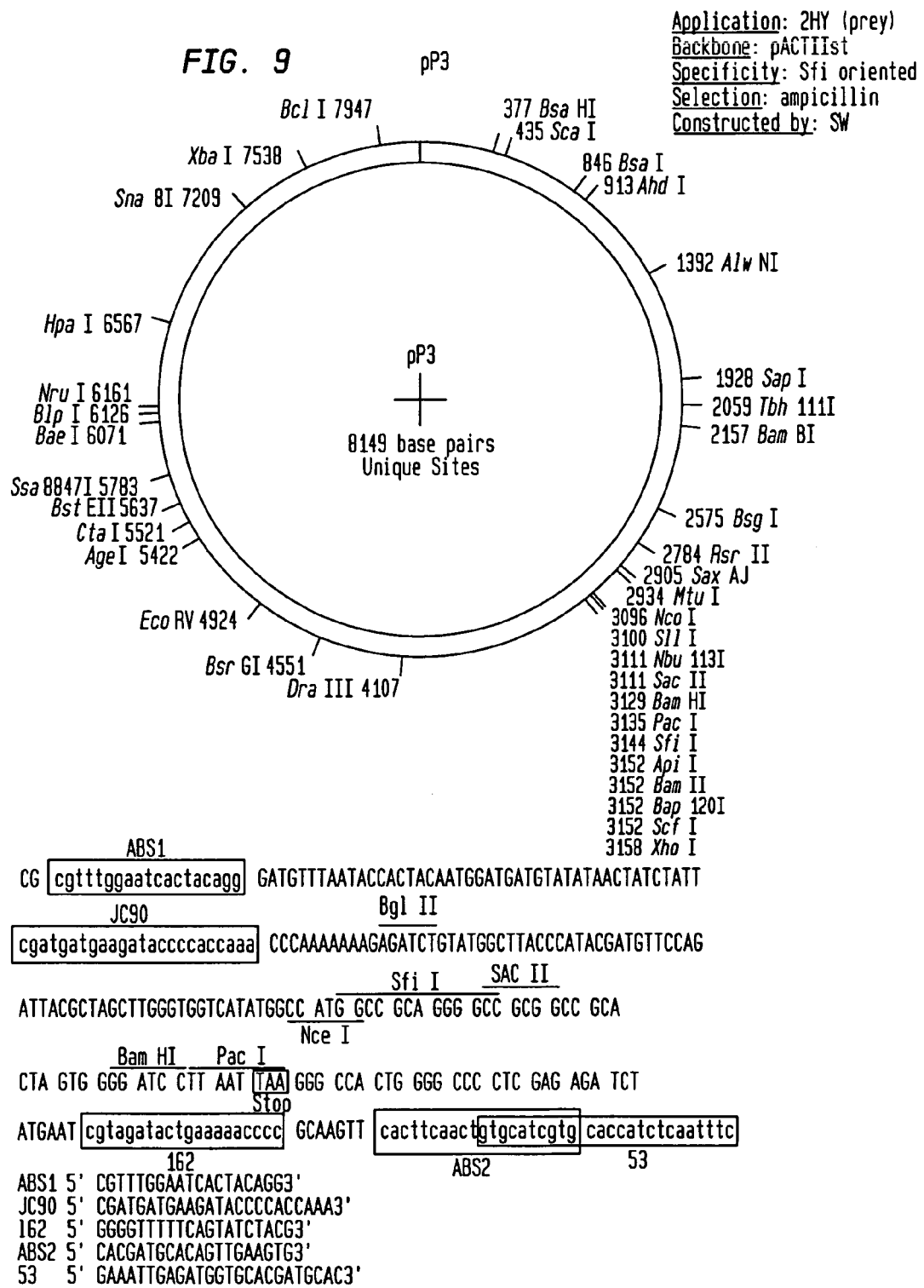
FIG. 9 is a schematic representation of the pP3 plasmid.

MCM7 fragments selected from the IN screen with the random primed and the oligo dT cDNA libraries indicate that MCM7 interacts with HIV-1 Integrase. The SID® on MCM7 for interaction with HIV-1 IN is located between amino acid residues 408-555 Of MCM7, as shown on Table 2. Silencing of MCM7 gene expression with specific siRNA prior HIV-1 infection, shows that HIV-1 infection and production of virus particles is strongly inhibited when MCM7 expression is impaired, to an extent of more than 50% inhibition (FIG. 19), slightly lower than that obtained with siRNA against Tsg101. This experiment demonstrates that the MCM7 protein is important for efficient infection and production of HIV-1 virion particles. Thus, targeting MCM7 or its cellular partners and disrupting the MCM7-IN interaction should allow to isolate novel anti-HIV molecules. As indicated in FIG. 24, treatment with siRNA against MCM7 resulted in strong inhibition of MCM7 protein expression detected by western blot using anti-MCM7 antibodies (SC-1966 from Santa-Cruz). As soon as cells were treated with 10 nM of MCM7 siRNA, more than 80% decrease of MCM7 expression level was obtained. At 30 nM MCM7 siRNA, MCM7 expression became almost undetectable (FIG. 6 left panel). This effect was specific for MCM7 siRNA since the siRNA Luc which targets Luciferase had no effect on the level of MCM7 (FIG. 24 right panel).

MCM7 is a member of the MCM protein family, which has been implicated in the regulatory machinery causing DNA to replicate only once in the S phase. Expression of MCM7 mRNA was repressed in quiescent cells but was induced at the late G1 to S phase by growth factor stimulation. MCM7 protein, together with other MCM proteins and other factors such as HBO1 Histone acetyl-transferase, participates in the regulation of mammalian DNA replication (Fujita, Kiyono et al. 1996). Thus, together with HBO1, MCM7 may participate to the chromatin remodeling which is concomitant to the integration of proviral HIV-1 DNA in the genome of HIV-1 infected cells.

6/ LEDGF Also Named PSIP2

LEDGE fragments corresponding to the p75 isoform (also named PSIP2 isoform), selected from the IN screen with the random and oligo dT primed cDNA libraries indicate that LEDGE interacts with HIV-1 Integrase. The multiple LEDGE polypeptide fragments interacting with HIV-1 IN isolated from the random primed and the oligo dT primed CEM cDNA libraries, demonstrate that this interaction of LEDGE with IN is highly specific, and allows to map the SID® on LEDGE for interaction with HIV-1 IN, as being located between LEDGE residues 243-345 (see Table 2). Secondary screen with LEDGE (fragment aa 341 to aa 507) as a bait against the library of HIV genome DNA random fragments shows that LEDGE interacts only with IN and not with any other protein of HIV-1 represented in the library. The great number of positive fragments (190 fragments) found in this screen allows us to define precisely the SID® on the HIV-1 IN protein for interaction with LEDGF as being located between IN residues 52 and 235:

(SEQ ID NO. 129)
SEQ: GGGCAAGTAGACTGTAGTCCAGGAATATGGCAACTAGATTGTACA
CATTTAGAAGGAAAAGTTATCCTGGTAGCAGTTCATGTAGCCAGTGGATA
TATAGAAGCAGAAGTTATTCCAGCAGAGACAGGGCAGGAAACAGCATACT
TTCTCTTAAAATTAGCAGGAAGATGGCCAGTAACAACAATACATACAGAC
AATGGCAGCAATTTCACCAGTGCTACAGTTAAAGCCGCCTGTTGGTGGGC
AGGGATCAAGCAGGAATTTGGCATTCCCTACAATCCCCAAAGTCAAGGAG
TAGTAGAATCTATGAATAAAGAATTAAAGAAAATTATAGGACAGGTAAGA
GATCAGGCTGAACATCTTAAGACAGCAGTACAAATGGCAGTATTCATCCA (SEQ ID NO. 130)
SEQ: GQVDCSPGIWQLDCTHLEGKVILVAVHVASGYIEAEVIPAETGQE
TAYFLLKLAGRWPVTTIHTDNGSNFTSATVKAACWWAGIKQEFGIPYNPQ
SQGVVESMNKELKKIIGQVRDQAEHLKTAVQMAVFI

Visualization of the SID® for interaction with LEDGF in HIV-1 IN is shown in the tertiary structure of the HIV-1 IN core domain (FIG. 23). This shows that the surface of interaction with LEDGF is located into one face of the core domain of IN and easily accessible. This should facilitate the isolation of molecules capable to disrupt IN-LEDGF interaction. Thus, both SID®s on LEDGF and IN are precisely defined. Silencing of LEDGF gene expression with specific siRNA prior HIV-1 infection, shows that HIV-1 infection and production of virus particles is strongly inhibited when LEDGF expression is impaired. The rate of inhibition of HIV replication reached was even higher than that obtained with siRNA against Tsg101 (84% versus 78%. This experiment demonstrates that the LEDGF protein is required for efficient infection and production of HIV-1 virion particles. Thus, targeting LEDGF or its cellular partners and disrupting the LEDGF-IN interaction should allow to isolate novel anti-HIV molecules. Interaction of LEDGF with HIV-1 IN has been confirmed recently by co-immunoprecipitation and in vitro interaction (Cherepanov, Maertens et al. 2002). Also it was shown that in vitro LEDGF enhances the activity of HIV-1 IN. Thus, LEDGF as a strong binder of HIV-1 IN, may play a role in the folding and in vivo activity of IN. In vitro, LEDGF could help to solubilize purified recombinant IN which usually aggregates in these conditions, and could allow crystallization of the full length IN protein which has not been yet realized.

LEDGF is a transcriptional coactivator which interacts with PC4 and SFRS1, and which exists under two isoforms resulting from alternative splicing, p75 (PSIP2) and p52 (PSIP1) (Ge, Si et al. 1998; Singh, Kimura et al. 2000). p52, functionally interacts also with the essential splicing factor ASF/SF2 (Ge, Si et al. 1998). It is expressed in various tissues. LEDGF stimulated growth of various cells including skin fibroblasts, and keratinocytes, and prolonged cell survival (Singh, Fatma et al. 2001). Thus, LEDGF is a regulatory transcriptional and splicing cofactor, which may play an important role in HIV-1 IN activity for integration of proviral DNA.

7-EIF3S3

EIF3S3 fragments selected from the IN screen with the random primed and the oligo dT cDNA libraries indicate that EIF3S3 interacts with HIV-1 Integrase. The SID® on EIF3S3 for interaction with HIV-1 IN is shown on Table 2. Silencing of EIF3S3 gene expression with specific siRNA prior HIV-1 infection, shows that HIV-1 infection and production of virus particles is strongly inhibited when EIF3S3 expression is impaired to an extent, 75% similar to that reached using siRNA against Tsg101 (see FIG. 19). This experiment demonstrates that the EIF3S3 protein is required for efficient infection and production of HIV-1 virion particles. Thus, targeting EIF3S3 or its cellular partners and disrupting the EIF3S3-IN interaction should allow to isolate novel anti-HIV molecules.

EIF3S3 is the p66 subunit 3 of the mammalian translation initiation factor 3 (eIF3) which is a multiprotein complex of approximately 600 kDa that binds to the 40 S ribosome and promotes the binding of methionyl-tRNAi and mRNA. EIF3S3 P66 is the major RNA binding subunit of the E1F3 complex. Deletion analyses of recombinant derivatives of eIF3-p66 show that the RNA-binding domain lies within an N-terminal 71-amino acid region rich in lysine and arginine. The N-terminal regions of human eIF3-p40 and eIF3-p47 are related to each other and to 17 other eukaryotic proteins, including murine Mov-34, a subunit of the 26 S proteasome.

8-PIASY

PIASy, is a nuclear matrix-associated SUMO E3 ligase. It has previously been reported that PIASY targets LEF1 to nuclear bodies and mediates repression of LEF activity (Sachdev, Bruhn et al. 2001).

Thus, as a novel interaction partner of HIV-1 Integrase, PIASY could similarly induce sumoylation of HIV-1 Integrase and targets it to the nuclear bodies to modulate its activity.

Example 19

HIV-1 Reverse Transcriptase

HIV-1 Reverse transcriptase (RT) is an heterotetramer constituted of two dimers of two subunits, encoded by the pol gene: the long polypeptide p66 which has the RNAse H domain at the C-terminus, and the shorter polypeptide p51 which is the result of a truncation of the p66. RT has been crystallized. Its three dimensional structure has been compared to that of a right palm with subdomains called fingers palm and thumb, and connecting domains. RT is the enzyme which in the cytoplasmic reverse transcription complex converts genomic RNA into proviral DNA before transport of the pre-integration complex to the nucleus occurs. Interactions between the RT complex and the cytoskeleton has been reported (Bukrinskaya, Brichacek et al. 1998), but no precise interactions of RT with cellular proteins have been reported yet. RT is with protease the principal target of efficient anti-retroviral treatments. However, numerous mutations in RT resulting from treatments with RT inhibitors have been reported. All RT inhibitors in use are directed against the RNA-dependent DNA polymerase catalytic activity. Thus, there is an urgent need to develop new RT inhibitors targeting other domains and other functions of RT to overcome the problem linked to the appearance of resistance.

Example 20

Novel Cellular Partners Interacting with HIV-1 RT

1/ Akap1=A Kinase Anchor Protein 1

Akap1 fragments selected from two-hybrid screen with p66 RT subunit as a bait indicate that Akap1 interacts with HIV-1 p66 RT. The SID® on Akap1 for interaction with HIV-1 p66 RT is located between amino acids 345-646 of Akap1 as shown on Table 2. On p66 RT, the SID® for interaction with Akap1 has been determined by screening the library of HIV genome DNA random fragments with Akap1 as a bait. The great number of positive fragments found in this screen (190 fragments) allows us to map precisely the Akap1 SID® on the HIV-1 p66 RT protein as being located between residues 464-561:

(SEQ ID NO. 131)
SEQ: AAGGTTGTCTCCCTAACTGACACAACAAATCAGAAGACTGAGTTA
CAAGCAATTTATCTAGCTTTGCAGGATTCGGGAUAGAAGTAAACATAGTA
ACAGACTCACAATATGCATTAGGAATCATTCAAGCACAACCAGATAGAAG
TGAATCAGAGTTAGTCAGTCAAATAATAGAGCAGTTAATAAAAAGGAAA
AGGTCTATCTGGCATGGGTACCAGCACACAAAGGAA (SEQ ID NO. 132)
SEQ: KVVSLTDTTNQKTELQAIYLALQDSGLEVNIVTDSQYALGIIQAQ
PDRSESELVSQIIEQLIKKEKVYLAWVPAHKG

Thus, both SID®s on Akap1 and RT have been precisely defined. Silencing of Akap1 gene expression with specific siRNA prior HIV-1 infection, shows that HIV-1 infection and production of virus particles is strongly inhibited when Akap1 expression is impaired, to the extent of more than 50% (see FIG. 20). This experiment demonstrates that the Akap1 protein is important for efficient infection and production of HIV-1 virion particles. Thus, targeting Akap1 or its cellular partners and disrupting the Akap1-RT interaction should allow to isolate novel anti-HIV molecules.

Several Akap proteins have been characterized. The role of Akap proteins is to anchor protein Kinase A in particular compartments of the cell and to control the intracellular localization of several isoforms of cAMP-dependent protein kinase (PKAs) involved in signal transduction (Trendelenburg, Hummel et al. 1996). An involvement of AKAP proteins in the anchoring of PKA isoforms in the cytoskeleton has been reported. Furthermore, Akap1 is characterized by the important new feature of the presence of an RNA-binding motif (KH domain). This domain together with the known characteristics of AKAPs suggests the involvement of AKAP1 in the phosphorylation-dependent regulation of RNA-processing (Herberg, Maleszka et al. 2000). Thus, these particular features of AKAP1 make this protein an excellent candidate to control the localization and to regulate the activity of HIV-1RT within infected cells. In particular it has been reported that HIV-1 RT interacts with cytoskeleton (Bukrinskaya, Brichacek et al. 1998). This interaction between RT and the cytoskeleton may well be dependent on the interaction between RT and Akap1. Thus, disruption of this RT-Akap1 interaction could be very useful to conceive new anti-HIV drugs aiming at the inhibition of this novel function of RT in connection with its interaction with Akap1.

2/ELAV1=Hu Antigen R

ELAV1 fragments selected from two-hybrid screen with p66 RT subunit as a bait indicate that ELAV1 interacts with HIV-1 p66 RT. The SID® on ELAV1 for interaction with HIV-1 p66 RT is located between amino acids 287-328 from ELAV1, as shown on Table 2. Silencing of ELAV1 gene expression with specific siRNA prior HIV-1 infection, shows that HIV-1 infection and production of virus particles is strongly inhibited when ELAV1 expression is impaired, to an extent of 58% (see FIG. 20). This experiment demonstrates that the ELAV1 protein is required for efficient infection and production of HIV-1 virion particles. Thus, targeting ELAV1 or its cellular partners and disrupting the ELAV1-RT interaction should allow to isolate novel anti-HIV molecules.

An important mechanism of posttranscriptional gene regulation in mammalian cells is the rapid degradation messenger RNAs (mRNAs) signaled by AU-rich elements (AREs) in their 3' untranslated regions. HuR, a ubiquitously expressed member of the Hu family of RNA-binding proteins related to *Drosophila* ELAV, selectively binds AREs and stabilizes ARE-containing mRNAs when overexpressed in cultured cells. mRNA decay signaled by AREs is a general form of gene regulation, and HuR and its Hu-family relatives play an important role in this phenomenon in antagonizing this mRNA degradation pathway (Brennan and Steitz 2001). In view of the fact that many HIV-1 splice sites are suboptimal (Olsen, Cochrane et al. 1992), it has been postulated that these HIV RNAs contain cis-active inhibitory sequences (INS) within their coding regions which decrease RNA stability and negatively regulate their expression (Schwartz, Felber et al. 1992). Distinct RNA sequences in the gag region of human immunodeficiency virus type 1 decrease RNA stability and inhibit expression in the absence of Rev protein (Graf, Bojak et al. 2000).

Thus, taking into account the function of ELAV1 in stabilization of mRNAs, one can conclude that ELAV1 may play an important role in reverse transcription of the HIV-1 genomic RNA by enhancement of HIV-1 RNA stability during this essential step of the virus life cycle.

Example 21

HIV-1 Protease

HIV-1 protease is an essential viral enzyme of 99 residues (10 kD as a monomère). The active enzyme is a dimer. Protease has been crystallized, and its catalytic core structure elucidated. Protease is encoded by the Gag-pro-pol precursor. It is responsible of the cleavages of the Gag-Pol precursor which give rise to the Gag mature products, MA, CA, NC, P6. For virions assembly, the Gag-pro-pol precursor is encapsidated and budding of virion particles occurs at the cell surface. These budding particles are immature, and maturation of the Gag-pol precursor takes place trough cleavages of the gag precursor by activated protease. These maturation cleavages occur during budding of the immature virion particles. Protease in the gag-pro-pol precursor is inactive and its activation mechanism is not yet elucidated. Protease is with RT the main target for anti-retroviral drugs. All protease inhibitors developed are inhibitors of the protease enzymatic activity. As for RT inhibitors, resistance mutants occur quite rapidly under treatment, and numerous mutations generating resistance to inhibitors have been mapped. No cellular proteins interacting with protease have been reported up to now. Thus, there is an urgent need of novel anti-protease molecules capable to target other functions of the protease in addition to the inhibitors already in use and which target its catalytic activity.

Example 22

Novel Cellular Partners Interacting with HIV-1 Protease

1/CSNK2B=Casein Kinase 2, Beta Polypeptide

Casein Kinase 2, beta polypeptide (CSNK2B) fragments selected from two-hybrid screen with HIV-1 protease as a bait indicate that CSNK2B interacts with HIV-1 protease. The SID® on CSNK2B for interaction with HIV-1 protease is located between CSNK2B amino acids 1-60 as shown on Table 2. Silencing of CSNK2B gene expression with specific siRNA prior HIV-1 infection, shows that HIV-1 infection and production of virus particles is strongly inhibited when CSNK2B expression is impaired, to an extent, 70%, similar to that produced by the siRNA against Tsg101 (65% in the experiment shown in FIG. 20). This experiment demonstrates that the CSNK2B protein is required for efficient infection and production of HIV-1 virion particles. Thus, targeting CSNK2B or its cellular partners and disrupting the CSNK2B-Protease interaction should allow to isolate novel anti-HIV molecules. Interestingly, (Haneda, Furuya et al. 2000) reported that recombinant CK2 could regulate the activity of HIV-1 protease in vitro, confirming the important role that CK2 can play in HIV-1 protease functions. Thus, these results showed that interaction takes place between the regulatory beta chain of CK2 and HIV-1 protease, pave the way to the isolation of new protease inhibitors aiming to disrupt the CSNK2B-HIV-1 protease interaction.

Protein kinase CK2 is a pleiotropic and ubiquitous serine or threonine kinase, which is highly conserved during evolution. The holoenzyme is composed of two regulatory beta-subunits and two catalytic alpha- or alpha'-subunits. There is now increasing evidence for individual functions of the subunits that are different from their functions in the holoenzyme. The crystal structure of the two subunits of protein kinase CK2 has been determined. Protein kinase CK2 is found in many organisms and tissues and nearly every subcellular compartment. There is ample evidence that protein kinase CK2 has different functions in these compartments and that the subcellular localization of protein kinase CK2 is tightly regulated. Therefore protein kinase CK2 may be a key to regulating HIV-1 protease activation and function.

2/AIM1=Absent in Melanoma

Absent In Melanoma (AIM1) fragments selected from two-hybrid screen with HIV-1 protease as a bait indicate that human AIM1 interacts with HIV-1 protease. The SID® on AIM1 for interaction with HIV-1 protease is located between amino acids 461-688 of AIM1 as shown on Table 2. Silencing of human AIM1 gene expression with specific siRNA prior HIV-1 infection, shows that HIV-1 infection and production of virus particles is inhibited to almost 30% when human AIM1 expression is impaired. This experiment demonstrates that the human AIM1 protein participates to the processes leading to efficient infection and production of HIV-1 virion particles. Thus, targeting AIM1 or its cellular partners and disrupting the AIM1-Protease interaction can allow to isolate novel anti-HIV molecules.

AIM1 is a novel non-lens member of the beta-gamma-crystallin superfamily. It is associated with the control of tumorigenicity in human malignant melanoma (Ray, Wistow et al. 1997). All known members of this superfamily contain two or four characteristic motifs arranged as one or two symmetrical domains. AIM1, in contrast, contains 12 beta-gamma motifs, suggesting a 6-domain structure resembling a trimer of beta- or gamma-crystallin subunits. Other parts of the predicted AIM1 protein sequence have weak similarity with filament or actin-binding proteins. AIM1 is a good candidate for the putative suppressor of malignant melanoma on chromosome 6, possibly exerting its effects through interactions with the cytoskeleton. Interaction of AIM1 with HIV-1 protease can be exploited to design new protease inhibitors aiming at the disruption of this interaction.

3/UBE1

UBE1 fragments selected from two-hybrid screen with HIV-1 protease as a bait indicate that human UBE1 interacts with HIV-1 protease. The SID® on UBE1 for interaction with HIV-1 protease is located between amino acids 929-1060 of UBE1 as shown on Table 2. Silencing of human UBE1 gene expression with specific siRNA prior HIV-1 infection, shows that HIV-1 infection and production of virus particles is strongly inhibited when human UBE1 expression is impaired, to an extent of 68%, similar to that obtained with siRNA against Tsg101 in this experiment. This experiment demonstrates that the human UBE1 protein is required for efficient infection and production of HIV-1 virion particles. UBE1 is a ubiquitin activating enzyme involved in the first step of Ubiquitin activation in the ubiquitin-proteasome pathway (Gong and Yeh 1999). Thus, targeting UBE1 or its cellular partners and disrupting the UBE1-Protease interaction should allow to isolate novel anti-HIV molecules.

Example 23

Pr55 Gag Precursor

The Pr55Gag is precursor of the maturation products of the Gag gene which results from protease cleavages: at the N-terminus of the Pr55 gag precursor, the Matrix Map17 is myristoylated and is important for the anchoring of Gag to the cell membrane. The capsid CA p24 is multimerized in capsid and encapsidates the viral genome. The nucleocapsid NC p7 decorates and protects the viral RNA genome and participates to the first steps of reverse transcription. The P6 is located at the C-terminus of Gag and is required for budding of viral particles.

Example 24

Novel Cellular Partners Interacting with HIV-1 Gag

1/BRCA1 Assoc. Prot.1=BAP1=Ubiquitin Hydrolase

BAP1 fragments selected from two-hybrid screen with HIV-1 Pr55 Gag as a bait indicate that human UBE1 interacts with Pr55 Gag HIV-1. The SID® on UBE1 for interaction with HIV-1 protease is located between UBE1 amino acids 929 and 131 as shown on Table 2. Interestingly, BAP1 was also found as interacting with Nucleocapsid NCp7, in the screen with NCp7 as a bait. Thus, the SID® on Pr55Gag for UBE1 interaction corresponds to NCp7. Silencing of human BAP1 gene expression with specific siRNA prior HIV-1 infection, shows that HIV-1 infection and production of virus particles is significantly inhibited when human BAP1 expression is impaired, to an extent of 43%. This experiment demonstrates that the human BAP1 protein is important for efficient infection and production of HIV-1 virion particles. Thus, targeting BAP1 or its cellular partners and disrupting the BAP1-Pr55 Gag interaction should allow to isolate novel anti-HIV molecules.

BAP1 binds to the RING finger domain of the Breast/Ovarian Cancer Susceptibility Gene product, BRCA1 (Jensen, Proctor et al. 1998). BAP1 is a nuclear-localized, ubiquitin carboxy-terminal hydrolase, suggesting that deubiquitinating enzymes may play a role in BRCA1 function. BAP1 binds to the wild-type BRCA1-RING finger, but not to germline mutants of the BRCA1-RING finger found in breast cancer kindreds. BAP1 and BRCA1 are temporally and spatially co-expressed during murine breast development and remodeling, and show overlapping patterns of subnuclear distribution. BAP1 resides on human chromosome 3p21.3; intragenic homozygous rearrangements and deletions of BAP1 have been found in lung carcinoma cell lines. BAP1 enhances BRCA1-mediated inhibition of breast cancer cell growth and is the first nuclear-localized ubiquitin carboxy-terminal hydrolase to be identified. Since the ubiquitin pathway has been found to be involved in P6-mediated budding of virus particles, with Tsg101 and Multi vesicular bodies (MVB), one can postulate that BAP1 as a ubiquitin hydrolase partner of pr55 Gag, is also involved in the process leading to the budding of viral particles.

Example 25

TM Gp41 HIV-1 Envelope Protein

HIV-1 envelope protein, like all retroviral envelope proteins, is composed of two subunits, the external subunit SU Gp120 which is involved in recognition of the receptor CD4 and the co-receptors CCR5 or CXCR4. The second subunit, TM Gp41 is the transmembrane subunit of the HIV-1 envelope protein. TM Gp41 is involved in fusion of viral membrane with the cell membrane. The cytoplasmic domain of TM Gp41 is involved in the traffic of the HIV-1 envelope protein in HIV-1 infected cells.

Example 26

Novel Cellular Partners of the TM Gp41 Cytoplasmic Domain

1/.Sterol Regulatory Element-Binding Proteins 1 and 2 (SREBP1 and 2):

SREBP1 and SREBP2 fragments selected from two-hybrid screen with the cytoplasmic domain of TM Gp41 (TM cyto) used as a bait indicate that SREBP1 and SREBP2 interact with TM cyto. The SID® on SREBP1 and on SREBP2 for interaction with TM cyto are located between amino acids 275-500 For SREBP1 and between amino acids 302-496 for SREBP2, as shown on Table 2. Silencing of SREBP1 gene expression with specific siRNA prior HIV-1 infection with the HXB2 isolate, shows that HIV-1 infection and production of virus particles is strongly inhibited when human SREBP1 expression is impaired, giving rise to an inhibition of HIV-1 replication of 88%, similar to that reached in the presence of siRNA against Tsg101, as shown in the experiment illustrated in FIG. 21. By contrast, in the same experiment, silencing SREBP2 has no effect on HIV-1 replication and infection. These experiments demonstrate that although SREBP1 and SREBP2 are closely related proteins, only the SREBP1 protein is required for efficient infection and production of HIV-1 virion particles, while the SREBP2 does not seem required for HIV-1 infection. Thus, targeting SREBP1 or its cellular partners and disrupting the SREBP1-TM cyto interaction should allow to isolate novel anti-HIV molecules.

Since anti-SREBP1 antibodies (2A4 from Santa Cruz, USA) were available, we could check by western blot that siRNA against SREBP1 resulted in the absence of detectable SREBP1 protein (see FIG. 23, lane 6) while ATF6 protein was not affected (see FIG. 23, lane 4), showing that the effect of siRNA against SREBP1 is specific. Interestingly, siRNA against SREBP1 resulted in inhibition of HIV-1 Gag maturation products (upper panel), as well as HIV-1 env protein produced (middle panel). This inhibition of viral protein expression paralleled the important inhibition of HIV-1 replication resulting from SREBP siRNA treatment. As a further proof of selectivity of siRNAs, siRNA against ATF6 had no effect on SREBP1 while it abolished expression of the ATF6 protein which became undetectable (FIG. 23, lane 4).

Sterol regulatory element-binding proteins (SREBPs) are basic helix-loop-helix (bHLH) type transcription factors that control expression of genes involved in biosynthesis of cholesterol and fatty acids (Brown, Ye et al. 2000; Hoppe, Rape et al. 2001; Horton, Goldstein et al. 2002). Dietary studies with normal, transgenic, and knockout mice have established SREBP-1 as a dominant transcription factor regulating gene expression of lipogenic enzyme in the liver. Polyunsaturated fatty acids inhibit hepatic lipogenic enzymes through suppressing SREBP-1. SREBP-1 and SREBP2 exert sterol regulation through cleavage of the membrane-bound precursor protein to liberate the active nuclear form into the nucleus. SREBP-1 and SREBP2 control lipogenic enzymes by self-regulating its own transcription level. SREBP-1 seems to be involved in energy metabolism including fatty acid and glucose/insulin metabolism, whereas SREBP-2 is specific to cholesterol synthesis. It has been shown by Caron et al. that the HIV protease inhibitor indinavir impairs sterol regulatory element-binding protein-1 intranuclear localization, inhibits preadipocyte differentiation, and induces insulin resistance (Caron, Auclair et al. 2001).

2/ ATF6 Alpha and Beta

ATF6 alpha and ATF6 beta fragments selected from two-hybrid screen with the cytoplasmic domain of TM Gp41 (TM cyto) used as a bait indicate that both ATF6 isoforms interact with TM cyto. The SID® on ATF6-alpha and ATF6-beta for interaction with TM cyto are located between amino acids 332-461 and amino acids 318-466 respectively as shown on Table 2. Silencing of ATF6 gene expression with specific siRNA prior HIV-1 infection with the HXB2 isolate, shows that HIV-1 infection and production of virus particles is strongly inhibited when ATF6 expression is impaired, to an extent of about 50% inhibition. This experiment demonstrated that the ATF6 protein is important for efficient infection and production of HIV-1 virion particles. Thus, targeting ATF6 or its cellular partners and disrupting the ATF6-TM cyto interaction should allow to isolate novel anti-HIV molecules.

As indicated for SREBP1, treatment with siRNA against ATF6 before HIV-1 infection resulted in inhibition of AT6 protein expression which became undetectable in western blot using anti-ATF6 alpha antibodies, as well as inhibition of production of viral proteins, Gag maturation products and Env (FIG. 23, lane 4) which paralleled the inhibition of virus replication. This effect was specific for ATF6 since the ATF6 siRNA had no effect on the level of SREBP1.

ATF6 is a basic leucine zipper (bZIP) protein, which functions as a transcription factor for ER stress response element, (ERSE) (Haze, Yoshida at al. 1999). ATF6 enhanced transcription of GRP genes in an ERSE-dependent manner. Endogenous ATF6 constitutively expressed as a 90-kD protein was converted to a 50-kD protein in ER-stressed cells, which appeared to be important for the cellular response to ER stress. When unfolded proteins accumulate in the ER, ATF6 is cleaved to release its cytoplasmic domain, which enters the nucleus. ATF6 is processed by site-1 protease S1P and site-2 protease (S2P), the enzymes that process sterol regulatory element-binding proteins (SREBPs) in response to cholesterol deprivation (Ye, Rawson et al. 2000).

The following results obtained from these Examples, as well as the teachings in the specification are set forth in the tables below.

While the invention has been described in terms of the various preferred embodiments, the skilled artisan will appreciate that various modifications, substitutions, omissions and changes may be made without departing from the scope thereof. Accordingly, it is intended that the present invention be limited by the scope of the following claims, including equivalents thereof.

Example 26

Vpu

Vpu is an accessory protein specifically expressed only in HIV-1, but not in the other primate lentiviruses. Vpu has an N-terminal transmembrane anchor domain, and a cytoplasmic phosphorylated tail. Several functions have been attributed to Vpu, enhancement of viral particles release from infected cells, induction of CD4 degradation, ion channel and pro-apoptotic activities. The mechanism by which Vpu mediates CD4 degradation has been elucidated. It was demonstrated that, by binding to the F-box WD40 protein □TrCP, the receptor component of the SCF ubiquitin ligase SCF betaTrCP, Vpu can subvert the cellular targeting pathways to the proteasome in order to promote CD4 degradation (Margottin, Bour et al. 1998). The mechanism by which Vpu enhances viral particle release is still unknown, except that this effect requires the N-terminal transmembrane anchor domain.

Example 27

Novel Cellular Partners of Vpu

1/PCBP1=PolyrC-Binding Protéin:

The protein encoded by this gene appears to be multifunctional. It along with PCBP-2 and hnRNPK corresponds to the major cellular poly(rC)-binding proteins. It contains three K-homologous (KH) domains which may be involved in RNA binding. This encoded protein together with PCBP-2 also functions as translational coactivators of poliovirus RNA via a sequence-specific interaction with stem-loop IV of the IRES and promote poliovirus RNA replication by binding to its 5'-terminal cloverleaf structure. It has also been implicated in translational control of the 15-lipoxygenase mRNA, human Papillomavirus type 16 L2 mRNA, and hepatitis A virus RNA. (Characterisation of two major cellular poly(rC)-binding human proteins, each containing three K-homologous (KH) domains (Leffers, Dejgaard et al., 1995). By binding to Vpu, PCBP1 could participate to the effect of Vpu in the enhancement of viral particle release. Interestingly, binding of PCBP1 to Vpu requires the N-terminal transmembrane anchor domain, the domain which is needed for the effect of Vpu on particle release. PCBP1 does not bind to the cytoplasmic tail of Vpu which is deleted of the N-ter membrane anchor domain, since it was not found in two-hybrid screens using the cytoplasmic tail of Vpu alone as a bait.

TABLE 1

| bait name and sequence | | | | | | |
|---|---|---|---|---|---|---|
| 1: Bait name | 2: Nucleic acid ID No. | 3: Nucleic acid sequence | 4: Nucleic Positions | 5: Amino acid ID No. | 6: Amino acid Sequence | 7: Bait construction |
| IN | 1 | ATGGAATAGATAAGGCCAAGAAGAACAT GAGAAATATCACAGTAATTGGAGAGCAA TGGCTAGTGATTTTAACCTGCCACCTGT AGTAGCAAAAGAAATAGTAGCCAGCTGT | [1-867] | 8 | FLDGIDKAQEEHEKYHSW WRAMASDFNLPPVVAKEI VASCDKCQLKGEAMHGQV DCSPGIWQLDCTHLEGKV | pB27 |

TABLE 1-continued bait name and sequence

| 1: Bait name | 2: Nucleic acid ID No. | 3: Nucleic acid sequence | 4: Nucleic Positions | 5: Amino acid ID No. | 6: Amino acid Sequence | 7: Bait construction |
|---|---|---|---|---|---|---|
| | | GATAAATGTCAGCTAAAAGGAGAAGCCA TGCATGGGCAAGTAGACTGTAGTCCAGG AATATGGCAACTAGATTGTACACATTTA GAAGGAAAAGTTATCCTGGTAGCAGTTC ATGTAGCCAGTGGATATATAGAAGCAGA AGTTATTCCAGCAGAGACAGGGCAGGAA ACAGCATACTTTCTCTTAAAATTAGCAG GAAGATGGCCAGTAACAACAATACATAC AGACAATGGCAGCAATTTCACCAGTGCT ACAGTTAAAGCCGCCTGTTGGTGGCAG GGATCAAGCAGGAATTTGGCATTCCCTA CAATCCCCAAAGTCAAGGAGTAGTAGAA TCTATGAATAAAGAATTAAAGAAAATTA TAGGACAGGTAAGAGATCAGGCTGAACA TCTTAAGACAGCAGTACAAATGGCAGTA TTCATCCACAATTTTAAAAGAAAAGGGG GGATTGGGGGGTACAGTGCAGGGGAAAG AATAGTAGACATAATAGCAACAGACATA CAAACTAAAGAACTACAGAAACAAATTA CAAAAATTCAAAATTTTCGGGTTTATTA CAGGGACAGCAGAGATCCACTTTGGAAA GGACCAGCAAAGCTCCTCTGGAAAGGTG AAGGGGCAGTAGTAATACAAGATAATAG TGACATAAAAGTAGTGCCAAGAAGAAAA GCAAAGATCATTAGGGATTATGGAAAAC AGATGGCAGGTGATGATTGTGTGGCAGG TAGACAGGATGAGGATTAG | | | ILVAVHVASGYIEAEVIP AETGQETAYFLLKLAGRW PVTTIETDNGSNFTSATV KAACWWAGIKQEFGIPYN PQSPGVVESMNKELKKII GQVRDQAEHLKTAVQMAV FIHNFKRKGGIGGYSAGE RIVDIIATDIQTKELQKQ ITKIQNFRVYYRDSRDPL WKGPAKLLWKGEGAVVIQ DNSDIKVVPRRKAKIIRD YGKQMAGDDCVAGRQDED | |
| RT_v1 | 2 | CCCATTAGTCCTATTGAAACTGTACCAG TAAAATTAAAGCCAGGAATGGATGGCCC AAAAGTTAAACAATGGCCATTGACAGAA GAAAAAATAAAAGCATTAGTAGAAATTT GTACAGAAATGGAAAAGGAAGGGAAAAT TTCAAAAATTGGGCCTGAAAACCCATAC AATACTCCAGTATTTGCCATAAAGAAAA AAGACAGTACTAAATGGAGAAAATTAGT AGATTTCAGAGAACTTAATAAGAGAACT CAAGACTTCTGGGAAGTTCAATTAGGAA TACCACATCCCGCAGGGTTAAAAAAGAA AAAATCAGTAACAGTACTGGATGTGGGT GATGCATATTTTTCAGTTCCCTTACATG AAGACTTCAGGAAGTATACTGCATTTAC CATACCTAGTATAAACAATGAGACACCA GGGATTAGATATCAGTACAATGTGCTTC CACAGGGATGGAAAGGGTCACCAGCAAT ATTCCAAAGTAGCATGACAACAATCTTA GAGCCTTTTAGAAAACAAAATCCAGACC TAGTTATCTATCAGTACATGGATGATTT GTACGTAGGATCTGACTTAGAAATAGGG CAGCATAGAACAAAAATAGAGGAACTGA GACAACATCTGTTGAGGTGGGGATTTAC CACACCAGACAAAAACATCAGAAAGAA CCTCCATTCCTTTGGATGGGTTATGAAC TCCATCCTGATAAATGGACAGTACAGCC TATAGTGCTGCCAGAAAAAGATAGCTGG ACTGTCAATGACATACAGAAGTTAGTGG GAAAATTGAATTGGGCAAGTCAGATTTA TGCAGGGATTAAAGTAAGGCAATTATGT AAACTCCTTAGGGGAACCAAAGCACTAA CAGAAGTAATACCACTAACAGAAGAAGC AGAACTAGAACTGGCAGAAAACAGGGAA ATTCTAAAAGAACCAGTACATGGAGTGT ATTATGACCCATCAAAAGACTTGATAGC AGAAATACAGAAGCAGGGGCAAGGCCAA TGGACATATCAAATTTATCAAGAGCCAT TTAAAAATCTGAAAACAGGAAAATATGC AAGAACGAGGGGTGCCCACACTAATGAT GTAAAACAATTAACAGAGGCAGTACAAA AAATAGCCACAGAAAGCATAGTAATATG GGGAAAGACTCCTAAATTTAAACTACCC ATACAAAAAGAAACATGGGAAACATGGT GGACAGAATATTGGCAAGCCACCTGGAT TCCTGAGTGGGAGTTTGTCAATACCCCT CCCTTAGTGAAATTATGGTACCAGTTAG | [1 1680] | 9 | PISPIETVPVKLKGMDGP KVKQWPLTEEKIKALVEI CTEMEKEGKISKIGPENP YNTPVFAIKKKDSTKWRK LVDFRELNKRTQDFWEVQ LGIPHPAGLKKKKSVTVL DVGDAYFSVPLHEDFRKY TAFTIPSINNETPGTRYQ YNVLPQGWKGSPAIFQSS MTTILEPFRKQNPDLVIY QYMDDLYVGSDLEIGQHR TKIEELRQHLLRWGFTTP DKKHQKEPPFLWMGYELH PDKWTVQPIVLPEKDSWT VNDIQKLVGKLNWASQIY AGIKVRQLCKLLRGTKAL TEVIPLTEEAELELAENR EILKEPVHGVYYDPSKDL IAEIQKQGQGQWTYQIYQ EPFKNLKTGKYARTRGAH TNDVKQLTEAVQKIATES IVIWGKTPKFKLPIQKET WETWWTEYWQATWIPEWE FVNTPPLVKLWYQLEKEP IIGAETFYVDGAANRETK LGKAGYVTNKGRQKVVSL TDTTNQKTELQAIYLALQ DSGLEVNIVTDSQYALCI IQAQPDRSESELVSQIIE QLIKKEKVYLAWVPAHKG IGGNEQVDKLVSAGIRKV L | pB6 |

TABLE 1-continued bait name and sequence

| 1: Bait name | 2: Nucleic acid ID No. | 3: Nucleic acid sequence | 4: Nucleic Positions | 5: Amino acid ID No. | 6: Amino acid Sequence | 7: Bait construction |
|---|---|---|---|---|---|---|
| | | AGAAGAACCCATAATAGGAGCAGAAACT TTCTATGTAGATGGGGCAGCTAACAGGG AGACTAAAATTAGGAAAAGCAGGATATGT TACTAACAAGGGAAGACAAAAGGTTGTC TCCCTAACTGACACAACAAATCAGAAGA CTGAGTTACAAGCAATTTATCTAGCTTT GCAGGATTCGGGATTAGAAGTAAACATA GTAACAGACTCACAATATGCATTAGGAA TCATTCAAGCACAACCAGATAGAAGTGA ATCAGAGTTAGTCAGTCAAATAATAGAG CAGTTAATAAAAAAGGAAAGGTCTATC TGGCATGGGTACCAGCACACAAAGGAAT TGGAGGAAATGAACAAGTAGATAAATTA GTCAGTGCTGGGATCAGGAAAGTACTA | | | | |
| PR_v1 | 3 | CCTCAGATCACTCTTTGGCAGCGACCCC TCGTCACAATAAAGATAGGGGGGCAACT AAAGGAAGCTCTATTAGATACAGGAGCA GATGATACAGTATTAGAAGAAATGAATT TGCCAGGAAGATGGAAACCAAAAATGAT AGGGGGAATTGGAGGTTTTATCAAAGTA AGACAGTATGATCAGATACCCATAGAAA TATGTGGACATAAAGCTATAGGTACAGT ATTAGTAGGACCTACACCTGTCAACATA ATTGGAAGAAATCTGTTGACTCAGATTG GTTGCACTTTAAATTTT | [1 297] | 10 | PQITLWQRPLVTIKIGGQ LKEALLDTGADDTVLEEM NLPGRWKPKMIGGIGGFI KVRQYDQIPIEICGHKAI GTVLVGPTPVNIIGRNLL TQIGCTLNF | pB27 |
| GAG_V1 | 4 | ATGGGTGCGAGAGCGTCAGTATTAAGTG CGGGGGAATTAGATAAGTGGGAAAAAAT TCGGTTAAGGCCAGGGGGAAAGAAACAA TATAGATTAAAACATATAGTATGGGCAA GCAGGGAGCTAGAACGATTCGCAGTTGA TCCTGGCCTGTTAGAAACATCAGAAGGC TGTAGACAAATACTGGGACAGCTACAAC CGTCCCTTCAGACAGGATCAGAAGAGCT TAGATCATTATATAATACAGTAGCCACC CTCTATTGTGTACATCAAAAGATAGAGG TAAAAGACACCAAGGAACTTTAGAGAAG ATAGAGGAAGAGCAAAACAAAAGTAAGA AAAAAGCACAGCAAGCAGCAGCTGACAC AGGAAACAGCAGCCAGGTCAGCCAAAAT TACCCTATAGTGCAGAACCTACAGGGGC AAATGGTACATCAGGCCATATCACCTAG AACTTTAAATGCATGGGTAAAAGTAGTG GAAGAGAAGGCGTTCAGCCCAGAAGTAA TACCCATGTTTTCAGCATTATCAGAAGG AGCCACCCCACAAGATTTAAACACCATG CTAAACACAGTGGGGGGACACCAAGCAG CCATGCAAATGTTAAAAGAGACCATCAA TGAGGAAGCTGCAGAATGGGATAGATTG CATCCAGTGCATGCAGGGCCTATTGCAC CAGGCCAGATGAGAGAACCAAGGGGAAG TGACATAGCAGGAACTACTAGTACCCTT CAGGAACAAATAGGATGGATGACAAATA ATCCACCTATCCCAGTAGGAGAAATCTA TAAAAGATGGATAATCCTGGGATTAAAT AAAATAGTAAGAATGTATAGTCCTACCA GCATTCTGGACATAAGACAAGGACCAAA GGAACCCTTTAGAGATTATGTAGACCGG TTCTATAAAACTCTAAGAGCCGAGCAAG CTTCACAGGAGGTAAAAAATTGGATGAC AGAAACCTTGTTGGTCCAAAATGCGAAC CCAGATTGTAAGACTATTTTAAAAGCAT TGGGACCAGCAGCTACACTAGAAGAAAT GATGACAGCATGTCAGGGAGTGGGGGGA CCCGGCCATAAAGCAAGAGTTTTGGCTG AAGCAATGAGCCAAGTAACAAATTCAGC TACCATAATGATGCAGAGAGGCAATTTT AGGAACCAAAGAAAAACTGTTAAGTGTT TCAATTGTGGCAAAGAAGGGCACATAGC CAAAAATTGCAGGGCTCCTAGGAAAAAG GGCTGTTGGAAATGTGGAAAGGAAGGAC ACCAAATGAAAGATTGTACTGAGAGACA GGCTAATTTTTTAGGGAAGATCTGGCCT | [1 1503] | 11 | MGARASVLSAGELDKWEK IRLRPGGKKQYRLKHIVW ASRELERFAVDPGLLETS EGCRQILGQLQPSLQTGS EELRSLYNTVATLYCVHQ KIEVKDTKEALEKIEEEQ NHSKKAQQAAADTGNSS QVSQNYPIVQNLQGQMVH QAISPRTLNAWVKVVEEK AFSPEVIPMFSALSEGAT PQDLNTMLNTVGGHQAAM QMLKETINEEAAEWDRLH PVHAGPIAPGQMREPRGS DIAGTTSTLQEQIGWMTN NPPIPVGEIYKRWIILGL NKIVRMYSPTSILDIRQG PKEPFRDYVDRFYKTLRA EQASQEVKNWMTETLLVQ NANPDCKTILKALGPAAT LEEMMTACQGVGGPGHKA RVLAEAMSQVTNSATIMM QRGWFRNQRKTVKCFNCG KEGHIAKNCRAPRKKGCW KCGKEGHQMKDCTERQAN FLGKIWPSHKGRPGNFLQ SRPEPTAPSEESVRFGEE TTTPSQKQEPIDKELYPL ASLRSLFGSDPSSQ | pB6 |

TABLE 1-continued bait name and sequence

| 1: Bait name | 2: Nucleic acid ID No. | 3: Nucleic acid sequence | 4: Nucleic Positions | 5: Amino acid ID No. | 6: Amino acid Sequence | 7: Bait construction |
|---|---|---|---|---|---|---|
| | | TCCCACAAGGGAAGGCCAGGAAATTTTC TTCAGAGCAGACCAGAGCCAACAGCCCC ATCAGAAGAGAGAGCGTCAGGTTTGGAG AAGAGACAACAACTCCCTCTCAGAAGCA GGAGCCGATAGACAAGGAACTGTATCCT TTAGCTTCCCTCAGATCACTCTTTGGCA GCGACCCCTCGTCACAATAA | | | | |
| NC_v1 | 5 | ATGCAGAGAGGCAATTTTAGGAACCAAA GAAAAACTGTTAAGTGTTTCAATTGTGG CAAAGAAGGGCACATAGCCAAAAATTGC AGGGCTCCTAGGAAAAAGGGCTGTTGGA AATGTGGAAAGGAAGGACACCAAATGAA AGATTGTACTGAGAGACAGGCTAAT | [1 165] | 12 | MQRGNFRNQRKTVKCFNC GKEGHIAKNCRAPPKKKG CWKCGKEGHQMKDCTERQ AN | pB6 |
| TM_v1 | 6 | GTTGTACTTTCTATAGTGAATAGAGTTA GGCAGGGATACTCACCATTATCGTTTCA GACCCACCTCCCAGCTCAGAGGGGACCC GACAGGCCCGACGGAATCGAAGAAGAAG GTGGAGAGAGAGACAGAGACAGATCCGG TCCATTAGTGGATGGCTTCTTAGCAATT ATCTGGGTCGACCTACGGAGCCTGTGCC TTTCAGCTACCACCGCTTGAGAGACTTA CTCTTGATTGTAACGAGGATTGTGGAAC TTCTGGGACGCAGGGGGTGGGGAGTCCT CAAATATTGGTGGAATCTCCTCCAGTAT TGGATTCAGGAACTAAAGAATAGTGCTG TTAGCTTGCTCAACGCCACAGCTATAGC AGTAGCTGAGGGAACAGATAGGGTTATA GAAATATTACAAAGAGCTTTTAGAGCTG TTCTTCACATACCTGTAAGAATAAGACA GGGCTTGGAAAGAGCTTTGCTATAA | [565 1038] | 13 | VVLSIVNRVRQGYSPLSF QTHLPAQRGPDRPDGIEE EGGERDRDRSCPLVDGFL AIIWVDLRSLCLFSYHRL RDLLLIVTRIVELLGRRG WGVLKYWWNLLQYWIQEL KNSAVSLLNATAIAVAEG TDRVIEILQRAFRAVLHI PVRIRQGLERALL | pB6 |
| VPU_v1 | 7 | CTGCAATCTTTACAAGTATTAGCAATAG TAGCATTAGTAGTAGCAACAATAATAGC AATAGTTGTGTGGACCATAGTATTCATA GAATATAGGAAAATATTAAGACAAAGGA AAATAGACAGGTTAATTAATAGAATAAC AGAAAGAGCAGAAGACAGTGGCAATGAG AGCGACGGAGATCAGGAAGAATTATCAG CACTTGTGGAAGGGGGCACCTTGCTCC TTGGGATGTTGATGATCTGTAG | [1 246] | 14 | LQSLQVLAIVALVVATII AIVVWTIVFIEYRKILRQ RKIDRLINRITERAEDSG NESDGDQEELSALVERGH LAPWDVDDL | pB27 |

TABLE 2 bait-prey interactions

| 1: Bait name | 2: Bait nucleic acid SEQ ID No. | 3: Bait construction | 4: Prey name | 5: Prey construction |
|---|---|---|---|---|
| IN | 1 | pB27 | prey024555 - Human VBP1 | dT |
| IN | 1 | pB27 | prey024555 - Human VBP1 | RP |
| IN | 1 | pB27 | prey007766 - Human TRN-SR | RP |
| IN | 1 | pB27 | prey024605 - Human RNUT1 | RP |
| IN | 1 | pB27 | prey001626 - Human HBOA | dT |
| IN | 1 | pB27 | prey001626 - Human HBOA | RP |
| IN | 1 | pB27 | prey007151 - Human MCM7 | dT |
| IN | 1 | pB27 | prey024567 - Human EIF3S3 | dT |
| IN | 1 | pB27 | prey024567 - Human EIF3S3 | RP |
| IN | 1 | pB27 | prey000022 - Human PIASY | RP |
| RT_v1 | 2 | pB27 | prey026778 - Human AKAP1 | RP |
| RT_v1 | 2 | pB27 | prey026784 - Human ELAVL1 | RP |
| PR_v1 | 3 | pB27 | prey47239 (CSNK2B) hCSNK2B | Human CEMC7 Random Primed |
| PR_v1 | 3 | pB27 | prey030612 - Human AIM1 | dT |
| PR_v1 | 3 | pB27 | prey030612 - Human AIM1 | RP |
| PR_v1 | 3 | pB27 | prey030679 - Human UBE1 | dT |
| GAG_v1 | 4 | pB6 | prey17662 (BAP1 KIAA0272; prey17663; prey17658) hBAP1 hBAP1 hhucep 6 | Human CEMC7 Random Primed |
| NC_v1 | 5 | pB6 | prey145885 (BAP1 HUCEP 6 HUCEP 13 KIAA0272) hBAP1 | Human CEMC7 Random Primed |
| TM_v1 | 6 | pB6 | prey34104 (ATF6; prey34106) hATF6 | Human CEMC7 Random Primed |

TABLE 2-continued bait-prey interactions

| 1: Bait name | 2: Bait nucleic acid SEQ ID No. | 3: Bait construction | 4: Prey name | 5: Prey construction |
|---|---|---|---|---|
| TM_v1 | 6 | pB6 | hgx33 hsterol regulatory element bindingprotein 2 hSREBF2 | Human CEMC7 Random Primed |
| TM_v1 | 6 | pB6 | prey15532 (SREBF1 SREBP1; prey15533) hSREBF1 hSREBP 1 | Human CEMC7 Random Primed |
| VPU_v1 | 7 | pB27 | prey6634 (PCBP1 HNRPE1 hnRNP E1 HNRPX hnRNP X; prey6635) hPCBP1 hhnRNP E1 | Human CEMC7 dT Primed |
| VPU_v1 | 7 | pB27 | prey6634 (PCBP1 HNRPE1 hnRNP E1 HNRPX hnRNP X; prey6635) hPCBP1 hhnRNP E1 | Human CEMC7 Random Primed |
| VPU_v1 | 7 | pB27 | prey7766 (TRN_SR TRN SR2 MTR10A; prey7769) hTRN_SR hMtr10a | Human CEMC7 Random Primed |

TABLE 3

SIDR

| 1: Bait name | 2: Bait nucleic acid SEQ ID No. | 3: Prey name | 4: SID nucleic acid SEQ ID No. | 5: SID nucleic acid sequence | 6: SID amino acid ID No. | 7: SID amino acid sequence |
|---|---|---|---|---|---|---|
| IN | 1 | prey0245 55 Human VBP1 | 15 | TTGTGGCAAAGGAGAAATGGCCACAGGGAATGGGCGGCGGC TCCACCTGGGGATTCCTGAGGCCGTGTTTGTGGAAGATGTA GATTCCTTCATGAAACAGCCTGGGAATGAGACTGCAGATAC AGTATTAAAGAAGCTGGATGAACAGTACCAGAACTATAAGT TTATGGAACTCAACCTTGCTCAAAAGAAAAGAAGGCTAAAA GGTCAGATTCCTGAAATTAAACAGACTTTGGAAATTCTAAA ATACATGCAGAAGAAAAAGAGTCCACCAACTCAATGGAGA CCAGATTCTTGCTGGCAGATAACCTGTATTGCAAAGCTTCA GTTCCTCCTACCGATAAAGTGTGTCTGTGGTTGGGGGCTAA TGTAATGCTTGAATATGATATTGATGAAGCTCAGGCATTGT TGGAAAAGAATTTATCGACTGCCACAAAGAATCTTGATTCC CTGGAGGAAGACCTTGACTTTCTTCGAGATCAATTTACTAC CACAGAAGTCAATATGGCCAGGGTTTATAATTGGGATGTAA AAAGAAGAAACAAGGATCACTCTACCAAGAACAAAGCATAA | 38 | CGKGEMATGNGRRLHLGIPEAV FVEDVDSFMKQPGNETADTVLK KLDEQYQKYKFMELNLAQKKRR LKGQIPEIKQTLEILKYMQKKK ESTNSMETRFLLADNLYCKASV PPTDKVCLWLGANVMLEYDIDE AQALLEKNLSTATKNLDSLEED LDFLRDQFTTTEVNMARVYNWD VKRRNKDDSTKNKA* |
| IN | 1 | prey0245 55 Human VBP1 | 16 | ATGGCGGCCGTTAAGGACAGTTGTGGCAAAGGAGAAATGGC CACAGGGAATGGGCGGCGGCTCCACCTGGGGATTCCTGAGT CCGTGTTTGTGGAAGATGTAGATTCCTTCATGAAACAGCCT GGGAATGAGACTGCAGATACAGTATTAAAGAAGCTGGATGA ACAGTACCAGAAGTATAAGTTTATGGAACTCAACCTTGCTC AAAAGAAAAGAAGGCTAAAAGGTCAGATTCCTGAAATTAAA CAGACTTTGGAAATTCTAAAATACATGCAGAAAAAAGAGTC CACCAACTCAATGGAGACCAGATTCTTGCTGGCAGATAACC TGTATTGCAAAGCTTCAGTTCCTCCTACCGATAAAGTGTGT CTGTGGTTGGGGGCTAATGTAATGCTTGAATATGATATTGA TGAAGCTCAGGCATTGTTGGAAAAGAATTTATCGACTGCCA CAAAGAATCTTGATTCCCTGGAGGAAGACCTTGACTTTCTT CGAGATCAATTTACTACCACAGAAGTCAATATGGCCAGGGT TTATAATTGGGATGTAAAAAGAAGAAACAAAGGATGACTCT ACCAAGAACAAAGCATAA | 39 | MAAVKDSCGKGEMATGNGRRLH LGIPEAVFVEDVDSFMKGPGNE TADTVLKKLDEGYGKYKFNELN LAGKKRRLKGGIPEIKQTLEIL KYMQKKKESTNSMETRFLLADN LYCKASVPPTDKVCLWLGANVM LEYDIDEAQALLEKNLSTATKN LDSLEEDLDFLRDGFTTTEVNM ARVYNWDVKRRNKDDSTKNKA* |
| IN | 1 | prey0077 66 Human TRN SR | 17 | TTTTGCTGCACAGACCATGAAAATGAAGATTCAGACCTCAT TTTATGAGCTCCCCACAGACTCTCATGCCTCTTTACGGGAC TCATTGCTAACCCATATCCAGAACTTGAAAGACTTGTCACC TGTTATTGTAACGCAGCTGGCTTTAGCAATAGCAGATCTTG CCCTACAGATGCCTTCCTGGAAGGGATGTGTGCAAACACTG GTGGAAAAATACAGCAATGATGTGACTTCTTTGCCTTTTTT GCTGGAGATCCTTACAGTGTTACCTGAAGAAGTACATAGTC GTTCCTTACGAATTGGAGCTAATCGGCGCACAGAAATTATA GAAGATTTGGCCTTCTACTCTAGTACAGTAGTATCTCTATT GATGACCTGTGTAGAAAAAGCAGGAACAGATGAGAAAATGC TTATGAAGGTTTTCGCTGTTTGGGAAGTTGGTTTAACTTG GGAGTTTTGAACAGTAACTTCATGGCTAACAATAAATTACT AGCACTCCTTTTTGAGGTTTTGCAACAGGATAAGACCTCGT CTAACCTACATGAAGCTGCTTCGGACTGTGTATGCTCAGCT CTCTATGCCATTGAGAATGTGGAGACTAACTTGCCATTAGC CATGCAACTTTTTCAGGGAGTGCTGACATTGGAGACTGCCT | 40 | FAAQTMKMKIQTSFYELPTDSH ASLRDSLLTHIQNLKDLSPVIV TQLALAIADLALQMPSWKGCVQ TLVEKYSNDVTSLPFLLEILTV LPEEVHSRSLRIGANRRTEIIE DLAFYSSTVVSLLMTCVEKAGT DEKMLMKVFRCLGSWFNLGVLD SNFMANNKLLALLPEVLQQDKT SSNLHEAASDCVCSALYAIENV ETNLPLAMQLFQGVLTLETAYH MAVAREDLDKVLNYCRIFTELC ETFLEKIVCTPGQGLGDLRTLE LLLICAGH |

TABLE 3-continued

SIDR

| 1: Bait name | 2: Bait nucleic acid SEQ ID No. | 3: Prey name | 4: SID nucleic acid ID No. | 5: SID nucleic acid sequence | 6: SID amino acid ID No. | 7: SID amino acid sequence |
|---|---|---|---|---|---|---|
| | | | | ATCATATGGCCGTGGCACGTGAAGATTTAGACAAAGTTCTG AATTACTGCCGTATTTTCACTGAACTATGTGAAACTTTTCT TGAAAAAATTGTTTGTACTCCAGGCCAAGGTCTTGGGGACC TTCGAACTCTGGAGCTGCTGCTTATCTGTGCAGGCCAT | | |
| IN | 1 | prey0246 05 Human RNUT1 | 18 | GTCCAAGTACAGTTCCTTGGAGCAGAGTGAGCGCCGCCGGA GGTTACTGGAACTGCAGAAATCCAAGCGGCTGGATTATGTG AACCATGCCACAAGACTGGCTGAAGATGACGACAGGGATGG AGAGTGAGGAGGAAAATAAGAAAGATGATGATGAAGAAATG ACATTGACACTGTCAAGAAGTTACCAAAACACTATGCTAAT CAATTGATGCTTTCTGAGTGGTTAATTGACGTTCCTTCAGA TTTGGGGCAGGAATGGATTGTGGTCGTGTGCCCTGTTGGAA AAAGAGCCCTTATCGTGGCCTCCAGGGGTTCTACCAGTGCC TACACCAAGAGTGGCTACTGTGTCAACAGGTTTTCTTCACT TCTGCCAGGAGGCAACAGGCGAAACTCAACACCAAAAGACT TCACCATTCTAGATTGCATTTACAATGAGGTAAACCAGACC TACTACGTTCTGGATGTGATGCTGGCGGGACACCCTTT TTATGATTGCCAGACTGATTTCCGATTCTACTGGATGCATT CAAAGTTACCAGAAGAAGAAGGACTGGGAGAGAAAACCAAG CTTAATCCTTTTAAATTTGTGGGGCTAAAGAACTTCCCTTG CACTCCCGAAAGCCTGTGTGATGTGCTATCTATGGATTTCC CTTTTGAGGTAGATGGACTTCTCTTCTACCACAAACAGACC CATTACAGCCC | 41 | SKYSSLEGSERRRRLLELGKSK RLDYVNHARRLAEDDWTGMESE EENKKDDEEMDIDTVKKLPKHY ANQLMLSEQLIDVPSDLGQEWI VVVCPVGKRALIVASRGSTSAY TKSGYCVNRFSSLLPGGNRRNS TAKDYTILDCIYNEVNQTYYVL DVMCWRGHPFYDCQTDFRFYWM HSKLPEEEGLGEKTKLNPFKFV GLKNFPCTPESLCDVLSMDFPF EVDGLLFYHKQTHYS |
| IN | 1 | prey0016 26 Human HBOA | 19 | GGGAAGCAACATGATTAAAACAATTGCTTTTGGCCGCTATG AGCTTGATACCTGGTATCATTCTCCATATCCTGAAGAATAT GCACGCCTGGGACGTCTCTATATGTGTGAATTCTGTTTAAA ATATATGAAGAGCCAAACGATACTCCGCCGGCACATGGCCA ATGTGTGTGGAAACACCCACCTGGTGATGAGATATATCGC AAAGGTTCAATCTCTGTGTTTGAAGTGGATGGCAAGAAAAA CAAGATCTACTGCCAAAACCTGTGCCTGTTGGCCAAACTTT TTCTGGACCACAAGACATTATATTATGATGTGGAGCCCTCC CTGTTCTATGTTATGACAGAGGCGGACAACACTGGCTGTCA CCTGATTGGATATTTTTCTAAGGAAAAGAATTCATTCCTCA ACTACAACGTCTCCTGTATCCTTACTATGCCTCAGTACATG AGACAGGGCTATGGCAAGATGCTTATTGATTTCAGTTATTT GCTTTCCAAAGTCGAAGAAAAAGTTGGCTCCCCAGAACGTC CACTCTCAGATCTGGGGCTTATAAGCTATCGCAGTTACTGG AAAGAAGTACTTCTCCGCTACCTGCATAATTTTCAAGGCAA AGAGATTTCTATCAAAGAAATCAGTCACGAGACGGCTGTGA ATCCTGTGCACATTGTCAGCACTCTGCAAGCCCTTCAGATG CTCAAATACTGGAAGGGAAAACACCTAGTTTTAAAGAGACA GGACCTGATTGATGAGTGGATAGCCAAAGAGGCCAAAAGGT CCAACTCCAATAAAACCATGGATCCCAGCTGCTTAAAATGG ACCCCTCCCAAGGGCACTTAA | 42 | GSNMIKTIAFGRYELDTWYHSP YPEEYARLGRLYMCEFCLKYMK SQTILRRHMAKCVWKHPPGDEI YRKGSISVFEVDGKKNKIYCQN LCLLAKLFLDHKTLYYDVEPFL FYVMTEADNTGCHLIGYFSKEK NSFLNYNVSCILTMPQYMRQGY GKMLIDFSYLLSKVEEKVGSPE RPLSDLGLISYRSYWKEVLLRY LHNFQGKEISIKEISQETAVNP VDIVSTLQALQMLKYWKGKHLV LKRQDLIDEWIAKEAKRSNSNK TMDPSCLKWTPPKGT* |
| IN | 1 | prey0016 26 Human HBOA | 20 | GATTAAAACAATTGCTTTTGGCCGCTATGAGCTTGATACCT GGTATCATTCTCCATATCCTGAAGAATATGCACGGCTGGGA CGTCTCTATATGTGTGAATTCTGTTTAAATATATGAAGAG CCAAACGATACTCCGCCGGCACATGGCCAATGTGTGTGGA AACACCCACCTGGTGATGAGATATATCGCAAAGGTTCAATC TCTGTGTTTGAAGTGGATGGCAAGAAAAACAAGATCTACTG CCAAAACCTGTGCCTGTTGGCCAAACTTTTTCTGGACCACA AGACATTATATTATGATGTGGAGCCCTTCCTGTTCTATGTT ATGACAGAGGCGGACAACACTGGCTGTCACCTGATTGGATA TTTTTCTAAGGAAAAGAATTCATTCCTCAACTACAACGTCT CCTGTATCCTTACTATGCCTCAGTACATGAGACAGGGCTAT GGCAAGATGCTTATTGATTTCAGTTATTTGCTTTCCAAAGT CGAAGAAAAAGTTGGCTCCCCAGAACGTCCACTCTCAGATC TGGGGCTTATAAGCTATCGCAGTTACTGGAAAGAAGTACTT CTCCGCTACCTGCATAATTTTCAAGGCAAAGAGATTTCTAT CAAAGAAATCAGTCAGGAGACGGCTGTGAATCCTGTGGACA TTGTCAGCACTCTGCAAGCCCTTCAGATGCTCAAATACTGG AAGGGAAAACACCTAGTTTTAAAGGACAGGACCTGATTGA TGAGTGGATAGCCAAAGAGGCCAAAAGGTCCAACTCCAATA AAACCATGGATCCCAGCTGCTTAAAAT | 43 | IKTIAFGRYELDTWYHSPYPEE YARLGRLYMCEFCLKYMKSQTI LRRHMAKCVWKHPPGDEIYRKG SISVFHVDGKKNKIYCQNLCLL AKLFLDHKTLYYDVEPFLFYVM TEADNTGCHLIGYFSKEKNSFL NYNVSCILTMPQYMRQGYGKML IDFSYLLSKVEEKVGSPERPLS DLGLISYRSYWKEVLLRYLHHF QGKEISIKEISQETAVNPVDIV STLQALQMLKYNKGKHLVLKRQ DLIDEWIAKEAKRSNSNKTMDP SCLK |
| IN | 1 | prey0071 51 Human MCM7 | 21 | AGCATACGTGGAGATGAGGCGAGAGGCTTGGGCTAGTAAGG ATGCCACCTATACTTCTGCCCGGACCCTGCTGGCTATCCTG CGCCTTTCCACTGCTCTGGCACGTCTGAGAATGGTGGATGT GGTGGAGAAGGAAGATGTGAATGAAGCCATCAGGCTAATGG AGAGTGTCAAAGGACTCTCTTCTAGGAGACAAGGGGCAGACA | 44 | AYVEMRREAWASKDATYTSART LLAILRLSTALARLRMVDVVEK EDVNEAIRLMEMSKDSLLGDKG QTARTQRPADVIFATVRELVSG GRSVRFSEAEQRCVSRGFTPAQ |

TABLE 3-continued

SIDR

| 1: Bait name | 2: Bait nucleic acid SEQ ID No. | 3: Prey name | 4: SID nucleic acid ID No. | 5: SID nucleic acid sequence | 6: SID amino acid ID No. | 7: SID amino acid sequence |
|---|---|---|---|---|---|---|
| | | | | GCTAGGACTCAGAGACCAGCAGATGTGATATTTGCCACCGT<br>CCGTGAACTGGTCTCAGGGGGCCGAAGTGTCCGGTTCTCTG<br>AGGCAGAGCAGCGCTGTGTATCTCGTGGCTTCACACCCGCC<br>CAGTTCCAGGCGGCTCTGGATGAATATGAGGAGCTCAATGT<br>CTGGCAGGTCAATGCTTCCCGGACACGGATCACTTTTGTCT<br>GA | | FQAALDEYEELNVWQVNASRTR<br>ITFV* |
| IN | 1 | prey0245<br>67<br>Human<br>EIF3S3 | 22 | GGAAGGTACCGGCTCTACTGCCACCTCTTCCAGCTCCACCG<br>CCGGCGCAGCAGGGAAAGGCAAAGGCAAAGGCGGCTCGGGA<br>GATTCAGCCGTGAAGCAAGTGCAGATAGATGGCCTTGTGGT<br>ATTAAAGATAATCAAACATTATCAAGAAGAAGGACAAGGAA<br>CTGAAGTTGTTCAAGGAGTGCTTTTGGGTCTGGTTGTAGAA<br>GATCGGCTTGAAATTACCAACTGTTTCCCTTCCCTCAGCAC<br>ACAGAGGATGATGCTGACTTTGATGAAGTCCAATATCAGAT<br>GGAAATGATGCGGAGCCTTCGCCATGTAAACATTGATCATC<br>TTCACGTGGGCTGGTATCAGTCCACATACTATGGCTCATTC<br>GTTACCCGGGCACTCCTGGACTCTCAGTTTAGTTACCAGCA<br>TGCCATTGAAGAATCTGTCGTTCTCATTTATGATCCCATAA<br>AAACTGCCCAAGGATCTCTCTCACTAAAGGCATACAGACTG<br>ACTCCTAAACTGATGGAAGTTTGTAAAGAAAAGGATTTTTC<br>CCCTGAAGCATTGAAAAAAGCAAATATCACCTTTGAGTACA<br>TGTTTGAAGAAGTGCCGATTGTAATTAAAAATTCACATCTG<br>ATCAATGTCCTAATGTGGGAACTTGAAAAGAAGTCAGCTGT<br>TGCAGATAAACATGAATTGCTCAGCCTTGCCAGCAGCAATC<br>ATTTGGGGAAGAATCTACAGTTGCTGATGGACAGAGTGGAT<br>GAAATGAGCCAAGATATAGTAATACAACACATACATGAGGA<br>ATACTAGTAAACAACAGCAGCAGAAACATCAGTATCAGCAG<br>CGTCGCCAGCAGGAGAATATGCAGCGCCAGAGCCGAGGACA<br>ACCCCCGCTCCCTGAGGAGGACCTGTCCAAACTCTTCAAAC<br>CACCACAGCCGCCTACCAGGATGGACTCGCTGCTCATTGCA<br>GGCCAGATAAACACTTACTGCCAGAACATCAAGGAGTCACT<br>GCCCAAACTTAGGCAAGCTCTTCATGGCCCAGGCTCTTCA<br>AGAATACAACAACTAA | 45 | EGTGSTATSSSSTAGAAGKGKG<br>KGGSGDSAVKQVQIDGLVVLKI<br>IKHYQEEGQGTEVVQGVLLGLV<br>VEDRLEITNCFPFPQHTEDDAD<br>FDEVQYQMEMNRSLRHVNIDHI<br>HVGWYQSTYYGSFVTRALLDSQ<br>FSYQHAIEESVVLIYDPIKTAQ<br>GSLSLKAYRLTPKLMEVCKEKD<br>FSPEALKKANITFEYMFEEVPI<br>VIKNSHLINVLMWELEKKSAVA<br>DKHELLSLASSNHLGKNLQLLM<br>DRVDEMSQDIVKYNTYMRNTSK<br>QQQQKHQYQQRRQQENMQRSR<br>GEPPLPEEDLSKLFKPPQPPAR<br>MDSLLIAGQINTYCQNIKEFTA<br>QNLGKLFMAQALQEYNN* |
| IN | 1 | prey0245<br>67<br>Human<br>EIF3S3 | 23 | CAAGGAAGGTACCGGCTCTACTGCCACCTCTTCCACCTCCA<br>CCGCCGGCGCAGCAGGGAAAGGCAAAGGCAAAGGCGGCTC<br>GGGAGATTCAGCCGTGAAGCAAGTGCAGATAGATGGCCTTGT<br>GGTATTAAAGATAATCAAACATTATCAAGAAGAAGGACAA<br>GAACTGAAGTTGTTCAAGGAGTGCTTTTGGGTCTGGTTGTA<br>GAAGATCGGCTTGAAATTACCAACTGCTTTTCCTTTCCCTC<br>AGCACACAGAGGATGATGCTGACTTTGATGAAGTCCAATAT<br>CAGATGGAAATGATGCGGAGCCTTCGCCATGTAAACATTGA<br>TCATCTTCACGTGGGCTGGTATCAGTCCACATACTATGGCT<br>CATTCGTTACCCGGGCACTCCTGACTCAGTTTAGTACCAGC<br>ATGCCATTGAAGAATCTGTCGTTCTCATTATGATCCCATAA<br>AAACTGCCCAAGGATCTCTCTCACTAAAGGCATACAGACGA<br>CTCCTAAACTGATGAAGTTTGTAAAGAAAAGGATTTTTCCC<br>CTGAAGCATTGAAAAAAGCAAATATCACCTTTGAGTACATG<br>TTTGAAGAAGTGCCGATTGTAATTAAAAATTCACATCTGAT<br>CAATGTCCTAATGTGGGAACTTGAAAAGAAGTCAGCTGTTG<br>CAGATAAACATGAATTGCTCAGCCTTGCCAGCAGCAATCAT<br>TTGGGGAAGAATCTACAGTTGCTGATGGACAGAGTGAATGA<br>AATGAGCCAAGATATAGTTAAATACAACACATACATGAGGA<br>ATACTAGTAAACAACAGCAGCAGAAACATCAGTATCAGCAG<br>CGTCGCCAGCAGGAGAATATGCAGCGCCAGAGCCGAGGAGA<br>ACCCCCGCTCCCTGAGGAGGACCTGTCCAAACTCTTCAAAC | 46 | KEGTGSTATSSSSTAGAAGKGK<br>GKGGSGDSAVKQVQIDGLVVLK<br>IIKHYQEEGQGTEVVQGVLLGL<br>VVEDRLEITNCFPFPQHTEDDA<br>DFDEVQYQMEMMRSLRHVNIDH<br>LHVGWYQSTYYGSFVTRALLDS<br>QFSYQHAIEESVVLIYDPIKTA<br>QGSLSLKAYRLTPKLMEVCKEK<br>DFSPEALKKANITFEYMFEEVP<br>IVIKNSHLINVLMWELEKKSAV<br>ADKHELLSLASSNHLGKNLQLL<br>MDRVDEMSQDIVKYNTYMRNTS<br>KQQQQKHQYQQRRQQENMQRQS<br>RGEPPLPEEDLSKLFK |
| IN | 1 | prey0000<br>22<br>Human<br>PIASY | 24 | ATGGCGGCGGAGCTGGTGGAGGCCAAAAACATGGTGATGAG<br>TTTTCGAGTCTCCGACCTTCAGATGCTCCTGGGTTTCGTGG<br>GCCGGAGTAAGAGTGGACTGAAGCACGAGCTCGTCACCAGG<br>GCCCTCCAGCTGGTGCAGTTTGACTGTAGCCCTGAGCTGTT<br>CAAGAAGATCAAGGAGCTGTACGAGACCCGCTACGCCAAGA<br>AGAACTCGGAGCCTGCCCCACAGCCGCACCGGCCCTGGAC<br>CCCCTGACATGCACTCACCTACGACCGGGCCGGCGCTGT<br>GCCCAGGACTCCGCTGGCAGGCCCCAATATTGACTACCCCG<br>TGCTCTACGGAAAGTACTTAAACGGACTGGGACGGTTGCCC<br>GCCAAGACCCTCAAGCCAGAAGTCCGCCTGGTGAAGCTGCC<br>GTTCTTTAATATGCTGGATGAGCTGCTGAAGCCCACCGAAT<br>TAG | 47 | MAAELVEAKNMVMSFRVSDLQM<br>LLGFVGRSKSGLKHELVTRALQ<br>LVQFDCSPBLFKKIKELYETRY<br>AKKNSEPAPQPHRPLDPLTMHS<br>TYDRAGAVPRTPLAGPNIDYPV<br>LYGKYLNGLGRLPAKTLKPEVR<br>LVKLPFFNMLDELLKPTEL |

TABLE 3-continued

SIDR

| 1: Bait name | 2: Bait nucleic acid SEQ ID No. | 3: Prey name | 4: SID nucleic acid ID No. | 5: SID nucleic acid sequence | 6: SID amino acid ID No. | 7: SID amino acid sequence |
|---|---|---|---|---|---|---|
| RT | 2 | prey0267 Human AKAP1 | 25 | TGTGTGTCACGCCAGTCAGCTCCAAGGGCAGAAGGAAGAGA GCTGTGTCCCAGTTCACCAGAAAACTGTCCTGGGCCCAGAC ACTGCGGAGCCTGCCACAGCAGAGGCAGCTGTTGCCCCGCC GGATGCTGGCCTCCCCTTGCCAGGCCTACCAGCAGAGGGCT CACCACCACCAAAGACCTACGTGAGCTGCCTGAAGAGCCTT CTGTCCAGCCCCACCAAGGACAGTAAGCCAAATATCTCTGC ACACCACATCTCCCTGGCCTCCTGCCTGGCACTGACCACCC CCAGTGAAGAGTTGCCGGACCGGGCAGGCATCCTGGTGGAA GATGCCACCTGTGTCACCTGCATGTCAGACAGCAGCCAAAG TGTCCCTTTGGTGGCTTCTCCAGGACACTGCTCAGATTCTT TCAGCACTTCAGGGCTTAAGACTCTTGCACAGAGACCAGC TCGAGCCCCAGGGACAAGGCCATCACCCCGCCACTGCCAGA AGTACTGTGCCCTTCAGCAATGGGGTGCTGAAGGGGGAGT TGTCAGACTTGGGGCTGAGGATGGATGGACCATGGATGCG GAAGCAGATCATTCAGGAGGTTCTGACAGGAACAGCATGGA TTCCGTGGATAGCTGTTGCAGTCTCAAGAAGACTGAGAGCT TCCAAAATGCCCAGGCAGGCTCCAACCCTAAGAAGGTCGAC CTCATCATCTGGGAGATCGAGGTGCCAAAGCACTTAGTCGG TCGGCTAATTGGCAAGCAGGGCGCTATGTGAGTTTTCTGA AGCAAACATCTGGTGCCAAGATCTACATTTCAAC | 45 | VCQASQLQGQKEESCVPVHQKT VLGPDTAEPATAEAAVAPPDAG LPLPGLPAEGSPPPKTYVSCLK SLLSSPTKDSKPNISAHHISLA SCLALTTPSEELPDRAGILVED ATCVTCMSDSSQSVPLVASPGH CSDSFSTSGLEDSCTETSSSPR DKAITPPLPESTVPFSNGVLKG ELSDLGAEDGWTMDAEADHSGG SDRNSMDSVDSCCSLKKTESFQ NAQAGSNPKKVDLIIWEIEVPK HLVGRLIGKQGRYVSFLKQTSG AXIYIS |
| RT | 2 | prey0267 Human ELAVL1 | 26 | GTTTGGCTTTGTGACCATGACAAACTATGAAGAAGCCGCGA TGGCCATAGCCAGCCTGAACGGCTACCGCCTGGGGGACAAA ATCTTACAGGTTTCCTTCAAAACCAACAAGTCCCACAAAT AA | 49 | FGFVTMTNYEEAAMAIASLNGY RLGDKILQVSFKTNKSHK* |
| PR_v1 | 3 | prey4723 | 27 | ATGAGCAGCTCAGAGGACGTGTCCTGGATTTCCTGGTTCTG TGGGCTCCGTGGCAATGAATTCTTCTGTGAAGTGGATGAAG ACTACATCCAGGACAAATTTAATCTTACTGGACTCAATGAG CAGGTCCCTCACTATCGACAAGCTCTAGACATGATCTTGGA CCTGGAGCCTGATGAAG | 50 | MSSSEEVSWISWFCGLRGNEFF CEVDEDYIQDKFNLTGLNEQVP HYRQALDMILDLEPDE |
| PR | 3 | prey0306 Human AIM1 | 28 | AGAAAGTCACCGGCTTTACATGATGCAGAACCTTGACACAA ATCCAAACAGAGACCCAAACGGCATCTGTGAACAGAGCGTC CTCTTCAAGTCCCTGCACACCAACACTAATGGGAACAGTGA GCCTCTGGTGATGCCGGAAATCAATGACAAAGAGAACAGGG ACGTCACAAATGGTGGCATGTAAGAGATCGAGACTAGAAAA AAGTGCACTTTTCTCAAGCTGTTATCTTTACCACAAG ACAAAATCTTTTCTCCTTCTGTGACATCAGTCAACACTATG ACCACGGCTTTCAGTACTTCTCAGAACGGTTCCCTATCTCA GTCTTCAGTGTCACAGCCCACGACTGAGGGTGCCCCGCCCT GTGGTTTGAACAAAGAACAGTCAAATCTTCTGCCCGACAAG TCCTTAAAGGTCTTCAATTTCAACTCGTCAAGTACATCACA CTCCAGTTTGAAAAGTCCAAGCCACATGGAAAAATACCCGC AAAAAGAGAAAACCAAAGAAGATCTGGATTCACGAAGCAAC CTACACTTGCCAGAAACTAAATTTTCTGAATTGTCAAAACT GAAGAATGATGATATGGAAAAGGCTAATATATTGAAAGTG TTATTAAATCAAACTTGCCAAACTGTGCAAACAGTGACACC GACTTCATGGGTCTTTTCAAATCAAGCCGGTATGACCCAAG CATTTCTTTTTCTGGAATGTCATTATCAGACACAATGACAC TTAGAGGAAGTGTCCAAAATAAACTCAATCCCCGACCTGCA AAGGTAGTGATATATAGTGAACCCGACGTCTCTGAGAAGTG CATTGAAGTTTTCAGTCACATTCAGGATTGCAGTTCTTGGA GCCTCTCTCCAGTGATACTCATAAAAGTEGTTAGAGGATGT TGGATTTGTATGAGCAACCAAATTTTGAAGGGCACTCCAT CCCCTTAGAAGAAGGAGAATTGGAACTCTCTGGTCTCTGGG GTATAGAAGACATTTTGGAAAGGCACGAAGAAGCAGAGTCT GATAAGCCAGTGGTGATTGGTTCCATCAGACATGTGGTCAG GATTACAGGTTAGTCACATTGACTTATTTACTGAACCAGA AGGGTTAGGAATCCTAAGTCCGACTTTGATGATACTGAAGA AATGCAGGGATTTGGTGTAATGCAGAAGACTTGTTCCATGA AAGTACATTGGGGCACGTGGCTGATTTATGAAGAACCTGGA TTTCAGGGTGTTCCTTTCATCCTGGAATTTGTGAATACCC TGACTTGTCCTTCTGGGATACAGAAGAAGCGTACATTGGAT CCATGCCCCCTCTGAAAATGGGTCCCCGTAAAGTTCAATTC CCTACAGATCCAAAGGTAGTTGTTTATGAAAAGCCTTTCTT TGAAGGAAATGTGTGGAACTAGAACAGGATGGTAGTTT TGTCATGCACGGAGGTGAAACAGAAGAGGCGACTGGAGACG ATCATTGCCGTTTACGTCAGTCGGTCTATGAAAGTTCTAA GAGGCATTTGGGTTGCATATGAGAAACCTCGATTTACCGGT CATCAGTATTTGCTAGAAGAAGGAGAATACAGGGACTGGAA ACCCTGGGGAGGTTACAATCGAGAGCTTCAGTCTTTACGAC | 51 | EMSPALHLMQNLDTKSKLRPKR ASAEQSVLFKSLHTNTNGNSEP LVNPEINDKENRDVTHGGIKRS RLEKSALFSSLLBSLPQDKIFS PSVTSVNTMTTAFSTSQNGBLS QSSVSQPTTEGAPPCGLNKEGS NLLPDNSLKVFNFNSSSTSHSS LKSPSHMEKYPQKBKTKEDLDS RSNLHLPETKFSELSKLKNDDM EKANHIESVIKSNLPNCANSDT DFMGLFKSSRYDPSISFSGMSL SDTWTLRGSVQNKLNPRPGKVV IYSEPDVSEKCIEVFSDIQDCS SWSLSPVILIKVVRGCWILYEQ PNFEGHSIPLEEGBLELSGLWG IEDILERHEEAESDKPVVIGSI RHVVQDYRVSHIDLFTEPEGLC ILSSYPDDTEEMQGFGVMQKTC SMKVHWGTWLIYEEPGFQGVPF ILEPGEYPDLSFWDTEEAYIGS MRPLKNGGRKVEFPTDPKVVVY EKPFFEGKCVELETCMCSFVME CGETEEEATGDDHLPFTSVGSMK VLRGIWVAYEKPGFTGHQYLLE EGEYRDWKAWGGYNGELQSLRP ILGDFSNAHMIMYSEKNFGSKG SSIDVLGIVANLKETGYGVKTQ SINVLSGVWVAYENPDFTGEQY ILDKGFYTSFEDWGGKNCKISS VQPICLDSFTGPRRRNQIHLFS EPQFQGHSQSFERTTSQIDDSF STKSCRVSGGSWVVYDGENFTG NQYVLEEGHYPCLSAMGCPPGA TFKSLRFIDVEFSEPTIILFER EDPGKKIELNAETVNLRSLGFN NTQIRSVQVIGGIWVTYEYGSY RGRQFLLSPAEVPNWYEFSGCR QIGSLRPFVQKRIYFRLRNKAT GLFMSTNGNLEDLKLLRIQVME DVGADDQIWIYQEGCIKCRIAE |

TABLE 3-continued

SIDR

| 1: Bait name | 2: Bait nucleic acid SEQ ID No. | 3: Prey name | 4: SID nucleic acid ID No. | 5: SID nucleic acid sequence | 6: SID amino acid ID No. | 7: SID amino acid sequence |
|---|---|---|---|---|---|---|
| | | | | CTATATTAGGTGATTTTTCAAATGCTCACATGATAATGTAC AGTGAAAAAAACTTTGGATCCAAAGGTTCCAGTATTGATGT ATTGGGAATTGTTGCTAATTTAAAGGAGACTGGATATGGAG TGAAGACACAGTCTATTAATGTACTGAGTGGAGTATGGGTA CCCTATCATCCTGACTTCACAGGAGAACAGTATATACTGCA TAAAGGATTTTATACCAGTTTGAGGACTGGGGAGGCAAAAA TTGTAAGATCTCTTCTCTTCAACCTATATGTTGCATTTTTC ACTCGCCCAAGCAGACGAAATCAGATTCACTTGTTTTCAGA ACCACAGTTTCAAGCTCACAGTCAAAGTTTTGAAGAAACAA CAAGTCAAATTGATGATTCATTTTCTACCAAGTCTTGCAGA GTTTCAGGAGGCAGCTGGGTCTATATGATGGAGAATTTCAC TGGTAATCAATACGTGTTGGAAGAAGGCCATTATCCTTGTC TGTCTGCAATGGGATGCCCGCCTGGAGCAACTTTCAACTCT CTTCGTTTTATAGATGTTGAATTTTCTGAACCAACAATTAT TCTCTTGAAACAGAAGACTTCAAAGAAAAACATTGAACTT AATGCAGAAACTGTCAATCCGATCCCTGGGATTCAACACAC AAATACGCTCGTTCAGGTTATTGGTGGCATATGGGTTACT TATGAATATGGCAGTTACAGAGGGCGACAGTTCCTATTGTC ACCTGCAGAAGTACCTAATTGGTATGAATTCAGTGGCTGTC GCCAAATAGGTTCTCTACGACCTTTTGTTCAGAAGCGAATT TATTTCAGACTTCGAAACAAAGCAACAGGGTTATTCATGTC AACCAATGGAAACTTAGAGGATCTGAAGCTTCTGAGGATAC AGGTCATGGAGGATGTCGGGGCCCGATGATCAGATTTGGAT CTATCAAGAAGGATGTATCAAATGCAGGATAGCAGAAGACT GCTGCCTGACGATTGTGGGCAGCCTGGTAACATCTGGCTCC AAGCTAGGCCTGGCCCTGGACCAGAATGCTGACAGCCAGTT CTGGAGCTTGAAGTCCGATGGCAGGATTTACAGCAAGTTGA AGCCAAATTTAGTTTTAGACATTAAAGGGGGCACACAGTAT GATCAAAATACACATTATCCTCAACACTGTCAGCAAGAGAAG TTTACACAAGTGTGGGAAGCCATGGTCCTATATACCTGA | | DCCLTIVGSLVTSGSKLGLALD QNADSQFWSLKSDGRIYSKLKP NLVLDIKGGTQYDQNHIILNTV SKEKFTQVWEAMVLYT* |
| PR_v1 | 3 | prey3061 | 29 | CAAACTCAGACCCAAACGTGCATCTCCTGAACGAGCGTCC TCTTCAAGTCCCGCACACCAACACTAATGGGACAGTGAGCC TCTGGTGATGCCGGAAATCAATGACAAAGAGAACAGGGACG TCACAAATGGTCGCATTAAGAGATCGAGACTAGAAAAAAGT GCACTTTCTCAACCTTGTTATCTTCTACCACAAGACAAAAT CTTTTCTCCTTCTGTGACATCAGTCAACACTATGACCACCG CTTCAGTACTTCTCAGAACCGTTCCCTATCTCAGTCTTCAG TGTCACAGCCCACGACTGACCGTCCCCCGCCCTGTGGTTTG AACAAAGAACAGTCAAATCTTCTGCCCGACAACTCCTTAAA GGTCTTCAATTTCAACTCGTCAAGTACATCACACTCCAGTT TGAAAAGTCCAAGCCACATGGAAAAATACCCGCAAAAAGAG AAAACCAAAGAAGATCTGGATTCACGAAGCAACCTACACTT GCCAGAAACTAAATTTTCTGAATTGTCAAAACTGAAGAATG ATGATATGGAAAAGGCTAATCATATTGAAAGTGTTATTAAA TCAAACGCCAAACTGGCAAACAGGACACCGACTTCATGGGT CTTTTCAAATCAAGCCGGTATGACCCAAGCATTTCTTTTTC TGGAATGTCATTATCAG | 52 | KLRPKRASAEQSVLFKSLHTNT NGNSEPLVMPEINDKENRDVTN GGIKRSRLEKSALFSSLLSSLP QDKIFSPSVTSVNTMTTAFSTS QNGSLSQSSVSQPTTEGAPPCG LNKEQSNLLPDNSLKVFNFNSS STSHSSLKSPSHMEKYPQKEKT KEDLDSRSNLHLPETKFSELSK LKNDDMEKANHIESVIKSNLPN CANSDTDFMGLFKSSRYDPSIS FSGMSLS |
| PR | 3 | prey0306 79 Human UEE1 | 30 | CTTGGCCCTGCCTTTCTTTGGTTTCTCTGAACCCCTTGCCG CACCACGTCACCAGTACTATAACCAAGAGTGACATTGTGG GATCGCTTTGAGCTACAAGGGCTGCAGCCTAATGGTGAGGA GATGACCCTCAAACAGTTCCTCGACTATTTTAAGACAGAGC ACAAATTAGAGATCACCATGCTGTCCCAGGGCGTGTCCATG CTCTATTCCTTCTTCATGCCAGCTGCCAAGCTCAAGGAACG GTTGGATCAGCCGATGACAGGTGCTTGAGCTGTGCTGTAAC GACGAGAGCGGCGAGGATGTCGAGGTTCCCTATGTCCGATA CACCATCCGCTGA | 53 | LALPFFGFSEPLAAPRHQYYNQ EWTLWDRFEVQGLQPNGEEMTL KQFLDYFKTEHKLEITMLSQGV SMLYSFFMPAAKLKERLDQPMT EIVSRVSKRKLGRHVRALVLEL CCNDESGEDVEVPYVRYTIR* |
| GAG_v1 | 4 | prey1766 | 31 | GCTGACAGAGGGTGGGAAGGGTTCCTCGCCCTCCATCAGAC CAATCCAAGGCAGCCAGGGGTCCAGCAGCCCAGTGGAGAAG GAGGTCGTGGAAGCCACGGACAGCAGAGAGAAGACGGGGAT GGTGGTCCTGGCGAGCCCTTGAGTGGGAGAAATACTACC CCAAGGAGCTGCTGGCACTGCTGAAGTGTGTGGAGGCTGAG ATTGCAAACTATGAGGCCTGCCTCAAGGAGGAGTAGAGAA GAGGAAGAAGTTCAAGATTGATGACCAGAGAAGGACCCACA ACTACGATGAGTTCATCTGCACCTTTATCTCCATGCTGCT CACGCAAGGCATGCTGGCCAACGTAGTGGAGCAGAACATCTC CGTGCGGCGGCGCAAGGGGTCAGCATCGGCCGGCTCCACA AGCAGCGGAAGCCTGACCGGCGGAAACGCTCTCGCCCCTAC AAGGCCAAGCGCCAGTGA | 54 | LTEGGKGSSPSIRPIQGSQGSS SPVEKEVVEATDSREKTGMVRP GEPLSGEKYSPKELLALLKCVE AEIANYEACLKEEVEKRKKFKI DDQRRTHNYDEFICTFISMLAQ EGMLANVLEGNISVRRRQGVSI GRLHKGRKPDRRKRSRPYKAKR Q |

TABLE 3-continued

SIDR

| 1: Bait name | 2: Bait nucleic acid SEQ ID No. | 3: Prey name | 4: SID nucleic acid ID No. | 5: SID nucleic acid sequence | 6: SID amino acid ID No. | 7: SID amino acid sequence |
|---|---|---|---|---|---|---|
| NC_v1 | 5 | prey1458 | 32 | GATTGATGACCAGAGAAGGACCCACAACTACGATGAGTTCA TCTGCACCTTTATCTCCATGCTGGCTCAGGAAGGCATGCTG GCCAACCTAGTGGAGCAGAACATCTCCGTGCGGCGGCGCCA AGGGGTCAGCATCGGCCGGCTCCACAAGCAGCGGAAGCCTG ACCGGCGGAACGCTCTCGCCCCTACAAGGCCAAGCGCCAGT GA | 55 | IDDQRRTHNYDEFICTFISMLA QEGMLANLVEQNISVRRRQGVS IGRLHKQRKPDRRKRSRPYKAK RQ |
| TM_v1 | 6 | prey3410 | 33 | GCTAGGGTTAGAGGCGAGATTAAAGGCTGCCCTCTCAGAAA ACGAGCAACTGAAGAAAGAAAATGGAACACTGAAGCGGCAG CTGGATGAAGTTGTGTCAGAGAACCAGAGGCTTAAAGTCCC TAGTCCAAAGCGAAGAGTTGTCTGTGTGATGATAGTATTGG CATTTATAATACTGAACTATGGACCTATGAGCATGTTGGAA CAGGATTCCAGGAGAATGAACCCAGTGTGGGACCTGCAAA TCAAAGGAGGCACCTTCTAGGATTTTCTGCTAAAGAGGCAC AGGACACATCAGATGGTATTATCCAGAAAAACAGCTACAGA TATGATCATTCTGTTTCAAATGACAAAGCCCTGATGGTGCT AACTGAAGAACCATTGCTT | 56 | LGLEARLKAALSENEQLKKENG TLKRQLDEVVSENQRLKVPSPK RRVVCVMIVLAFIILNYGPMSM LEQDSRRMNPSVGPANQRRHLL GFSAKEAQDTSDGIIQKNSYRY DHSVSNDKALMVLTEEPLL |
| TM_v1 | 6 | hgx33 | 34 | AATGCCTGTAATGATGGGCAAGAGAAAGTGCCCATTAAGC AGGTACCTGGGGGAGTCAAGCAGCTTGAGCCCCCCAAAGAA GGAGAAAGGCGGACAACCCATAATATCATTGAGAAACGATA TCGCTCCTCCATCAATGACAAAATCATCGAATTGAAAGACC TGGTCATGGGGACAGACGCCAAGATGCACAAGTCTGGCGTT CTGAGGAAGGCCATTGATTACATCAAATACTTGCAGCAGGT CAATCATAAACTGCGCCAGGAGAACATGGTGCTGAAGCTGG CAAATCAAAAGAACAAGCTTCTAAAGCGATCGACCTAGGC AGTCTGGTGGACAATGAGGTGGACCTGAAGATCGAGGACTT TAATCACAATGTCCTTCTGATGTCCCCCCCAGCCTCTGACT CAGGGGTCCCAGGCTGGCTTCTCTCCCTACTCCATTGACTCT GAGCCAGGAAGCCCTCTATTGGATGATGCAAAGGTCAAAGA TGAGCCAGACTCTCCTCCTGTGGCGCTGGGCATGGTAGACC GCTCACGCATTCTTCGGTGTGTCCTCACCTTCCTGTGCCTC TCCTTTAAC | 57 | MPVMMGQEKVPIKQVPGGVKQL EPPKEGERRTTHNIIEKRYRSS INDKIIELKDLVMGTDAKMHKS GVLRKAIDYIKYLQQVNHKLRQ ENMVLKLANQKNKLLKGIDLGS LVDNEVDLKIEDFNQNVLLMSP PASDSGSQAGFSPYSIDSEPGS PLLDDAKVKDEPDSPPVALGMV DRSRILLCVLTFLCLSFN |
| VPU_v1 | 7 | prey6634 | 35 | CCTGAGGCTGGTGGTGCCGGCCACCCAGTGCGGCTCCCTGA TTGGGAAAGGCGGGTGTAAGATCAAAGAGATCCGCAGAGT ACGGGGCGCAGGTCCAGGTGGCGGGGGATATGCTGCCCAA CTCCACCGAGCGGGCCATCACCATCGCTGGCGTGCCGCAGT CTGTCACCGAGTGTGTCAAGCAGATTTGCCTGGTCATGCTG GAGACGCTCTCCCAGTCTCCGCAAGGGAGAGTCATGACCAT TCCGTACCAGCCCATGCCGGCCAGCTCCCCAGTCATCTGCG CGGGCGGCCAAGATCGGTGCAGCGACGCTGTGGGCTACCCC CATGCCACCCATGACCTGGAGGGACCACCTCTAGATGCCTA CTCGATTCAAGGACAACACACCTTTCTCCGCTCGATCTTG CCAAGCTGAACCAGGTGGCAAGACAACAGTCTCACTTTGCC ATGATGCACGGCGGGACCCGATTCGCCGGAATTGACTCCAG CTCTCCCAGAGGTGAAAGGCTATTGGGCAAGTTTGGATGCAT CTACTCAAACCACCCATGAACTCACCATCCAAATAACTTAA TTGGCTGCATAATCGGGCGCCAAGGCGCCAACATTAATGAG ATCCGCCAGATGTCCGGGGCCCAGATCAAAATGCCAACCCA GTGGAAGGCTCCTCTGGTAGGCAGGTTACTATCACTGGCTC TGCTGCCAGTATTAGTCTGGCCCAGTATCTAATCAATGCCA GGCTTTCCTCTGAGAAGGGCATGGGGTGCAGCTAG | 58 | LRLVVPATQCGSLIGKGGCKIK EIRESTGAQVQVAGDMLPNSTE RAITIAGVPQSVTECVKQICLV MLETLSQSPQGRVMTIPYQMP ASSPVICAGGQDRCSDAVGYPH ATHDLEGPPLDAYSIQGQHTIS PLDLAKLNQVARQQSHFAMMHG GTGFAGIDSSSPEVKGYWASLD ASTQTTHELTIPNNLIGCIIGR QGANINEIRQMSGAQIKIANPV EGSSGRQVTITGSAASISLAQY LINARLSSEKGMGCS |
| VPU_v1 | 7 | prey6634 | 36 | GGGGGATATGCTGCCCAACTCCACCGAGCGGGCCATCACCA TCGCTGGCGTGCCGCAGTCTGTCACCGAGTGTGTCAAGCAG ATTTGCCTGGTCATGCTGGAGACGCTCTCCCAGTCTCCGCA AGGGAGAGTCATGACCATTCC | 59 | GDMLPNSTERAITIAGVPQSVT ECVKQICLVMLETLSQSPQGRV MTI |
| VPU_v1 | 7 | prey7766 | 37 | CGCCTTGGCTCGACACTGCCAGCTGGAACCAGACCATGAGG GGGTTCCTGAGGAGACTGATGACTTTGGGGAGTTTCGCATG AGGGTATCAGACCTGGTAAAGGACTTGATTTTCTTGATAGG GTCTATGGAGTGTTTTGCTCAGTTATATTCTACTCTGAAAG AAGGCAACCCACCCTGGGAGGTGACAGAAGCGGTTCTCTTT ATCATGGCTGCTATAGCAAAGAGTGTTGATCCGGAAACAA TCCAACACTTGTGGAAGTCCTAGAAGGAGTTGTCCGCCTCC CGGAGACCGTACATACGGC | 60 | ALARHCQLEPDHEGVPEETDDF GEFRMRVSDLVKDLIFLIGSME CFAQLYSTLKEGNPPWEVTEAV LFIMAAIAKSVDPENNPTLVEV LEGVVRLPETVHT |

REFERENCES

Brennan, C. M. and J. A. Steitz (2001). "HuR and mRNA stability." *Cell Mol Life Sci* 58(2): 266-77.

Brown, M. S., J. Ye, et al. (2000). "Regulated intramembrane proteolysis: a control mechanism conserved from bacteria to humans." *Cell* 100(4): 391-8.

Bukrinskaya, A., B. Brichacek, et al. (1998). "Establishment of a functional human immunodeficiency virus type 1 (HIV-1) reverse transcription complex involves the cytoskeleton." *J Exp Med* 188(11): 2113-25.

Caron, M., M. Auclair, et al. (2001). "The HIV protease inhibitor indinavir impairs sterol regulatory element-binding protein-1 intranuclear localization, inhibits preadipocyte differentiation, and induces insulin resistance." *Diabetes* 50(6): 1378-88.

Cherepanov, P., G. Maertens, et al. (2002). "HIV-1 integrase forms stable tetramers and associates with LEDGF/p75 protein in human cells." *J Biol Chem* 28: 28.

Diaz, E. and S. R. Pfeffer (1998). "TIP47: a cargo selection device for mannose 6-phosphate receptor trafficking." *Cell* 93(3): 433-43.

Elbashir, S. M., J. Harborth, et al. (2001). "Duplexes of 21-nucleotide RNAs mediate RNA interference in cultured mammalian cells." *Nature* 411(6836): 494-8.

Freed, E. O. and M. A. Martin (1994). "HIV-1 infection of non-dividing cells." *Nature* 369(6476): 107-8.

Fujita, M., T. Kiyono, et al. (1996). "hCDC47, a human member of the MCM family. Dissociation of the nucleus-bound form during S phase." *J Biol Chem* 271(8): 4349-54.

Garrus, J. E., U. K. von Schwedler, et al. (2001). "Tsg101 and the vacuolar protein sorting pathway are essential for HIV-1 budding." *Cell* 107(1): 55-65.

Ge, H., Y. Si, et al. (1998). "Isolation of cDNAs encoding novel transcription coactivators p52 and p75 reveals an alternate regulatory mechanism of transcriptional activation." *Embo J* 17(22): 6723-9.

Ge, H., Y. Si, et al. (1998). "A novel transcriptional coactivator, p52, functionally interacts with the essential splicing factor ASF/SF2." *Mol Cell* 2(6): 751-9.

Gong, L. and E. T. Yeh (1999). "Identification of the activating and conjugating enzymes of the NEDD8 conjugation pathway." *J Biol Chem* 274(17): 12036-42.

Graf, M., A. Bojak, et al. (2000). "Concerted action of multiple cis-acting sequences is required for Rev dependence of late human immunodeficiency virus type 1 gene expression." *J Virol* 74(22): 10822-6.

Greene, W. C. and B. M. Peterlin (2002). "Charting HIV's remarkable voyage through the cell: Basic science as a passport to future therapy." *Nat Med* 8(7): 673-80.

Haneda, E., T. Furuya, et al. (2000). "Biochemical characterization of casein kinase II as a protein kinase responsible for stimulation of HIV-1 protease in vitro." *Biochem Biophys Res Commun* 275(2): 434-9.

Hartl, F. U. and M. Hayer-Hartl (2002). "Molecular chaperones in the cytosol: from nascent chain to folded protein." *Science* 295(5561): 1852-8.

Haze, K., H. Yoshida, et al. (1999). "Mammalian transcription factor ATF6 is synthesized as a transmembrane protein and activated by proteolysis in response to endoplasmic reticulum stress." *Mol Biol Cell* 10(11): 3787-99.

Herberg, F. W., A. Maleszka, et al. (2000). "Analysis of A-kinase anchoring protein (AKAP) interaction with protein kinase A (PKA) regulatory subunits: PKA isoform specificity in AKAP binding." *J Mol Biol* 298(2): 329-39.

Hoppe, T., M. Rape, et al. (2001). "Membrane-bound transcription factors: regulated release by RIP or RUP." *Curr Opin Cell Biol* 13(3): 344-8.

Horton, J. D., J. L. Goldstein, et al. (2002). "SREBPs: activators of the complete program of cholesterol and fatty acid synthesis in the liver." *J Clin Invest* 109(9): 1125-31.

Huber, J., U. Cronshagen, et al. (1998). "Snurportin1, an m3G-cap-specific nuclear import receptor with a novel domain structure." *Embo J* 17(14): 4114-26.

Lizuka, M. and B. Stillman (1999). "Histone acetyltransferase HBO1 interacts with the ORC1 subunit of the human initiator protein." *J Biol Chem* 274(33): 23027-34.

Jensen, D. E., M. Proctor, et al. (1998). "BAP1: a novel ubiquitin hydrolase which binds to the BRCA1 RING finger and enhances BRCA1-mediated cell growth suppression." *Oncogene* 16(9): 1097-112.

Kalpana, G. V., S. Marmon, et al. (1994). "Binding and stimulation of HIV-1 integrase by a human homolog of yeast transcription factor SNF5." *Science* 266(5193): 2002-6.

Kataoka, N., J. L. Bachorik, et al. (1999). "Transportin-SR, a nuclear import receptor for SR proteins." *J Cell Biol* 145 (6): 1145-52.

Leffers, H., K. Dejgaard, et al. (1995). "Characterisation of two major cellular poly(rC)-binding human proteins, each containing three K-homologous (KH) domains." *Eur J Biochem* 230(2): 447-53.

Margottin, F., S. P. Bour, et al. (1998). "A novel human WD protein, h-beta TrCp, that interacts with HIV-1 Vpu connects CD4 to the ER degradation pathway through an F-box motif." *Mol Cell* 1(4): 565-74.

Nair, V. (2002). "HIV integrase as a target for antiviral chemotherapy." *Rev Med Virol* 12(3): 179-93.

Olsen, H. S., A. W. Cochrane, et al. (1992). "Interaction of cellular factors with intragenic cis-acting repressive sequences within the HIV genome." *Virology* 191(2): 709-15.

Paraskeva, E., E. Izaurralde, et al. (1999). "CRM1-mediated recycling of snurportin 1 to the cytoplasm." *J Cell Biol* 145(2): 255-64.

Ratner, L., W. Haseltine, et al. (1985). "Complete nucleotide sequence of the AIDS virus, HTLV-III." *Nature* 313(6000): 277-84.

Ray, M. E., G. Wistow, et al. (1997). "AIM1, a novel non-lens member of the betagamma-crystallin superfamily, is associated with the control of tumorigenicity in human malignant melanoma." *Proc Natl Acad Sci USA* 94(7): 3229-34

Sachdev, S., L. Bruhn, et al. (2001). "PIASy, a nuclear matrix-associated SUMO E3 ligase, represses LEF1 activity by sequestration into nuclear bodies." *Genes Dev* 15(23): 3088-103.

Schwartz, S., B. K. Felber, et al. (1992). "Distinct RNA sequences in the gag region of human immunodeficiency virus type 1 decrease RNA stability and inhibit expression in the absence of Rev protein." *J Virol* 66(1): 150-9.

Singh, D. P., N. Fatma, et al. (2001). "LEDGF binds to heat shock and stress-related element to activate the expression of stress-related genes." *Biochem Biophys Res Commun* 283(4): 943-55.

Singh, D. P., A. Kimura, et al. (2000). "Lens epithelium-derived growth factor (LEDGF/p75) and p52 are derived from a single gene by alternative splicing." *Gene* 242(1-2): 265-73.

Trendelenburg, G., M. Hummel, et al. (1996). "Molecular characterization of AKAP149, a novel A kinase anchor protein with a KH domain." *Biochem Biophys Res Commun* 225(1): 313-9.

Turelli, P., V. Doucas, et al. (2001). "Cytoplasmic recruitment of INN and PML on incoming HIV preintegration complexes: interference with early steps of viral replication." *Mol Cell* 7(6): 1245-54.

Vainberg, I. E., S. A. Lewis, et al. (1998). "Prefoldin, a chaperone that delivers unfolded proteins to cytosolic chaperonin." *Cell* 93(5): 863-73.

Ye, J., R. B. Rawson, et al. (2000). "ER stress induces cleavage of membrane-bound ATF6 by the same proteases that process SREBPs." *Mol Cell* 6(6): 1355-64.

---

What is claimed is:

1. An isolated and purified HIV integrase/p75 isoform complex, wherein the HIV integrase has a selected interacting domain having a sequence designated as SEQ ID NO.: 130, and the p75 isoform has a selected interacting domain comprising amino acids 341-507 thereof.

* * * * *

UNITED STATES PATENT AND TRADEMARK OFFICE
CERTIFICATE OF CORRECTION

PATENT NO. : 7,763,254 B2  Page 1 of 1
APPLICATION NO. : 10/853807
DATED : July 27, 2010
INVENTOR(S) : Pierre Legrain et al.

It is certified that error appears in the above-identified patent and that said Letters Patent is hereby corrected as shown below:

Column 183, line 20, after "isoform" insert --of a LEDGF protein--.

Column 184, line 20, delete "thereof" and insert therefor --of the LEDGF protein--.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,763,254 B2
APPLICATION NO. : 10/853807
DATED : July 27, 2010
INVENTOR(S) : Pierre Legrain et al.

It is certified that error appears in the above-identified patent and that said Letters Patent is hereby corrected as shown below:

Column 3, line 10, "leukaemia)" should read --leukemia)--.
Column 6, line 61, "kind" should read --kinds--.
Column 30, line 44, "Strand)" should read --Strand) The Following siRNAs were obtained from GENSET:--.
Column 34, line 38, "24 h" should read --24h--.

Signed and Sealed this
Eighteenth Day of October, 2011

David J. Kappos
*Director of the United States Patent and Trademark Office*

SEQUENCE LISTING

<160> NUMBER OF SEQ ID NOS: 162

<210> SEQ ID NO 1
<211> LENGTH: 860
<212> TYPE: DNA
<213> ORGANISM: Human immunodeficiency virus

<400> SEQUENCE: 1

```
atggaataga taaggcccaa gaagaacatg agaaatatca cagtaattgg agagcaatgg      60
ctagtgattt taacctgcca cctgtagtag caaaagaaat agtagccagc tgtgataaat     120
gtcagctaaa aggagaagcc atgcatggac aagtagactg tagtccagga atatggcaac     180
tagattgtac acatttagaa ggaaaagtta tcctggtagc agttcatgta gccagtggat     240
atatagaagc agaagttatt ccagcagaga cagggcagga aacagcatac tttctcttaa     300
aattagcagg aagatggcca gtaacaacaa tacatacaga caatggcagc aatttcacca     360
gtgctacagt taaagccgcc tgttggtggg cagggatcaa gcaggaattt ggcattccct     420
acaatcccca aagtcaagga gtagtagaat ctatgaataa agaattaaag aaaattatag     480
gacaggtaag agatcaggct gaacatctta agacagcagt acaaatggca gtattcatcc     540
acaattttaa aagaaaaggg gggattgggg ggtacagtgc aggggaaaga atagtagaca     600
taatagcaac agacatacaa actaaagaac tacagaaaca aattacaaaa attcaaaatt     660
ttcgggttta ttacagggac agcagagatc cactttggaa aggaccagca aagctcctct     720
ggaaaggtga aggggcagta gtaatacaag ataatagtga cataaaagta gtgccaagaa     780
gaaaagcaaa gatcattagg gattatggaa aacagatggc aggtgatgat tgtgtggcag     840
gtagacagga tgaggattag                                                   860
```

<210> SEQ ID NO 2
<211> LENGTH: 1680
<212> TYPE: DNA
<213> ORGANISM: Human immunodeficiency virus

<400> SEQUENCE: 2

```
cccattagtc ctattgaaac tgtaccagta aaattaaagc caggaatgga tggcccaaaa      60
gttaaacaat ggccattgac agaagaaaaa ataaaagcat tagtagaaat ttgtacagaa     120
atggaaaagg aagggaaaat ttcaaaaatt gggcctgaaa acccatacaa tactccagta     180
tttgccataa agaaaaaaga cagtactaaa tggagaaaat tagtagattt cagagaactt     240
aataagagaa ctcaagactt ctgggaagtt caattaggaa taccacatcc cgcagggtta     300
aaaaagaaaa aatcagtaac agtactggat gtgggtgatg catattttc agttccctta     360 catgaagact tcaggaagta tactgcattt accataccta gtataaacaa tgagacacca     420
```

```
gggactagat atcagtacaa tgtgcttcca cagggatgga aagggtcacc agcaatattc    480
caaagtagca tgacaacaat cttagagcct tttagaaaac aaaatccaga cctagttatc    540
tatcagtaca tggatgattt gtacgtagga tctgacttag aataggcca gcatagaaca    600 aaaatagagg aactgagaca acatctgttg aggtgggat ttaccacacc agacaaaaaa    660
catcagaaag aacctccatt cctttggatg ggttatgaac tccatcctga taaatggaca    720
gtacagccta tagtgctgcc agaaaaagat agctggactg tcaatgacat acagaagtta    780
gtgggaaaat tgaattgggc aagtcagatt tatgcaggga ttaaagtaag gcaattatgt    840
aaactcctta ggggaaccaa agcactaaca gaagtaatac cactaacaga agaagcagaa    900
ctagaactgg cagaaaacag ggaaattcta aagaaccag tacatggagt gtattatgac    960
ccatcaaaag acttgatagc agaaatacag aagcagggc aaggccaatg gacatatcaa   1020
atttatcaag agccatttaa aaatctgaaa acaggaaaat atgcaagaac gagggggtgcc   1080 cacactaatg atgtaaaaca attaacagag gcagtacaaa aaatagccac agaaagcata   1140
gtaatatggg gaaagactcc taaatttaaa ctacccatac aaaaagaaac atgggaaaca   1200
tggtggacag aatattggca agccacctgg attcctgagt gggagtttgt caataccct   1260 cccttagtga aattatggta ccagttagag aaagaaccca ataggagc agaaactttc   1320 tatgtagatg gggcagctaa cagggagact aaattaggaa aagcaggata tgttactaac   1380
aagggaagac aaaaggttgt ctccctaact gacacaacaa atcagaagac tgagttacaa   1440
gcaatttatc tagcttgca ggattcggga ttagaagtaa acatagtaac agactcacaa   1500
tatgcattag gaatcattca agcacaacca gatagaagtg aatcagagtt agtcagtcaa   1560
ataatagagc agttaataaa aaaggaaaag gtctatctgg catgggtacc agcacacaaa   1620
ggaattggag gaaatgaaca agtagataaa ttagtcagtg ctgggatcag gaaagtacta   1680

<210> SEQ ID NO 3
<211> LENGTH: 297
<212> TYPE: DNA
<213> ORGANISM: Human immunodeficiency virus

<400> SEQUENCE: 3
cctcagatca ctctttggca gcgacccctc gtcacaataa agataggggg gcaactaaag     60
gaagctctat tagatacagg agcagatgat acagtattag aagaaatgaa tttgccagga    120
agatggaaac caaaaatgat agggggaatt ggaggttta tcaaagtaag acagtatgat    180
cagataccca tagaaatatg tggacataaa gctataggta cagtattagt aggacctaca    240
cctgtcaaca taattggaag aaatctgttg actcagattg gttgcacttt aaatttt      297

<210> SEQ ID NO 4
<211> LENGTH: 1503
<212> TYPE: DNA
<213> ORGANISM: Human immunodeficiency virus

<400> SEQUENCE: 4
atgggtgcga gagcgtcagt attaagtgcg ggggaattag ataagtggga aaaaattcgg     60
ttaaggccag ggggaaagaa acaatataga ttaaaacata tagtatgggc aagcagggag    120
ctagaacgat tcgcagttga tcctggcctg ttagaaacat cagaaggctg tagacaaata    180
ctgggacagc tacaaccgtc ccttcagaca ggatcagaag agcttagatc attatataat    240
acagtagcca ccctctattg tgtacatcaa aagatagagg taaaagacac caaggaagct    300
```

-continued

```
ttagagaaga tagaggaaga gcaaaacaaa agtaagaaaa aagcacagca agcagcagct    360
gacacaggaa acagcagcca ggtcagccaa aattacccta tagtgcagaa cctacagggg    420
caaatggtac atcaggccat atcacctaga actttaaatg catgggtaaa agtagtggaa    480
gagaaggcgt tcagcccaga agtaataccc atgttttcag cattatcaga aggagccacc    540
ccacaagatt taaacaccat gctaaacaca gtggggggac accaagcagc catgcaaatg    600
ttaaaagaga ccatcaatga ggaagctgca gaatgggata gattgcatcc agtgcatgca    660
gggcctattg caccaggcca gatgagagaa ccaaggggaa gtgacatagc aggaactact    720
agtacccttc aggaacaaat aggatggatg acaaataatc cacctatccc agtaggagaa    780
atctataaaa gatggataat cctgggatta aataaaatag taagaatgta tagtcctacc    840
agcattctgg acataagaca aggaccaaag gaacccttta gagattatgt agaccggttc    900
tataaaactc taagagccga gcaagcttca caggaggtaa aaaattggat gacagaaacc    960
ttgttggtcc aaaatgcgaa cccagattgt aagactattt taaaagcatt gggaccagca   1020
gctacactag aagaaatgat gacagcatgt cagggagtgg ggggacccgg ccataaagca   1080
agagttttgg ctgaagcaat gagccaagta acaaattcag ctaccataat gatgcagaga   1140
ggcaatttta ggaaccaaag aaaaactgtt aagtgtttca attgtggcaa agaagggcac   1200
atagccaaaa attgcagggc tcctaggaaa aagggctgtt ggaaatgtgg aaaggaagga   1260
caccaaatga agattgtac tgagagacag gctaattttt tagggaagat ctggccttcc   1320
cacaagggaa ggccaggaaa ttttcttcag agcagaccag agccaacagc cccatcagaa   1380
gagagcgtca ggtttggaga agacaaca actccctctc agaagcagga gccgatagac   1440
aaggaactgt atcctttagc ttccctcaga tcactctttg gcagcgaccc ctcgtcacaa   1500
taa                                                                 1503

<210> SEQ ID NO 5
<211> LENGTH: 165
<212> TYPE: DNA
<213> ORGANISM: Human immunodeficiency virus

<400> SEQUENCE: 5
atgcagagag gcaattttag gaaccaaaga aaaactgtta agtgtttcaa ttgtggcaaa     60
gaagggcaca tagccaaaaa ttgcagggct cctaggaaaa agggctgttg gaaatgtgga    120
aaggaaggac accaaatgaa agattgtact gagagacagg ctaat                   165

<210> SEQ ID NO 6
<211> LENGTH: 474
<212> TYPE: DNA
<213> ORGANISM: Human immunodeficiency virus

<400> SEQUENCE: 6
gttgtacttt ctatagtgaa tagagttagg cagggatact caccattatc gtttcagacc     60
cacctcccag ctcagagggg acccgacagg cccgacggaa tcgaagaaga aggtggagag    120
agagacagag acagatccgg tccattagtg gatggcttct tagcaattat ctgggtcgac    180
ctacggagcc tgtgcctttt cagctaccac cgcttgagag acttactctt gattgtaacg    240
aggattgtgg aacttctggg acgcaggggg tgggagtcc tcaaatattg gtggaatctc    300
ctccagtatt ggattcagga actaaagaat agtgctgtta gcttgctcaa cgccacagct    360
atagcagtag ctgagggaac agatagggtt atagaaatat acaaagagc ttttagagct    420
gttcttcaca tacctgtaag aataagacag ggcttggaaa gagctttgct ataa          474
```

<210> SEQ ID NO 7
<211> LENGTH: 246
<212> TYPE: DNA
<213> ORGANISM: Human immunodeficiency virus

<400> SEQUENCE: 7

```
ctgcaatctt tacaagtatt agcaatagta gcattagtag tagcaacaat aatagcaata      60
gttgtgtgga ccatagtatt catagaatat aggaaaatat taagacaaag gaaaatagac     120
aggttaatta atagaataac agaaagagca gaagacagtg gcaatgagag cgacggagat     180
caggaagaat tatcagcact tgtggaaagg gggcaccttg ctccttggga tgttgatgat     240
ctgtag                                                                246
```

<210> SEQ ID NO 8
<211> LENGTH: 288
<212> TYPE: PRT
<213> ORGANISM: Human immunodeficiency virus

<400> SEQUENCE: 8

```
Phe Leu Asp Gly Ile Asp Lys Ala Gln Glu Glu His Glu Lys Tyr His
 1               5                  10                  15

Ser Asn Trp Arg Ala Met Ala Ser Asp Phe Asn Leu Pro Pro Val Val
                20                  25                  30

Ala Lys Glu Ile Val Ala Ser Cys Asp Lys Cys Gln Leu Lys Gly Glu
            35                  40                  45

Ala Met His Gly Gln Val Asp Cys Ser Pro Gly Ile Trp Gln Leu Asp
        50                  55                  60

Cys Thr His Leu Glu Gly Lys Val Ile Leu Val Ala Val His Val Ala
 65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Thr Thr
           100                 105                 110

Ile His Thr Asp Asn Gly Ser Asn Phe Thr Ser Ala Thr Val Lys Ala
       115                 120                 125

Ala Cys Trp Trp Ala Gly Ile Lys Gln Glu Phe Gly Ile Pro Tyr Asn
   130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
               165                 170                 175

Gln Met Ala Val Phe Ile His Asn Phe Lys Arg Lys Gly Gly Ile Gly
           180                 185                 190

Gly Tyr Ser Ala Gly Glu Arg Ile Val Asp Ile Ile Ala Thr Asp Ile
       195                 200                 205

Gln Thr Lys Glu Leu Gln Lys Gln Ile Thr Lys Ile Gln Asn Phe Arg
   210                 215                 220

Val Tyr Tyr Arg Asp Ser Arg Asp Pro Leu Trp Lys Gly Pro Ala Lys
225                 230                 235                 240

Leu Leu Trp Lys Gly Glu Gly Ala Val Val Ile Gln Asp Asn Ser Asp
               245                 250                 255

Ile Lys Val Val Pro Arg Arg Lys Ala Lys Ile Ile Arg Asp Tyr Gly
           260                 265                 270

Lys Gln Met Ala Gly Asp Asp Cys Val Ala Gly Arg Gln Asp Glu Asp
```

```
                275                 280                 285

<210> SEQ ID NO 9
<211> LENGTH: 560
<212> TYPE: PRT
<213> ORGANISM: Human immunodeficiency virus

<400> SEQUENCE: 9

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu His Glu Asp Phe Arg Lys Tyr Thr
        115                 120                 125

Ala Phe Thr Ile Pro Ser Ile Asn Asn Glu Thr Pro Gly Thr Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Thr Ile Leu Glu Pro Phe Arg Lys Gln Asn Pro
                165                 170                 175

Asp Leu Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Phe Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Ala
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Thr Arg Gly Ala His Thr Asn Asp Val Lys Gln Leu
        355                 360                 365
```

```
Thr Glu Ala Val Gln Lys Ile Ala Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Ile Gly Ala Glu Thr Phe Tyr Val Asp Gly Ala Ala Asn Arg
        435                 440                 445

Glu Thr Lys Leu Gly Lys Ala Gly Tyr Val Thr Asn Lys Gly Arg Gln
    450                 455                 460

Lys Val Val Ser Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Arg
            500                 505                 510

Ser Glu Ser Glu Leu Val Ser Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Val Leu
545                 550                 555                 560

<210> SEQ ID NO 10
<211> LENGTH: 99
<212> TYPE: PRT
<213> ORGANISM: Human immunodeficiency virus

<400> SEQUENCE: 10

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Pro Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 11
<211> LENGTH: 500
<212> TYPE: PRT
<213> ORGANISM: Human immunodeficiency virus

<400> SEQUENCE: 11

Met Gly Ala Arg Ala Ser Val Leu Ser Ala Gly Glu Leu Asp Lys Trp
1               5                   10                  15

Glu Lys Ile Arg Leu Arg Pro Gly Gly Lys Lys Gln Tyr Arg Leu Lys
            20                  25                  30

His Ile Val Trp Ala Ser Arg Glu Leu Glu Arg Phe Ala Val Asp Pro
```

-continued

```
            35                  40                  45
Gly Leu Leu Glu Thr Ser Glu Gly Cys Arg Gln Ile Leu Gly Gln Leu
 50                  55                  60
Gln Pro Ser Leu Gln Thr Gly Ser Glu Glu Leu Arg Ser Leu Tyr Asn
 65                  70                  75                  80
Thr Val Ala Thr Leu Tyr Cys Val His Gln Lys Ile Glu Val Lys Asp
                 85                  90                  95
Thr Lys Glu Ala Leu Glu Lys Ile Glu Glu Gln Asn Lys Ser Lys
                100                 105                 110
Lys Lys Ala Gln Gln Ala Ala Ala Asp Thr Gly Asn Ser Ser Gln Val
                115                 120                 125
Ser Gln Asn Tyr Pro Ile Val Gln Asn Leu Gln Gly Gln Met Val His
    130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
                180                 185                 190
Gly His Gln Ala Ala Met Gln Met Leu Lys Glu Thr Ile Asn Glu Glu
                195                 200                 205
Ala Ala Glu Trp Asp Arg Leu His Pro Val His Ala Gly Pro Ile Ala
    210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
                260                 265                 270
Ile Val Arg Met Tyr Ser Pro Thr Ser Ile Leu Asp Ile Arg Gln Gly
                275                 280                 285
Pro Lys Glu Pro Phe Arg Asp Tyr Val Asp Arg Phe Tyr Lys Thr Leu
    290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
                340                 345                 350
Val Gly Gly Pro Gly His Lys Ala Arg Val Leu Ala Glu Ala Met Ser
                355                 360                 365
Gln Val Thr Asn Ser Ala Thr Ile Met Met Gln Arg Gly Asn Phe Arg
    370                 375                 380
Asn Gln Arg Lys Thr Val Lys Cys Phe Asn Cys Gly Lys Glu Gly His
385                 390                 395                 400
Ile Ala Lys Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
                420                 425                 430
Phe Leu Gly Lys Ile Trp Pro Ser His Lys Gly Arg Pro Gly Asn Phe
                435                 440                 445
Leu Gln Ser Arg Pro Glu Pro Thr Ala Pro Ser Glu Glu Ser Val Arg
    450                 455                 460
```

```
Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 12
<211> LENGTH: 55
<212> TYPE: PRT
<213> ORGANISM: Human immunodeficiency virus

<400> SEQUENCE: 12

Met Gln Arg Gly Asn Phe Arg Asn Gln Arg Lys Thr Val Lys Cys Phe
1               5                   10                  15

Asn Cys Gly Lys Glu Gly His Ile Ala Lys Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn
    50                  55

<210> SEQ ID NO 13
<211> LENGTH: 157
<212> TYPE: PRT
<213> ORGANISM: Human immunodeficiency virus

<400> SEQUENCE: 13

Val Val Leu Ser Ile Val Asn Arg Val Arg Gln Gly Tyr Ser Pro Leu
1               5                   10                  15

Ser Phe Gln Thr His Leu Pro Ala Gln Arg Gly Pro Asp Arg Pro Asp
            20                  25                  30

Gly Ile Glu Glu Gly Gly Glu Arg Asp Arg Asp Arg Ser Gly Pro
        35                  40                  45

Leu Val Asp Gly Phe Leu Ala Ile Ile Trp Val Asp Leu Arg Ser Leu
50                  55                  60

Cys Leu Phe Ser Tyr His Arg Leu Arg Asp Leu Leu Leu Ile Val Thr
65                  70                  75                  80

Arg Ile Val Glu Leu Leu Gly Arg Arg Gly Trp Gly Val Leu Lys Tyr
                85                  90                  95

Trp Trp Asn Leu Leu Gln Tyr Trp Ile Gln Glu Leu Lys Asn Ser Ala
                100                 105                 110

Val Ser Leu Leu Asn Ala Thr Ala Ile Ala Val Ala Glu Gly Thr Asp
            115                 120                 125

Arg Val Ile Glu Ile Leu Gln Arg Ala Phe Arg Ala Val Leu His Ile
        130                 135                 140

Pro Val Arg Ile Arg Gln Gly Leu Glu Arg Ala Leu Leu
145                 150                 155

<210> SEQ ID NO 14
<211> LENGTH: 81
<212> TYPE: PRT
<213> ORGANISM: Human immunodeficiency virus

<400> SEQUENCE: 14

Leu Gln Ser Leu Gln Val Leu Ala Ile Val Ala Leu Val Val Ala Thr
1               5                   10                  15
```

```
Ile Ile Ala Ile Val Val Trp Thr Ile Val Phe Ile Glu Tyr Arg Lys
            20                  25                  30

Ile Leu Arg Gln Arg Lys Ile Asp Arg Leu Ile Asn Arg Ile Thr Glu
        35                  40                  45

Arg Ala Glu Asp Ser Gly Asn Glu Ser Asp Gly Asp Gln Glu Glu Leu
    50                  55                  60

Ser Ala Leu Val Glu Arg Gly His Leu Ala Pro Trp Asp Val Asp Asp
65                  70                  75                  80

Leu

<210> SEQ ID NO 15
<211> LENGTH: 574
<212> TYPE: DNA
<213> ORGANISM: Homo sapiens

<400> SEQUENCE: 15
ttgtggcaaa ggagaaatgg ccacagggaa tgggcggcgg ctccacctgg ggattcctga      60
ggccgtgttt gtggaagatg tagattcctt catgaaacag cctgggaatg agactgcaga     120
tacagtatta aagaagctgg atgaacagta ccagaagtat aagtttatgg aactcaacct     180
tgctcaaaag aaaagaaggc taaaggtca gattcctgaa attaaacaga ctttggaaat      240
tctaaaatac atgcagaaga aaaagagtc caccaactca atggagacca gattcttgct      300
ggcagataac ctgtattgca agcttcagt tcctcctacc gataaagtgt gtctgtggtt      360
gggggctaat gtaatgcttg aatatgatat tgatgaagct caggcattgt tggaaaagaa     420
tttatcgact gccacaaaga atcttgattc cctggaggaa gaccttgact tcttcgaga      480 tcaatttact accacagaag tcaatatggc cagggtttat aattgggatg taaaaagaag     540
aaacaaggat gactctacca agaacaaagc ataa                                 574

<210> SEQ ID NO 16
<211> LENGTH: 594
<212> TYPE: DNA
<213> ORGANISM: Homo sapiens

<400> SEQUENCE: 16
atggcggccg ttaaggacag ttgtggcaaa ggagaaatgg ccacagggaa tgggcggcgg      60
ctccacctgg ggattcctga ggccgtgttt gtggaagatg tagattcctt catgaaacag     120
cctgggaatg agactgcaga tacagtatta aagaagctgg atgaacagta ccagaagtat     180
aagtttatgg aactcaacct tgctcaaaag aaaagaaggc taaaggtca gattcctgaa      240 attaaacaga ctttggaaat tctaaaatac atgcagaaga aaaagagtc caccaactca      300 atggagacca gattcttgct ggcagataac ctgtattgca agcttcagt tcctcctacc      360 gataaagtgt gtctgtggtt gggggctaat gtaatgcttg aatatgatat tgatgaagct     420
caggcattgt tggaaaagaa tttatcgact gccacaaaga atcttgattc cctggaggaa     480
gaccttgact tcttcgaga tcaatttact accacagaag tcaatatggc cagggtttat      540
aattgggatg taaaaagaag aaacaaggat gactctacca agaacaaagc ataa           594

<210> SEQ ID NO 17
<211> LENGTH: 817
<212> TYPE: DNA
<213> ORGANISM: Homo sapiens

<400> SEQUENCE: 17
ttttgctgca cagaccatga aaatgaagat tcagacctca ttttatgagc tccccacaga      60
```

| | |
|---|---|
| ctctcatgcc tctttacggg actcattgct aacccatatc cagaacttga aagacttgtc | 120 |
| acctgttatt gtaacgcagc tggctttagc aatagcagat cttgccctac agatgccttc | 180 |
| ctggaaggga tgtgtgcaaa cactggtgga aaaatacagc aatgatgtga cttcttttgcc | 240 |
| ttttttgctg agatccttca cagtgttacc tgaagaagta catagtcgtt ccttacgaat | 300 |
| tggagctaat cggcgcacag aaattataga agatttggcc ttctactcta gtacagtagt | 360 |
| atctctattg atgacctgtg tagaaaaagc aggaacagat gagaaaatgc ttatgaaggt | 420 |
| ttttcgctgt ttgggaagtt ggtttaactt gggagttttg acagtaact tcatggctaa | 480 |
| caataaatta ctagcactcc tttttgaggt tttgcaacag gataagacct cgtctaacct | 540 |
| acatgaagct gcttcggact gtgtatgctc agctctctat gccattgaga atgtggagac | 600 |
| taacttgcca ttagccatgc aacttttttca gggagtgctg acattggaga ctgcctatca | 660 |
| tatggccgtg gcacgtgaag atttagacaa agttctgaat tactgccgta ttttcactga | 720 |
| actatgtgaa acttttcttg aaaaaattgt ttgtactcca ggccaaggtc ttggggacct | 780 |
| tcgaactctg gagctgctgc ttatctgtgc aggccat | 817 |

<210> SEQ ID NO 18
<211> LENGTH: 708
<212> TYPE: DNA
<213> ORGANISM: Homo sapiens

<400> SEQUENCE: 18

| | |
|---|---|
| gtccaagtac agttccttgg agcagagtga gcgccgccgg aggttactgg aactgcagaa | 60 |
| atccaagcgg ctggattatg tgaaccatgc cagaagactg gctgaagatg actggacagg | 120 |
| gatggagagt gaggaagaaa ataagaaaga tgatgaagaa atggacattg acactgtcaa | 180 |
| gaagttacca aaacactatg ctaatcaatt gatgctttct gagtggttaa ttgacgttcc | 240 |
| ttcagatttg gggcaggaat ggattgtggt cgtgtgccct gttggaaaaa gagcccttat | 300 |
| cgtggcctcc aggggttcta ccagtgccta caccaagagt ggctactgtg tcaacaggtt | 360 |
| ttcttcactt ctgccaggag gcaacaggcg aaactcaaca gcaaaagact acaccattct | 420 |
| agattgcatt tacaatgagg taaaccagac ctactacgtt ctggatgtga tgtgctggcg | 480 |
| gggacaccct tttatgatt gccagactga tttccgattc tactgatgc attcaaagtt | 540 |
| accagaagaa gaaggactgg gagagaaaac caagcttaat cctttttaaat ttgtggggct | 600 |
| aaagaacttc ccttgcactc ccgaaagcct gtgtgatgtg ctatctatgg atttcccttt | 660 |
| tgaggtagat ggacttctct tctaccacaa acagacccat tacagccc | 708 |

<210> SEQ ID NO 19
<211> LENGTH: 841
<212> TYPE: DNA
<213> ORGANISM: Homo sapiens

<400> SEQUENCE: 19

| | |
|---|---|
| gggaagcaac atgattaaaa caattgcttt tggccgctat gagcttgata cctggtatca | 60 |
| ttctccatat cctgaagaat atgcacggct gggacgtctc tatatgtgtg aattctgttt | 120 |
| aaaatatatg aagagccaaa cgatactccg ccggcacatg gccaaatgtg tgtgaaaaca | 180 |
| cccacctggt gatgagatat atcgcaaagg ttcaatctct gtgtttgaag tggatggcaa | 240 |
| gaaaaacaag atctactgcc aaaacctgtg cctgttggcc aaacttttc tggaccacaa | 300 |
| gacattatat tatgatgtgg agcccttcct gttctatgtt atgacagagg cggacaacac | 360 |

```
tggctgtcac ctgattggat attttttctaa ggaaaagaat tcattcctca actacaacgt    420
ctcctgtatc cttactatgc ctcagtacat gagacagggc tatggcaaga tgcttattga    480
tttcagttat ttgctttcca aagtcgaaga aaaagttggc tccccagaac gtccactctc    540
agatctgggg cttataagct atcgcagtta ctggaaagaa gtacttctcc gctacctgca    600
taattttcaa ggcaaagaga tttctatcaa agaaatcagt caggagacgg ctgtgaatcc    660
tgtggacatt gtcagcactc tgcaagccct tcagatgctc aaatactgga agggaaaaca    720
cctagtttta aagagacagg acctgattga tgagtggata gccaaagagg ccaaaaggtc    780
caactccaat aaaaccatgg atcccagctg cttaaaatgg acccctccca agggcactta    840
a                                                                    841

<210> SEQ ID NO 20
<211> LENGTH: 806
<212> TYPE: DNA
<213> ORGANISM: Homo sapiens

<400> SEQUENCE: 20
gattaaaaca attgcttttg gccgctatga gcttgatacc tggtatcatt ctccatatcc     60
tgaagaatat gcacggctgg gacgtctcta tatgtgtgaa ttctgtttaa aatatatgaa    120
gagccaaacg atactccgcc ggcacatggc caaatgtgtg tggaaacacc cacctggtga    180
tgagatatat cgcaaaggtt caatctctgt gtttgaagtg gatggcaaga aaaacaagat    240
ctactgccaa aacctgtgcc tgttggccaa acttttttctg gaccacaaga cattatatta    300
tgatgtggag ccccttcctgt tctatgttat gacagaggcg gacaacactg gctgtcacct    360 gattggtatat ttttctaagg aaaagaattc attcctcaac tacaacgtct cctgtatcct    420
tactatgcct cagtacatga gacagggcta tggcaagatg cttattgatt tcagttattt    480
gctttccaaa gtcgaagaaa agttggctc cccagaacgt ccactctcag atctggggct    540
tataagctat cgcagttact ggaaagaagt acttctccgc tacctgcata ttttcaagg    600 caaagagatt tctatcaaag aaatcagtca ggagacggct gtgaatcctg tggacattgt    660
cagcactctg caagcccttc agatgctcaa atactggaag ggaaaacacc tagttttaaa    720
gagacaggac ctgattgatg agtggatagc caaagaggcc aaaaggtcca actccaataa    780
aaccatggat cccagctgct taaaat                                         806

<210> SEQ ID NO 21
<211> LENGTH: 412
<212> TYPE: DNA
<213> ORGANISM: Homo sapiens

<400> SEQUENCE: 21
agcatacgtg gagatgaggc gagaggcttg ggctagtaag gatgccacct atacttctgc     60
ccggaccctg ctggctatcc tgcgcctttc cactgctctg gcacgtctga aatggtgga    120 tgtggtggag aaagaagatg tgaatgaagc catcaggcta atggagatgt caaaggactc    180
tcttctagga gacaaggggc agacagctag gactcagaga ccagcagatg tgatatttgc    240
caccgtccgt gaactggtct caggggggccg aagtgtccgg ttctctgagg cagagcagcg    300
ctgtgtatct cgtggcttca cccgcccaa gttccaggcg ctctggatg aatatgagga    360 gctcaatgtc tggcaggtca atgcttcccg gacacggatc acttttgtct ga            412

<210> SEQ ID NO 22
<211> LENGTH: 1045
```

<212> TYPE: DNA
<213> ORGANISM: Homo sapiens

<400> SEQUENCE: 22

| | | | | | |
|---|---|---|---|---|---|
| ggaaggtacc | ggctctactg | ccacctcttc | cagctccacc | gccggcgcag | cagggaaagg | 60 |
| caaaggcaaa | ggcggctcgg | gagattcagc | cgtgaagcaa | gtgcagatag | atggccttgt | 120 |
| ggtattaaag | ataatcaaac | attatcaaga | agaaggacaa | ggaactgaag | ttgttcaagg | 180 |
| agtgcttttg | ggtctggttg | tagaagatcg | gcttgaaatt | accaactgct | tccttttccc | 240 |
| tcagcacaca | gaggatgatg | ctgactttga | tgaagtccaa | tatcagatgg | aaatgatgcg | 300 |
| gagccttcgc | catgtaaaca | ttgatcatct | tcacgtgggc | tggtatcagt | ccacatacta | 360 |
| tggctcattc | gttacccggg | cactcctgga | ctctcagttt | agttaccagc | atgccattga | 420 |
| agaatctgtc | gttctcattt | atgatcccat | aaaaactgcc | caaggatctc | tctcactaaa | 480 |
| ggcatacaga | ctgactccta | aactgatgga | agtttgtaaa | gaaaggatt | tttcccctga | 540 |
| agcattgaaa | aaagcaaata | tcacctttga | gtacatgttt | gaagaagtgc | cgattgtaat | 600 |
| taaaaattca | catctgatca | atgtcctaat | gtgggaactt | gaaaagaagt | cagctgttgc | 660 |
| agataaacat | gaattgctca | gccttgccag | cagcaatcat | ttggggaaga | atctacagtt | 720 |
| gctgatggac | agagtggatg | aaatgagcca | agatatagtt | aaatacaaca | catacatgag | 780 |
| gaatactagt | aaacaacagc | agcagaaaca | tcagtatcag | cagcgtcgcc | agcaggagaa | 840 |
| tatgcagcgc | cagagccgag | agaaccccc | gctccctgag | gaggacctgt | ccaaactctt | 900 |
| caaaccacca | cagccgcctg | ccaggatgga | ctcgctgctc | attgcaggcc | agataaacac | 960 |
| ttactgccag | aacatcaagg | agttcactgc | ccaaaactta | ggcaagctct | tcatggccca | 1020 |
| ggctcttcaa | gaatacaaca | actaa | | | | 1045 |

<210> SEQ ID NO 23
<211> LENGTH: 908
<212> TYPE: DNA
<213> ORGANISM: Homo sapiens

<400> SEQUENCE: 23

| | | | | | |
|---|---|---|---|---|---|
| caaggaaggt | accggctcta | ctgccacctc | ttccagctcc | accgccggcg | cagcagggaa | 60 |
| aggcaaaggc | aaaggcggct | cgggagattc | agccgtgaag | caagtgcaga | tagatggcct | 120 |
| tgtggtatta | aagataatca | aacattatca | agaagaagga | caaggaactg | aagttgttca | 180 |
| aggagtgctt | ttgggtctgg | ttgtagaaga | tcggcttgaa | attaccaact | gctttccttt | 240 |
| ccctcagcac | acagaggatg | atgctgactt | tgatgaagtc | caatatcaga | tggaaatgat | 300 |
| gcggagcctt | cgccatgtaa | acattgatca | tcttcacgtg | ggctggtatc | agtccacata | 360 |
| ctatggctca | ttcgttaccc | gggcactcct | ggactctcag | tttagttacc | agcatgccat | 420 |
| tgaagaatct | gtcgttctca | tttatgatcc | cataaaaact | gcccaaggat | ctctctcact | 480 |
| aaaggcatac | agactgactc | ctaaactgat | ggaagtttgt | aaagaaaagg | attttttccc | 540 |
| tgaagcattg | aaaaaagcaa | atatcacctt | tgagtacatg | tttgaagaag | tgccgattgt | 600 |
| aattaaaaat | tcacatctga | tcaatgtcct | aatgtgggaa | cttgaaaaga | agtcagctgt | 660 |
| tgcagataaa | catgaattgc | tcagccttgc | cagcagcaat | catttgggga | agaatctaca | 720 |
| gttgctgatg | gacagagtgg | atgaaatgag | ccaagatata | gttaaataca | acacatacat | 780 |
| gaggaatact | agtaaacaac | agcagcagaa | acatcagtat | cagcagcgtc | gccagcagga | 840 |
| gaatatgcag | cgccagagcc | gaggagaacc | cccgctccct | gaggaggacc | tgtccaaact | 900 |

-continued cttcaaac                                                                908

<210> SEQ ID NO 24
<211> LENGTH: 454
<212> TYPE: DNA
<213> ORGANISM: Homo sapiens

<400> SEQUENCE: 24
atggcggcgg agctggtgga ggccaaaaac atggtgatga gttttcgagt ctccgacctt    60
cagatgctcc tgggtttcgt gggccggagt aagagtggac tgaagcacga gctcgtcacc   120
agggccctcc agctggtgca gtttgactgt agccctgagc tgttcaagaa gatcaaggag   180
ctgtacgaga cccgctacgc caagaagaac tcggagcctg ccccacagcc gcaccggccc   240
ctggaccccc tgaccatgca ctccacctac gaccgggccg cgctgtgcc caggactccg    300 ctggcaggcc ccaatattga ctaccccgtg ctctacggaa agtacttaaa cggactggga   360
cggttgcccg ccaagaccct caagccgaaa gtccgcctgg tgaagctgcc gttctttaat   420
atgctggatg agctgctgaa gcccaccgaa ttag                                454

<210> SEQ ID NO 25
<211> LENGTH: 813
<212> TYPE: DNA
<213> ORGANISM: Homo sapiens

<400> SEQUENCE: 25
tgtgtgtcag gccagtcagc tccaagggca gaaggaagag agctgtgtcc cagttcacca    60
gaaaactgtc ctgggcccag acactgcgga gcctgccaca gcagaggcag ctgttgcccc   120
gccggatgct ggcctcccct tgccaggcct accagcagag gctcaccac caccaaagac   180 ctacgtgagc tgcctgaaga gccttctgtc cagccccacc aaggacagta agccaaatat    240
ctctgcacac cacatctccc tggcctcctg cctggcactg accacccca gtgaagagtt     300 gccggaccgg gcaggcatcc tggtggaaga tgccacctgt gtcacctgca tgtcagacag    360
cagccaaagt gtcccttttgg tggcttctcc aggacactgc tcagattctt tcagcacttc    420
agggcttgaa gactcttgca cagagaccag ctcgagcccc agggacaagg ccatcacccc   480
gccactgcca gaaagtactg tgcccttcag caatggggtg ctgaagggg agttgtcaga    540 cttggggggct gaggatggat ggaccatgga tgcggaagca gatcattcag gaggttctga   600
caggaacagc atggattccg tggatagctg ttgcagtctc aagaagactg agagcttcca   660
aaatgcccag gcaggctcca accctaagaa ggtcgacctc atcatctggg agatcgaggt    720
gccaaagcac ttagtcggtc ggctaattgg caagcagggg cgctatgtga gttttctgaa   780
gcaaacatct ggtgccaaga tctacatttc aac                                 813

<210> SEQ ID NO 26
<211> LENGTH: 124
<212> TYPE: DNA
<213> ORGANISM: Homo sapiens

<400> SEQUENCE: 26
gtttggcttt gtgaccatga caaactatga agaagccgcg atggccatag ccagcctgaa    60
cggctaccgc ctgggggaca aaatcttaca ggtttccttc aaaaccaaca gtcccacaa    120 ataa                                                                 124

<210> SEQ ID NO 27
<211> LENGTH: 181

```
<212> TYPE: DNA
<213> ORGANISM: Homo sapiens

<400> SEQUENCE: 27
atgagcagct cagaggaggt gtcctggatt tcctggttct gtgggctccg tggcaatgaa    60
ttcttctgtg aagtggatga agactacatc caggacaaat ttaatcttac tggactcaat   120
gagcaggtcc ctcactatcg acaagctcta gacatgatct tggacctgga gcctgatgaa   180
g                                                                   181

<210> SEQ ID NO 28
<211> LENGTH: 2890
<212> TYPE: DNA
<213> ORGANISM: Homo sapiens

<400> SEQUENCE: 28
agaaatgtca ccggctttac atttgatgca gaaccttgac acaaaatcca aactgagacc    60
caaacgtgca tctgctgaac agagcgtcct cttcaagtcc ctgcacacca acactaatgg   120
gaacagtgag cctctggtga tgccggaaat caatgacaaa gagaacaggg acgtcacaaa   180
tggtggcatt aagagatcga gactagaaaa aagtgcactt ttctcaagct tgttatcttc   240
tttaccacaa gacaaaatct tttctccttc tgtgacatca gtcaacacta tgaccacggc   300
tttcagtact tctcagaacg gttccctatc tcagtcttca gtgtcacagc ccacgactga   360
gggtgccccg ccctgtggtt tgaacaaaga cagtcaaat cttctgcccg acaactcctt   420
aaaggtcttc aatttcaact cgtcaagtac atcacactcc agtttgaaaa gtccaagcca   480
catggaaaaa tacccgcaaa aagagaaaac caagaagat ctggattcac gaagcaacct   540
acacttgcca gaaactaaat tttctgaatt gtcaaaactg aagaatgatg atatggaaaa   600
ggctaatcat attgaaagtg ttattaaatc aaacttgcca aactgtgcaa acagtgacac   660
cgacttcatg ggtcttttca atcaagccg gtatgaccca agcatttctt tttctggaat   720
gtcattatca gacacaatga cacttagagg aagtgtccaa aataaactca atccccgacc   780
tggaaaggta gtgatatata gtgaacccga cgtctctgag aagtgcattg aagttttcag   840
tgacattcag gattgcagtt cttggagcct ctctccagtg atactcataa agttgttag    900 aggatgttgg attttgtatg agcaaccaaa ttttgaaggg cactccatcc ccttagaaga   960
aggagaattg gaactctctg gtctctgggg tatagaagac attttggaaa ggcacgaaga  1020
agcagagtct gataagccag tggtgattgg ttccatcaga catgtggttc aggattacag  1080
agttagtcac attgacttat ttactgaacc agaagggtta ggaatcctaa gttcctactt  1140
tgatgatact gaagaaatgc agggatttgg tgtaatgcag aagacttgtt ccatgaaagt  1200 acattgggc acgtggctga tttatgaaga acctggattt cagggtgttc cttttcatcct  1260 ggaacctggt gaataccctg acttgtcctt ctgggataca aagaagcgt acattggatc  1320 catgcggcct ctgaaaatgg gtggccgtaa agttgaattc cctacagatc caaaggtagt  1380
tgtttatgaa aagccttct ttgaaggaaa atgtgtggaa ctagaaacag gaatgtgtag  1440
ttttgtcatg gagggaggtg aaacagaaga ggcgactgga gacgatcatt tgccgtttac  1500
gtcagtgggg tctatgaaag ttctaagagg catttgggtt gcatatgaga aacctggatt  1560
taccggtcat cagtatttgc tagaagaagg agaatacagg gactggaaag cctggggagg  1620
ttacaatgga gagcttcagt ctttacgacc tatattaggt gatttttcaa atgctcacat  1680
gataatgtac agtgaaaaaa actttggatc caaaggttcc agtattgatg tattgggaat  1740
```

```
tgttgctaat ttaaaggaga ctggatatgg agtgaagaca cagtctatta atgtactgag    1800
tggagtatgg gtagcctatg aaaatcctga cttcacagga gaacagtata tactggataa    1860
aggattttat accagttttg aggactgggg aggcaaaaat tgtaagatct cttctgttca    1920
acctatatgt ttggattctt tcactggccc aaggagacga aatcagattc acttgttttc    1980
agaaccacag tttcaaggtc acagtcaaag ttttgaagaa caacaagtc aaattgatga     2040 ttcattttct accaagtctt gcagagtttc aggaggcagc tgggttgtat atgatggaga    2100
aaatttcact ggtaatcaat acgtgttgga agaaggccat tatccttgtc tgtctgcaat    2160
gggatgcccg cctggagcaa ctttcaagtc tcttcgtttt atagatgttg aattttctga    2220
accaacaatt attctctttg aaagagaaga cttcaaagga aaaaagattg aacttaatgc    2280
agaaactgtc aatctccgat ccctgggatt caacacacaa atacgctctg ttcaggttat    2340
tggtggcata tgggttactt atgaatatgg cagttacaga gggcgacagt tcctattgtc    2400
acctgcagaa gtacctaatt ggtatgaatt cagtggctgt cgccaaatag gttctctacg    2460
accttttgtt cagaagcgaa tttatttcag acttcgaaac aaagcaacag gttattcat     2520 gtcaaccaat ggaaacttag aggatctgaa gcttctgagg atacaggtca tggaggatgt    2580
cggggccgat gatcagattt ggatctatca agaaggatgt atcaaatgca ggatagcaga    2640
agactgctgc ctgacgattg tgggcagcct ggtaacatct ggctccaagc taggcctggc    2700
cctggaccag aatgctgaca gccagttctg gagcttgaag tccgatggca ggatttacag    2760
caagttgaag ccaaatttag ttttagacat taaggggggc acacagtatg atcaaaatca    2820
cattatcctc aacactgtca gcaaagagaa gtttacacaa gtgtgggaag ccatggtcct    2880
atatacctga                                                           2890

<210> SEQ ID NO 29
<211> LENGTH: 683
<212> TYPE: DNA
<213> ORGANISM: Homo sapiens

<400> SEQUENCE: 29
caaactgaga cccaaacgtg catctgctga acagagcgtc ctcttcaagt ccctgcacac      60
caacactaat gggaacagtg agcctctggt gatgccggaa atcaatgaca aagagaacag     120
ggacgtcaca aatggtggca ttaagagatc gagactagaa aaaagtgcac ttttctcaag     180
cttgttatct tctttaccac aagacaaaat cttttctcct tctgtgacat cagtcaacac     240
tatgaccacg gctttcagta cttctcagaa cggttcccta tctcagtctt cagtgtcaca     300
gcccacgact gagggtgccc cgccctgtgg tttgaacaaa gaacagtcaa atcttctgcc     360
cgacaactcc ttaaaggtct tcaatttcaa ctcgtcaagt acatcacact ccagtttgaa     420
aagtccaagc cacatggaaa ataccccgca aaagagaaa accaaagaag atctggattc     480
acgaagcaac ctacacttgc cagaaactaa attttctgaa ttgtcaaaac tgaagaatga     540
tgatatggaa aaggctaatc atattgaaag tgttattaaa tcaaacttgc caaactgtgc     600
aaacagtgac accgacttca tgggtctttt caaatcaagc cggtatgacc caagcatttc     660 ttttttctgga atgtcattat cag                                            683

<210> SEQ ID NO 30
<211> LENGTH: 394
<212> TYPE: DNA
<213> ORGANISM: Homo sapiens

<400> SEQUENCE: 30
```

```
cttggccctg cctttctttg gtttctctga accccttgcc gcaccacgtc accagtacta      60
taaccaagag tggacattgt gggatcgctt tgaggtacaa gggctgcagc ctaatggtga     120
ggagatgacc ctcaaacagt tcctcgacta ttttaagaca gagcacaaat tagagatcac     180
catgctgtcc cagggcgtgt ccatgctcta ttccttcttc atgccagctg ccaagctcaa     240
ggaacggttg gatcagccga tgacagagat tgtgagccgt gtgtcgaagc gaaagctggg     300
ccgccacgtg cgggcgctgg tgcttgagct gtgctgtaac gacgagagcg gcgaggatgt     360
cgaggttccc tatgtccgat acaccatccg ctga                                 394

<210> SEQ ID NO 31
<211> LENGTH: 469
<212> TYPE: DNA
<213> ORGANISM: Homo sapiens

<400> SEQUENCE: 31
gctgacagag ggtgggaagg gttcctcgcc ctccatcaga ccaatccaag gcagccaggg      60
gtccagcagc ccagtggaga aggaggtcgt ggaagccacg gacagcagag agaagacggg     120
gatggtgagg cctggcgagc ccttgagtgg ggagaaatac tcacccaagg agctgctggc     180
actgctgaag tgtgtggagg ctgagattgc aaactatgag gcgtgcctca aggaggaggt     240
agagaagagg aagaagttca agattgatga ccagagaagg acccacaact acgatgagtt     300
catctgcacc tttatctcca tgctggctca ggaaggcatg ctggccaacc tagtggagca     360
gaacatctcc gtgcggcggc gccaagggggt cagcatcggc cggctccaca gcagcggaa     420 gcctgaccgg cggaaacgct ctcgccccta caaggccaag cgccagtga                 469

<210> SEQ ID NO 32
<211> LENGTH: 208
<212> TYPE: DNA
<213> ORGANISM: Homo sapiens

<400> SEQUENCE: 32
gattgatgac cagagaagga cccacaacta cgatgagttc atctgcacct ttatctccat      60
gctggctcag gaaggcatgc tggccaacct agtggagcag aacatctccg tgcggcggcg     120 ccaagggggtc agcatcggcc ggctccacaa gcagcggaag cctgaccggc ggaaacgctc     180
tcgcccctac aaggccaagc gccagtga                                        208

<210> SEQ ID NO 33
<211> LENGTH: 388
<212> TYPE: DNA
<213> ORGANISM: Homo sapiens

<400> SEQUENCE: 33
gctagggtta gaggcgagat taaaggctgc cctctcagaa acgagcaac tgaagaaaga       60 aaatggaaca ctgaagcggc agctggatga agttgtgtca gagaaccaga ggcttaaagt     120
ccctagtcca aagcgaagag ttgtctgtgt gatgatagta ttggcattta taatactgaa     180 ctatggaccct atgagcatgt tggaacagga ttccaggaga atgaaccta gtgtgggacc     240 tgcaaatcaa aggaggcacc ttctaggatt ttctgctaaa gaggcacagg acacatcaga    300
tggtattatc cagaaaaaca gctacagata tgatcattct gtttcaaatg acaaagccct    360
gatggtgcta actgaagaac cattgctt                                       388

<210> SEQ ID NO 34
```

<211> LENGTH: 583
<212> TYPE: DNA
<213> ORGANISM: Homo sapiens

<400> SEQUENCE: 34

```
aatgcctgta atgatggggc aagagaaagt gcccattaag caggtacctg ggggagtcaa      60
gcagcttgag ccccccaaag aaggagaaag gcggacaacc cataatatca ttgagaaacg     120
atatcgctcc tccatcaatg acaaaatcat cgaattgaaa gacctggtca tggggacaga     180
cgccaagatg cacaagtctg gcgttctgag gaaggccatt gattacatca aatacttgca     240
gcaggtcaat cataaactgc gccaggagaa catggtgctg aagctggcaa atcaaaagaa     300
caagcttcta aagggcatcg acctaggcag tctggtggac aatgaggtgg acctgaagat     360
cgaggacttt aatcagaatg tccttctgat gtccccccca gcctctgact cagggtccca     420
ggctggcttc tctccctact ccattgactc tgagccagga agccctctat ggatgatgc      480
aaaggtcaaa gatgagccag actctcctcc tgtggcgctg gcatggtag accgctcacg      540
gattcttctg tgtgtcctca ccttcctgtg cctctccttt aac                       583
```

<210> SEQ ID NO 35
<211> LENGTH: 775
<212> TYPE: DNA
<213> ORGANISM: Homo sapiens

<400> SEQUENCE: 35

```
cctgaggctg gtggtgccgg ccacccagtg cggctccctg attgggaaag gcgggtgtaa      60
gatcaaagag atccgcgaga gtacgggggc gcaggtccag gtggcggggg atatgctgcc     120
caactccacc gagcgggcca tcaccatcgc tggcgtgccg cagtctgtca ccgagtgtgt     180
caagcagatt tgcctggtca tgctggagac gctctcccag tctccgcaag ggagagtcat     240
gaccattccg taccagccca tgccggccag ctccccagtc atctgcgcgg gcggccaaga     300
tcggtgcagc gacgctgtgg gctaccccca tgccacccat gacctggagg gaccacctct     360
agatgcctac tcgattcaag acaacacac catttctccg ctcgatctgg ccaagctgaa      420
ccaggtggca agacaacagt ctcactttgc catgatgcac ggcgggaccg gattcgccgg     480
aattgactcc agctctccag aggtgaaagg ctattgggca gtttggatg catctactca      540
aaccacccat gaactcacca ttccaaataa cttaattggc tgcataatcg ggcgccaagg     600
cgccaacatt aatgagatcc gccagatgtc cggggcccag atcaaaattg ccaacccagt     660
ggaaggctcc tctggtaggc aggttactat cactggctct gctgccagta ttagtctggc     720
ccagtatcta atcaatgcca ggctttcctc tgagaagggc atggggtgca gctag          775
```

<210> SEQ ID NO 36
<211> LENGTH: 144
<212> TYPE: DNA
<213> ORGANISM: Homo sapiens

<400> SEQUENCE: 36

```
gggggatatg ctgcccaact ccaccgagcg ggccatcacc atcgctggcg tgccgcagtc      60
tgtcaccgag tgtgtcaagc agatttgcct ggtcatgctg gagacgctct cccagtctcc     120
gcaagggaga gtcatgacca ttcc                                            144
```

<210> SEQ ID NO 37
<211> LENGTH: 306
<212> TYPE: DNA
<213> ORGANISM: Homo sapiens

<400> SEQUENCE: 37

```
cgccttggct cgacactgcc agctggaacc agaccatgag ggggttcctg aggagactga      60
tgactttggg gagtttcgca tgagggtatc agacctggta aaggacttga ttttcttgat     120
agggtctatg gagtgttttg ctcagttata ttctactctg aaagaaggca acccaccctg     180
ggaggtgaca gaagcggttc tctttatcat ggctgctata gcaaagagtg ttgatccgga     240
aaacaatcca acacttgtgg aagtcctaga aggagttgtc cgcctcccgg agaccgtaca     300
tacggc                                                               306
```

<210> SEQ ID NO 38
<211> LENGTH: 190
<212> TYPE: PRT
<213> ORGANISM: Homo sapiens

<400> SEQUENCE: 38

```
Cys Gly Lys Gly Glu Met Ala Thr Gly Asn Gly Arg Arg Leu His Leu
1               5                   10                  15

Gly Ile Pro Glu Ala Val Phe Val Glu Asp Val Asp Ser Phe Met Lys
            20                  25                  30

Gln Pro Gly Asn Glu Thr Ala Asp Thr Val Leu Lys Lys Leu Asp Glu
        35                  40                  45

Gln Tyr Gln Lys Tyr Lys Phe Met Glu Leu Asn Leu Ala Gln Lys Lys
    50                  55                  60

Arg Arg Leu Lys Gly Gln Ile Pro Glu Ile Lys Gln Thr Leu Glu Ile
65                  70                  75                  80

Leu Lys Tyr Met Gln Lys Lys Glu Ser Thr Asn Ser Met Glu Thr
                85                  90                  95

Arg Phe Leu Leu Ala Asp Asn Leu Tyr Cys Lys Ala Ser Val Pro Pro
            100                 105                 110

Thr Asp Lys Val Cys Leu Trp Leu Gly Ala Asn Val Met Leu Glu Tyr
        115                 120                 125

Asp Ile Asp Glu Ala Gln Ala Leu Leu Glu Lys Asn Leu Ser Thr Ala
    130                 135                 140

Thr Lys Asn Leu Asp Ser Leu Glu Glu Asp Leu Asp Phe Leu Arg Asp
145                 150                 155                 160

Gln Phe Thr Thr Thr Glu Val Asn Met Ala Arg Val Tyr Asn Trp Asp
                165                 170                 175

Val Lys Arg Arg Asn Lys Asp Asp Ser Thr Lys Asn Lys Ala
            180                 185                 190
```

<210> SEQ ID NO 39
<211> LENGTH: 197
<212> TYPE: PRT
<213> ORGANISM: Homo sapiens

<400> SEQUENCE: 39

```
Met Ala Ala Val Lys Asp Ser Cys Gly Lys Gly Glu Met Ala Thr Gly
1               5                   10                  15

Asn Gly Arg Arg Leu His Leu Gly Ile Pro Glu Ala Val Phe Val Glu
            20                  25                  30

Asp Val Asp Ser Phe Met Lys Gln Pro Gly Asn Glu Thr Ala Asp Thr
        35                  40                  45

Val Leu Lys Lys Leu Asp Glu Gln Tyr Gln Lys Tyr Lys Phe Met Glu
    50                  55                  60
```

```
Leu Asn Leu Ala Gln Lys Lys Arg Leu Lys Gly Gln Ile Pro Glu
 65                  70                  75                  80

Ile Lys Gln Thr Leu Glu Ile Leu Lys Tyr Met Gln Lys Lys Lys Glu
                 85                  90                  95

Ser Thr Asn Ser Met Glu Thr Arg Phe Leu Leu Ala Asp Asn Leu Tyr
            100                 105                 110

Cys Lys Ala Ser Val Pro Pro Thr Asp Lys Val Cys Leu Trp Leu Gly
        115                 120                 125

Ala Asn Val Met Leu Glu Tyr Asp Ile Asp Glu Ala Gln Ala Leu Leu
    130                 135                 140

Glu Lys Asn Leu Ser Thr Ala Thr Lys Asn Leu Asp Ser Leu Glu Glu
145                 150                 155                 160

Asp Leu Asp Phe Leu Arg Asp Gln Phe Thr Thr Thr Glu Val Asn Met
                165                 170                 175

Ala Arg Val Tyr Asn Trp Asp Val Lys Arg Arg Asn Lys Asp Asp Ser
            180                 185                 190

Thr Lys Asn Lys Ala
            195

<210> SEQ ID NO 40
<211> LENGTH: 272
<212> TYPE: PRT
<213> ORGANISM: Homo sapiens

<400> SEQUENCE: 40

Phe Ala Ala Gln Thr Met Lys Met Lys Ile Gln Thr Ser Phe Tyr Glu
 1               5                  10                  15

Leu Pro Thr Asp Ser His Ala Ser Leu Arg Asp Ser Leu Leu Thr His
                 20                  25                  30

Ile Gln Asn Leu Lys Asp Leu Ser Pro Val Ile Val Thr Gln Leu Ala
             35                  40                  45

Leu Ala Ile Ala Asp Leu Ala Leu Gln Met Pro Ser Trp Lys Gly Cys
         50                  55                  60

Val Gln Thr Leu Val Glu Lys Tyr Ser Asn Asp Val Thr Ser Leu Pro
 65                  70                  75                  80

Phe Leu Leu Glu Ile Leu Thr Val Leu Pro Glu Glu Val His Ser Arg
                 85                  90                  95

Ser Leu Arg Ile Gly Ala Asn Arg Arg Thr Glu Ile Ile Glu Asp Leu
            100                 105                 110

Ala Phe Tyr Ser Ser Thr Val Val Ser Leu Leu Met Thr Cys Val Glu
        115                 120                 125

Lys Ala Gly Thr Asp Glu Lys Met Leu Met Lys Val Phe Arg Cys Leu
    130                 135                 140

Gly Ser Trp Phe Asn Leu Gly Val Leu Asp Ser Asn Phe Met Ala Asn
145                 150                 155                 160

Asn Lys Leu Leu Ala Leu Leu Phe Glu Val Leu Gln Gln Asp Lys Thr
                165                 170                 175

Ser Ser Asn Leu His Glu Ala Ala Ser Asp Cys Val Cys Ser Ala Leu
            180                 185                 190

Tyr Ala Ile Glu Asn Val Glu Thr Asn Leu Pro Leu Ala Met Gln Leu
        195                 200                 205

Phe Gln Gly Val Leu Thr Leu Glu Thr Ala Tyr His Met Ala Val Ala
    210                 215                 220

Arg Glu Asp Leu Asp Lys Val Leu Asn Tyr Cys Arg Ile Phe Thr Glu
225                 230                 235                 240
```

Leu Cys Glu Thr Phe Leu Glu Lys Ile Val Cys Thr Pro Gly Gln Gly
                245                 250                 255

Leu Gly Asp Leu Arg Thr Leu Glu Leu Leu Ile Cys Ala Gly His
                260                 265                 270

<210> SEQ ID NO 41
<211> LENGTH: 235
<212> TYPE: PRT
<213> ORGANISM: Homo sapiens

<400> SEQUENCE: 41

Ser Lys Tyr Ser Ser Leu Glu Gln Ser Glu Arg Arg Arg Arg Leu Leu
1               5                   10                  15

Glu Leu Gln Lys Ser Lys Arg Leu Asp Tyr Val Asn His Ala Arg Arg
            20                  25                  30

Leu Ala Glu Asp Asp Trp Thr Gly Met Glu Ser Glu Glu Glu Asn Lys
        35                  40                  45

Lys Asp Asp Glu Glu Met Asp Ile Asp Thr Val Lys Lys Leu Pro Lys
50                  55                  60

His Tyr Ala Asn Gln Leu Met Leu Ser Glu Trp Leu Ile Asp Val Pro
65                  70                  75                  80

Ser Asp Leu Gly Gln Glu Trp Ile Val Val Cys Pro Val Gly Lys
                85                  90                  95

Arg Ala Leu Ile Val Ala Ser Arg Gly Ser Thr Ser Ala Tyr Thr Lys
            100                 105                 110

Ser Gly Tyr Cys Val Asn Arg Phe Ser Ser Leu Leu Pro Gly Gly Asn
        115                 120                 125

Arg Arg Asn Ser Thr Ala Lys Asp Tyr Thr Ile Leu Asp Cys Ile Tyr
130                 135                 140

Asn Glu Val Asn Gln Thr Tyr Tyr Val Leu Asp Val Met Cys Trp Arg
145                 150                 155                 160

Gly His Pro Phe Tyr Asp Cys Gln Thr Asp Phe Arg Phe Tyr Trp Met
                165                 170                 175

His Ser Lys Leu Pro Glu Glu Glu Gly Leu Gly Glu Lys Thr Lys Leu
            180                 185                 190

Asn Pro Phe Lys Phe Val Gly Leu Lys Asn Phe Pro Cys Thr Pro Glu
        195                 200                 205

Ser Leu Cys Asp Val Leu Ser Met Asp Phe Pro Phe Glu Val Asp Gly
    210                 215                 220

Leu Leu Phe Tyr His Lys Gln Thr His Tyr Ser
225                 230                 235

<210> SEQ ID NO 42
<211> LENGTH: 279
<212> TYPE: PRT
<213> ORGANISM: Homo sapiens

<400> SEQUENCE: 42

Gly Ser Asn Met Ile Lys Thr Ile Ala Phe Gly Arg Tyr Glu Leu Asp
1               5                   10                  15

Thr Trp Tyr His Ser Pro Tyr Pro Glu Glu Tyr Ala Arg Leu Gly Arg
            20                  25                  30

Leu Tyr Met Cys Glu Phe Cys Leu Lys Tyr Met Lys Ser Gln Thr Ile
        35                  40                  45

Leu Arg Arg His Met Ala Lys Cys Val Trp Lys His Pro Pro Gly Asp
    50                  55                  60

```
Glu Ile Tyr Arg Lys Gly Ser Ile Ser Val Phe Glu Val Asp Gly Lys
 65                  70                  75                  80

Lys Asn Lys Ile Tyr Cys Gln Asn Leu Cys Leu Leu Ala Lys Leu Phe
                 85                  90                  95

Leu Asp His Lys Thr Leu Tyr Tyr Asp Val Glu Pro Phe Leu Phe Tyr
            100                 105                 110

Val Met Thr Glu Ala Asp Asn Thr Gly Cys His Leu Ile Gly Tyr Phe
        115                 120                 125

Ser Lys Glu Lys Asn Ser Phe Leu Asn Tyr Asn Val Ser Cys Ile Leu
    130                 135                 140

Thr Met Pro Gln Tyr Met Arg Gln Gly Tyr Gly Lys Met Leu Ile Asp
145                 150                 155                 160

Phe Ser Tyr Leu Leu Ser Lys Val Glu Lys Val Gly Ser Pro Glu
                165                 170                 175

Arg Pro Leu Ser Asp Leu Gly Leu Ile Ser Tyr Arg Ser Tyr Trp Lys
            180                 185                 190

Glu Val Leu Leu Arg Tyr Leu His Asn Phe Gln Gly Lys Glu Ile Ser
        195                 200                 205

Ile Lys Glu Ile Ser Gln Glu Thr Ala Val Asn Pro Val Asp Ile Val
    210                 215                 220

Ser Thr Leu Gln Ala Leu Gln Met Leu Lys Tyr Trp Lys Gly Lys His
225                 230                 235                 240

Leu Val Leu Lys Arg Gln Asp Leu Ile Asp Glu Trp Ile Ala Lys Glu
                245                 250                 255

Ala Lys Arg Ser Asn Ser Asn Lys Thr Met Asp Pro Ser Cys Leu Lys
            260                 265                 270

Trp Thr Pro Pro Lys Gly Thr
            275

<210> SEQ ID NO 43
<211> LENGTH: 268
<212> TYPE: PRT
<213> ORGANISM: Homo sapiens

<400> SEQUENCE: 43

Ile Lys Thr Ile Ala Phe Gly Arg Tyr Glu Leu Asp Thr Trp Tyr His
  1               5                  10                  15

Ser Pro Tyr Pro Glu Glu Tyr Ala Arg Leu Gly Arg Leu Tyr Met Cys
                 20                  25                  30

Glu Phe Cys Leu Lys Tyr Met Lys Ser Gln Thr Ile Leu Arg Arg His
             35                  40                  45

Met Ala Lys Cys Val Trp Lys His Pro Pro Gly Asp Glu Ile Tyr Arg
         50                  55                  60

Lys Gly Ser Ile Ser Val Phe Glu Val Asp Gly Lys Lys Asn Lys Ile
 65                  70                  75                  80

Tyr Cys Gln Asn Leu Cys Leu Leu Ala Lys Leu Phe Leu Asp His Lys
                 85                  90                  95

Thr Leu Tyr Tyr Asp Val Glu Pro Phe Leu Phe Tyr Val Met Thr Glu
            100                 105                 110

Ala Asp Asn Thr Gly Cys His Leu Ile Gly Tyr Phe Ser Lys Glu Lys
        115                 120                 125

Asn Ser Phe Leu Asn Tyr Asn Val Ser Cys Ile Leu Thr Met Pro Gln
    130                 135                 140

Tyr Met Arg Gln Gly Tyr Gly Lys Met Leu Ile Asp Phe Ser Tyr Leu
```

-continued

```
              145                 150                 155                 160
Leu Ser Lys Val Glu Lys Val Gly Ser Pro Glu Arg Pro Leu Ser
                    165                 170                 175

Asp Leu Gly Leu Ile Ser Tyr Arg Ser Tyr Trp Lys Glu Val Leu Leu
            180                 185                 190

Arg Tyr Leu His Asn Phe Gln Gly Lys Glu Ile Ser Ile Lys Glu Ile
            195                 200                 205

Ser Gln Glu Thr Ala Val Asn Pro Val Asp Ile Val Ser Thr Leu Gln
            210                 215                 220

Ala Leu Gln Met Leu Lys Tyr Trp Lys Gly Lys His Leu Val Leu Lys
225                 230                 235                 240

Arg Gln Asp Leu Ile Asp Glu Trp Ile Ala Lys Glu Ala Lys Arg Ser
                245                 250                 255

Asn Ser Asn Lys Thr Met Asp Pro Ser Cys Leu Lys
            260                 265

<210> SEQ ID NO 44
<211> LENGTH: 136
<212> TYPE: PRT
<213> ORGANISM: Homo sapiens

<400> SEQUENCE: 44

Ala Tyr Val Glu Met Arg Arg Glu Ala Trp Ser Lys Asp Ala Thr
1               5                   10                  15

Tyr Thr Ser Ala Arg Thr Leu Leu Ala Ile Leu Arg Leu Ser Thr Ala
                20                  25                  30

Leu Ala Arg Leu Arg Met Val Asp Val Val Glu Lys Glu Asp Val Asn
            35                  40                  45

Glu Ala Ile Arg Leu Met Glu Met Ser Lys Asp Ser Leu Leu Gly Asp
        50                  55                  60

Lys Gly Gln Thr Ala Arg Thr Gln Arg Pro Ala Asp Val Ile Phe Ala
65                  70                  75                  80

Thr Val Arg Glu Leu Val Ser Gly Gly Arg Ser Val Arg Phe Ser Glu
                85                  90                  95

Ala Glu Gln Arg Cys Val Ser Arg Gly Phe Thr Pro Ala Gln Phe Gln
            100                 105                 110

Ala Ala Leu Asp Glu Tyr Glu Leu Asn Val Trp Gln Val Asn Ala
            115                 120                 125

Ser Arg Thr Arg Ile Thr Phe Val
        130                 135

<210> SEQ ID NO 45
<211> LENGTH: 347
<212> TYPE: PRT
<213> ORGANISM: Homo sapiens

<400> SEQUENCE: 45

Glu Gly Thr Gly Ser Thr Ala Thr Ser Ser Ser Thr Ala Gly Ala
1               5                   10                  15

Ala Gly Lys Gly Lys Gly Lys Gly Gly Ser Gly Asp Ser Ala Val Lys
                20                  25                  30

Gln Val Gln Ile Asp Gly Leu Val Val Leu Lys Ile Ile Lys His Tyr
            35                  40                  45

Gln Glu Glu Gly Gln Gly Thr Glu Val Val Gln Gly Val Leu Leu Gly
        50                  55                  60

Leu Val Val Glu Asp Arg Leu Glu Ile Thr Asn Cys Phe Pro Phe Pro
```

```
                65                  70                  75                  80
Gln His Thr Glu Asp Asp Ala Asp Phe Asp Glu Val Gln Tyr Gln Met
                    85                  90                  95
Glu Met Met Arg Ser Leu Arg His Val Asn Ile Asp His Leu His Val
            100                 105                 110
Gly Trp Tyr Gln Ser Thr Tyr Tyr Gly Ser Phe Val Thr Arg Ala Leu
        115                 120                 125
Leu Asp Ser Gln Phe Ser Tyr Gln His Ala Ile Glu Glu Ser Val Val
    130                 135                 140
Leu Ile Tyr Asp Pro Ile Lys Thr Ala Gln Gly Ser Leu Ser Leu Lys
145                 150                 155                 160
Ala Tyr Arg Leu Thr Pro Lys Leu Met Glu Val Cys Lys Glu Lys Asp
                165                 170                 175
Phe Ser Pro Glu Ala Leu Lys Lys Ala Asn Ile Thr Phe Glu Tyr Met
            180                 185                 190
Phe Glu Glu Val Pro Ile Val Ile Lys Asn Ser His Leu Ile Asn Val
        195                 200                 205
Leu Met Trp Glu Leu Glu Lys Lys Ser Ala Val Ala Asp Lys His Glu
    210                 215                 220
Leu Leu Ser Leu Ala Ser Ser Asn His Leu Gly Lys Asn Leu Gln Leu
225                 230                 235                 240
Leu Met Asp Arg Val Asp Glu Met Ser Gln Asp Ile Val Lys Tyr Asn
                245                 250                 255
Thr Tyr Met Arg Asn Thr Ser Lys Gln Gln Gln Lys His Gln Tyr
            260                 265                 270
Gln Gln Arg Arg Gln Gln Glu Asn Met Gln Arg Gln Ser Arg Gly Glu
        275                 280                 285
Pro Pro Leu Pro Glu Glu Asp Leu Ser Lys Leu Phe Lys Pro Pro Gln
    290                 295                 300
Pro Pro Ala Arg Met Asp Ser Leu Leu Ile Ala Gly Gln Ile Asn Thr
305                 310                 315                 320
Tyr Cys Gln Asn Ile Lys Glu Phe Thr Ala Gln Asn Leu Gly Lys Leu
                325                 330                 335
Phe Met Ala Gln Ala Leu Gln Glu Tyr Asn Asn
            340                 345

<210> SEQ ID NO 46
<211> LENGTH: 302
<212> TYPE: PRT
<213> ORGANISM: Homo sapiens

<400> SEQUENCE: 46

Lys Glu Gly Thr Gly Ser Thr Ala Thr Ser Ser Ser Thr Ala Gly
1               5                   10                  15
Ala Ala Gly Lys Gly Lys Gly Lys Gly Ser Gly Asp Ser Ala Val
            20                  25                  30
Lys Gln Val Gln Ile Asp Gly Leu Val Val Leu Lys Ile Ile Lys His
        35                  40                  45
Tyr Gln Glu Glu Gly Gln Gly Thr Glu Val Val Gln Gly Val Leu Leu
    50                  55                  60
Gly Leu Val Val Glu Asp Arg Leu Glu Ile Thr Asn Cys Phe Pro Phe
65                  70                  75                  80
Pro Gln His Thr Glu Asp Asp Ala Asp Phe Asp Glu Val Gln Tyr Gln
                85                  90                  95
```

```
Met Glu Met Met Arg Ser Leu Arg His Val Asn Ile Asp His Leu His
             100                 105                 110
Val Gly Trp Tyr Gln Ser Thr Tyr Tyr Gly Ser Phe Val Thr Arg Ala
         115                 120                 125
Leu Leu Asp Ser Gln Phe Ser Tyr Gln His Ala Ile Glu Glu Ser Val
     130                 135                 140
Val Leu Ile Tyr Asp Pro Ile Lys Thr Ala Gln Gly Ser Leu Ser Leu
145                 150                 155                 160
Lys Ala Tyr Arg Leu Thr Pro Lys Leu Met Glu Val Cys Lys Glu Lys
                165                 170                 175
Asp Phe Ser Pro Glu Ala Leu Lys Lys Ala Asn Ile Thr Phe Glu Tyr
            180                 185                 190
Met Phe Glu Glu Val Pro Ile Val Ile Lys Asn Ser His Leu Ile Asn
        195                 200                 205
Val Leu Met Trp Glu Leu Glu Lys Lys Ser Ala Val Ala Asp Lys His
    210                 215                 220
Glu Leu Leu Ser Leu Ala Ser Ser Asn His Leu Gly Lys Asn Leu Gln
225                 230                 235                 240
Leu Leu Met Asp Arg Val Asp Glu Met Ser Gln Asp Ile Val Lys Tyr
                245                 250                 255
Asn Thr Tyr Met Arg Asn Thr Ser Lys Gln Gln Gln Lys His Gln
            260                 265                 270
Tyr Gln Gln Arg Arg Gln Gln Glu Asn Met Gln Arg Gln Ser Arg Gly
        275                 280                 285
Glu Pro Pro Leu Pro Glu Glu Asp Leu Ser Lys Leu Phe Lys
    290                 295                 300

<210> SEQ ID NO 47
<211> LENGTH: 151
<212> TYPE: PRT
<213> ORGANISM: Homo sapiens

<400> SEQUENCE: 47

Met Ala Ala Glu Leu Val Glu Ala Lys Asn Met Val Met Ser Phe Arg
1               5                   10                  15
Val Ser Asp Leu Gln Met Leu Leu Gly Phe Val Gly Arg Ser Lys Ser
            20                  25                  30
Gly Leu Lys His Glu Leu Val Thr Arg Ala Leu Gln Leu Val Gln Phe
        35                  40                  45
Asp Cys Ser Pro Glu Leu Phe Lys Lys Ile Lys Glu Leu Tyr Glu Thr
    50                  55                  60
Arg Tyr Ala Lys Lys Asn Ser Glu Pro Ala Pro Gln Pro His Arg Pro
65                  70                  75                  80
Leu Asp Pro Leu Thr Met His Ser Thr Tyr Asp Arg Ala Gly Ala Val
                85                  90                  95
Pro Arg Thr Pro Leu Ala Gly Pro Asn Ile Asp Tyr Pro Val Leu Tyr
            100                 105                 110
Gly Lys Tyr Leu Asn Gly Leu Gly Arg Leu Pro Ala Lys Thr Leu Lys
        115                 120                 125
Pro Glu Val Arg Leu Val Lys Leu Pro Phe Phe Asn Met Leu Asp Glu
    130                 135                 140
Leu Leu Lys Pro Thr Glu Leu
145                 150

<210> SEQ ID NO 48
```

```
<211> LENGTH: 270
<212> TYPE: PRT
<213> ORGANISM: Homo sapiens

<400> SEQUENCE: 48

Val Cys Gln Ala Ser Gln Leu Gln Gly Gln Lys Glu Glu Ser Cys Val
1               5                   10                  15

Pro Val His Gln Lys Thr Val Leu Gly Pro Asp Thr Ala Glu Pro Ala
            20                  25                  30

Thr Ala Glu Ala Ala Val Ala Pro Asp Ala Gly Leu Pro Leu Pro
        35                  40                  45

Gly Leu Pro Ala Glu Gly Ser Pro Pro Lys Thr Tyr Val Ser Cys
    50                  55                  60

Leu Lys Ser Leu Leu Ser Ser Pro Thr Lys Asp Ser Lys Pro Asn Ile
65                  70                  75                  80

Ser Ala His His Ile Ser Leu Ala Ser Cys Leu Ala Leu Thr Thr Pro
                85                  90                  95

Ser Glu Glu Leu Pro Asp Arg Ala Gly Ile Leu Val Glu Asp Ala Thr
                100                 105                 110

Cys Val Thr Cys Met Ser Asp Ser Ser Gln Ser Val Pro Leu Val Ala
            115                 120                 125

Ser Pro Gly His Cys Ser Asp Ser Phe Ser Thr Ser Gly Leu Glu Asp
        130                 135                 140

Ser Cys Thr Glu Thr Ser Ser Pro Arg Asp Lys Ala Ile Thr Pro
145                 150                 155                 160

Pro Leu Pro Glu Ser Thr Val Pro Phe Ser Asn Gly Val Leu Lys Gly
                165                 170                 175

Glu Leu Ser Asp Leu Gly Ala Glu Asp Gly Trp Thr Met Asp Ala Glu
            180                 185                 190

Ala Asp His Ser Gly Gly Ser Asp Arg Asn Ser Met Asp Ser Val Asp
        195                 200                 205

Ser Cys Cys Ser Leu Lys Lys Thr Glu Ser Phe Gln Asn Ala Gln Ala
    210                 215                 220

Gly Ser Asn Pro Lys Lys Val Asp Leu Ile Ile Trp Glu Ile Glu Val
225                 230                 235                 240

Pro Lys His Leu Val Gly Arg Leu Ile Gly Lys Gln Gly Arg Tyr Val
                245                 250                 255

Ser Phe Leu Lys Gln Thr Ser Gly Ala Lys Ile Tyr Ile Ser
            260                 265                 270

<210> SEQ ID NO 49
<211> LENGTH: 40
<212> TYPE: PRT
<213> ORGANISM: Homo sapiens

<400> SEQUENCE: 49

Phe Gly Phe Val Thr Met Thr Asn Tyr Glu Glu Ala Ala Met Ala Ile
1               5                   10                  15

Ala Ser Leu Asn Gly Tyr Arg Leu Gly Asp Lys Ile Leu Gln Val Ser
            20                  25                  30

Phe Lys Thr Asn Lys Ser His Lys
        35                  40

<210> SEQ ID NO 50
<211> LENGTH: 60
<212> TYPE: PRT
<213> ORGANISM: Homo sapiens
```

<400> SEQUENCE: 50

Met Ser Ser Ser Glu Val Ser Trp Ile Ser Trp Phe Cys Gly Leu
1               5                   10                  15

Arg Gly Asn Glu Phe Phe Cys Glu Val Asp Glu Asp Tyr Ile Gln Asp
            20                  25                  30

Lys Phe Asn Leu Thr Gly Leu Asn Glu Gln Val Pro His Tyr Arg Gln
            35                  40                  45

Ala Leu Asp Met Ile Leu Asp Leu Glu Pro Asp Glu
    50                  55                  60

<210> SEQ ID NO 51
<211> LENGTH: 962
<212> TYPE: PRT
<213> ORGANISM: Homo sapiens

<400> SEQUENCE: 51

Glu Met Ser Pro Ala Leu His Leu Met Gln Asn Leu Asp Thr Lys Ser
1               5                   10                  15

Lys Leu Arg Pro Lys Arg Ala Ser Ala Glu Gln Ser Val Leu Phe Lys
            20                  25                  30

Ser Leu His Thr Asn Thr Asn Gly Asn Ser Glu Pro Leu Val Met Pro
            35                  40                  45

Glu Ile Asn Asp Lys Glu Asn Arg Asp Val Thr Asn Gly Gly Ile Lys
    50                  55                  60

Arg Ser Arg Leu Glu Lys Ser Ala Leu Phe Ser Ser Leu Leu Ser Ser
65                  70                  75                  80

Leu Pro Gln Asp Lys Ile Phe Ser Pro Ser Val Thr Ser Val Asn Thr
            85                  90                  95

Met Thr Thr Ala Phe Ser Thr Ser Gln Asn Gly Ser Leu Ser Gln Ser
            100                 105                 110

Ser Val Ser Gln Pro Thr Thr Glu Gly Ala Pro Pro Cys Gly Leu Asn
            115                 120                 125

Lys Glu Gln Ser Asn Leu Leu Pro Asp Asn Ser Leu Lys Val Phe Asn
    130                 135                 140

Phe Asn Ser Ser Thr Ser His Ser Ser Leu Lys Ser Pro Ser His
145                 150                 155                 160

Met Glu Lys Tyr Pro Gln Lys Glu Lys Thr Lys Glu Asp Leu Asp Ser
                165                 170                 175

Arg Ser Asn Leu His Leu Pro Glu Thr Lys Phe Ser Glu Leu Ser Lys
            180                 185                 190

Leu Lys Asn Asp Asp Met Glu Lys Ala Asn His Ile Glu Ser Val Ile
            195                 200                 205

Lys Ser Asn Leu Pro Asn Cys Ala Asn Ser Thr Asp Phe Met Gly
    210                 215                 220

Leu Phe Lys Ser Ser Arg Tyr Asp Pro Ser Ile Ser Phe Ser Gly Met
225                 230                 235                 240

Ser Leu Ser Asp Thr Met Thr Leu Arg Gly Ser Val Gln Asn Lys Leu
                245                 250                 255

Asn Pro Arg Pro Gly Lys Val Val Ile Tyr Ser Glu Pro Asp Val Ser
            260                 265                 270

Glu Lys Cys Ile Glu Val Phe Ser Asp Ile Gln Asp Cys Ser Ser Trp
            275                 280                 285

Ser Leu Ser Pro Val Ile Leu Ile Lys Val Val Arg Gly Cys Trp Ile
    290                 295                 300

-continued

```
Leu Tyr Glu Gln Pro Asn Phe Glu Gly His Ser Ile Pro Leu Glu Glu
305                 310                 315                 320

Gly Glu Leu Glu Leu Ser Gly Leu Trp Gly Ile Glu Asp Ile Leu Glu
            325                 330                 335

Arg His Glu Glu Ala Glu Ser Asp Lys Pro Val Val Ile Gly Ser Ile
            340                 345                 350

Arg His Val Val Gln Asp Tyr Arg Val Ser His Ile Asp Leu Phe Thr
            355                 360                 365

Glu Pro Glu Gly Leu Gly Ile Leu Ser Ser Tyr Phe Asp Asp Thr Glu
370                 375                 380

Glu Met Gln Gly Phe Gly Val Met Gln Lys Thr Cys Ser Met Lys Val
385                 390                 395                 400

His Trp Gly Thr Trp Leu Ile Tyr Glu Glu Pro Gly Phe Gln Gly Val
            405                 410                 415

Pro Phe Ile Leu Glu Pro Gly Glu Tyr Pro Asp Leu Ser Phe Trp Asp
            420                 425                 430

Thr Glu Glu Ala Tyr Ile Gly Ser Met Arg Pro Leu Lys Met Gly Gly
            435                 440                 445

Arg Lys Val Glu Phe Pro Thr Asp Pro Lys Val Val Tyr Glu Lys
450                 455                 460

Pro Phe Phe Glu Gly Lys Cys Val Glu Leu Glu Thr Gly Met Cys Ser
465                 470                 475                 480

Phe Val Met Glu Gly Gly Glu Thr Glu Ala Thr Gly Asp Asp His
            485                 490                 495

Leu Pro Phe Thr Ser Val Gly Ser Met Lys Val Leu Arg Gly Ile Trp
            500                 505                 510

Val Ala Tyr Glu Lys Pro Gly Phe Thr Gly His Gln Tyr Leu Leu Glu
            515                 520                 525

Glu Gly Glu Tyr Arg Asp Trp Lys Ala Trp Gly Gly Tyr Asn Gly Glu
            530                 535                 540

Leu Gln Ser Leu Arg Pro Ile Leu Gly Asp Phe Ser Asn Ala His Met
545                 550                 555                 560

Ile Met Tyr Ser Glu Lys Asn Phe Gly Ser Lys Gly Ser Ser Ile Asp
                565                 570                 575

Val Leu Gly Ile Val Ala Asn Leu Lys Glu Thr Gly Tyr Gly Val Lys
            580                 585                 590

Thr Gln Ser Ile Asn Val Leu Ser Gly Val Trp Val Ala Tyr Glu Asn
            595                 600                 605

Pro Asp Phe Thr Gly Glu Gln Tyr Ile Leu Asp Lys Gly Phe Tyr Thr
            610                 615                 620

Ser Phe Glu Asp Trp Gly Gly Lys Asn Cys Lys Ile Ser Ser Val Gln
625                 630                 635                 640

Pro Ile Cys Leu Asp Ser Phe Thr Gly Pro Arg Arg Asn Gln Ile
            645                 650                 655

His Leu Phe Ser Glu Pro Gln Phe Gln Gly His Ser Gln Ser Phe Glu
            660                 665                 670

Glu Thr Thr Ser Gln Ile Asp Asp Ser Phe Ser Thr Lys Ser Cys Arg
            675                 680                 685

Val Ser Gly Gly Ser Trp Val Val Tyr Asp Gly Glu Asn Phe Thr Gly
            690                 695                 700

Asn Gln Tyr Val Leu Glu Glu Gly His Tyr Pro Cys Leu Ser Ala Met
705                 710                 715                 720
```

```
Gly Cys Pro Pro Gly Ala Thr Phe Lys Ser Leu Arg Phe Ile Asp Val
                725                 730                 735

Glu Phe Ser Glu Pro Thr Ile Ile Leu Phe Glu Arg Glu Asp Phe Lys
            740                 745                 750

Gly Lys Lys Ile Glu Leu Asn Ala Glu Thr Val Asn Leu Arg Ser Leu
        755                 760                 765

Gly Phe Asn Thr Gln Ile Arg Ser Val Gln Val Ile Gly Gly Ile Trp
    770                 775                 780

Val Thr Tyr Glu Tyr Gly Ser Tyr Arg Gly Arg Gln Phe Leu Leu Ser
785                 790                 795                 800

Pro Ala Glu Val Pro Asn Trp Tyr Glu Phe Ser Gly Cys Arg Gln Ile
                805                 810                 815

Gly Ser Leu Arg Pro Phe Val Gln Lys Arg Ile Tyr Phe Arg Leu Arg
            820                 825                 830

Asn Lys Ala Thr Gly Leu Phe Met Ser Thr Asn Gly Asn Leu Glu Asp
        835                 840                 845

Leu Lys Leu Leu Arg Ile Gln Val Met Glu Asp Val Gly Ala Asp Asp
    850                 855                 860

Gln Ile Trp Ile Tyr Gln Glu Gly Cys Ile Lys Cys Arg Ile Ala Glu
865                 870                 875                 880

Asp Cys Cys Leu Thr Ile Val Gly Ser Leu Val Thr Ser Gly Ser Lys
                885                 890                 895

Leu Gly Leu Ala Leu Asp Gln Asn Ala Asp Ser Gln Phe Trp Ser Leu
            900                 905                 910

Lys Ser Asp Gly Arg Ile Tyr Ser Lys Leu Lys Pro Asn Leu Val Leu
        915                 920                 925

Asp Ile Lys Gly Gly Thr Gln Tyr Asp Gln Asn His Ile Ile Leu Asn
    930                 935                 940

Thr Val Ser Lys Glu Lys Phe Thr Gln Val Trp Glu Ala Met Val Leu
945                 950                 955                 960

Tyr Thr

<210> SEQ ID NO 52
<211> LENGTH: 227
<212> TYPE: PRT
<213> ORGANISM: Homo sapiens

<400> SEQUENCE: 52

Lys Leu Arg Pro Lys Arg Ala Ser Ala Glu Gln Ser Val Leu Phe Lys
1               5                   10                  15

Ser Leu His Thr Asn Thr Asn Gly Asn Ser Glu Pro Leu Val Met Pro
            20                  25                  30

Glu Ile Asn Asp Lys Glu Asn Arg Asp Val Thr Asn Gly Gly Ile Lys
        35                  40                  45

Arg Ser Arg Leu Glu Lys Ser Ala Leu Phe Ser Ser Leu Leu Ser Ser
    50                  55                  60

Leu Pro Gln Asp Lys Ile Phe Ser Pro Ser Val Thr Ser Val Asn Thr
65                  70                  75                  80

Met Thr Thr Ala Phe Ser Thr Ser Gln Asn Gly Ser Leu Ser Gln Ser
                85                  90                  95

Ser Val Ser Gln Pro Thr Thr Glu Gly Ala Pro Pro Cys Gly Leu Asn
            100                 105                 110

Lys Glu Gln Ser Asn Leu Leu Pro Asp Asn Ser Leu Lys Val Phe Asn
        115                 120                 125
```

```
Phe Asn Ser Ser Ser Thr Ser His Ser Ser Leu Lys Ser Pro Ser His
    130                 135                 140

Met Glu Lys Tyr Pro Gln Lys Glu Lys Thr Lys Glu Asp Leu Asp Ser
145                 150                 155                 160

Arg Ser Asn Leu His Leu Pro Glu Thr Lys Phe Ser Glu Leu Ser Lys
                165                 170                 175

Leu Lys Asn Asp Asp Met Glu Lys Ala Asn His Ile Glu Ser Val Ile
            180                 185                 190

Lys Ser Asn Leu Pro Asn Cys Ala Asn Ser Asp Thr Asp Phe Met Gly
        195                 200                 205

Leu Phe Lys Ser Ser Arg Tyr Asp Pro Ser Ile Ser Phe Ser Gly Met
    210                 215                 220

Ser Leu Ser
225

<210> SEQ ID NO 53
<211> LENGTH: 130
<212> TYPE: PRT
<213> ORGANISM: Homo sapiens

<400> SEQUENCE: 53

Leu Ala Leu Pro Phe Phe Gly Phe Ser Glu Pro Leu Ala Ala Pro Arg
1               5                   10                  15

His Gln Tyr Tyr Asn Gln Glu Trp Thr Leu Trp Asp Arg Phe Glu Val
            20                  25                  30

Gln Gly Leu Gln Pro Asn Gly Glu Glu Met Thr Leu Lys Gln Phe Leu
        35                  40                  45

Asp Tyr Phe Lys Thr Glu His Lys Leu Glu Ile Thr Met Leu Ser Gln
    50                  55                  60

Gly Val Ser Met Leu Tyr Ser Phe Phe Met Pro Ala Ala Lys Leu Lys
65                  70                  75                  80

Glu Arg Leu Asp Gln Pro Met Thr Glu Ile Val Ser Arg Val Ser Lys
                85                  90                  95

Arg Lys Leu Gly Arg His Val Arg Ala Leu Val Leu Glu Leu Cys Cys
            100                 105                 110

Asn Asp Glu Ser Gly Glu Asp Val Glu Val Pro Tyr Val Arg Tyr Thr
        115                 120                 125

Ile Arg
    130

<210> SEQ ID NO 54
<211> LENGTH: 155
<212> TYPE: PRT
<213> ORGANISM: Homo sapiens

<400> SEQUENCE: 54

Leu Thr Glu Gly Gly Lys Gly Ser Ser Pro Ser Ile Arg Pro Ile Gln
1               5                   10                  15

Gly Ser Gln Gly Ser Ser Ser Pro Val Glu Lys Glu Val Val Glu Ala
            20                  25                  30

Thr Asp Ser Arg Glu Lys Thr Gly Met Val Arg Pro Gly Glu Pro Leu
        35                  40                  45

Ser Gly Glu Lys Tyr Ser Pro Lys Glu Leu Leu Ala Leu Leu Lys Cys
    50                  55                  60

Val Glu Ala Glu Ile Ala Asn Tyr Glu Ala Cys Leu Lys Glu Glu Val
65                  70                  75                  80
```

```
Glu Lys Arg Lys Lys Phe Lys Ile Asp Asp Gln Arg Arg Thr His Asn
                85                  90                  95

Tyr Asp Glu Phe Ile Cys Thr Phe Ile Ser Met Leu Ala Gln Glu Gly
            100                 105                 110

Met Leu Ala Asn Leu Val Glu Gln Asn Ile Ser Val Arg Arg Arg Gln
        115                 120                 125

Gly Val Ser Ile Gly Arg Leu His Lys Gln Arg Lys Pro Asp Arg Arg
    130                 135                 140

Lys Arg Ser Arg Pro Tyr Lys Ala Lys Arg Gln
145                 150                 155

<210> SEQ ID NO 55
<211> LENGTH: 68
<212> TYPE: PRT
<213> ORGANISM: Homo sapiens

<400> SEQUENCE: 55

Ile Asp Asp Gln Arg Arg Thr His Asn Tyr Asp Glu Phe Ile Cys Thr
1               5                   10                  15

Phe Ile Ser Met Leu Ala Gln Glu Gly Met Leu Ala Asn Leu Val Glu
            20                  25                  30

Gln Asn Ile Ser Val Arg Arg Arg Gln Gly Val Ser Ile Gly Arg Leu
        35                  40                  45

His Lys Gln Arg Lys Pro Asp Arg Arg Lys Arg Ser Arg Pro Tyr Lys
    50                  55                  60

Ala Lys Arg Gln
65

<210> SEQ ID NO 56
<211> LENGTH: 129
<212> TYPE: PRT
<213> ORGANISM: Homo sapiens

<400> SEQUENCE: 56

Leu Gly Leu Glu Ala Arg Leu Lys Ala Ala Leu Ser Glu Asn Glu Gln
1               5                   10                  15

Leu Lys Lys Glu Asn Gly Thr Leu Lys Arg Gln Leu Asp Glu Val Val
            20                  25                  30

Ser Glu Asn Gln Arg Leu Lys Val Pro Ser Pro Lys Arg Arg Val Val
        35                  40                  45

Cys Val Met Ile Val Leu Ala Phe Ile Ile Leu Asn Tyr Gly Pro Met
    50                  55                  60

Ser Met Leu Glu Gln Asp Ser Arg Arg Met Asn Pro Ser Val Gly Pro
65                  70                  75                  80

Ala Asn Gln Arg Arg His Leu Leu Gly Phe Ser Ala Lys Glu Ala Gln
                85                  90                  95

Asp Thr Ser Asp Gly Ile Ile Gln Lys Asn Ser Tyr Arg Tyr Asp His
            100                 105                 110

Ser Val Ser Asn Asp Lys Ala Leu Met Val Leu Thr Glu Glu Pro Leu
        115                 120                 125

Leu

<210> SEQ ID NO 57
<211> LENGTH: 194
<212> TYPE: PRT
<213> ORGANISM: Homo sapiens

<400> SEQUENCE: 57
```

```
Met Pro Val Met Met Gly Gln Glu Lys Val Pro Ile Lys Gln Val Pro
1               5                   10                  15

Gly Gly Val Lys Gln Leu Glu Pro Pro Lys Glu Gly Glu Arg Arg Thr
            20                  25                  30

Thr His Asn Ile Ile Glu Lys Arg Tyr Arg Ser Ser Ile Asn Asp Lys
        35                  40                  45

Ile Ile Glu Leu Lys Asp Leu Val Met Gly Thr Asp Ala Lys Met His
    50                  55                  60

Lys Ser Gly Val Leu Arg Lys Ala Ile Asp Tyr Ile Lys Tyr Leu Gln
65                  70                  75                  80

Gln Val Asn His Lys Leu Arg Gln Glu Asn Met Val Leu Lys Leu Ala
                85                  90                  95

Asn Gln Lys Asn Lys Leu Leu Lys Gly Ile Asp Leu Gly Ser Leu Val
            100                 105                 110

Asp Asn Glu Val Asp Leu Lys Ile Glu Asp Phe Asn Gln Asn Val Leu
        115                 120                 125

Leu Met Ser Pro Pro Ala Ser Asp Ser Gly Ser Gln Ala Gly Phe Ser
    130                 135                 140

Pro Tyr Ser Ile Asp Ser Glu Pro Gly Ser Pro Leu Leu Asp Asp Ala
145                 150                 155                 160

Lys Val Lys Asp Glu Pro Asp Ser Pro Val Ala Leu Gly Met Val
                165                 170                 175

Asp Arg Ser Arg Ile Leu Leu Cys Val Leu Thr Phe Leu Cys Leu Ser
                180                 185                 190

Phe Asn

<210> SEQ ID NO 58
<211> LENGTH: 257
<212> TYPE: PRT
<213> ORGANISM: Homo sapiens

<400> SEQUENCE: 58

Leu Arg Leu Val Val Pro Ala Thr Gln Cys Gly Ser Leu Ile Gly Lys
1               5                   10                  15

Gly Gly Cys Lys Ile Lys Glu Ile Arg Glu Ser Thr Gly Ala Gln Val
            20                  25                  30

Gln Val Ala Gly Asp Met Leu Pro Asn Ser Thr Glu Arg Ala Ile Thr
        35                  40                  45

Ile Ala Gly Val Pro Gln Ser Val Thr Glu Cys Val Lys Gln Ile Cys
    50                  55                  60

Leu Val Met Leu Glu Thr Leu Ser Gln Ser Pro Gln Gly Arg Val Met
65                  70                  75                  80

Thr Ile Pro Tyr Gln Pro Met Pro Ala Ser Ser Pro Val Ile Cys Ala
                85                  90                  95

Gly Gly Gln Asp Arg Cys Ser Asp Ala Val Gly Tyr Pro His Ala Thr
            100                 105                 110

His Asp Leu Glu Gly Pro Pro Leu Asp Ala Tyr Ser Ile Gln Gly Gln
        115                 120                 125

His Thr Ile Ser Pro Leu Asp Leu Ala Lys Leu Asn Gln Val Ala Arg
    130                 135                 140

Gln Gln Ser His Phe Ala Met Met His Gly Thr Gly Phe Ala Gly
145                 150                 155                 160

Ile Asp Ser Ser Ser Pro Glu Val Lys Gly Tyr Trp Ala Ser Leu Asp
                165                 170                 175
```

```
Ala Ser Thr Gln Thr Thr His Glu Leu Thr Ile Pro Asn Asn Leu Ile
            180                 185                 190

Gly Cys Ile Ile Gly Arg Gln Gly Ala Asn Ile Asn Glu Ile Arg Gln
        195                 200                 205

Met Ser Gly Ala Gln Ile Lys Ile Ala Asn Pro Val Glu Gly Ser Ser
    210                 215                 220

Gly Arg Gln Val Thr Ile Thr Gly Ser Ala Ala Ser Ile Ser Leu Ala
225                 230                 235                 240

Gln Tyr Leu Ile Asn Ala Arg Leu Ser Ser Glu Lys Gly Met Gly Cys
                245                 250                 255

Ser
```

<210> SEQ ID NO 59
<211> LENGTH: 47
<212> TYPE: PRT
<213> ORGANISM: Homo sapiens

<400> SEQUENCE: 59

```
Gly Asp Met Leu Pro Asn Ser Thr Glu Arg Ala Ile Thr Ile Ala Gly
1               5                   10                  15

Val Pro Gln Ser Val Thr Glu Cys Val Lys Gln Ile Cys Leu Val Met
            20                  25                  30

Leu Glu Thr Leu Ser Gln Ser Pro Gln Gly Arg Val Met Thr Ile
        35                  40                  45
```

<210> SEQ ID NO 60
<211> LENGTH: 101
<212> TYPE: PRT
<213> ORGANISM: Homo sapiens

<400> SEQUENCE: 60

```
Ala Leu Ala Arg His Cys Gln Leu Glu Pro Asp His Glu Gly Val Pro
1               5                   10                  15

Glu Glu Thr Asp Asp Phe Gly Glu Phe Arg Met Arg Val Ser Asp Leu
            20                  25                  30

Val Lys Asp Leu Ile Phe Leu Ile Gly Ser Met Glu Cys Phe Ala Gln
        35                  40                  45

Leu Tyr Ser Thr Leu Lys Glu Gly Asn Pro Pro Trp Glu Val Thr Glu
    50                  55                  60

Ala Val Leu Phe Ile Met Ala Ala Ile Ala Lys Ser Val Asp Pro Glu
65                  70                  75                  80

Asn Asn Pro Thr Leu Val Glu Val Leu Glu Gly Val Val Arg Leu Pro
                85                  90                  95

Glu Thr Val His Thr
            100
```

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tcccccgggc ggaggctaga aggagagaga tgggtg                                 36

<210> SEQ ID NO 62

```
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tcccccgggg ctctaggtta ggatctactg gctccat                               37

<210> SEQ ID NO 63
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggccacgaa                                                             10

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ttcgtggccc ctg                                                         13

<210> SEQ ID NO 65
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
atcccggacg aaggcc                                                      16

<210> SEQ ID NO 66
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggccttcgtc cgg                                                         13

<210> SEQ ID NO 67
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tagccatggc cgcaggggcc gcggccgcac tagtggggat ccttaattaa gggccactgg      60
ggccccc                                                                67
```

<210> SEQ ID NO 68
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68 tcgaggggc cccagtggcc cttaattaag gatccccact agtgcggccg cggcccctgc    60
ggccatgg                                                            68

<210> SEQ ID NO 69
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ctagccatgg ccgcaggggc cgcggccgca ctagtgggga tccttaatta agggccactg    60
gggcccc                                                             67

<210> SEQ ID NO 70
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 tcgaggggc cccagtggcc cttaattaag gatccccact agtgcggccg cggcccctgc    60
ggccatggc                                                           69

<210> SEQ ID NO 71
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ctagccatgg ccgcaggggc cgcggccgca ctagtgggga tccttaatta agggccactg    60
gggcccccc                                                           68

<210> SEQ ID NO 72
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72 tcgaggggc cccagtggcc cttaattaag gatccccact agtgcggccg cggcccctgc    60
ggccatgg                                                            68

<210> SEQ ID NO 73
<211> LENGTH: 76
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 73
aattcggggc cggacgggcc gcggccgcac tagtggggat ccttaattaa gggccactgg      60 ggccccctcga cctgca                                                     76

<210> SEQ ID NO 74
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggtcgagggg ccccagtggc ccttaattaa ggatccccac tagtgcggcc gcggcccgtc      60
cggccccg                                                               68

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcgtttggaa tcactacagg                                                  20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cacgatgcac gttgaagtg                                                   19

<210> SEQ ID NO 77
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 77
ggagugcuuu ugggucuggt t                                                21

<210> SEQ ID NO 78
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
```

-continued

<400> SEQUENCE: 78
ccagacccaa aagcacucct t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 79
gugauggcac aucccgacgt t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 80
cgucgggaug ugccaucact t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 81
guuccugaug gagcuguaat t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 82
uuacagcucc aucaggaact t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 83
gaagcaguuc aaguaugggt t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 84
cccauacuug aacugcuuct t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 85
ccaugccaga agacuggcut t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 86
agccagucuu cuggcauggt t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
ggagcgcgcc ucuuuuuggt t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic -continued oligonucleotide

<400> SEQUENCE: 88
ccaaaaagag gcgcgcucct t                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 89
ccuccagucu ucucucguct t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 90
gacgagagaa gacuggaggt t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 91
cagccuggga augagacugt t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 92
cagucucauu cccaggcugt t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

-continued

<223> OTHER INFORMATION: Description of Artificial Sequence: Synthetic
      oligonucleotide

<400> SEQUENCE: 93
gaaagugaaa ucuccgcggt t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 94
ccgcggagau uucacuuuct t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 95
ggaaccucuc cccguggaat t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 96
uuccacgggg agagguucct t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 97
ugagacguau gaaaacaaut t                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide

```
<220> FEATURE:
<223> OTHER INFORMATION: Description of Artificial Sequence: Synthetic
      oligonucleotide

<400> SEQUENCE: 98
auuguuuuca uacgucucat t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 99
guggaggaga ucuacgacct t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 100
ggucguagau cuccuccact t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 101
gaacuggaag acaaccccat t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 102
ugggguuguc uuccaguuct t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
      Synthetic oligonucleotide
<220> FEATURE:
<223> OTHER INFORMATION: Description of Artificial Sequence: Synthetic
      oligonucleotide

<400> SEQUENCE: 103
gccuguucag cagcauuggt t                                               21

<210> SEQ ID NO 104
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 104
ccaaugcugc ugaacaggct t                                               21

<210> SEQ ID NO 105
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 105
cuagagaucc cucagaccct t                                               21

<210> SEQ ID NO 106
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 106
gggucugagg gaucucuagt t                                               21

<210> SEQ ID NO 107
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 107
cguacgcgga auacuucgat t                                               21

<210> SEQ ID NO 108
<211> LENGTH: 21
<212> TYPE: DNA
<213> ORGANISM: Artificial Sequence
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 108
ucgaaguauu ccgcguacgt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 109
caaugacuua caaggcagct t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 110
gcugccuugu aagucauugt t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 111
gaguggacug aagcacgagt t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 112
cucgugcuuc aguccacuct t                                              21

<210> SEQ ID NO 113
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 113
ggaaguagga agcaucauut t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 114
aaugaugcuu ccuacuucct t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 115
gagauacccc ucacucuggt t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 116
ccagagugag ggguaucuct t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 117
gacaugcuuc agcuuaucat t                                              21

<210> SEQ ID NO 118
<211> LENGTH: 21
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 118
ugauaagcug aagcauguct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 119
ucaaguggga gaguucccut t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 120
agggaacucu cccacuugat t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 121
ccaacggaau ggccaagaat t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 122
uucuuggcca uuccguuggt t                                              21

<210> SEQ ID NO 123
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gacugucugc gacgcagcat t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 124
ugcugcgucg cagacaguct t                                              21

<210> SEQ ID NO 125
<211> LENGTH: 458
<212> TYPE: DNA
<213> ORGANISM: Homo sapiens

<400> SEQUENCE: 125
cagctaaaag gagaagccat gcatgggcaa gtagactgta gtccaggaat atggcaacta    60
gattgtacac atttagaagg aaaagttatc ctggtagcag ttcatgtagc cagtggatat   120
atagaagcag aagttattcc agcagagaca gggcaggaaa cagcatactt tctcttaaaa   180
ttagcaggaa gatggccagt aacaacaata catacagaca atggcagcaa tttcaccagt   240
gctacagtta aagccgcctg ttggtgggca gggatcaagc aggaatttgg cattccctac   300
aatccccaaa gtcaaggagt agtagaatct atgaataaag aattaaagaa aattatagga   360
caggtaagag atcaggctga acatcttaag acagcagtac aaatggcagt attcatccac   420
aattttaaaa gaaaaggggg gattgggggg tacagtgc                            458

<210> SEQ ID NO 126
<211> LENGTH: 152
<212> TYPE: PRT
<213> ORGANISM: Homo sapiens

<400> SEQUENCE: 126

Gln Leu Lys Gly Glu Ala Met His Gly Gln Val Asp Cys Ser Pro Gly
1               5                   10                  15

Ile Trp Gln Leu Asp Cys Thr His Leu Glu Gly Lys Val Ile Leu Val
            20                  25                  30

Ala Val His Val Ala Ser Gly Tyr Ile Glu Ala Glu Val Ile Pro Ala
        35                  40                  45

Glu Thr Gly Gln Glu Thr Ala Tyr Phe Leu Leu Lys Leu Ala Gly Arg
    50                  55                  60

Trp Pro Val Thr Thr Ile His Thr Asp Asn Gly Ser Asn Phe Thr Ser
65                  70                  75                  80

Ala Thr Val Lys Ala Ala Cys Trp Trp Ala Gly Ile Lys Gln Glu Phe
                85                  90                  95

Gly Ile Pro Tyr Asn Pro Gln Ser Gln Gly Val Val Glu Ser Met Asn
            100                 105                 110
```

```
Lys Glu Leu Lys Lys Ile Ile Gly Gln Val Arg Asp Gln Ala Glu His
        115                 120                 125

Leu Lys Thr Ala Val Gln Met Ala Val Phe Ile His Asn Phe Lys Arg
    130                 135                 140

Lys Gly Gly Ile Gly Gly Tyr Ser
145                 150
```

<210> SEQ ID NO 127
<211> LENGTH: 159
<212> TYPE: DNA
<213> ORGANISM: Homo sapiens

<400> SEQUENCE: 127

```
actagattgt acacatttag aaggaaaagt tatcctggta gcagttcatg tagccagtgg    60
atatatagaa gcagaagtta ttccagcaga gacagggcag gaaacagcat actttctctt   120
aaaattagca ggaagatggc cagtaacaac aatacatac                          159
```

<210> SEQ ID NO 128
<211> LENGTH: 52
<212> TYPE: PRT
<213> ORGANISM: Homo sapiens

<400> SEQUENCE: 128

```
Leu Asp Cys Thr His Leu Glu Gly Lys Val Ile Leu Val Ala Val His
1               5                   10                  15

Val Ala Ser Gly Tyr Ile Glu Ala Glu Val Ile Pro Ala Glu Thr Gly
            20                  25                  30

Gln Glu Thr Ala Tyr Phe Leu Leu Lys Leu Ala Gly Arg Trp Pro Val
        35                  40                  45

Thr Thr Ile His
    50
```

<210> SEQ ID NO 129
<211> LENGTH: 395
<212> TYPE: DNA
<213> ORGANISM: Homo sapiens

<400> SEQUENCE: 129

```
gggcaagtag actgtagtcc aggaatatgg caactagatt gtacacattt agaaggaaaa    60
gttatcctgg tagcagttca tgtagccagt ggatatatag aagcagaagt tattccagca   120
gagacagggc aggaaacagc atactttctc ttaaaattag caggaagatg gccagtaaca   180
acaatacata cagacaatgg cagcaatttc accagtgcta cagttaaagc cgcctgttgg   240
tgggcaggga tcaagcagga atttggcatt ccctacaatc cccaaagtca aggagtagta   300
gaatctatga ataaagaatt aagaaaatt ataggacagg taagagatca ggctgaacat    360
cttaagacag cagtacaaat ggcagtattc atcca                              395
```

<210> SEQ ID NO 130
<211> LENGTH: 131
<212> TYPE: PRT
<213> ORGANISM: Homo sapiens

<400> SEQUENCE: 130

```
Gly Gln Val Asp Cys Ser Pro Gly Ile Trp Gln Leu Asp Cys Thr His
1               5                   10                  15

Leu Glu Gly Lys Val Ile Leu Val Ala Val His Val Ala Ser Gly Tyr
            20                  25                  30
```

```
Ile Glu Ala Glu Val Ile Pro Ala Glu Thr Gly Gln Glu Thr Ala Tyr
            35                  40                  45

Phe Leu Leu Lys Leu Ala Gly Arg Trp Pro Val Thr Thr Ile His Thr
        50                  55                  60

Asp Asn Gly Ser Asn Phe Thr Ser Ala Thr Val Lys Ala Ala Cys Trp
 65                  70                  75                  80

Trp Ala Gly Ile Lys Gln Glu Phe Gly Ile Pro Tyr Asn Pro Gln Ser
                85                  90                  95

Gln Gly Val Val Glu Ser Met Asn Lys Glu Leu Lys Lys Ile Ile Gly
            100                 105                 110

Gln Val Arg Asp Gln Ala Glu His Leu Lys Thr Ala Val Gln Met Ala
        115                 120                 125

Val Phe Ile
    130

<210> SEQ ID NO 131
<211> LENGTH: 232
<212> TYPE: DNA
<213> ORGANISM: Homo sapiens

<400> SEQUENCE: 131
aaggttgtct ccctaactga cacaacaaat cagaagactg agttacaagc aatttatcta      60
gctttgcagg attcgggatt agaagtaaac atagtaacag actcacaata tgcattagga    120
atcattcaag cacaaccaga tagaagtgaa tcagagttag tcagtcaaat aatagagcag    180
ttaataaaaa aggaaaaggt ctatctggca tgggtaccag cacacaaagg aa            232

<210> SEQ ID NO 132
<211> LENGTH: 77
<212> TYPE: PRT
<213> ORGANISM: Homo sapiens

<400> SEQUENCE: 132

Lys Val Val Ser Leu Thr Asp Thr Thr Asn Gln Lys Thr Glu Leu Gln
  1               5                  10                  15

Ala Ile Tyr Leu Ala Leu Gln Asp Ser Gly Leu Glu Val Asn Ile Val
            20                  25                  30

Thr Asp Ser Gln Tyr Ala Leu Gly Ile Ile Gln Ala Gln Pro Asp Arg
        35                  40                  45

Ser Glu Ser Glu Leu Val Ser Gln Ile Ile Glu Gln Leu Ile Lys Lys
    50                  55                  60

Glu Lys Val Tyr Leu Ala Trp Val Pro Ala His Lys Gly
 65                  70                  75

<210> SEQ ID NO 133
<211> LENGTH: 9706
<212> TYPE: DNA
<213> ORGANISM: Human immunodeficiency virus

<400> SEQUENCE: 133
tggaagggct aattcactcc caacaaagac aagatatcct tgatctgtgg gtctaccaca      60
cacaaggcta cttccctgat ggcagaact acacaccagg ggggactaga tggccactga    120
cctttggatg gtgcttcaag ctagtaccag ttgagccaga aagatagaa gaggccaatg    180 caggagagaa caactgcttg ttacacccta tgagccagca tggaatggat gacccggaga    240
gagaagggtt agagtggagg tttgacagcc gcctagcatt tcatcacgtg gcccgagagc    300
tgcatccgga gtactacaag aactgatgac ctcgagcttt ctacaaggga ctttccgctg    360
```

```
gggactttcc agggaagcgt ggcctgggcg ggactgggga gtggcgagcc ctcagatgct    420
gcatataagc agctgctttt gcctgtactg ggtctctctg gttagaccag atctgagcct    480
gggagctctc tggctagcta ggaaacccac tgcttaagcc tcaataaagc ttgccttgag    540
tgctttaagt agtgtgtgcc cgtctgttgt gtgactctgg taactagaga tccctcagac    600
ccttttagtc agtgtggaaa atctctagca gtggcgcccg aacagggact tgaaagcgaa    660
aggaaaacca gaggagctct ctcgacgcag gactcggctt gctgaagcgc gcacggcaag    720
aggcgagggg cggcgactgg tgagtacgcc aaaaattttt gactagcgg aggctagaag    780
gagagagatg ggtgcgagag cgtcagtatt aagtgcgggg gaattagata agtgggaaaa    840
aattcggtta aggccagggg gaaagaaaca atatagatta aaacatatag tatgggcaag    900
cagggagcta gaacgattcg cagttgatcc tggcctgtta gaaacatcag aaggctgtag    960
acaaatactg ggacagctac aaccgtccct tcagacagga tcagaagagc ttagatcatt   1020
atataataca gtagccaccc tctattgtgt acatcaaaag atagaggtaa aagacaccaa   1080
ggaagcttta gagaagatag aggaagagca aaacaaaagt aagaaaaaag cacagcaagc   1140
agcagctgac acaggaaaca gcagccaggt cagccaaaat taccctatag tgcagaacct   1200
acaggggcaa atggtacatc aggccatatc acctagaact ttaaatgcat gggtaaaagt   1260
agtggaagag aaggcgttca gcccagaagt aatacccatg ttttcagcat tatcagaagg   1320
agccacccca caagatttaa acaccatgct aaacacagtg gggggacacc aagcagccat   1380
gcaaatgtta aaagagacca tcaatgagga agctgcagaa tgggatagat tgcatccagt   1440
gcatgcaggg cctattgcac caggccagat gagagaacca aggggaagtg acatagcagg   1500
aactactagt acccttcagg aacaaatagg atggatgaca aataatccac ctatcccagt   1560
aggagaaatc tataaaagat ggataatcct gggattaaat aaaatagtaa gaatgtatag   1620
tcctaccagc attctggaca taagacaagg accaaaggaa cccttagag attatgtaga   1680
ccggttctat aaaactctaa gagccgagca agcttcacag gaggtaaaaa attggatgac   1740
agaaaccttg ttggtccaaa atgcgaaccc agattgtaag actatttaa aagcattggg   1800
accagcagct acactagaag aaatgatgac agcatgtcag ggagtggggg gacccggcca   1860
taaagcaaga gttttggctg aagcaatgag ccaagtaaca aattcagcta ccataatgat   1920
gcagagaggc aattttagga accaaagaaa aactgttaag tgtttcaatt gtggcaaaga   1980
agggcacata gccaaaaatt gcagggctcc taggaaaaag ggctgttgga aatgtggaaa   2040
ggaaggacac caaatgaaag attgtactga gagacaggct aattttttag ggaagatctg   2100
gccttcccac aagggaaggc caggaaattt tcttcagagc agaccagagc caacagcccc   2160
atcagaagag agcgtcaggt ttggagaaga gacaacaact ccctctcaga agcaggagcc   2220
gatagacaag gaactgtatc ctttagcttc cctcagatca ctctttggca gcgacccctc   2280
gtcacaataa agatagggg gcaactaaag gaagctctat tagatacagg agcagatgat   2340
acagtattag aagaaatgaa tttgccagga agatggaaac caaaaatgat aggggaatt   2400
ggaggtttta tcaaagtaag acagtatgat cagatacccca tagaaatatg tggacataaa   2460
gctataggta cagtattagt aggacctaca cctgtcaaca taattggaag aaatctgttg   2520
actcagattg gttgcacttt aaattttccc attagtccta ttgaaactgt accagtaaaa   2580
ttaaagccag gaatggatgg cccaaaagtt aaacaatggc cattgacaga agaaaaaata   2640
aaagcattag tagaaatttg tacagaaatg gaaaaggaag ggaaaatttc aaaaattggg   2700
```

```
cctgaaaacc catacaatac tccagtattt gccataaaga aaaagacag tactaaatgg    2760 agaaaattag tagatttcag agaacttaat aagagaactc aagacttctg ggaagttcaa    2820
ttaggaatac cacatcccgc aggttaaaa agaaaaaat cagtaacagt actggatgtg    2880
ggtgatgcat attttcagt tcccttacat gaagacttca ggaagtatac tgcatttacc    2940
atacctagta taaacaatga dacaccaggg actagatatc agtacaatgt gcttccacag    3000
ggatggaaag ggtcaccagc aatattccaa gtagcatga caacaatctt agagcctttt    3060
agaaaacaaa atccagacct agttatctat cagtacatgg atgatttgta cgtaggatct    3120
gacttagaaa tagggcagca tagaacaaaa atagaggaac tgagacaaca tctgttgagg    3180
tggggattta ccacaccaga caaaaaacat cagaaagaac ctccattcct ttggatgggt    3240
tatgaactcc atcctgataa atggacagta cagcctatag tgctgccaga aaagatagc    3300 tggactgtca atgacataca gaagttagtg ggaaaattga attgggcaag tcagatttat    3360
gcagggatta aagtaaggca attatgtaaa ctccttaggg gaaccaaagc actaacagaa    3420
gtaataccac taacagaaga agcagaacta gaactggcag aaaacaggga aattctaaaa    3480
gaaccagtac atggagtgta ttatgaccca tcaaagact tgatagcaga atacagaag    3540 caggggcaag gccaatggac atatcaaatt tatcaagagc catttaaaaa tctgaaaaca    3600
ggaaaatatg caagaacgag gggtgcccac actaatgatg taaaacaatt aacagaggca    3660
gtacaaaaaa tagccacaga aagcatagta atatggggaa agactcctaa atttaaacta    3720
cccatacaaa aagaaacatg gaaacatgg tggacagaat attggcaagc cacctggatt    3780
cctgagtggg agtttgtcaa tacccctccc ttagtgaaat tatggtacca gttagagaaa    3840
gaacccataa taggagcaga aactttctat gtagatgggg cagctaacag ggagactaaa    3900
ttaggaaaag caggatatgt tactaacaag ggaagacaaa aggttgtctc cctaactgac    3960
acaacaaatc agaagactga gttacaagca atttatctag ctttgcagga ttcgggatta    4020
gaagtaaaca tagtaacaga ctcacaatat gcattaggaa tcattcaagc acaaccagat    4080
agaagtgaat cagagttagt cagtcaaata atagagcagt taataaaaaa ggaaaaggtc    4140
tatctggcat gggtaccagc acacaaagga attggaggaa atgaacaagt agataaatta    4200
gtcagtgctg gatcaggaa agtactattt ttagatggaa tagataaggc ccaagaagaa    4260
catgagaaat atcacagtaa ttggagagca atggctagtg attttaacct gccacctgta    4320
gtagcaaaag aaatagtagc cagctgtgat aaatgtcagc taaaaggaga agccatgcat    4380
gggcaagtag actgtagtcc aggaatatgg caactagatt gtacacattt agaaggaaaa    4440
gttatcctgg tagcagttca tgtagccagt ggatatatag aagcagaagt tattccagca    4500
gagacagggc aggaaacagc atactttctc ttaaaattag caggaagatg gccagtaaca    4560
acaatacata cagacaatgg cagcaatttc accagtgcta cagttaaagc cgcctgttgg    4620
tgggcaggga tcaagcagga atttggcatt ccctacaatc cccaaagtca aggagtagta    4680
gaatctatga ataaagaatt aaagaaaatt ataggacagg taagagatca ggctgaacat    4740
cttaagacag cagtacaaat ggcagtattc atccacaatt ttaaaagaaa aggggggatt    4800
ggggggtaca gtgcagggga agaatagta gacataatag caacagacat acaaactaaa    4860
gaactacaga aacaaattac aaaaattcaa aattttcggg tttattacag ggacagcaga    4920
gatccacttt ggaaaggacc agcaaagctc ctctggaaag gtgaagggc agtagtaata    4980 caagataata gtgacataaa agtagtgcca agaagaaaag caaagatcat tagggattat    5040
ggaaaacaga tggcaggtga tgattgtgtg gcaggtagac aggatgagga ttagagcatg    5100
```

```
gaaaagttta gtaaaacacc atatgtatat ttcagggaaa gctaggggat ggttttatag    5160
acatcactat gaaagtcctc atccaagaat aagttcagaa gtacacatcc cactagggga    5220
tgctaaattg gtaataacaa catattgggg tctgcacaca ggagaaagag actggcattt    5280
gggtcaggga gtctccatag aatggaggaa aaagagatat agcacacaag tagaccctga    5340
cctagcagac caactaattc atctgtatta ctttgattgt ttttcagaat ctgctataag    5400
aaaggccata ttaggatata gagttagtcc taggtgtgaa tatcaagcag gacataacaa    5460
ggtaggatct ctacagtact tggcactaac agcattaata acaccaaaaa agacaaagcc    5520
acctttgcct agtgttaaaa aactgacaga ggatagatgg aacaagcccc agaagaccaa    5580
gggccacaga gggagccgca caatgaatgg acactagagc ttttagagga gcttaagaga    5640
gaagctgtta gacattttcc taggccatgg ctacatggct taggacaaca tatctatgaa    5700
acttatggag atacttgggc aggagtggaa gccataataa gaattctgca acaactgctg    5760
tttattcatt tcagaattgg gtgtcaacat agcagaatag gcattattca acagaggaga    5820
gcaagaagaa atggagccag tagatcctaa cctagcccc tggaagcatc caggaagtca    5880
gcctaggact gcttgtaaca attgctattg taaaaagtgt tgctttcatt gccaagtttg    5940
ttttacaaaa aaaggcttag gcatctccta tggcaggaag aagcggagac agcgacgaag    6000
acctcctcag gacagtcaga ctcatcaaag ttctctatca aagcagtaag tagtacatgt    6060
actgcaatct ttacaagtat tagcaatagt agcattagta gtagcaacaa taatagcaat    6120
agttgtgtgg accatagtat tcatagaata taggaaaata ttaagacaaa ggaaaataga    6180
caggttaatt aatagaataa cagaaagagc agaagacagt ggcaatgaga gcgacggaga    6240
tcaggaagaa ttatcagcac ttgtggaaag ggggcacctt gctccttggg atgttgatga    6300
tctgtagtgc tgcagaacaa ttgtgggtca cagtctatta tggggtacct gtgtggaaag    6360
aagcaaccac cactctattt tgtgcatcag atgctaaagc atatgataca gaggtacata    6420
atgtttgggc cacacatgcc tgtgtaccca cagaccccaa cccacaagaa gtaaaattgg    6480
aaaatgtgac agaaaatttt aacatgtgga aaaataacat ggtagaacaa atgcatgagg    6540
atataatcag tttatgggat caaagcctaa agccatgtgt aaaattaact ccactctgtg    6600
ttactttaaa ttgcactgat ttaaggaatg ctactaatac cactagtagt agctgggaaa    6660
cgatggagaa aggagaaata aaaaactgct ctttcaatat caccacaagc ataagagata    6720
aggtacagaa agaatatgca ctttttata accttgatgt agtaccaata gataatgcta    6780
gctataggtt gataagttgt aacacctcag tcattacaca ggcctgtcca aggtatcct    6840 ttgagccaat tcccatacat tattgtgccc cggctggttt tgcgattcta aaatgtaatg    6900
ataaaaagtt caatggaaca ggaccatgta caaatgtcag cacagtacaa tgtacacatg    6960
gaattaggcc agtagtatca actcaactgc tgttaaatgg cagtctagca gaagaagaga    7020
tagtaattag atctgaaaat ttcacaaaca atgctaaaac tataatagta cagctgaacg    7080
aatctgtagt aattaattgt acaagaccca acaacaatac aagaaaaagt ataaatatag    7140
gaccagggag agcattgtat acaacaggag aaataatagg agatataaga caagcacatt    7200
gtaaccttag taaaacacaa tgggaaaaca ctttagaaca gatagctata aaattaaaag    7260
aacaatttgg gaataataaa acaataatct ttaatccatc ctcaggaggg gacccagaaa    7320
ttgtaacaca cagttttaat tgtggagggg aattttccta ctgtaattca acacaactgt    7380
ttacttggaa tgatactaga aagttaaata acactggaag aaatatcaca ctcccatgta    7440
```

```
gaataaaaca aattatataaat atgtggcagg aagtaggaaa agcaatgtat gcccctccca    7500
tcagaggaca aattagatgt tcatcaaata ttacagggct gctattaaca agagatggtg    7560
gtaaggacac gaacgggact gagatcttca gacctggagg aggagatatg agggacaatt    7620
ggagaagtga attatataaa tataaagtag taaaaattga accattagga gtagcaccca    7680
ccaaggcaaa gagaagagtg gtgcagagag aaaaaagagc agtgggacta ggagctttgt    7740
tccttgggtt cttgggagca gcaggaagca ctatgggcgc agcgtcaata acgctgacgg    7800
tacaggccag acaattattg tctggtatag tgcaacagca gaacaatctg ctgagggcta    7860
ttgaggcgca acagcacctg ttgcaactca cagtctgggg catcaagcag ctccaggcaa    7920
gagtcctggc tgtggaaaga tacctaaggg atcaacagct cctagggatt tggggttgct    7980
ctggaaaact catttgcacc actactgtgc cttggaatac tagttggagt aataaatctc    8040
tgaatgaaat ttgggataac atgacttgga tgaagtggga agagaaaatt gacaattaca    8100
cacacataat atactcctta attgaacaat cgcagaacca acaagaaaag aatgaacaag    8160
aattattggc attagataaa tgggcaagtt tgtggaattg gtttgacata acaaaatggc    8220
tgtggtatat aaaaatattc ataatgatag taggaggctt gataggttta agaatagttt    8280
ttgttgtact ttctatagtg aatagagtta ggcagggata ctcaccatta tcgtttcaga    8340
cccacctccc agctcagagg ggacccgaca ggcccgacgg aatcgaagaa gaaggtggag    8400
agagagacag agacagatcc ggtccattag tggatggctt cttagcaatt atctgggtcg    8460
acctacggag cctgtgcctt ttcagctacc accgcttgag agacttactc ttgattgtaa    8520
cgaggattgt ggaacttctg ggacgcaggg ggtggggagt cctcaaatat tggtggaatc    8580
tcctccagta ttggattcag gaactaaaga atagtgctgt tagcttgctc aacgccacag    8640
ctatagcagt agctgaggga acagataggg ttatagaaat attacaaaga gcttttagag    8700
ctgttcttca catacctgta agaataagac agggcttgga aagagctttg ctataagatg    8760
ggtggcaagt ggtcaaaacg tagtatggct ggatggccta ctgtaaggga agaatgaga    8820 cgagccgagc cagcagcaga aagaatgaga cgagctgagc cagcagcaga tggggtggga    8880
gcagtatctc gagacctgga aagacatgga gcaatcacaa gtagcaatac agcagctact    8940
aatgctgatt gtgcctggct agaagcacaa gaggaggagg aggtgggttt tccagtcaga    9000
cctcaggtac ctttaagacc aatgactcac aaggcagcta tggatcttag ccactttta    9060 aaagaaaagg ggggactgga agggctaatt cactcccaac aaagacaaga tatccttgat    9120
ctgtgggtct accacacaca aggctacttc cctgattggc agaactacac accagggggg    9180
actagatggc cactgacctt tggatggtgc ttcaagctag taccagttga gccagagaag    9240
atagaagagg ccaatgcagg agagaacaac tgcttgttac accctatgag ccagcatgga    9300
atggatgacc cggagagaga agggttagag tggaggtttg acagccgcct agcatttcat    9360
cacgtggccc gagagctgca tccggagtac tacaagaact gatgacctcg agctttctac    9420
aagggacttt ccgctgggga ctttccaggg aagcgtggcc tgggcgggac tggggagtgg    9480
cgagccctca gatgctgcat ataagcagct gctttgcct gtactgggtc tctctggtta    9540
gaccagatct gagcctggga gctctctggc tagctaggaa acccactgct taagcctcaa    9600
taaagcttgc cttgagtgct ttaagtagtg tgtgcccgtc tgttgtgtga ctctggtaac    9660
tagagatccc tcagaccctt ttagtcagtg tggaaaatct ctagca           9706
```

<210> SEQ ID NO 134
<211> LENGTH: 114

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gagagtagta acaaaggtca aagacagttg actgtatcgc cggaatttat ggccatggag    60
gccccgggga tccgtcgacc tgcagccaag ctaattccgg gcgaatttct tatg         114

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gagagtagta acaaaggtc                                                 19

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cataagaaat tcgcccgg                                                  18

<210> SEQ ID NO 137
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gagagtagta acaaaggtca aagacagttg actgtatcgc cggaatttat ggccatggcc    60 gcagggccg cggccgcact agtggggatc cttaattaag ggccactggg gccctcgac     120 ctgcagccaa gctaattccg ggcgaatttc ttatg                              155

<210> SEQ ID NO 138
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gagagtagta acaaaggtca aagacagttg actgtatcgc cggaatttat ggccatggcc    60
ggacgggccg cggccgcact agtggggatc cttaattaag ggccactggg gccctcgac   120 ctgcagccaa gctaattccg ggcgaatttc ttatg                              155

<210> SEQ ID NO 139
<211> LENGTH: 78
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139
gaattcgggg ccggacgggc cgcggccgca ctagtgggga tccttaatta agggccactg      60
gggcccctcg acctgcag      78

<210> SEQ ID NO 140
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
cgtttggaat cactacaggg atgtttaata ccactacaat ggatgatgta tataactatc      60
tattcgatga tgaagatacc ccaccaaacc caaaaaaaga gatctgtatg gcttacccat     120
acgatgttcc agattacgct agcttgggtg gtcatatggc catggaggcc ccggggatcc     180
gaattcgagc tcgactagct agctgactcg agagatctat gaatcgtaga tactgaaaaa     240
ccccgcaagt tcacttcaac tgtgcatcgt gcaccatctc aatttc                    286

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
cgtttggaat cactacagg      19

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
cgatgatgaa gatacccccac caaa      24

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143 ggggttttc agtatctacg      20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144

```
cacgatgcac agttgaagtg                                                 20

<210> SEQ ID NO 145
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gaaattgaga tggtgcacga tgcac                                           25

<210> SEQ ID NO 146
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
cgcgtttgga atcactacag ggatgtttaa taccactaca atggatgatg tatataacta     60
tctattcgat gatgaagata ccccaccaaa cccaaaaaaa gagatctgta tggcttaccc    120
atacgatgtt ccagattacg ctagcttggg tggtcatatg gccatggccg caggggccgc    180
ggccgcacta gtgggatcc ttaattaagg gccactgggg cccctcgaga gatctatgaa    240
tcgtagatac tgaaaaaccc cgcaagttca cttcaactgt gcatcgtgca ccatctcaat    300
ttc                                                                  303

<210> SEQ ID NO 147
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
cgcgtttgga atcactacag ggatgtttaa taccactaca atggatgatg tatataacta     60
tctattcgat gatgaagata ccccaccaaa cccaaaaaaa gagatctgta tggcttaccc    120
atacgatgtt ccagattacg ctagcttggg tggtcatatg gccatggccg acgggccgc    180 ggccgcacta gtgggatcc ttaattaagg gccactgggg cccctcgaga gatctatgaa    240
tcgtagatac tgaaaaaccc cgcaagttca cttcaactgt gcatcgtgca ccatctcaat    300
ttc                                                                  303

<210> SEQ ID NO 148
<211> LENGTH: 358
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
cgtttggaat cactacaggg atgtttaata ccactacaat ggatgatgta taaactatc      60 tattcgatga tgaagatacc caccaaaacc caaaaaaaga gatcctagaa ctagccatgg    120
ccgcaggggc gcggccgca ctagtgggga tccttaatta agggccactg ggcccctcg    180 agtagctagt gtctagaggc ccggtaccca attcgcccta tagtgagtcg tattacaatt    240
```

```
cactggccgt cgttttacaa cgtcgtgact gggaaaaccc tgatctatga atcgtagata      300
ctgaaaaacc ccgcaagttc acttcaactg tgcatcgtgc accatctcaa tttctttc       358

<210> SEQ ID NO 149
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
cgtttggaat cactacaggg atgtttaata ccactacaat ggatgatgta tataactatc      60
tattcgatga tgaagatacc ccaccaaacc caaaaaaaga gatcctagaa ctagccatgg     120
ccggacgggc cgcggccgca ctagtgggga tccttaatta agggccactg ggcccctcg      180 agtagctagt gtctagaggc ccggtaccca attcgcccta tagtgagtcg tattacaatt     240
cactggccgt cgttttacaa cgtcgtgact gggaaaaccc tgatctatga atcgtagata     300
ctgaaaaacc ccgcaagttc acttcaactg tgcatcgtgc accatctcaa tttcttt       357

<210> SEQ ID NO 150
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(42)

<400> SEQUENCE: 150 gct gca ggg tcg act cta gag gat ccc cgg gta cct aag taa              42
Ala Ala Gly Ser Thr Leu Glu Asp Pro Arg Val Pro Lys
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Ala Gly Ser Thr Leu Glu Asp Pro Arg Val Pro Lys
1               5                   10

<210> SEQ ID NO 152
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(75)

<400> SEQUENCE: 152 atg acc atg att acg cca agc ttg cat gcc tgc agg tcg act cta gag      48
Met Thr Met Ile Thr Pro Ser Leu His Ala Cys Arg Ser Thr Leu Glu
1               5                   10                  15 gat ccc cgg gta ccg agc tcg aat tca                                  75
```

Asp Pro Arg Val Pro Ser Ser Asn Ser
            20                  25

<210> SEQ ID NO 153
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Met Thr Met Ile Thr Pro Ser Leu His Ala Cys Arg Ser Thr Leu Glu
1               5                   10                  15

Asp Pro Arg Val Pro Ser Ser Asn Ser
            20                  25

<210> SEQ ID NO 154
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(54)

<400> SEQUENCE: 154 gcc tgc agg tcg act cta gag gat ccc cgg gta ccg agc tcg aat tca         48
Ala Cys Arg Ser Thr Leu Glu Asp Pro Arg Val Pro Ser Ser Asn Ser
1               5                   10                  15 tgc ata taa                                                             57
Cys Ile <210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Cys Arg Ser Thr Leu Glu Asp Pro Arg Val Pro Ser Ser Asn Ser
1               5                   10                  15

Cys Ile

<210> SEQ ID NO 156
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)

<400> SEQUENCE: 156 gct gca ggg tcg act cta gag gat ccc cgg gta cct aag taactaagaa          49
Ala Ala Gly Ser Thr Leu Glu Asp Pro Arg Val Pro Lys
1               5                   10 ttc                                                                     52

<210> SEQ ID NO 157

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Ala Gly Ser Thr Leu Glu Asp Pro Arg Val Pro Lys
1               5                   10

<210> SEQ ID NO 158
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(57)

<400> SEQUENCE: 158 tgg gta ccg ggc ccc ccc tcg agg tcg acg gta tcg ata agc ttg ata      48
Trp Val Pro Gly Pro Pro Ser Arg Ser Thr Val Ser Ile Ser Leu Ile
1               5                   10                  15 tcg aat tcc                                                          57
Ser Asn Ser <210> SEQ ID NO 159
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Trp Val Pro Gly Pro Pro Ser Arg Ser Thr Val Ser Ile Ser Leu Ile
1               5                   10                  15

Ser Asn Ser

<210> SEQ ID NO 160
<211> LENGTH: 264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
aaagtcgaac tgttgccaga aaatagcgag tttaaaccaa ttgtcgtaat cttcgtcagc     60
agagcttcac cattgaaggg ctggcggttg gggttattcg caacggcgac tggctggaat    120
tcggggccgg acgggccgcg gccgcactag tgggatcct taattaaggg ccactggggc     180
ccctcgacct gcagccaagc taattccggg cgaatttctt atgatttatg attttttatta   240 ttaaataagt tataaaaaaa ataa                                            264

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 161
tgttgccaga aaatagcgag                                              20

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aattcgcccg gaattagc                                                18
```